United States Patent
Nitz et al.

(10) Patent No.: US 11,236,122 B2
(45) Date of Patent: Feb. 1, 2022

(54) TRITERPENE AMINE DERIVATIVES

(71) Applicants: DFH THERAPEUTICS, Gaithersburg, MD (US); The United States of America, as represented by the Secretary, Department of Health and Human Services, Bethesda, MD (US)

(72) Inventors: Theodore J. Nitz, Boyds, MD (US); Carl T. Wild, Gaithersburg, MD (US); David E. Martin, Shawnee, OK (US); Eric O. Freed, Frederick, MD (US)

(73) Assignees: DFH THERAPEUTICS, Gaithersburg, MD (US); The United States Of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 17/254,189

(22) PCT Filed: Jun. 28, 2019

(86) PCT No.: PCT/US2019/039981
§ 371 (c)(1),
(2) Date: Dec. 18, 2020

(87) PCT Pub. No.: WO2020/006510
PCT Pub. Date: Jan. 2, 2020

(65) Prior Publication Data
US 2021/0253627 A1    Aug. 19, 2021

Related U.S. Application Data

(60) Provisional application No. 62/692,071, filed on Jun. 29, 2018.

(51) Int. Cl.
*C07J 63/00* (2006.01)

(52) U.S. Cl.
CPC .................... *C07J 63/008* (2013.01)

(58) Field of Classification Search
CPC ........................................... C07J 63/08
USPC .......................................... 514/176
See application file for complete search history.

(56) References Cited

U.S. PATENT DOCUMENTS 9,505,800 B2 * 11/2016 Nitz ...................... C07J 63/008
2013/0072465 A1   3/2013 Liu et al.
2014/0221361 A1   8/2014 Swidorski et al.

FOREIGN PATENT DOCUMENTS

WO    2017/149518 A1    9/2017

OTHER PUBLICATIONS

Urano, Antimicrobial Agents and Chemotherapy (2016), 60(1), 190-197.*
International Search Report and Written Opinion in PCT/US2019/039981, dated Oct. 29, 2019.

* cited by examiner

*Primary Examiner* — Nizal S Chandrakumar
(74) *Attorney, Agent, or Firm* — Medler Ferro Woodhouse & Mills PLLC

(57) ABSTRACT

The present invention concerns novel pharmaceutically active triterpene amine derivatives, pharmaceutical compositions containing the same, their use as medicaments, and the use of the compounds for the manufacture of specific medicaments. The present invention also concerns a method of treatment involving administration of the triterpene amine compounds. Specifically, the compounds are derivatives of betulinic acid having substitutions at one or more of the C-3, C-28 and C-19 positions as further described herein. The novel compounds are useful as antiretroviral agents. In particular, the novel compounds are useful for the treatment of Human Immunodeficiency Virus-1 (HIV-1).

14 Claims, No Drawings

TRITERPENE AMINE DERIVATIVES

GOVERNMENT LICENSE RIGHTS

This invention was supported by the U.S. Federal government using intramural funding from the the National Cancer Institute, National Institutes of Health. As such, the government may have certain rights in the invention.

FIELD OF THE INVENTION

The present invention concerns novel pharmaceutically active triterpene amine derivatives, pharmaceutical compositions containing the same, their use as medicaments, and the use of the compounds for the manufacture of specific medicaments. The present invention also concerns a method of treatment involving administration of the triterpene amine compounds. Specifically, the compounds are derivatives of betulin and betulinic acid having substitutions at one or more of the C-3, C-28 and C-19 positions as further described herein. The novel compounds are useful as antiretroviral agents. In particular, the novel compounds are useful for the treatment of Human Immunodeficiency Virus-1 (HIV-1).

BACKGROUND OF THE INVENTION

HIV-1 is a member of the lentiviruses, a subfamily of retroviruses. HIV-1 infects and invades cells of the immune system; it breaks down the body's immune system and renders the patient susceptible to opportunistic infections and neoplasms. The immune defect appears to be progressive and irreversible, with a high mortality rate that approaches 100% over several years.

U.S. Pat. No. 5,679,828 mentions betulinic acid and diliydrobetulinic acid derivatives, including 3-O-(3',3'-dimethylsuccinyl)betulinic acid (also known as (3β)-3-(carboxy-3-methyl-1-oxobutoxy)-lup-20(29)-en-28-oic acid), as potent anti-HIV agents.

U.S. Pat. No. 6,642,217 mentions the use of betulin and analogs thereof for treating fungal and yeast infections.

U.S. Patent Application No. 20050239748 mentions V-methylglucamine, potassium, and sodium pharmaceutical salts of 3-O-(3',3'-dimethylsuccinyl)betulinic acid that are useful in the treatment of HIV and related diseases.

U.S. Patent Application No. 20030186945 mentions method of preparing and use of prodrugs of betulinic acid derivatives.

WO application WO 00/46235 mentions novel betulinic acid derivatives, processes for preparing such derivatives and its use as cancer growth inhibitors.

An American Chemical Society Abstract entitled "Novel Synthetic Analogs of Betulinic Acid and their Biological Activity" by Pranab K. Gupta and Bashir Kaskar bearing a publication date of March 2002 mentions betulinic acid analogs having antitumor activity against human melanoma.

It is well known in the art that highly water soluble medicinal preparations, when administered orally, result in efficient absorption of such preparations from the gastrointestinal tract into systemic circulation. Another hallmark of such preparations is the rapid rate at which they are absorbed into the systemic circulation resulting in a high concentration of the active agent in the blood. Despite recent progress in the development of HIV therapeutic options, there remains a need for drugs having different or enhanced anti-HIV properties relative to currently marketed pharmaceuticals.

BRIEF SUMMARY OF THE INVENTION

It has been discovered that compounds of Formula I are unique compositions exhibiting superior antiretroviral properties:

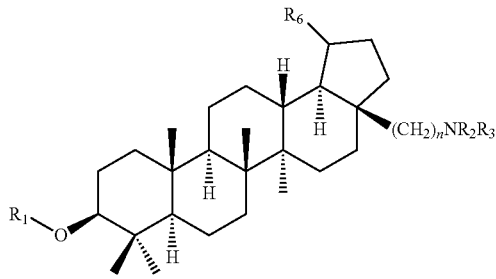

Formula I

Thus, m some embodiments, the disclosure provides for C-28 amine compounds of Formula I, wherein $R_1$, $R_2$, $R_3$, $R_6$ and n are as described herein. In some embodiments, the disclosure provides for pharmaceutically acceptable salts, tautomers, or esters of Formula I.

In some embodiments, the disclosure provides for a compound of Formula I, wherein $R_2$ is hydrido, and $R_3$ is selected with one or more groups from the group consisting of heteroaryl$(CR_aR_b)_m$—, heterocyclyl$(CR_aR_b)_m$—, and $R_4R_5N(CR_aR_b)_m$—, wherein $R_a$, $R_b$, $R_4$, $R_5$ and m are as defined herein. In some embodiments, the heteroaryl of heteroaryl$(CR_aR_b)_m$— or the heterocyclyl of heterocyclyl $(CR_aR_b)_m$ is a nitrogen containing heteroaryl or nitrogen containing heterocyclyl. In some embodiments, $R_3$ is heterocyclyl$(CR_aR_b)_m$—, and the heterocyclyl of heterocyclyl $(CR_aR_b)_m$— is selected from the group consisting of a pyrrolidinyl, a morpholinyl, a pipendinyl, a piperazinyl, a thiomorpholinyl, an imidazolyl, or an oxazolyl.

In some embodiments, the compound of Formula I is a compound of Formula II, Formula III, Formula IV, or Formula V:

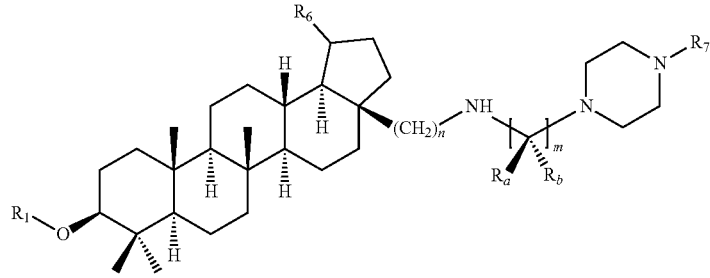

Formula II

Formula III

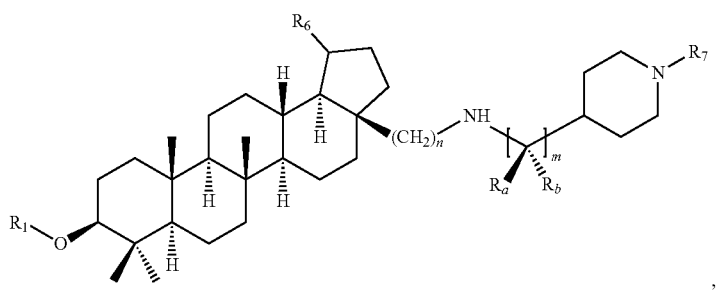

,

Formula IV

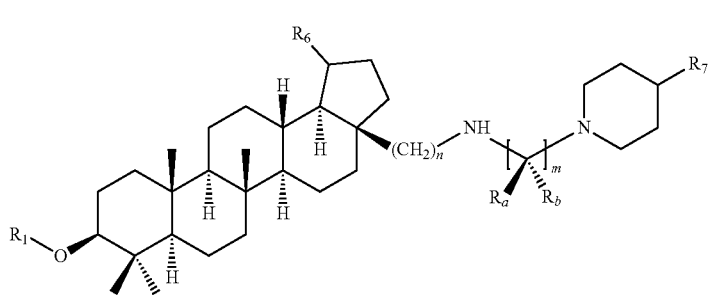

or

Formula V

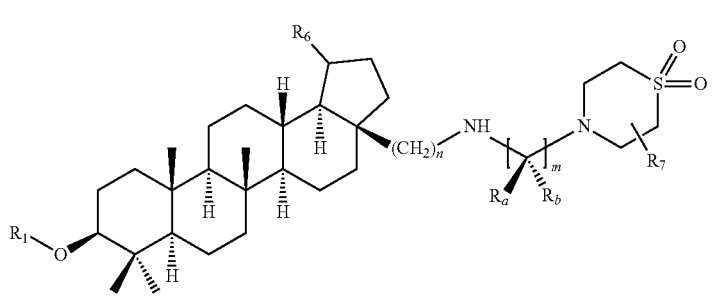

wherein $R_1$, $R_6$, $R_7$, $R_a$, $R_b$, n and m are described herein.

In some embodiments, the disclosure provides a pharmaceutical composition comprising (a) a compound as described herein, and (b) a pharmaceutically acceptable carrier.

In some embodiments, the disclosure provides a pharmaceutical composition as described herein, further comprising at least one antiretroviral selected from the group consisting of HIV protease inhibitors, non-nucleoside HIV reverse transcriptase inhibitors, nucleoside HIV reverse transcriptase inhibitors, nucleotide HIV reverse transcriptase inhibitors, HIV maturation inhibitors, and HIV fusion inhibitors.

In some embodiments, the disclosure provides for a method of inhibiting HIV virion maturation in a subject in need thereof which comprises the step of administering to a subject a therapeutically effective amount of a compound as described herein.

In some embodiments, the disclosure provides a method of preventing or treating infection by HIV in a subject in need thereof which comprises the step of administering to a subject a therapeutically effective amount of a compound as described herein. In some embodiments, the disclosure provides for a method of preventing, treating or delaying the onset of AIDS in a subject in need thereof which comprises administering to the subject a therapeutically effective amount of a compound as described herein. In some embodiments, the disclosure provides for a method for treating a lentiviral condition mediated by the cleavage of a Gag structural protein from at least one adjacent spacer protein in a human in need of such treatment comprising administering a therapeutically effective, Gag cleavage inhibiting amount of a compound as described herein. In some embodiments, the disclosure it directed to a process of synthesizing a triterpene derivative animated at the C-28 position, comprising reductive animation of a triterpene comprising a C-28 aldehyde or a C-28 homologated aldehyde with an amine.

In some embodiments, the disclosure provides a process of synthesizing a triterpene derivative aminated at the C-28 position, comprising reductive animation of a triterpene comprising a C-28 primary amine or a C-28 homologated primary amine with an aldehyde or an aldehyde acetal, or a ketone or a ketone ketal.

DETAILED DESCRIPTION OF THE INVENTION

The present disclosure provides for unique C-28 triterpene derivatives of Formula I, exhibiting superior antiretroviral properties:

Formula I

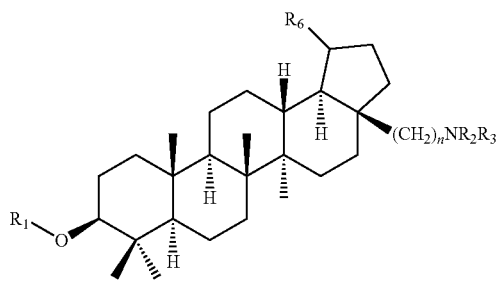

wherein $R_1$, $R_2$, $R_3$, $R_6$ and n are as described herein.

The C-28 amine compounds as disclosed herein differ from previously disclosed compounds in structure, pharmacological activity, or pharmacological potency. Some compounds of the invention not only act favorably in terms of their capability to inhibit the replication of HIV-1, but also by their improved ability to inhibit the replication of mutant strains, in particular strains which have become resistant to commercially available drugs.

Previously, U.S. Pat. No. 9,505,800 reported betulinic acid derivatives compounds exhibiting anti-retroviral properties. The present disclosure has improved certain properties of existing triterpene derivatives. In some embodiments, the present disclosure provides for C-28 amine triterpene derivatives having increase in vivo solubility. In some embodiments, the present disclosure provides for C-28 amine triterpene derivatives having increase solubility to facilitate the manufacture and formulation of pharmaceuticals having improved pharmaceutical properties. In some embodiments, the present disclosure provides for C-28 amine triterpene derivatives having increased antiretroviral activity, especially anti-HIV activity, with improved biodistribution properties. In some embodiments, the present disclosure provides for C-28 amine triterpene derivatives possessing potent antiretroviral activity, especially anti-HIV-1 activity, with superior drug-plasma protein binding properties.

The compounds of the present invention have utility in antiretroviral applications. Exemplary uses include anti-lentiviral applications, and anti-HIV applications. In some embodiments, the treatment of HIV is a preferred use. All forms of HIV-1 are potentially treatable with compounds of the present invention. In some embodiments, compounds of the present invention have utility in treating protease inhibitor resistant HIV, reverse transcriptase inhibitor resistant HIV, and entry/fusion inhibitor resistant HIV. Compounds of the present invention can have utility in treating HIV groups M, N, and O. Compounds of the present invention can have utility in treating HIV-1, including subtypes A1, A2, B, C, D, F1, F2, G, H, J; and circulating recombinant HIV forms. Compounds of the present invention can have utility in treating CCR5 tropic HIV strains as well as CXCR4 tropic HIV strains.

Without wishing to be bound by theory, some triterpene derivatives of the present invention inhibit cleavage of the Capsid-SP1 polypeptide resulting in the release of virus-like particles that are incapable of maturing into infectious virions.

The compounds of the present invention exhibit one or more of the following superior properties thereby satisfying an advance in the art of virology and augmenting pharmaceutical options for clinicians providing antiretroviral treatment to those in need thereof. These superior properties include, but are not limited to, one or more of the following:

(1) enhanced activity against HIV;
(2) enhanced activity against HIV in the presence of human serum;
(3) activity against a broader variety of HIV strains;
(4) improved bioavailability;
(5) reduced protein binding;
(6) improved composition compressibility; and,
(7) improved composition flow properties.

Abbreviations

The term "Ac" refers to acetyl.

The term "acid halide forming agent" means any agent capable of converting a carboxylic acid moiety to an acid halide moiety. Illustrative acid chloride forming agents include oxalyl chloride, oxalyl bromide, thionyl chloride, thionyl bromide, phosphorus oxychloride, phosphorus oxybromide, phosphorus pentachloride, phosphorus pentabromide, phosphorus trichloride, and phosphorus tribromide.

The term "alkyl", as used alone or within other terms such as "haloalkyl" and "alkylsulfonyl", means an acyclic alkyl radical, linear or branched, preferably containing from 1 to about 10 carbon atoms and more preferably containing from 1 to about 6 carbon atoms. "Alkyl" also encompasses the sub-genus of cyclic alkyl radicals containing from 3 to about 7 carbon atoms, preferably from 3 to 5 carbon atoms. Said alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, ten-butyl, pentyl, aminopentyl, isoamyl, hexyl, and octyl.

The term "alkenyl" refers to an unsaturated, acyclic hydrocarbon radical, linear or branched, in so much as it contains at least one double bond. Such radicals containing from 2 to about 6 carbon atoms, preferably from 2 to about 4 carbon atoms, more preferably from 2 to about 3 carbon atoms. "Alkenyl" also encompasses the sub-genus of cyclic alkyl radicals containing from 3 to about 7 carbon atoms, preferably from 3 to 5 carbon atoms. Said alkenyl radicals may be optionally substituted with groups as defined below. Examples of suitable alkenyl radicals include propenyl, isopropenyl, 2-chloropropenyl, buten-1-yl, isobutenyl, penten-1-yl, 2-methylbuten-1-yl, 3-methylbuten-1-yl, hexen-1-yl, 3-hydroxyhexen-1-yl, hepten-1-yl, and octen-1-yl.

The term "alkynyl" refers to an unsaturated, acyclic hydrocarbon radical, linear or branched, in so much as it contains one or more triple bonds, such radicals containing 2 to about 6 carbon atoms, preferably from 2 to about 4 carbon atoms, more preferably from 2 to about 3 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, and 3,3-dimethylbutyn-1-yl radicals.

The term "alkoxy" embraces linear or branched oxy-containing radicals each having alkyl portions of 1 to about 6 carbon atoms, preferably 1 to about 3 carbon atoms, such as a methoxy radical. The term "alkoxyalkyl" also embraces alkyl radicals having one or more alkoxy radicals attached to the alkyl radical, that is, to form, monoalkoxyalkyl and dialkoxyalkyl radicals. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term, "alkylthio" embraces radicals containing a linear or branched alkyl radical, of 1 to about 6 carbon atoms, attached to a divalent sulfur atom. An example of lower alkylthio is methylthio ($CH_3S$).

The term "alkylthioalkyl" embraces alkylthio radicals, attached to an alkyl group. An example of alkylthioalkyl is methylthiomethyl.

The term "amu" means atomic mass unit.

The term "antiretroviral activity" or "anti-HIV activity" means the ability to inhibit at least one of:
(1) retroviral attachment to cells;
(2) viral entry into cells;
(3) viral pro-DNA integration into host cell genome;
(4) cellular metabolism which permits viral replication;
(5) inhibition of intercellular spread of the virus;
(6) synthesis of viral antigens;
(7) cellular expression of viral antigens
(8) viral budding or maturation;
(9) activity of virus-coded enzymes (such as reverse transcriptase, integrase and proteases); or
(10) any known retroviral or HIV pathogenic actions, such as, for example, immunosuppression.

The term "aryl" means a fully unsaturated mono- or multi-ring carbocycle. Examples of such radicals include substituted or unsubstituted phenyls, naphthyls, and anthracenyls. The term "aryl", as used alone or within other terms, means a mono- or multi-ring aromatic ring structure containing between one and four rings wherein such rings may be attached together in a pendent manner or may be fused. Such an "aryl" group may have 1 or more substituents such as, but not limited to, lower alkyl, hydroxy, halo, haloalkyl, nitro, cyano, alkoxy and lower alkylamino. The term "aryl" refers to both cyclic structures consisting only of carbon (carboaryls), and cyclic structures comprising carbon and one or more heteroatoms selected from the group consisting of nitrogen, sulfur and oxygen (heteroaryls).

The term "BOC" or "Boc" refers to tert-butoxycarbonyl.

The term "br" refers to broad (spectral).

The term "n-Bu" refers to normal (primary) butyl.

The term "t-Bu" refers to tert-butyl.

The term "Bzl" refers to benzyl.

The term "° C." refers to degrees Celsius.

The term "CA" refers to capsid protein.

The term "calcd" refers to calculated.

The term "carbocycle", as used alone or within other terms, means a mono- or multi-ring aromatic ring structure consisting only of carbon containing between one and four rings wherein such rings may be attached together in a pendent manner or may be fused. The term "carbocycle" refers to fully saturated and unsaturated ring systems as well as partially unsaturated ring systems. The term "carbocycle" additionally encompasses spiro systems wherein one cycloalkyl ring has a carbon ring atom in common with another cycloalkyl ring. The term "carbocycle" additionally encompasses bridged systems. Illustrative examples of monocyclic, bicyclic or tricyclic saturated carbocycles include cyclopropyl, cyclobutyl, cyclopentyl, cyclohexyl, cycloheptyl, cyclooctyl, bicyclo[2.2.1]heptyl, bicyclo[2.2.2] octyl, bicyclo[4.2.0]octyl, cyclononanyl, cyclodecanyl, decahydronapthalenyl, and tetradecahydroanthracenyl. Illustrative examples of monocyclic, bicyclic or tricyclic partially saturated carbocycles include cyclopropenyl, cyclobutenyl, cyclopentenyl, cyclohexenyl, cycloheptenyl, cyclooctenyl, bicyclo[3.2.2]nonenyl, bicyclo[4.2.0]octenyl, cyclononenyl, cyclodecenyl, octahydronaphthalenyl, 1,2,3,4-tetrahydronaphthalenyl, and 1,2,3,4,4a,9,9a,10-octahydroanthracenyl. Illustrative examples of monocyclic, bicyclic or tricyclic aromatic carbocycles include phenyl, naphthalenyl, and anthracenyl. Thus, the term "carbocycle" includes the following exemplary structures:

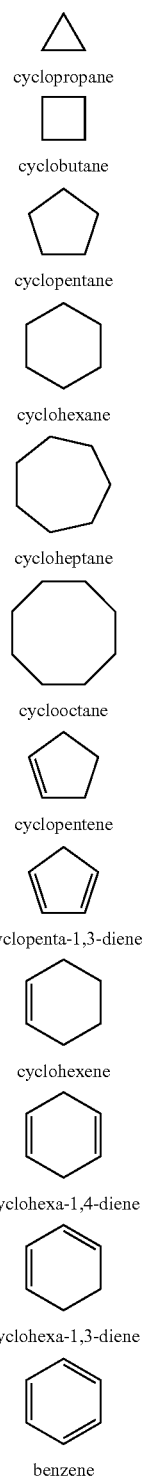

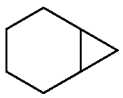
bicyclo[4.1.0]heptane

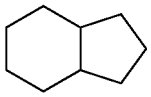
octahydro-1H-indene

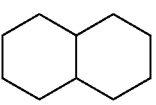
decahydronaphthalene

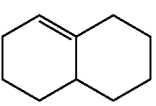
1,2,3,4,4a,5,6,7-octahydronaphthalene

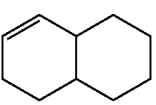
1,2,3,4,4a,5,6,8a-octahydronaphthalene

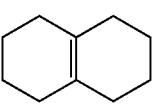
1,2,3,4,5,6,7,8-octahydronaphthalene

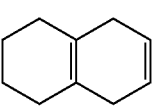
1,2,3,4,5,8-hexahydronaphthalene

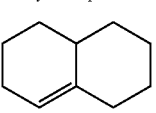
1,2,3,4,4a,5,6,7-octahydronaphthalene

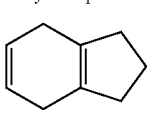
2,3,4,7-tetrahydro-1H-indene

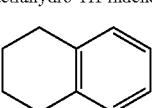
1,2,3,4-tetrahydronaphthalene

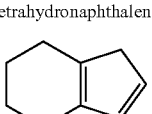
4,5,6,7-tetrahydro-1H-indene

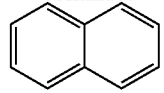
naphthalene

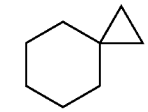
spiro[2.5]octane

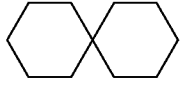
spiro[5.5]undecane

The term "cat" refers to catalytic.

The term "CC" refers to cytotoxic concentration.

The term, "combination therapy" refers to the administration of a compound of the present invention with one or more anti-infective or pharmaceutical agents as part of a specific treatment regimen intended to provide a beneficial effect from the co-action of these therapeutic agents. In some embodiments, the term, "combination therapy" refers to the administration of a compound of the present invention with two additional anti-infective or pharmaceutical agents. The beneficial effect of the combination includes, but is not limited to, pharmacokinetic or pharmacodynamic co-action resulting from the combination of therapeutic agents. Administration of these therapeutic agents in combination typically is carried out over a defined tune period (usually minutes, hours, days or weeks depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention comprises a reverse transcriptase inhibitor and a maturation inhibitor administered as separate agents at the same or different times or they can be formulated as a single, co-formulated pharmaceutical composition comprising the two compounds. As another example, a combination of the present invention comprises a reverse transcriptase inhibitor and a maturation inhibitor formulated as separate pharmaceutical compositions that can be administered at the same or different time. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, one component of a particular combination may be administered by intravenous injection while the other component(s) of the combination may be administered orally. The components may be administered in any therapeutically effective sequence.

The term "coned" refers to concentrated.

The term "δ" refers to the chemical shift in parts per million downfield from tetramethylsilane.

The term "d" in reference to time means day(s); in reference to spectral data means doublet.

The term "DCC" refers to N,N-dicyclohexylcarbodiimide.

The term "DCE" refers to 1,2-dichloroethane.

The term "DCM" refers to dichloromethane.

The term "DIPEA" refers to N,N-diisopropylethylamine.

The term "DMAP" refers to 4-(dimethylamino)pyridine.

The term "DMF" refers to N,N-dimethylformamide.

The term "DMSQ" refers to dimethylsulfoxide.

The term "equ" or refers to equivalent.

The term "ELS" refers to evaporative light scattering.

The term "ELSD" refers to evaporative light scattering detector.

The term "ES+" refers to electrospray ionization.

The term "Et" refers to ethyl.

The term "EtOAc" means ethyl acetate.

The term "EtOH" refers to ethanol.

The term "FCC" refers to flash column chromatography.

The term "g" refers to gram(s).

The term "h" refers to hour(s).

The term "halo" means a halogen radical derived from fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have one atom selected from the group consisting of iodo, bromo, chloro and fluoro atoms within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrido radicals replaced with fluoro atoms. Examples include trifluoromethyl and pentafluoroethyl.

The term "heterocyclyl" means a saturated or unsaturated mono- or multi-ring carbocycle wherein one or more carbon atoms is replaced by N, S, P, or O. The term "heterocycle" refers to fully saturated and unsaturated ring systems as well as partially unsaturated ring systems. The term "heterocycle" is intended to include all the possible isomeric forms of the heterocycles, for example, pyrrolyl comprises 1H-pyrrolyl and 2H-pyrrolyl. Preferred heterocycles comprise at least one atom selected from the group consisting of nitrogen, oxygen and sulfur. Illustrative examples of monocyclic, bicyclic or tricyclic saturated heterocycle substituents include tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyranyl, pyrazolidinyl, piperidinyl, hexahydropyrimidinyl, hexahydropyrazinyl, dioxanyl, morpholinyl, dithianyl, thiomorpholinyl, piperazinyl, trithianyl, diazabicyclo[2.2.1]heptanyl, oxazabicyclo[2.2.1]heptanyl, thiazabicyclo[2.2.1]heptanyl, decahydroquinolyl, and octahydromdolyl. Illustrative examples of monocyclic, bicyclic or tricyclic partially saturated heterocycles include azetyl, pyrrolinyl, imidazolinyl, pyrazolinyl, 2,3-dihydrobenzofuranyl, 1,3-benzodioxolyl, 2,3dihydro-1,4-benzodioxinyl, indolinyl and the like. Illustrative examples of monocyclic, bicyclic or tricyclic aromatic heterocycles include pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridinyl, pyrimidinyl, pyrazinyl, pyridazinyl, triazinyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthyridinyl, pteridinyl, benzopyranyl, pyrrolopyridyl, thienopyridinyl, furopyridinyl, isothiazolopyndinyl, thiazolopyridinyl, isoxazolopyridinyl, oxazolopyridinyl, pyrazolopyndinyl, imidazopyridinyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopynmidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridinyl, tluadiazolopyridinyl, triazolopyridinyl, oxadiazolopyrazinyl, thiadiazolopyrazinyl, triazolopyrazinyl, oxadiazolopyrimidinyl, thiadiazolopyrinndinyl, triazolopyrmndinyl, oxadiazolopyridazinyl, thiadiazolopyridazinyl, triazoiopyridazinyl, imidazooxazolyl, imidazothiazolyl, imidazoimidazolyl, isoxazolotriazinyl, isothiazolotriazinyl, pyrazolotriazinyl, oxazolotriazinyl, thiazoiotriazinyl, imidazotriazinyl, oxadiazolotriazinyl, thiadiazolotriazinyl, triazolotriazinyl, carbazolyl, acridinyl, phenazinyl, phenothiazinyl, and phenoxazinyl. Thus, the term "heterocycle" includes the following exemplary structures:

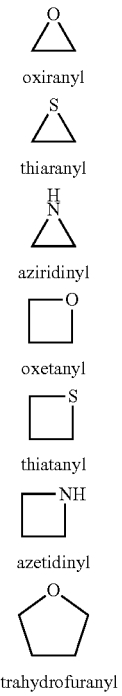

tetrahydrothiphenyl
pyrrolidinyl
tetrahydropyranyl
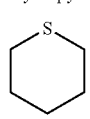
tetrahydrothio
pyranyl
piperidinyl
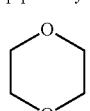
1,4-dioxanyl
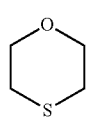
1,4-oxathianyl
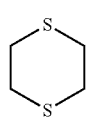
1,4-thianyl
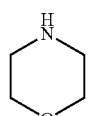
morpholinyl
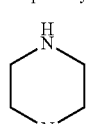
piperazinyl
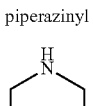
1,4-azathianyl
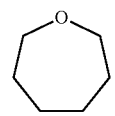
oxepanyl
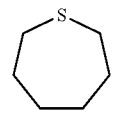
thiepanyl
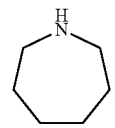
azepanyl
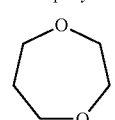
1,4-dioxepanyl
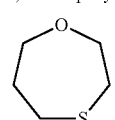
1,4-oxathiepanyl
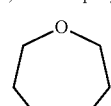
1,4-oxaazapanyl
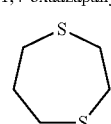
1,4-dithiepanyl
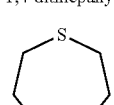
1,4-thieazapanyl
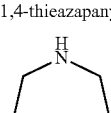
1,4-diazapanyl
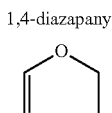
3,4-dihydro-2H-pyranyl
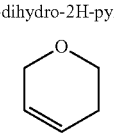
5,6-dihydro-2H-pyranyl -continued
2H-pyranyl
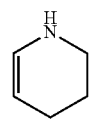
1,2,3,4-tetrahydropyridinyl
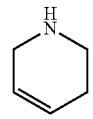
1,2,5,6-tetrahydropyridinyl
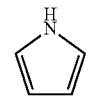
pyrrolyl
furanyl
thiophenyl
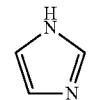
imidazolyl
pyrazolyl
oxazolyl
isoxazolyl
thiazolyl
isothiazolyl
-continued
1,2,3-triazolyl
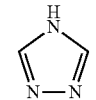
1,2,4-triazolyl
1-oxa-2,4-diazolyl
1-oxa-2,5-diazolyl
1-oxa-3,4-diazolyl
1-oxa-2,3-diazolyl
1-thia-2,4-diazolyl
1-thia-2,5-diazolyl
1-thia-3,4-diazolyl
1-thia-2,3-diazolyl
tetrazolyl
pyridinyl
pyridazinyl -continued

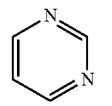
pyrimidinyl

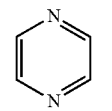
pyrzainyl

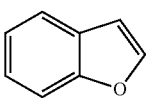
benzofuranyl

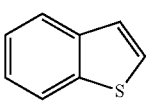
benzothiopehnyl

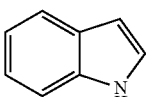
indoyly

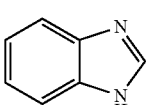
benzimidazolyl

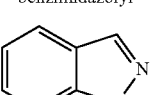
indazolyl

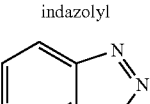
benzotriazolyl

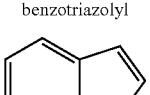
pyrrolo[2,3-b]
pyridinyl

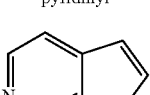
pyrrolo[2,3-c]
pyridinyl

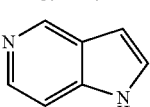
pyrrolo[3,2-c]
pyridinyl

-continued

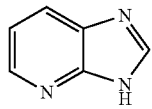
imidazo[4,5-b]
pyridinyl

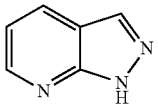
pyrrazolo[3,4-b]
pyridinyl

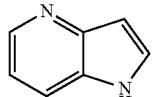
pyrrolo[3,2-b]
pyridinyl

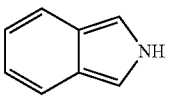
isoindolyl

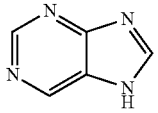
purinyl

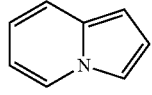
indolinyl

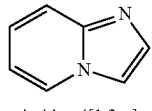
imidazol[1,2-a]
pyridinyl

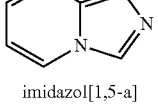
imidazol[1,5-a]
pyridinyl

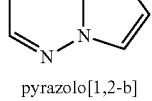
pyrazolo[1,2-b]
pyridazinyl

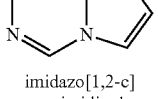
imidazo[1,2-c]
pyrimidinyl

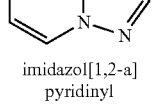
imidazol[1,2-a]
pyridinyl

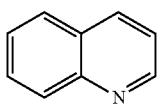
quinolinyl

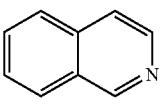
isoquinolinyl

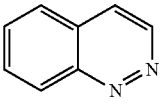
cinnolinyl

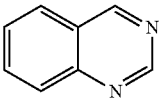
quinazolinyl

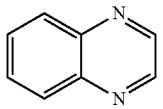
quinoxalinyl

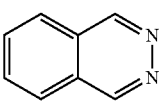
phthalazinyl

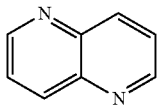
1,6-naphthyridinyl

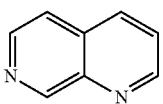
1,7-naphthyridinyl

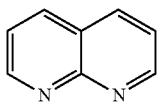
1,8-naphthyridinyl

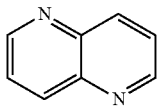
1,5-naphthyridinyl

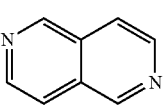
2,6-naphthyridinyl

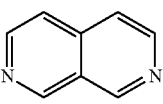
2,7-naphthyridinyl

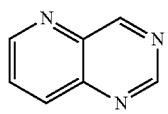
1,6-naphthyridinyl

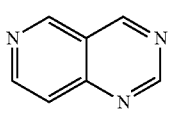
pyrido[3,2-d]
pyrimidinyl

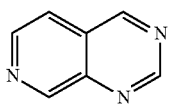
pyrido[4,3-d]
pyrimidinyl

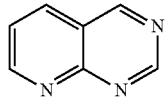
pyrido[2,3-d]
pyrimidinyl

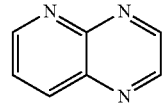
pyrido[2,3-b]
pyrazinyl

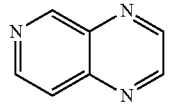
pyrido[3,4-b]
pyrazinyl

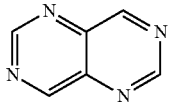
pyrimido[5,4-b]
pyrimidinyl

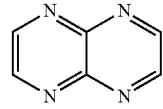
pyrazino[2,3-b]
pyrazinyl

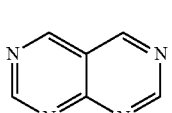
pyrimido[4,5-b]
pyrimidinyl

The term "heteroaryl" means a fully unsaturated heterocycle.

The terms "C-3", "C-19", and "C-28" refer to certain substitutable positions of a triterpene core as numbered in accordance with CAS rules (positions depicted below with respect to an illustrative triterpene);

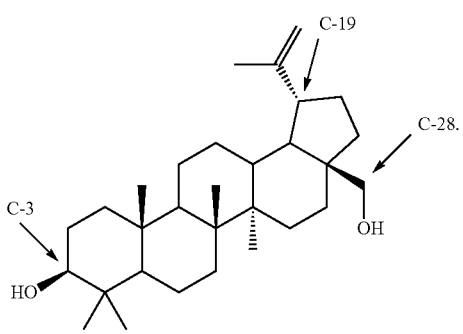

The "C-28 amines" of the present disclosure provide for a chain comprising one to six carbons at the C-28 position prior to a nitrogen group With regards to any of "carbocycle," "aryl," "heterocycle," or "heteroaryl", the point of attachment to the molecule of interest can be at the heteroatom or elsewhere within the ring. For terms such as aralkyl, and heteroarylalkyl, the moiety may be linked through any ring atom or through any atom of the alkyl portion so long as the resultant molecule is chemically stable. The presence of charge, for example when a pyridinyl radical is attached via the ring nitrogen to yield a quaternary nitrogen, does not in and of itself mean that the resultant molecule is not chemically stable. The use of "carbocycle," "aryl," "heterocycle," and "heteroaryl" moieties includes divalent attachment at appropriate substitutable sites.

The term "HOAc" refers to acetic acid.

The term "homologation" means the addition of at least one methylene group to a linear, branched or cyclic moiety. Similarly, a homologated compound comprises at least one additional methylene group relative to the parent compound. In some embodiments, homologation comprises adding one to six methylene groups.

The term "HPLC" refers to high performance liquid chromatography.

The term "Human Serum" means type AB clotted serum collected from a male human.

The term "hydrido" means a Single hydrogen atom (H). This hydrido radical may be attached, for example, to an oxygen atom to form a hydroxyl radical (—OH) or two hydrido radicals may be attached to a carbon atom to form a methylene (—CH$_2$—) radical.

The term "Hz" refers to hertz.

The term "IBX" refers to 2-iodoxybenzoic acid.

The term "IC$_{50}$" means the drug concentration that results in inhibition of 50% of the viral growth.

The term "IR ATR" refers to attenuated total reflection infrared spectroscopy.

The term "isopropenyl" means:

The term "L" refers to liter(s).
The term "LAH" refers to lithium aluminum hydride.
The term "LC" refers to liquid chromatography.
The term "LDA" means lithium diisopropylamide.
The term "µ" refers to micro.

The term "m" in reference to spectral data means multiplet; in reference to units of measurements means milli.

The term "M" in reference to concentration means molar (moles per liter); in reference to mass spectrometry means parent molecular ion; in reference to units of measurements means mega.

The term "Me" refers to methyl.
The term "MeOH" refers to methanol.
The term "MHz" refers to megahertz.
The term "1-methyl-1-cyclopropyl" means:

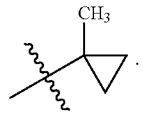

The term "min" refers to minute(s).
The term "mol" refers to mole(s).
The term "mp" refers to melting point.
The term "MS" refers to mass spectrometry.
The term "MT-2 cells" refers to human T-cell leukemia cells isolated from cord blood lymphocytes and co-cultured with cells from patients with adult T-cell leukemia. The MT-2 cell line was acquired from the AIDS Research and Reference Reagent Program.

The term "m/z" refers to mass-to-charge ratio.
The term "NaHMDS" refers to sodium hexamethyldisilazide.
The term "NCS" refers to N-chlorosuccinimide.
The term "nM" refers to nanomolar.
The term "NMP" refers to N-methyl-2-pyrrolidinone.
The term "NMR" refers to nuclear magnetic resonance.
The term "obs" refers to obscured (spectral).
The term "oxo" means a doubly bonded oxygen.
The term "Ph" refers to phenyl.
The term "PPTS" refers to pyridinium p-toluenesulfonate.

The term "prodrug" means a chemical derivative of an active parent drug that requires, upon spontaneous or enzymatic biotransformation, release of the active parent drug. The term "prodrug" includes variations or derivatives of the compounds of this invention which have groups cleavable under metabolic conditions including solvolysis or enzymatic degradation. In some embodiments of the present invention the prodrug is either pharmacologically inactive or exhibits reduced activity relevant to its active parent drug.

The term "q" refers to quartet (spectral).
The term "R$_f$" refers to retention factor, in the context of thin-layer chromatography.
The term "R$_t$" refers to retention time, in the context of liquid chromatography.
The term "rt" refers to ambient (room) temperature.
The term "s" refers to singlet (spectral).
The term "satd" refers to saturated.
The term "serum shift" means the ratio of IC$_{50}$ in 10% Human Serum to the IC$_{50}$ in 20% Human Serum.
The term "selective" as referring to a particular event means that the particular event occurs with greater frequency than other potential event(s).
The term "sept" refers to septet (spectral).
The term "solvate" means a molecular complex comprising a compound of the present invention and a proportional number of solvent molecules. The term "hydrate" means a solvate where the solvent is water. In some embodiments of the present invention the solvate comprises a fractional amount of a solvent molecule per molecule of the present invention, for example, a hemisolvate. In some embodiments of the present invention the solvate comprises one solvent molecule per molecule of the present invention, for example, a monosolvate. In some embodiments of the present invention the solvate comprises two solvent molecules per molecule of the present invention, for example, a disolvate.

The term "solvolysis" means a nucleophilic substitution, for example via an $S_N1$ mechanism, where the nucleophile is a solvent molecule.

The term "SP1" refers to spacer protein 1, or spacer peptide 1.

The term "STAB" refers to sodium triacetoxyborohydride.

The term "t" refers to triplet (spectral).

The term "TBAC" refers to tetra-n-butylammonium chloride.

The term "TBAF" refers to tetra-n-butylammonium fluoride.

The term "TBDMS" refers to t-butyldimethylsilyl.

The term "TBME" refers to t-butyl methyl ether.

The term "TEA" refers to triethylamine.

The term "TEMPO" refers to 2,2,6,6-tetramethyl-1-piperidinyloxy.

The term "TFA" refers to trifluoroacetic acid.

"Therapeutic effect" as used herein means some extent of relief of one or more of the symptoms of an HIV-related disorder. In reference to the treatment of HIV, a therapeutic effect refers to one or more of the following: 1) reduction in the number of infected cells; 2) reduction in the number of virions present in serum; 3) inhibition (i.e., slowing to some extent, preferably stopping) of the rate of HIV replication; 4) relieving or reducing to some extent one or more of the symptoms associated with HIV; and 5) relieving or reducing the side effects associated with the administration of other antiretroviral agents.

"Therapeutically effective amount" as used herein means the amount required to achieve a therapeutic effect.

The term "THF" refers to tetrahydrofuran.

The term "TLC" refers to thin layer chromatography.

The term "IMS" refers to trimethylsilyl.

"Weight percent" as used herein means the weight percent of a specified ingredient based upon the total weight of all ingredients of the composition.

In some embodiments, the disclosure is directed to a compound according to Formula I:

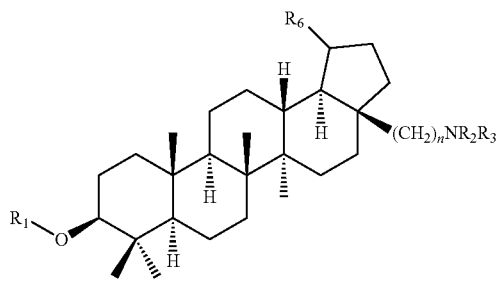

Formula I or a pharmaceutically acceptable salt, tautomer, or ester thereof, wherein $R_1$ is selected from the group consisting of substituted or unsubstituted $C_3$-$C_{20}$ alkanoyl, carboxyalkanoyl, carboxyalkenoyl, carboxyalkynoyl, carboxycyloalkylalkanoyl, carboxyalkylcycloalkylalkanoyl, carboxycyloalkylcarbonyl, carboxyalkylcycloalkylcarbonyl, alkoxycarbonylcyloalkylcarbonyl, alkoxycarbonylalkylcycloalkylcarbonyl, trialkylsilylalkoxycarbonylcyloalkylcarbonyl, trialkylsilylalkoxycarbonylalkylcycloalkylcarbonyl, arylalkyloxycarbonylcycloalkylcarbonyl, arylalkyloxycarbonylalkylcycloalkylcarbonyl, alkoxycarbonylalkanoyl, alkoxycarbonylalkenoyl, alkoxycarbonylalkynoyl, alkoxycarbonylcyloalkylalkanoyl, alkoxycarbonylalkylcycloalkylalkanoyl, trialkylsilylalkoxycarbonylalkanoyl, trialkylsilylalkoxycarbonylalkenoyl, trialkylsilylalkoxycarbonylalkynoyl, trialkylsilylalkoxycarbonylcyloalkylalkanoyl, trialkylsilylalkoxycarbonylalkylcycloalkylalkanoyl, arylalkyloxycarbonylalkanoyl, arylalkyloxycarbonylalkenoyl, arylalkyloxycarbonylalkynoyl, arylalkyloxycarbonylcyloalkylalkanoyl, and arylalkyloxycarbonylalkylcycloalkylalkanoyl wherein any alkyl, cycloalkyl, alkenyl, or alkynyl group are independently substituted with one or more groups selected from the group consisting of hydrido, halo, or $C_1$-$C_6$ alkyl groups;

In some embodiments, n is an integer from one to six, from one to five, from one to four, from one to three or from one to two. In some embodiments, n is an integer from two to six, from two to five, from two to four, or from two to three. In some embodiments, n is one, two, three, four, five or six. In some embodiments, n is two or three. In some embodiments, n is one.

$R_2$ and $R_3$ are substituents attached to the nitrogen located off the C-28 position. In some embodiments, $R_2$ and $R_3$, are independently selected with one or more groups from the group consisting of hydride, heteroaryl$(CR_aR_b)_m$—, heterocyclyl$(CR_aR_b)_m$—, and $R_4R_5N(CR_aR_b)_m$—, wherein said heteroaryl, or heterocyclyl is independently substituted with one or more groups selected from the group consisting of alkyl, oxo, hydroxy, halo, cyano, alkoxy, cycloalkyl, aryl, heteroaryl, heterocyclyl, cycloalkylalkyl, hydroxyalkyl, alkoxyalkyl, arylalkyl, heteroarylalkyl, heterocyclylalkyl, haloalkyl, haloalkyl carbonyl, $(R_cR_dN)$alkyl, hydroxyalkyl carbonyl, alkoxyalkyl carbonyl, $(R_cR_dN)$alkyl carbonyl, alkoxy carbonyl, $(R_cR_dN)$carbonyl, aryl carbonyl, heteroaryl carbonyl, heterocyclylcarbonyl, alkylsulfonyl, haloalkyl sulfonyl, arylsulfonyl, heteroarylsulfonyl, heterocyclylsulfonyl, $(R_cR_dN)$sulfonyl, $(R_cR_dN)$sulfonylalkyl, carboxyalkyl, alkoxycarbonylalkyl, cyanoalkyl, alkylcarbonylaminoalkyl, alkylsulfonylaminoalkyl, and $(R_cR_dN)$carbonylalkyl. In some embodiments, the heteroaryl or heterocyclyl are independently substituted at one or more of positions on the ring structure, e.g., 1', 2', 3', 4', 5', 6', etc.

One of skill in the art can appreciate that substitution(s) on any of the heterocyclyl and or heteroaryl substituents can be made at various positions on the ring. In some embodiments, the substitution on the ring is made at one or more heteroatoms. In some embodiments, the substitution(s) on the ring is made at one or more carbon atoms on the ring. For example, on a 5-membered ring (either heteroaryl or heterocyclyl), a substitution can be made at any position on the ring, for example, at the 1 position, the 2 position, 3 position, 4 position or 5 position, etc. Likewise, on a 6-membered ring (either heteroaryl or heterocyclyl), a substitution can be made at any position on the ring, for example, at the 1 position, the 2 position, 3 position, 4 position, 5 position, 6 position, etc.

In some embodiments, $R_2$ is hydrido, and $R_3$ is selected with one or more groups from the group consisting of heteroaryl$(CR_aR_b)_m$—, heterocyclyl $(CR_aR_b)_m$—, and —$(CR_aR_b)_mNR_4R_5$. In some embodiments, $R_2$ is hydrido, and $R_3$ is heteroaryl$(CR_aR_b)_m$— or heterocyclyl $(CR_aR_b)_m$—. Various heteroaryls or heterocyclyls as described herein can be use when $R_3$ is heteroaryl($CR_aR_b$)$_m$— or heterocyclyl ($CR_aR_b$)$_m$—. In some embodiments, the heteroaryl of heteroaryl($CR_aR_b$)$_m$— or the heterocyclyl of heteroaryl($CR_aR_b$)$_m$— is a nitrogen containing heteroaryl or nitrogen containing heterocyclyl. In some embodiments, the heteroaryl of heteroaryl($CR_aR_b$)$_m$— or the heterocyclyl of heteroaryl($CR_aR_b$)$_m$— is substituted with one or more arylalkyl, heteroarylalkyl, cycloalkylalkyl, heterocyclylalkyl, or combinations thereof.

In some embodiments, the heteroaryl of heteroaryl ($CR_aR_b$)$_m$— or the heterocyclyl of heterocyclyl($CR_aR_b$)$_m$— is substituted with one or more arylalkyl, heteroarylalkyl, cycloalkylalkyl, heterocyclylalkyl, arylcarbonyl, heteroaryl carbonyl, arylsulfonyl, heteroarylsulfonyl, or combinations thereof, and the arylalkyl, heteroarylalkyl, cycloalkylalkyl, heterocyclylalkyl, arylcarbonyl, heteroarylcarbonyl, arylsulfonyl, heteroarylsulfonyl, or combinations thereof is substituted with one or more halogens or $C_1$-$C_3$ alkyl. In some embodiments, the arylalkyl, heteroarylalkyl, cycloalkylalkyl, heterocyclylalkyl, arylcarbonyl, heteroarylcarbonyl, arylsulfonyl, heteroarylsulfonyl, or combinations thereof is substituted with a fluoro, difluoro, chloro or dichloro. In some embodiments, the arylalkyl, heteroarylalkyl, cycloalkylalkyl, heterocyclylalkyl, arylcarbonyl, heteroarylcarbonyl, arylsulfonyl, heteroarylsulfonyl, or combinations thereof is substituted with methyl, dimethyl, ethyl, diethyl, isopropyl, or propyl. In some embodiments, the arylalkyl, heteroarylalkyl, cycloalkylalkyl, heterocyclylalkyl, arylcarbonyl, heteroarylcarbonyl, arylsulfonyl, heteroarylsulfonyl, or combinations thereof is substituted with $C_1$-$C_3$ alkoxy, $C_1$-$C_3$ dialkylamine, or cyano.

In some embodiments, the heteroaryl of heteroaryl ($CR_aR_b$)$_m$— or the heterocyclyl of heterocyclyl($CR_aR_b$)$_m$— is substituted with one or more arylalkyl, heteroarylalkyl, cycloalkylalkyl, heterocyclylalkyl, arylcarbonyl, heteroarylcarbonyl, arylsulfonyl, heteroarylsulfonyl, or combinations thereof, and the arylalkyl, heteroarylalkyl, cycloalkylalkyl, heterocyclylalkyl, arylcarbonyl, heteroarylcarbonyl, arylsulfonyl, heteroarylsulfonyl, or combinations thereof is substituted with one or more alkyl, alkoxy, alkoxyalkyl, alkoxyalkoxy, hydroxyalkyl, hydroxyalkoxy, hydroxy, haloalkyl, formyl, alkylcarbonyl, arylcarbonyl, amino, alkylamino, dialkylamino, dialkylaminoalkyl, dialkylaminoalkoxy, alkylthio, alkylsulfinyl, alkylsulfonyl, arylsulfonyl, dialkylaminosulfonyl, alkylsulfonylamino, cyano, cyanoalkyl, oxo, nitro, aryl, heteroaryl, heterocycyl, alkylcarbonylamino, hydroxyalkylcarbonyl, dialkylaminoalkylcarbonyl, or combinations thereof. In some embodiments, the alkyl, alkoxy, haloalkyl, alkylamino, alkylsulfonyl, arylsulfonyl, alkylsulfonylamino, cyanoalkyl, hydroxyalkylcarbonyl, aminoalkylcarbonyl is substituted with one or more halogens or $C_1$-$C_3$ alkyl. In some embodiments, the alkyl, alkoxy, haloalkyl, alkylamino, alkylsulfonyl, arylsulfonyl, alkylsulfonylamino, cyanoalkyl, hydroxyalkylcarbonyl, aminoalkylcarbonyl is substituted with a fluoro, difluoro, chloro or dichloro. In some embodiments, alkyl, alkoxy, haloalkyl, alkylamino, alkylsulfonyl, arylsulfonyl, alkylsulfonylamino, cyanoalkyl, hydroxyalkylcarbonyl, aminoalkylcarbonyl is substituted with methyl, dimethyl, ethyl, diethyl, isopropyl, or propyl. In some embodiments, the alkyl, alkoxy, haloalkyl, alkylamino, alkylsulfonyl, arylsulfonyl, alkylsulfonylamino, cyanoalkyl, hydroxyalkylcarbonyl, aminoalkylcarbonyl is substituted with $C_1$-$C_3$ alkoxy, $C_1$-$C_3$ dialkylamine, or cyano.

In some embodiments, the heteroaryl of heteroaryl ($CR_aR_b$)$_m$— or the heterocyl of heterocyclyl($CR_aR_b$)$_m$— is substituted with arylcarbonyl, heteroarylcarbonyl, cycloalkylcarbonyl, or heterocycyl carbonyl, any of which can be optionally substituted with a halogen, $C_1$-$C_3$ alkyl, $C_1$-$C_3$ alkoxy, $C_1$-$C_3$ dialkylamine, cyano, or combination thereof. In some embodiments, the heteroaryl of heteroaryl ($CR_aR_b$)$_m$— or the heterocycyl of heterocycyl($CR_aR_b$)$_m$— is substituted with alkylsulfonyl, haloalkylsulfonyl, alkylaminosulfonyl, arylsulfonyl, heteroarylsulfonyl, heterocyclylsulfonyl, wherein the arylsulfonyl, the heteroarylsulfonyl and the heterocyclylsulfonyl, are optionally substituted with halogen, alkyl, alkoxy, alkoxycarbonylamino, haloalkyl, or combinations thereof.

In some embodiments, the heteroaryl of heteroaryl ($CR_aR_b$)$_m$— or the heterocyl of heterocyclyl($CR_aR_b$)$_m$— is substituted with one or more of the group consisting of aminocarbonyl, alkylaminocarbonyl, dialkylaminocarbonyl, alkoxyalkylcarbonyl, hydroxyalkylcarbonyl, alkylaminoalkylcarbonyl, dialkylaminoalkylcarbonyl, cyanoalkyl, alkoxycarbonylalkyl, alkylaminocarbonylalkyl, alkylcarbonylaminoalkyl, alkylsulfonylaminoalkyl, cycloalkylalkyl, aryl, heteroaryl, hydroxyalkyl, alkoxyalkyl, haloalkyl, haloalkylcarbonyl, alkylcarbonyl, alkoxycarbonyl, carboxyalkyl or combinations thereof.

In some embodiments, the heteroaryl of heteroaryl ($CR_aR_b$)$_m$— or the heterocyclyl of heterocyclyl($CR_aR_b$)$_m$— is substituted with one or more sulfur containing groups. For example, in some embodiments, the heteroaryl of heteroaryl ($CR_aR_b$)$_m$— or the heterocyclyl of heterocyclyl($CR_aR_b$)$_m$— is substituted with one or more of the group consisting of alkylsulfonyl, haloalkylsulfonyl, arylsulfonyl, heteroarylsulfonyl, heterocyclylsulfonyl, ($R_cR_dN$)sulfonyl, and ($R_cR_dN$)sulfonylalkyl.

In some embodiments, $R_3$ and/or $R_2$ is heterocycyl ($CR_aR_b$)$_m$—. Various heterocyclyls are known to the skilled artisan and are encompassed within the term heterocyclyl ($CR_aR_b$)$_m$—. In some embodiments, $R_3$ and/or $R_2$ is heterocyclyl($CR_5R_6$)$_m$—, and heterocyclyl is as defined herein. In some embodiments, $R_3$ and/or $R_2$ is heterocyclyl($CR_aR_b$)$_m$—, and heterocyclyl is a monocyclic ring.

In some embodiments, $R_3$ and/or $R_2$ is heterocyclyl ($CR_aR_b$)$_m$—, and heterocyclyl comprises a nitrogen, sulfur or oxygen. In some embodiments, $R_3$ and/or $R_2$ is heterocyclyl($CR_aR_b$)$_m$—, and heterocyclyl comprises one or more nitrogens. In some embodiments, $R_3$ and/or $R_2$ is heterocyclyl($CR_aR_b$)$_m$—, wherein the heterocyclyl of heterocyclyl ($CR_aR_b$)$_m$— is selected from the group consisting of oxiranyl, thiaranyl, aziridinyl, oxetanyl, thiatanyl, azetidinyl, dihydrofuranyl, tetrahydrofuranyl, dihydrothiophenyl, tetrahydrothiophenyl, pyrrolinyl, pyrrolidinyl, pyrazolinyl, pyrazolidinyl, imidazolinyl, imidazolidinyl, isoxazolinyl, isoxazolidinyl, oxazolinyl, oxazolyl, isothiazolinyl, isothiazolidinyl, thiazolinyl, thiazolidinyl, dihydropyranyl, tetrahydropyranyl, tetrahydrothiopyranyl, dihydropyridinyl, tetrahydropyridinyl, piperidinyl, dioxanyl, oxathianyl, dithianyl, oxazinyl, morpholinyl, piperazinyl, thiazinyl, thiomorpholinyl, oxepanyl, thiepanyl, azepanyl, dioxepanyl, oxathiepanyl, oxazapanyl, dithiepanyl, thieazapanyl, diazapanyl, diazabicyclo[2.2.1]heptanyl, oxazabicyclo[2.2.1]heptanyl, thiazabicyclo[2.2.1]heptanyl, diazabicyclo[2.2.2]octanyl, oxazabicyclo[2.2.2]octanyl, and thiazabicyclo[2.2.2]octanyl.

In some embodiments, $R_3$ is heterocyclyl($CR_aR_b$)$_m$—, and the heterocyclyl of heterocyclyl($CR_aR_b$)$_m$— is selected from the group consisting of a pyrrolidinyl, a morpholinyl, a piperidinyl, a piperazinyl, an imidazolyl, or an oxazolyl.

In some embodiments, $R_3$ and/or $R_2$ is heterocyclyl ($CR_aR_b$)$_m$—, and the heterocyclyl of heterocyclyl($CR_aR_b$)$_m$— is piperazinyl. In some embodiments, $R_2$ is hydrido, and $R_3$ is heterocyclyl$(CR_aR_b)_m$—, and the heterocyclyl of heterocyclyl$(CR_aR_b)_m$— is piperazinyl.
In some embodiments, $NR_2R_3$ of Formula I, is selected from the group consisting of:
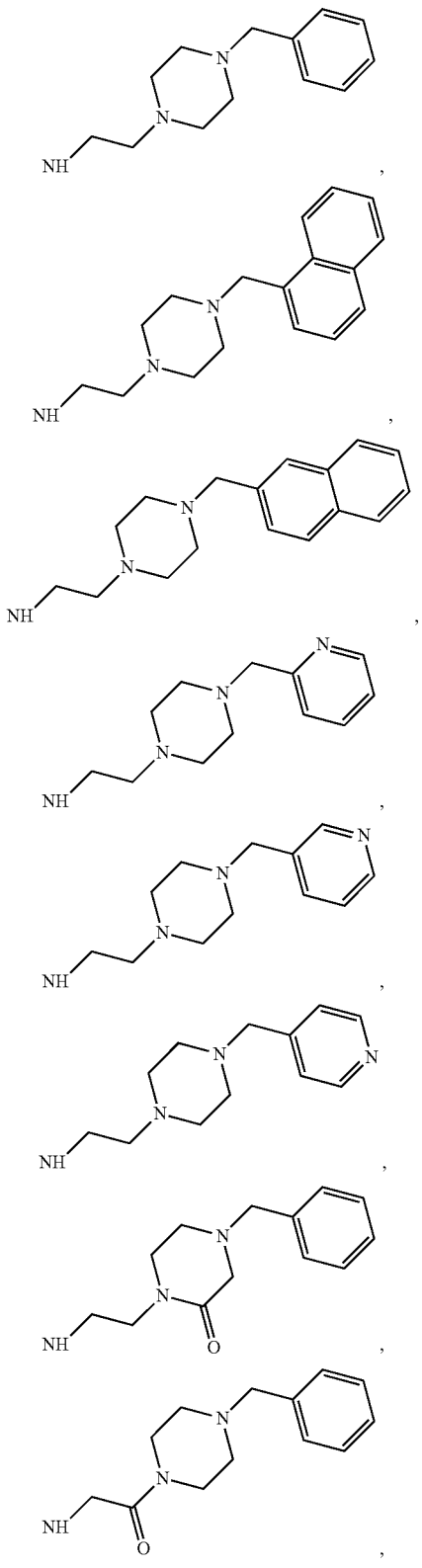
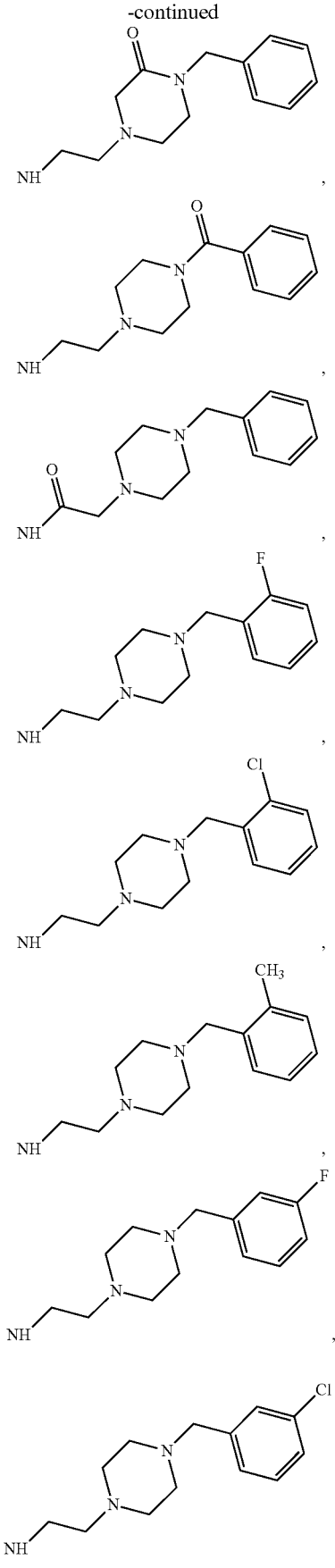

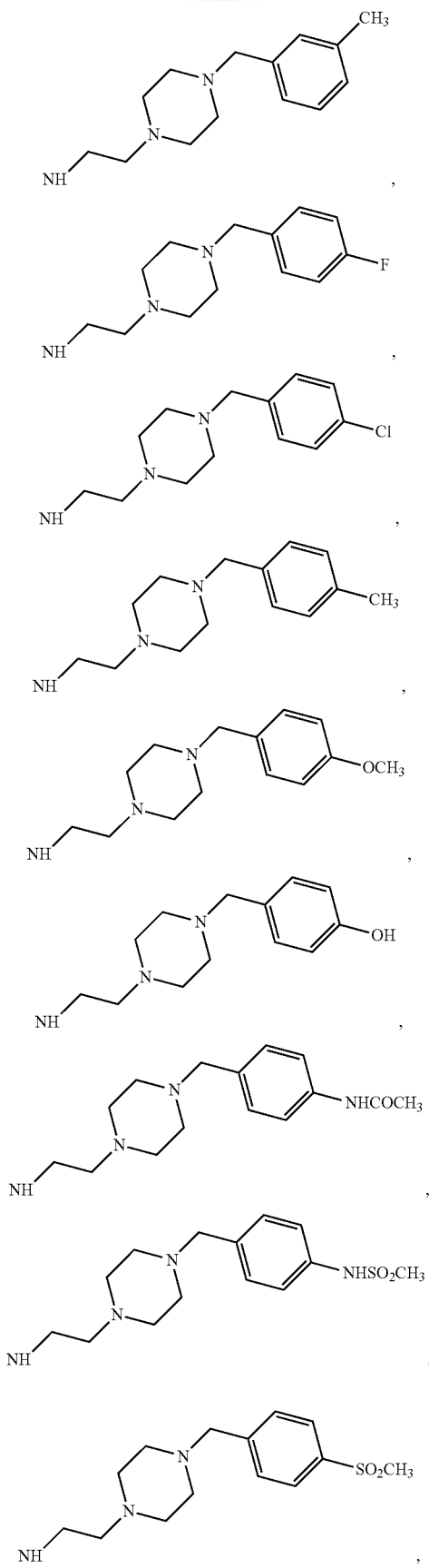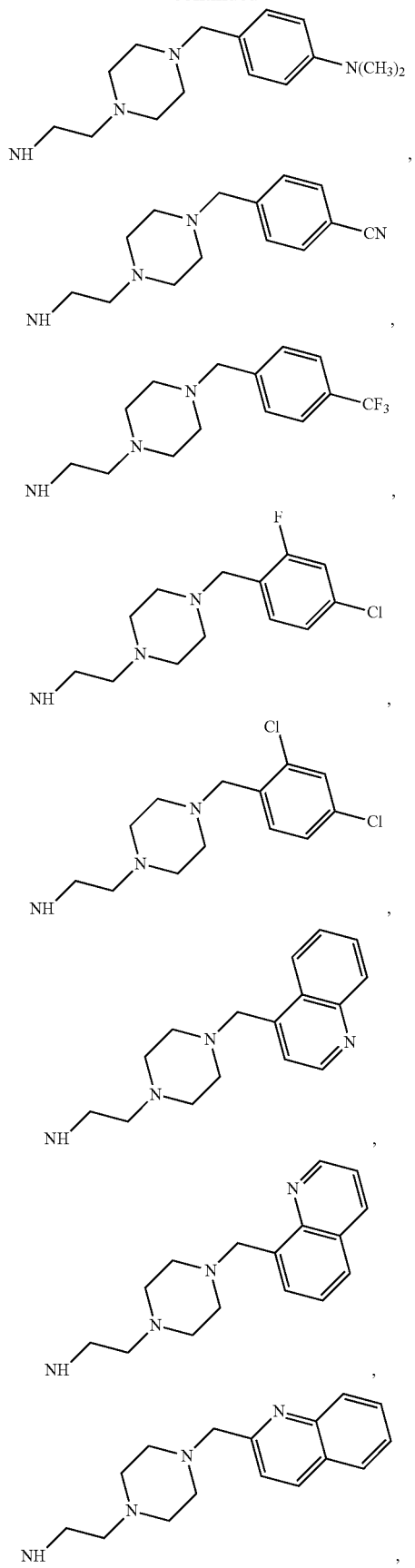

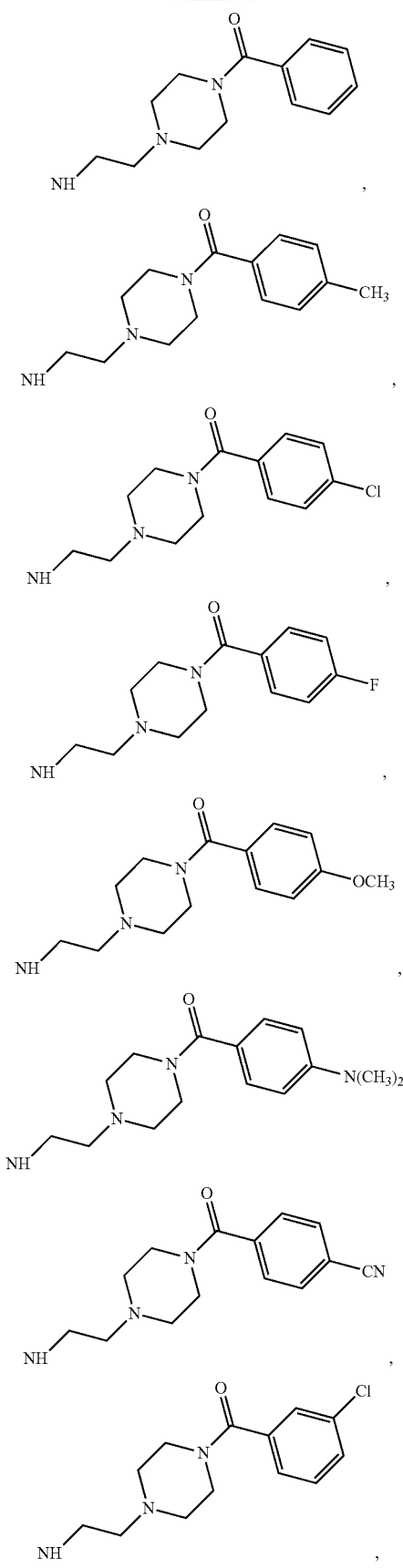
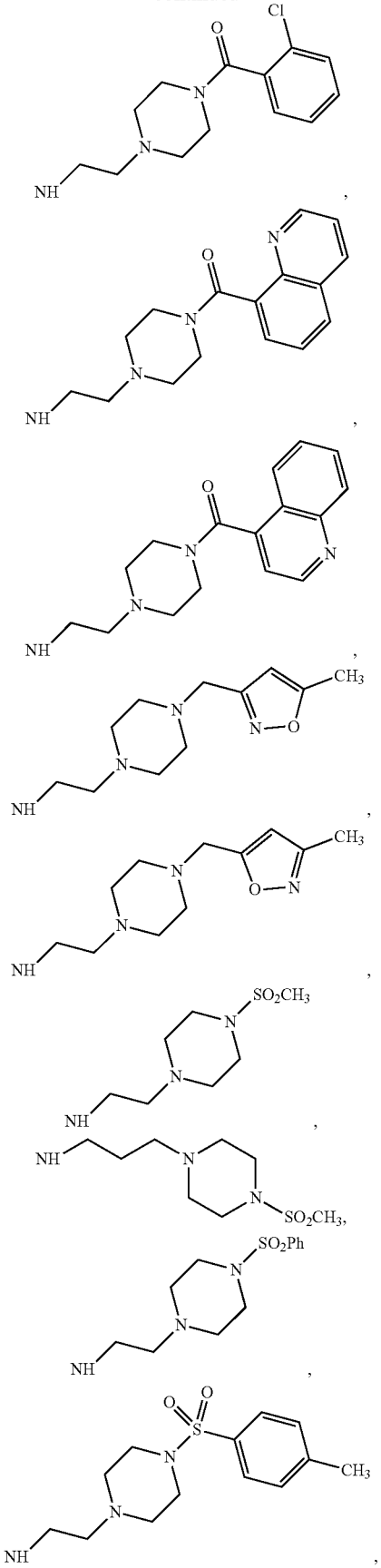

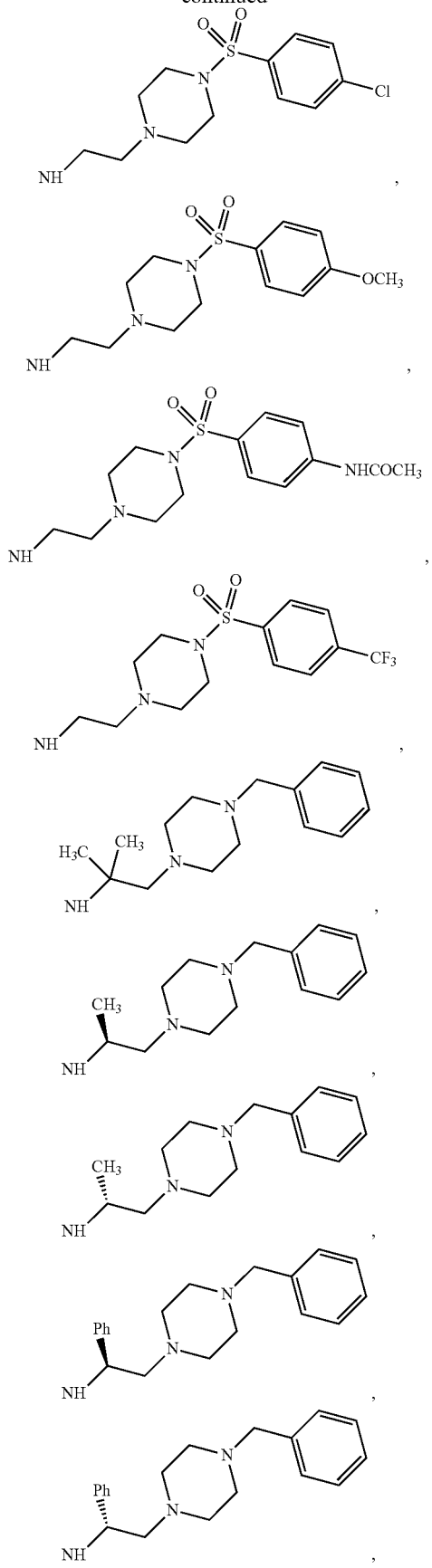
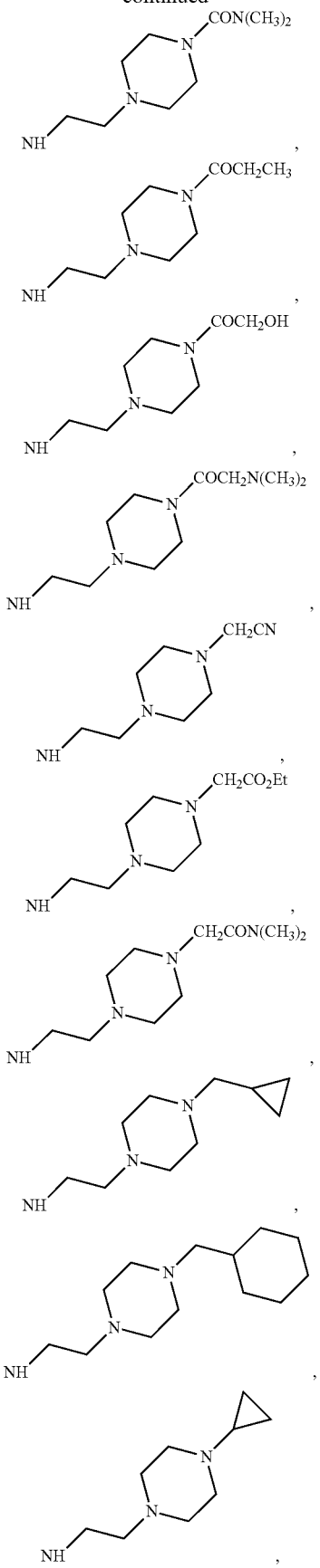

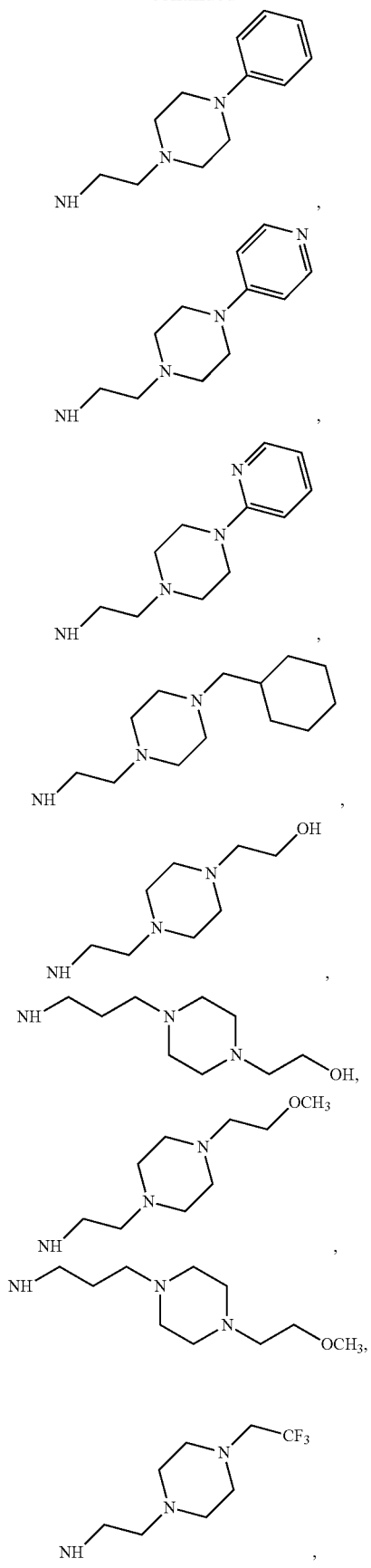
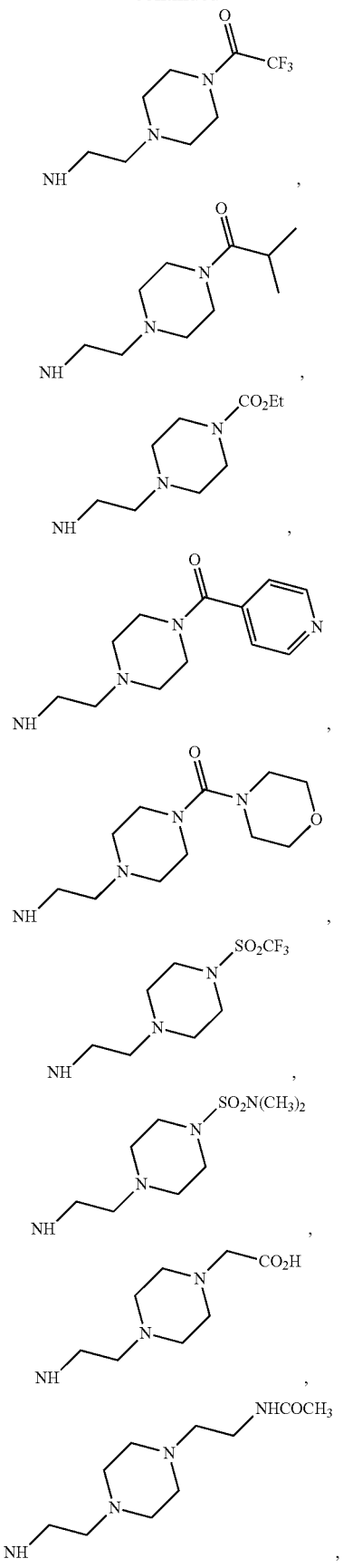

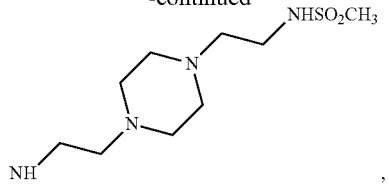,
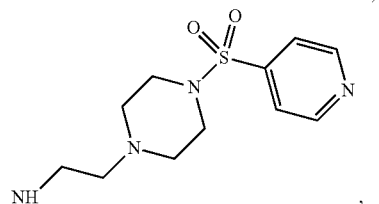,
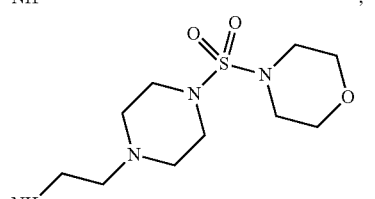,
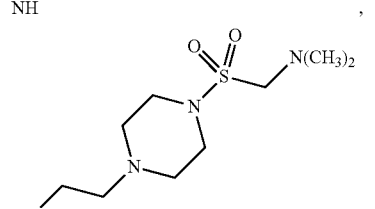,
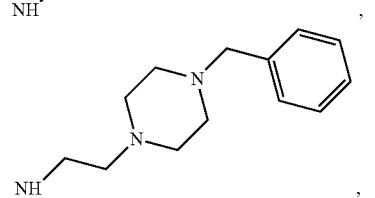,
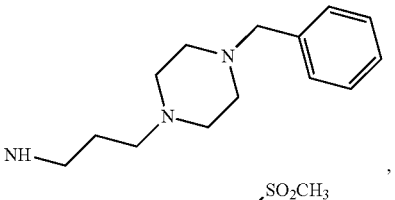,
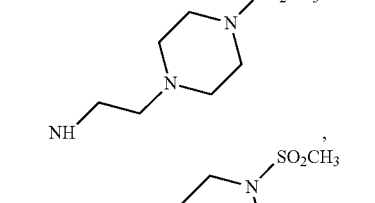,
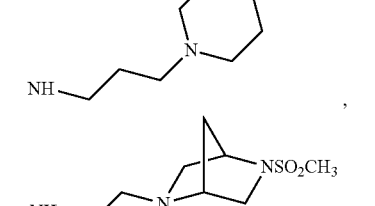,
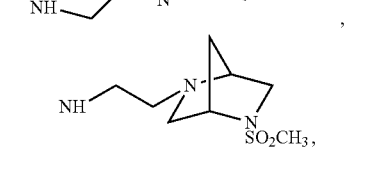,
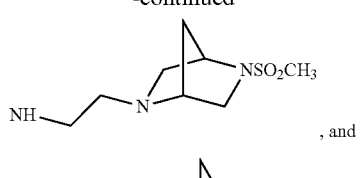, and
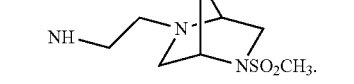.
In some embodiments, $R_3$ and/or $R_2$ is heterocyclyl$(CR_aR_b)_m$—, and the heterocyclyl of heterocyclyl$(CR_aR_b)_m$— is piperidinyl. In some embodiments, $R_2$ is hydrido, and $R_3$ is heterocyclyl$(CR_aR_b)_m$—, and the heterocyclyl of heterocyclyl$(CR_aR_b)_m$— is piperidinyl.
In some embodiments, $NR_2R_3$ of Formula I, is selected from the group consisting of:
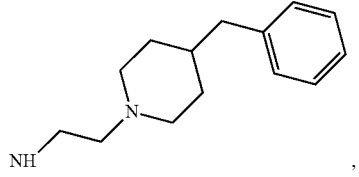,
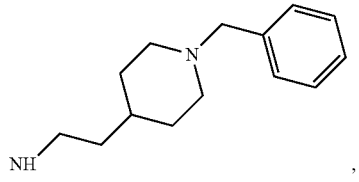,
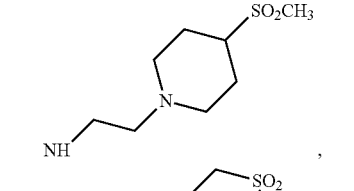,
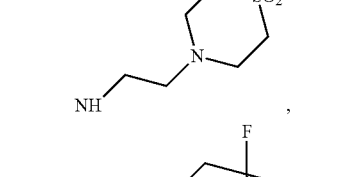,
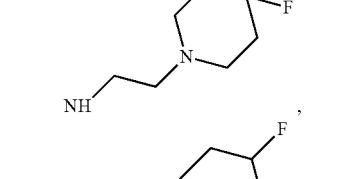,
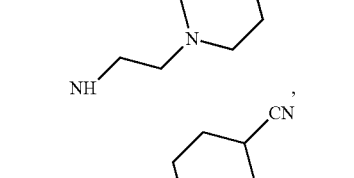,
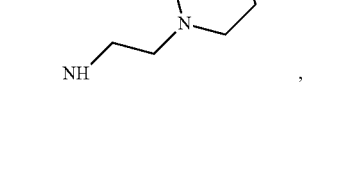,

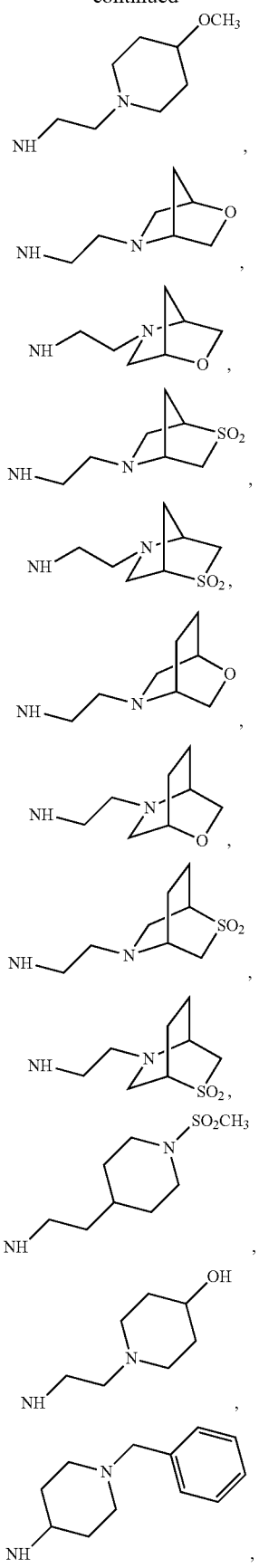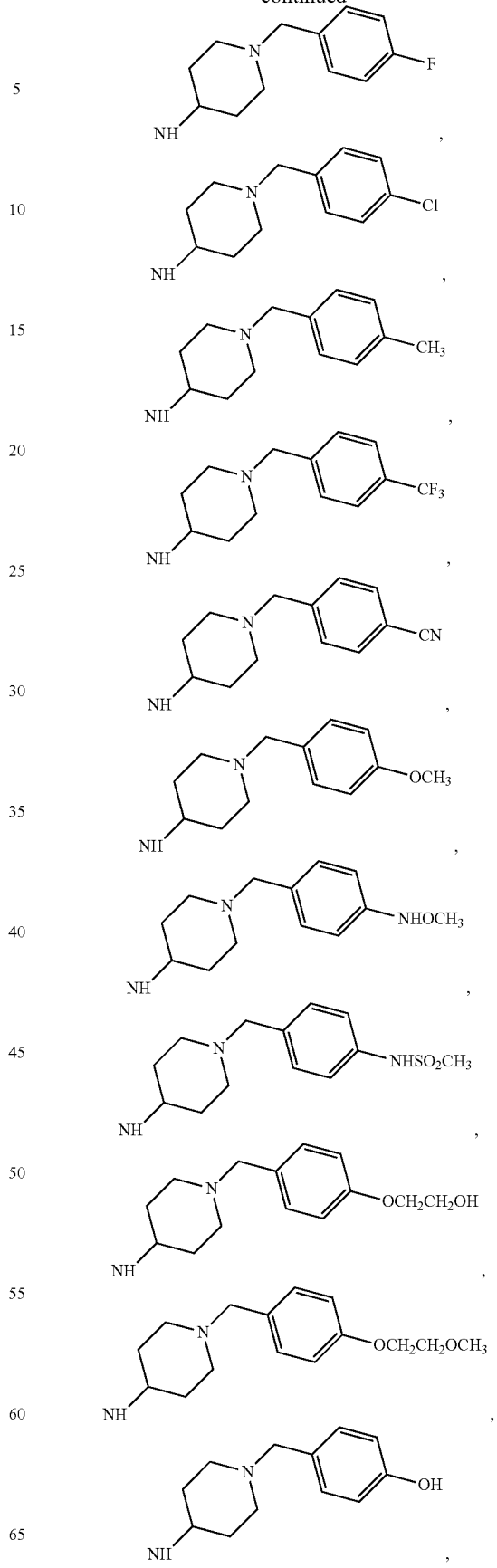

-continued
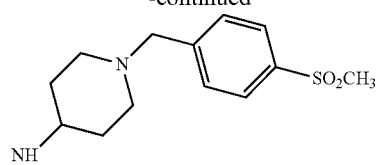
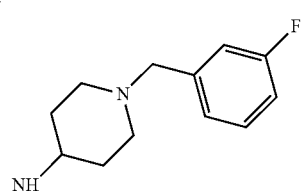
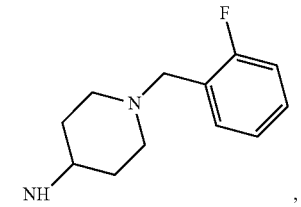
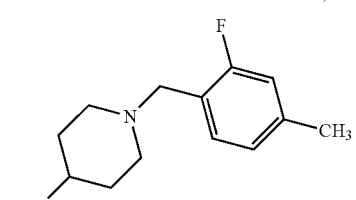
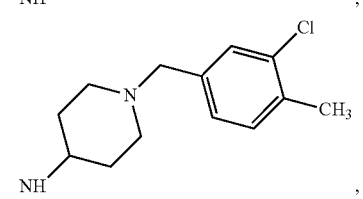
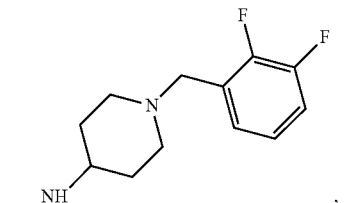
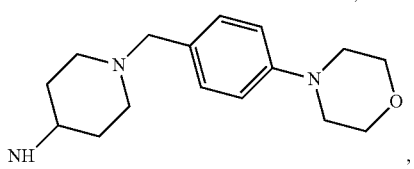
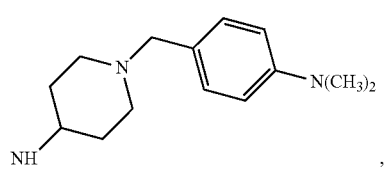
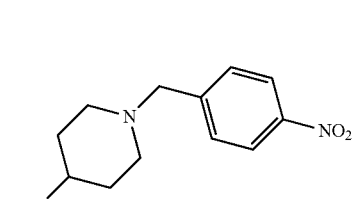
-continued
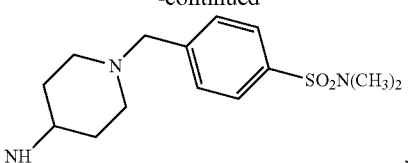
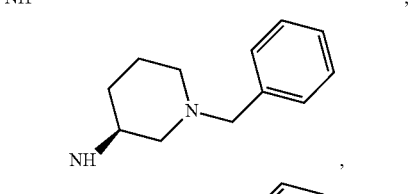
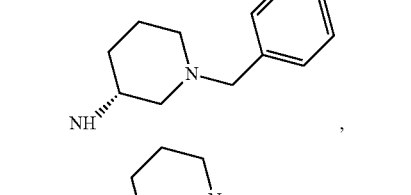
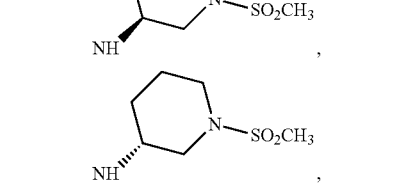
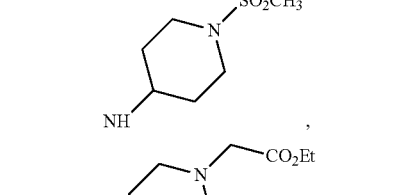
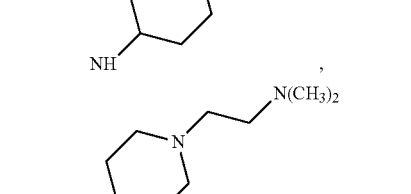
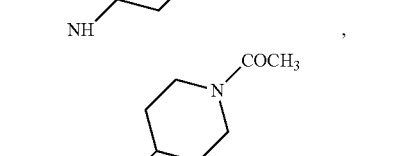
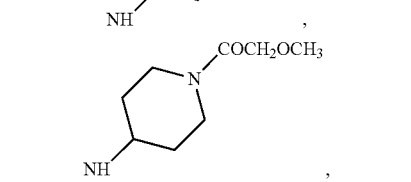
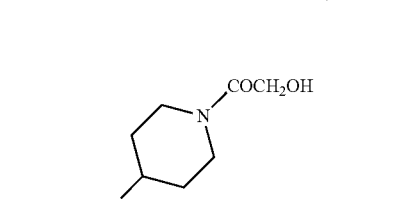
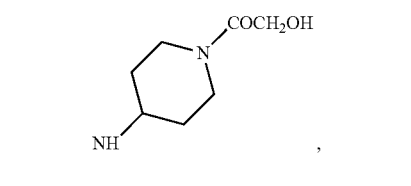

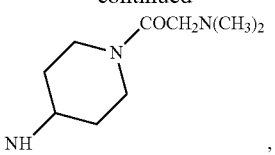,
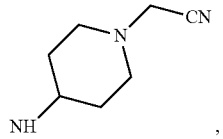,
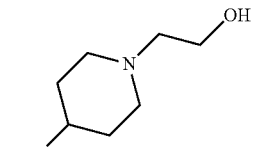,
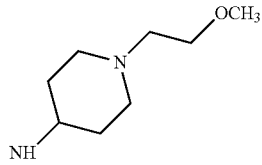,
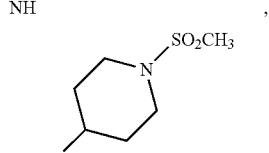,
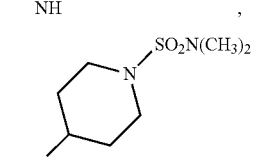,
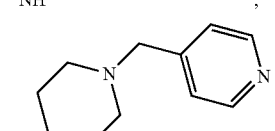,
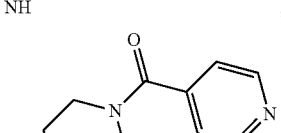,
,
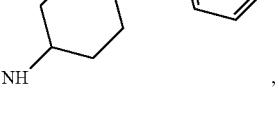,
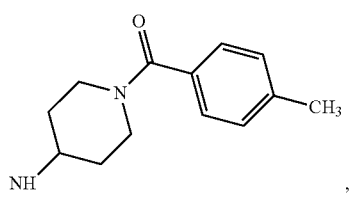,
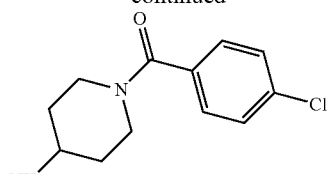,
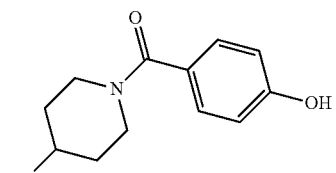,
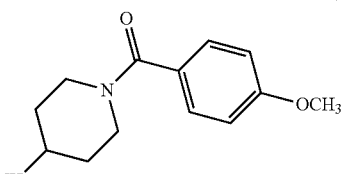,
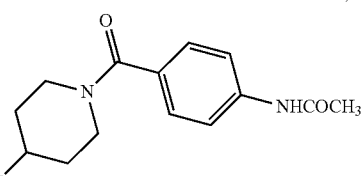,
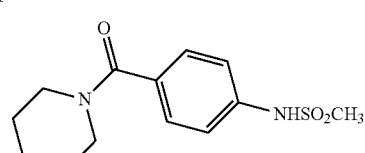,
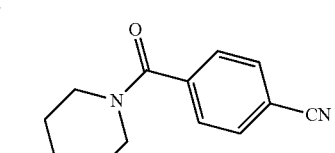,
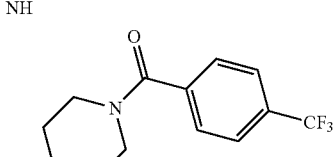,
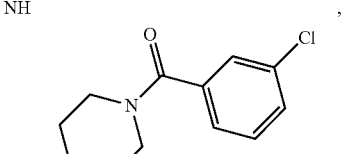,
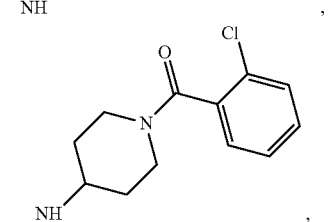, -continued

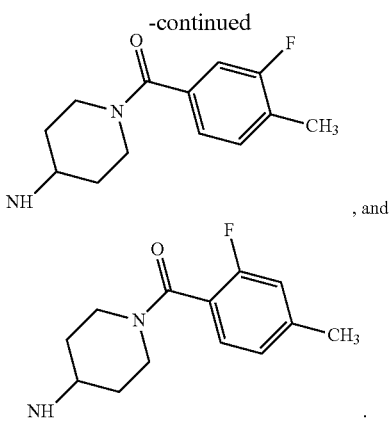

, and

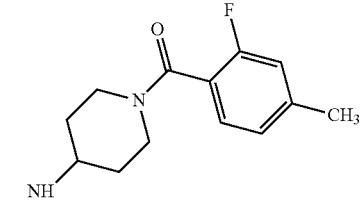

In some embodiments, NR₂R₃ is selected from the group consisting of:

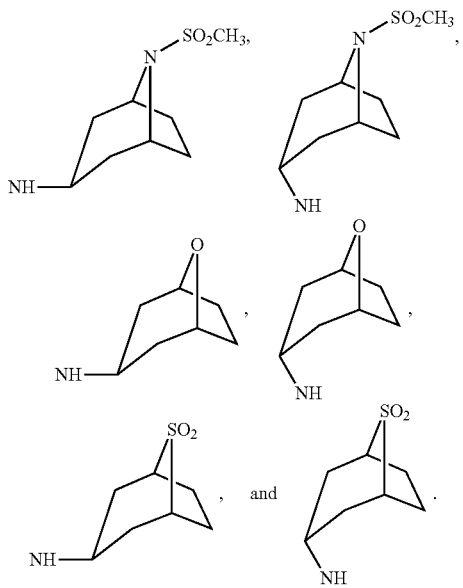

In some embodiments, R₃ and/or R₂ is heteroaryl(CR$_a$R$_b$)$_m$—. Various heteroaryls are known to the skilled artisan and are encompassed within the term heteroaryl(CR$_a$R$_b$)$_m$—. In some embodiments, R₃ and/or R₂ is heteroaryl (CR$_a$R$_b$)$_m$—, and heteroaryl is as defined herein. In some embodiments, R₃ and/or R₂ is heteroaryl(CR$_a$R$_b$)$_m$—, and heteroaryl is a monocyclic ring.

In some embodiments, R₃ and/or R₂ is heteroaryl(CR$_a$R$_b$)$_m$—, and heteroaryl comprises a nitrogen, sulfur or oxygen. In some embodiments, R₃ and/or R₂ is heteroaryl (CR$_a$R$_b$)$_m$—, and heteroaryl comprises one or more nitrogens. In some embodiments, R₂ is hydrido, and R₃ is heteroaryl(CR$_a$R$_b$)$_m$—. In some embodiments, R₂ is hydrido, and R₃ is heteroaryl(CR$_a$R$_b$)$_m$—, wherein the heteroaryl of heteroaryl(CR$_a$R$_b$)$_m$— is selected from the group consisting of the group consisting of furanyl, thiophenyl, pyrrolyl, isoxazolyl, oxazolyl, isothiazolyl, thiazolyl, pyrazolyl, imidazolyl, triazolyl, oxadiazolyl, thiadiazolyl, tetrazolyl, pyridinyl, pyrimidinyl, pyrazinyl, benzofuranyl, benzothiophenyl, indolyl, benzopyrrolidinyl, benzimidizolyl, indazolyl, benzotriazolyl, benzisoxazolyl, benzoxazolyl, benzisothiazolyl, benzothiazolyl, dihydroquinolinyl, tetrahydroquinolinyl, benzoxazinyl, quinolinyl, and isoquinolinyl. In some embodiments, the heteroaryl of heteroaryl (CR$_a$R$_b$)$_m$— is a pyridinyl.

In some embodiments, NR₂R₃ comprises a benzyl ring, e.g., NR₂R₃ is

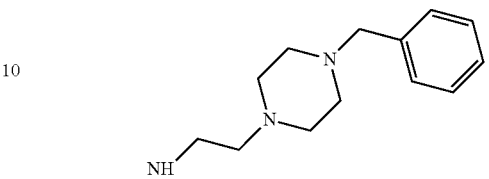

The present disclosure specifically describes wherein the benzyl ring found within NR₂R₃ can be substituted with one or more halogens, e.g., chloro or fluoro, one or more C₁-C₃ alkyls, e.g., methyl, or one or more halogenated C₁-C₃ alkyls, e.g., —CH₂Cl or CF₃. In some embodiments, the disclosure provides wherein the benzyl ring found within NR₂R₃ can be substituted with one, two or three halogens, e.g., chloro or fluoro. In some embodiments, the disclosure provides wherein the benzyl ring found within NR₂R₃ can be substituted at any position on the benzyl ring, e.g., at position 2', 3', 4', 5', or 6'.

In some embodiments, R₃ and/or R₂ is R₄R₅N(CR$_a$R$_b$)$_m$—. In some embodiments, R₂ is hydrido, and R₃ is R₄R₅N(CR$_a$R$_b$)$_m$—. In some embodiments, R₂ is alkyl, and R₃ is R₄R₅N(CR$_a$R$_b$)$_m$— R₄ and R₅ are independently selected from the group consisting of hydrido, alkyl, cyano, cycloalkyl, cycloalkylalkyl, hydroxyalkyl, alkoxyalkyl, aryl, heteroaryl, heterocyclyl, arylalkyl, heteroarylalkyl, heterocyclylalkyl, haloalkyl, haloalkylcarbonyl, hydroxyalkylcarbonyl, alkoxyalkylcarbonyl, (R$_c$R$_d$N)alkylcarbonyl, alkoxycarbonyl, (R$_c$R$_d$N)carbonyl, arylcarbonyl, heteroarylcarbonyl, heterocyclylcarbonyl, alkylsulfonyl, haloalkylsulfonyl, arylsulfonyl, heteroarylsulfonyl, heterocyclylsulfonyl, (R$_c$R$_d$N)sulfonyl, (R$_c$R$_d$N)sulfonylalkyl, (R$_c$R$_d$N)carbonylalkyl, carboxyalkyl, alkoxycarbonylalkyl, cyanoalkyl, alkylcarbonylaminoalkyl, alkylsulfonylalkyl, alkylsulfonylaminoalkyl, and (R$_c$R$_d$N)carbonylalkyl. In some embodiments, R₄ is alkyl, and R₅ is selected from the group consisting of cycloalkyl, cycloalkylalkyl, hydroxyalkyl, alkoxyalkyl, arylalkyl, heteroarylalkyl, heterocyclylalkyl, haloalkyl, haloalkylcarbonyl, hydroxyalkylcarbonyl, alkoxyalkylcarbonyl, —(R$_c$R$_d$N)alkylcarbonyl, alkoxycarbonyl, (R$_c$R$_d$N)carbonyl, arylcarbonyl, heteroarylcarbonyl, heterocyclylcarbonyl, alkylsulfonyl, haloalkylsulfonyl, arylsulfonyl, heteroarylsulfonyl, heterocyclylsulfonyl, (R$_c$R$_d$N)sulfonyl, (R$_c$R$_d$N)sulfonylalkyl, carboxyalkyl, alkoxycarbonylalkyl, cyanoalkyl, alkylcarbonylaminoalkyl, alkylsulfonylaminoalkyl, and (R$_c$R$_d$N)carbonylalkyl. In some embodiments, R₄ is alkyl, and R₅ is selected from the group consisting of cycloalkylalkyl, hydroxyalkyl, alkoxyalkyl, alkoxycarbonylalkyl, alkylsulfonyl, cyanoalkyl, alkylsulfonylalkyl, and alkylaminocarbonylalkyl.

In some embodiments, the disclosure is directed to compounds of Formula I, wherein NR₂R₃ is selected from the group consisting of:

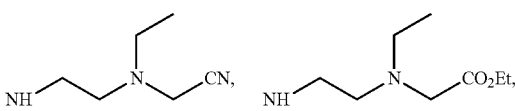

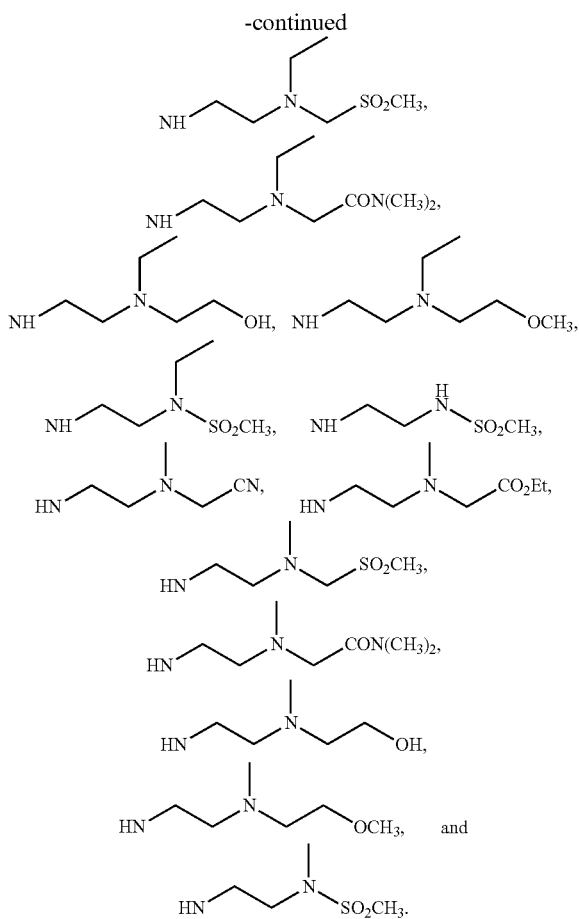

In some embodiments, $R_a$ and $R_b$ are independently selected from the group consisting of hydrido, $C_1$-$C_6$ alkyl, alkoxyalkyl, hydroxyalkyl, alkylthioalkyl, alkylsulfinylalkyl, alkylsulfonylalkyl, cyano, cyanoalkyl, carboxyalkyl, aminocarbonylalkyl, alkylaminocarbonylalkyl, dialkylaminocarbonylalkyl, hydroxyl, halo, aryl, arylalkyl, heteroaryl, heteroarylalkyl, heterocyclyl, and heterocyclylalkyl groups. In some embodiments, $R_a$ and $R_b$ are taken together with the carbon atom to form an oxo or substituted or unsubstituted cycloalkyl or heterocyclyl ring, with said cycloalkyl or heterocycloalkyl ring substituted with one or more hydrido, oxo, or $C_1$-$C_6$ alkyl groups, and wherein the heterocyclyl can optionally include one or more heteroatoms selected from the group consisting of nitrogen, sulfur and oxygen. In some embodiments, $R_a$ and $R_b$ are independently selected from the group consisting of hydrido, $C_1$-$C_6$ alkyl, hydroxyalkyl, hydroxyl, halo, aryl, arylalkyl, heterocyclyl, and heterocyclylalkyl. In some embodiments, $R_a$ and $R_b$ are independently selected from the group consisting of hydrido, methyl, ethyl, hydroxymethyl, methoxymethyl, phenyl, benzyl, or hydroxyl.

In some embodiments, $R_c$ and $R_d$ are independently selected from the group consisting of hydrido, $C_1$-$C_6$ alkyl, cycloalkyl, cycloalkylalkyl, alkoxyalkyl, hydroxyalkyl, alkylthioalkyl, alkylsulfinylalkyl, alkylsulfonylalkyl, cyano, cyanoalkyl, carboxyalkyl, alkoxycarbonylalkyl, aminocarbonylalkyl, alkylaminocarbonylalkyl, dialkylaminocarbonylalkyl, hydroxyl, aryl, arylalkyl, heteroaryl, heteroarylalkyl, heterocyclyl, and heterocyclylalkyl groups. In some embodiments, $R_c$ and $R_d$ can together with the nitrogen atom to which they are attached form a heterocyclyl or heteroaryl group, wherein the heterocyclyl or heteroaryl can optionally include one or more heteroatoms selected from the group consisting of nitrogen, sulfur and oxygen.

As defined herein, "m" is an integer from zero to six, zero to five, zero to four, zero to three, zero to two or zero to one. In some embodiments, "m" is an integer from one to six, one to five, one to four, one to three, one to two. In some embodiments, "m" is zero. In some embodiments, "m" is one. In some embodiments, "m" is two. In some embodiments, "in" is three.

As defined herein, "n" is an integer from one to six, one to five, one to four, one to three, or one to two. In some embodiments, "n" is one. In some embodiments, "n" is two. In some embodiments, "n" is three.

As defined herein, $R_1$ can include any substituent selected from the group consisting of substituted or unsubstituted $C_3$-$C_{20}$ alkanoyl, carboxyalkanoyl, carboxyalkenoyl, carboxylalkynoyl, carboxycyloalkylalkanoyl, carboxyalkylcycloalkylalkanoyl, carboxycyloalkylcarbonyl, carboxyalkylcycloalkylcarbonyl, alkoxycarbonylcyloalkylcarbonyl, alkoxycarbonylalkylcycloalkylcarbonyl, trialkylsilylalkoxycarbonylcyloalkylcarbonyl, trialkylsilylalkoxycarbonylalkylcycloalkylcarbonyl, arylalkyloxycarbonylcycloalkylcarbonyl, arylalkyloxycarbonylalkylcycloalkylcarbonyl, alkoxycarbonylalkanoyl, alkoxycarbonylalkenoyl, alkoxycarbonylalkynoyl, alkoxycarbonylcyloalkylalkanoyl, alkoxycarbonylalkylcycloalkylalkanoyl, trialkylsilylalkoxycarbonylalkanoyl, trialkylsilylalkoxycarbonylalkenoyl, trialkylsilylalkoxycarbonylalkynoyl, trialkylsilylalkoxycarbonylcyloalkylalkanoyl, trialkylsilylalkoxycarbonylalkylcycloalkylalkanoyl, arylalkyloxycarbonylalkanoyl, arylalkyloxycarbonylalkenoyl, arylalkyloxycarbonylalkynoyl, arylalkyloxycarbonylcyloalkylalkanoyl, and arylalkyloxycarbonylalkylcycloalkylalkanoyl wherein any alkyl, cycloalkyl, alkenyl, or alkynyl group are independently substituted with one or more groups selected from the group consisting of hydrido, halo, or $C_1$-$C_6$ alkyl groups.

In some embodiments, $R_1$ is selected from the group consisting of a $C_3$-$C_{20}$ carboxyalkanoyl, $C_3$-$C_{20}$ carboxyalkenoyl, and $C_3$-$C_{20}$ carboxyalkanoyl. In some embodiments, $R_1$ is a $C_3$-$C_6$ carboxyalkanoyl, wherein the carboxyalkanoyl is optionally substituted with one or more $C_1$-$C_6$ alkyl groups. In some embodiments, $R_1$ is a $C_3$-$C_6$ carboxyalkanoyl, wherein the carboxyalkanoyl is optionally substituted with one or more methyl or ethyl groups. In some embodiments, $R_1$ is selected from the group consisting of a $C_4$-$C_5$ carboxyalkanoyl, optionally substituted with one or more methyl or ethyl groups. In some embodiments, $R_1$ is 3'-methylsuccinyl, 3'-methylglutaryl, 3',3'-dimethylsuccinyl or 3',3'-dimethylglutaryl.

$R_6$ as described herein can include isopropyl, isopropenyl, or 1-methyl-1-cyclopropyl. In some embodiments, $R_6$ is isopropyl. In some embodiments, $R_6$ is isopropenyl. In some embodiments, $R_6$ is 1-methyl-1-cyclopropyl.

Various compounds of the present disclosure are excluded. For example, in some embodiments, the compounds of Formula I do not encompass wherein (i) $R_2$ and $R_3$ are not both hydrido, (ii) $R_4$ and $R_5$ are not both alkyl, and (iii) wherein $R_2$ is not hydrido when $R_3$ is alkyl.

In some embodiments, the compounds of the present disclosure can be described as in Formula II:

Formula II

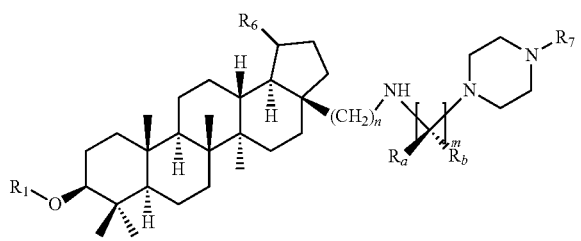

Formula V

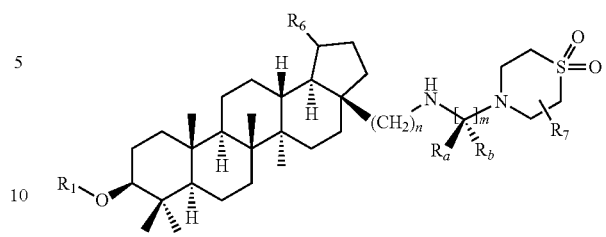

wherein $R_7$ is selected from the group consisting of cycloalkyl, cycloalkylalkyl, hydroxyalkyl, alkoxyalkyl, aryl, arylalkyl, heteroarylalkyl, heterocyclylalkyl, haloalkyl, haloalkylcarbonyl, hydroxyalkylcarbonyl, alkoxyalkylcarbonyl, $(R_cR_dN)$alkylcarbonyl, alkoxycarbonyl, $(R_cR_dN)$carbonyl, arylcarbonyl, heteroarylcarbonyl, heterocyclylcarbonyl, alkylsulfonyl, haloalkylsulfonyl, arylsulfonyl, heteroarylsulfonyl, heterocyclylsulfonyl, $(R_cR_dN)$sulfonyl, $(R_cR_dN)$sulfonylalkyl, carboxyalkyl, alkoxycarbonylalkyl, cyanoalkyl, alkylcarbonylaminoalkyl, alkylsulfonylaminoalkyl, and $(R_cR_dN)$carbonylalkyl.

In some embodiments, $R_c$ and $R_d$ of Formula II are independently selected from the group consisting of hydrido, $C_1$-$C_6$ alkyl, alkoxyalkyl, hydroxyalkyl, cyanoalkyl, carboxyalkyl, hydroxyl, aryl, arylalkyl, heteroaryl, heteroarylalkyl, heterocyclyl, and heterocyclylalkyl groups, or $R_c$ and $R_d$ can together with the nitrogen atom to which they are attached form a heterocyclyl or heteroaryl group, wherein the heterocyclyl or heteroaryl can optionally include one or more heteroatoms selected from the group consisting of nitrogen, sulfur and oxygen.

In some embodiments, $R_a$ and $R_b$ of Formula II are independently selected from the group consisting of hydrido, cyano, oxo, $C_1$-$C_6$ alkyl, hydroxyalkyl, hydroxyl, halo, and aryl groups.

In some embodiments, m of Formula II is 1 to 3.

In some embodiments, the compounds of the present disclosure can be described as in Formula III, Formula IV, or Formula V:

Formula III

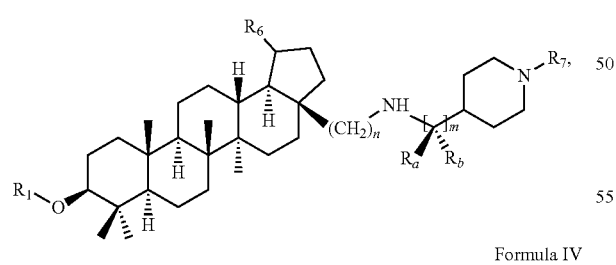

Formula IV

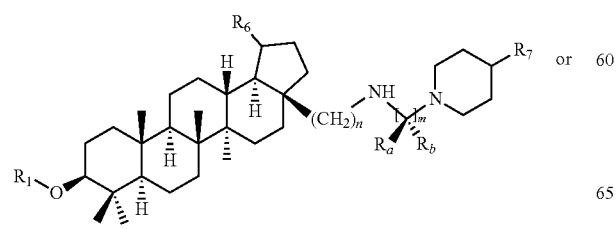

wherein $R_7$ is selected from the group consisting of cyano, halo, alkoxy, cycloalkyl, hydroxy, cycloalkylalkyl, hydroxyalkyl, alkoxyalkyl, arylalkyl, heteroarylalkyl, heterocyclylalkyl, haloalkyl, haloalkylcarbonyl, hydroxyalkylcarbonyl, alkoxyalkylcarbonyl, $(R_cR_dN)$alkylcarbonyl, alkoxycarbonyl, $(R_cR_dN)$carbonyl, arylcarbonyl, heteroarylcarbonyl, heterocyclylcarbonyl, alkylsulfonyl, haloalkylsulfonyl, arylsulfonyl, heteroarylsulfonyl, heterocyclylsulfonyl, $(R_cR_dN)$sulfonyl, $(R_cR_dN)$sulfonylalkyl, carboxyalkyl, alkoxycarbonylalkyl, cyanoalkyl, alkylcarbonylaminoalkyl, alkylsulfonylaminoalkyl, and $(R_cR_dN)$carbonylalkyl. When Formula IV, then $R_7$ can be oxo.

In some embodiments, the $R_c$ and $R_d$ of Formula III and/or Formula IV are independently selected from the group consisting of hydrido, $C_1$-$C_6$ alkyl, alkoxyalkyl, hydroxyalkyl, cyanoalkyl, carboxyalkyl, hydroxyl, aryl, arylalkyl, heteroaryl, heteroarylalkyl, heterocyclyl, and heterocyclylalkyl groups, or $R_c$ and $R_d$ can together with the nitrogen atom to winch they are attached form a heterocyclyl or heteroaryl group, wherein the heterocyclyl or heteroaryl can optionally include one or more heteroatoms selected from the group consisting of nitrogen, sulfur and oxygen.

In some embodiments, $R_a$ and $R_b$ of Formula III and/or Formula IV are independently selected from the group consisting of hydrido, $C_1$-$C_6$ alkyl, hydroxyalkyl, hydroxyl, halo, and aryl groups.

In some embodiments, m as defined in of Formula III and/or Formula IV is zero to two.

In some embodiments, the compounds of the present invention are selected from the group consisting of:
(i) wherein $R_1$ is 3',3'-dimethylsuccinyl, n is 2, and $NR_2R_3$ is

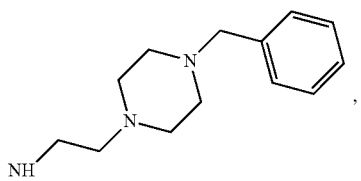 [SMILES: NCCN1CCN(Cc2ccccc2)CC1]

$R_6$ is isopropenyl;
(ii) wherein $R_1$ is 3',3'-dimethylsuccinyl, n is 2, and $NR_2R_3$ is

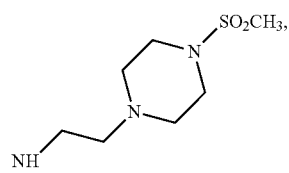 [SMILES: CS(=O)(=O)N1CCN(CCN)CC1]

$R_6$ is isopropenyl;

(iii) wherein $R_1$ is 3',3'-dimethylsuccinyl, n is 2, and $NR_2R_3$ is

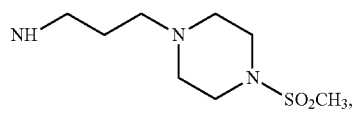

$R_6$ is isopropenyl;

(iv) wherein $R_1$ is 3',3'-dimethylglutaryl, n is 2, and $NR_2R_3$ is

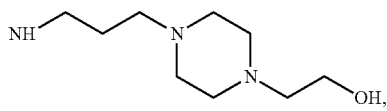

$R_6$ is isopropenyl;

(v) wherein $R_1$ is 3',3'-dimethylglutaryl, n is 2, and $NR_2R_3$ is

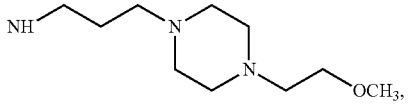 [SMILES: COCCN1CCN(CCCN)CC1]

$R_6$ is isopropenyl;

(vi) wherein $R_1$ is 3',3'-dimethylsuccinyl, n is 2, and $NR_2R_3$ is

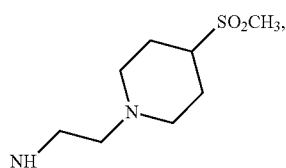

$R_6$ is isopropenyl;

(vii) wherein R; is 3',3'-dimethylsuccinyl, n is 2, and $NR_2R_3$ is

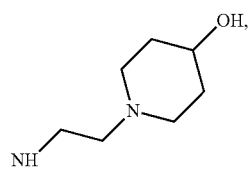

$R_6$ is isopropenyl;

(viii) wherein $R_1$ is 3',3'-dimethylglutaryl, n is 2, and $NR_2R_3$ is

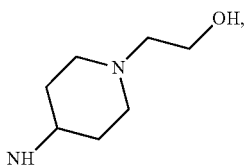

$R_6$ is isopropenyl;

(ix) wherein $R_1$ is 3',3'-dimethylglutaryl, n is 2, and $NR_2R_3$ is

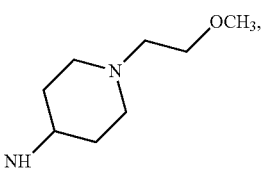 [SMILES: COCCN1CCC(N)CC1]

$R_6$ is isopropenyl;

(x) wherein $R_1$ is 3',3'-dimethylglutaryl, n is 2, and $NR_2R_3$ is

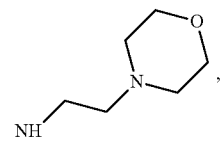

$R_6$ is isopropenyl;

(xi) wherein $R_1$ is 3',3'-dimethylsuccinyl, n is 2, and $NR_2R_3$ is

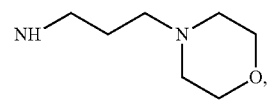

$R_6$ is isopropenyl;

(xii) wherein $R_1$ is 3',3'-dimethylglutaryl, n is 2, and $NR_2R_3$ is

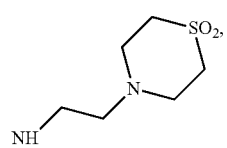

$R_6$ is isopropenyl;

(xiii) wherein $R_1$ is 3',3'-dimethylsuccinyl, n is 2, and $NR_2R_3$ is

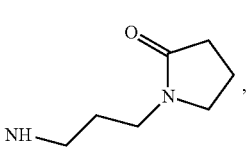

$R_6$ is isopropenyl;

(xiv) wherein $R_1$ is 3',3'-dimethylglutaryl, n is 2, and $NR_2R_3$

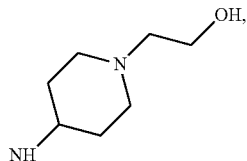

$R_6$ is 1-methyl-1-cyclopropyl;

(xv) wherein $R_1$ is 3',3'-dimethylglutaryl, n is 2, and $NR_2R_3$ is

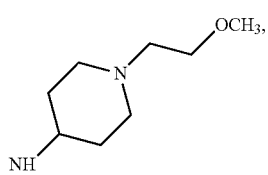

$R_6$ is 1-methyl-1-cyclopropyl;

(xvi) wherein $R_1$ is 3',3'-dimethylglutaryl, n is 2, and $NR_2R_3$ is

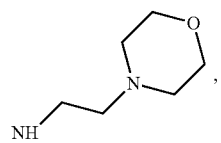

$R_6$ is 1-methyl-1-cyclopropyl; and (xvii) wherein $R_1$ is 3',3'-dimethylsuccinyl, n is 2, and $NR_2R_3$ is

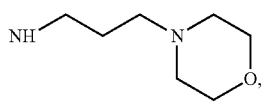

$R_6$ is 1-methyl-1-cyclopropyl.

In some embodiments, the disclosure provides a compound of Formula I, (i) wherein $R_1$ is 3',3'-dimethylglutaryl, n is 2, and $NR_2R_3$ is

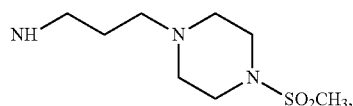

$R_6$ is isopropenyl;

(ii) wherein $R_1$ is 3',3'-dimethylsuccinyl, n is 2, and $NR_2R_3$ is

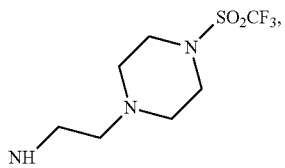

$R_6$ is isopropenyl;

(iii) wherein $R_1$ is 3',3'-dimethylsuccinyl, n is 2, and $NR_2R_3$ is

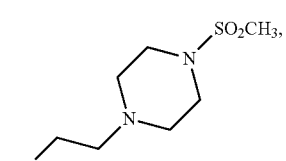

$R_6$ is isopropenyl;

(iv) wherein $R_1$ is 3',3'-dimethylsuccinyl, n is 2, and $NR_2R_3$ is

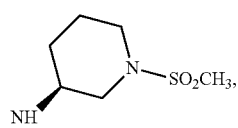

$R_6$ is isopropenyl;

(v) wherein $R_1$ is 3',3'-dimethylsuccinyl, n is 2, and $NR_2R_3$ is

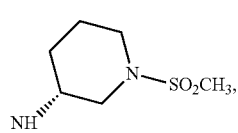

$R_6$ is isopropenyl;

(vi) wherein $R_1$ is 3',3'-dimethylsuccinyl, n is 2, and $NR_2R_3$ is

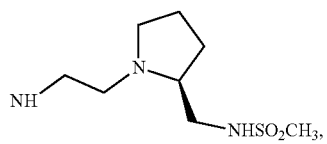

$R_6$ is isopropenyl;

(vii) wherein $R_1$ is 3',3'-dimethylsuccinyl, n is 2, and $NR_2R_3$ is

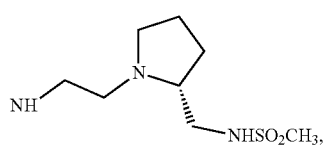

$R_6$ is isopropenyl;

(viii) wherein $R_1$ is 3',3'-dimethylsuccinyl, n is 2, and $NR_2R_3$ is

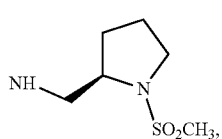

$R_6$ is isopropenyl;

(ix) wherein $R_1$ is 3',3'-dimethylsuccinyl, n is 2, and $NR_2R_3$ is

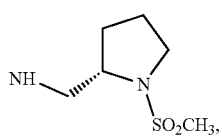

$R_6$ is isopropenyl;

(x) wherein $R_1$ is 3',3'-dimethylsuccinyl, n is 2, and $NR_2R_3$ is

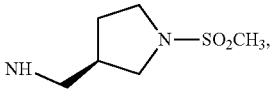

$R_6$ is isopropenyl;

(xi) wherein $R_1$ is 3',3'-dimethylsuccinyl, n is 2, and $NR_2R_3$ is

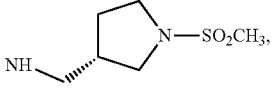

$R_6$ is isopropenyl;

(xii) wherein $R_1$ is 3',3'-dimethylglutaryl, n is 2, and $NR_2R_3$ is

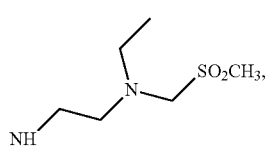

$R_6$ is isopropenyl;

(xiii) wherein $R_1$ is 3',3'-dimethylsuccinyl, n is 2, and $NR_2R_3$ is

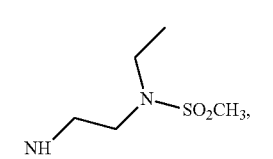

$R_6$ is isopropenyl;

(xiv) wherein $R_1$ is 3',3'-dimethylsuccinyl, n is 2, and $NR_2R_3$ is

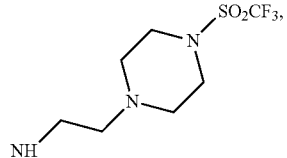 [SMILES: CS(=O)(=O)N1CCN(CCN)CC1]

$R_6$ is isopropenyl;

(xv) wherein $R_1$ is 3',3'-dimethylsuccinyl, n is 2, and $NR_2R_3$ is

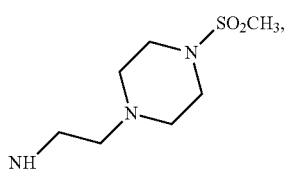

$R_6$ is isopropenyl;

(xvi) wherein $R_1$ is 3',3'-dimethylsuccinyl, n is 2, and $NR_2R_3$ is

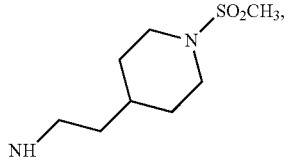

$R_6$ is isopropenyl;

(xvii) wherein $R_1$ is 3',3'-dimethylsuccinyl, n is 2, and $NR_2R_3$ is

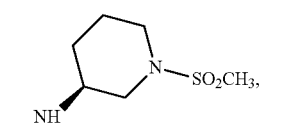 [SMILES: CS(=O)(=O)N1CCC[C@H](N)C1]

$R_6$ is isopropenyl;

(xviii) wherein $R_1$ is 3',3'-dimethylsuccinyl, n is 2, and $NR_2R_3$ is

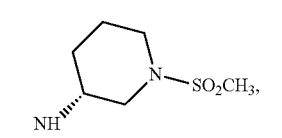

$R_6$ is isopropenyl;

(xix) wherein $R_1$ is 3',3'-dimethylsuccinyl, n is 2, and $NR_2R_3$ is (xx) wherein $R_1$ is 3',3'-dimethylsuccinyl, n is 2, and $NR_2R_3$ is

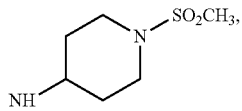

$R_6$ is isopropenyl;

(xxi) wherein $R_1$ is 3',3'-dimethylglutaryl, n is 2, and $NR_2R_3$ is

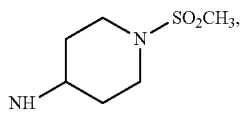

$R_6$ is isopropenyl;

(xxii) wherein $R_1$ is 3',3'-dimethylsuccinyl, n is 2, and $NR_2R_3$ is

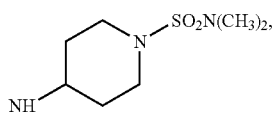

$R_6$ is isopropenyl;

(xxiii) wherein $R_1$ is 3',3'-dimethylsuccinyl, n is 2, and $NR_2R_3$ is

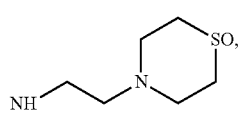

$R_6$ is is isopropenyl;

(xxiv) wherein $R_1$ is 3',3'-dimethylsuccinyl, n is 2, and $NR_2R_3$ is

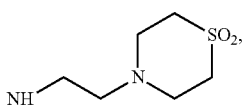

$R_6$ is isopropenyl;

(xxv) wherein $R_1$ is 3',3'-dimethylsuccinyl, n is 2, and $NR_2R_3$ is

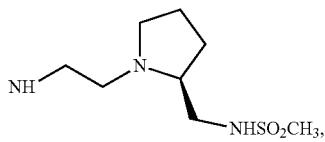

$R_6$ is isopropenyl;

(xxvi) wherein $R_1$ is 3',3'-dimethylsuccinyl, n is 2, and $NR_2R_3$ is

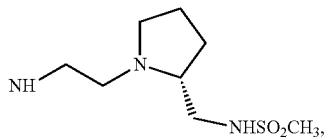

$R_6$ is isopropenyl;

(xxvii) wherein $R_1$ is 3',3'-dimethylsuccinyl, n is 2, and $NR_2R_3$ is

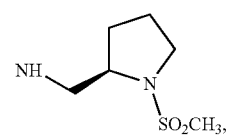

$R_6$ is isopropenyl;

(xxviii) wherein $R_1$ is 3',3'-dimethylsuccinyl, n is 2, and $NR_2R_3$ is

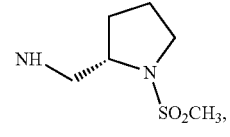

$R_6$ is isopropenyl;

(xxix) wherein $R_1$ is 3',3'-dimethylsuccinyl, n is 2, and $NR_2R_3$ is

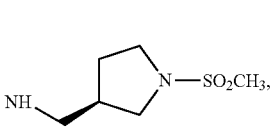 [SMILES: CS(=O)(=O)N1CC[C@H](CN)C1]

$R_6$ is isopropenyl;

(xxx) wherein $R_1$ is 3',3'-dimethylsuccinyl, n is 2, and $NR_2R_3$ is

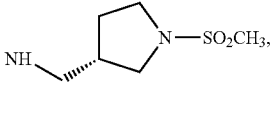

$R_6$ is isopropenyl;

(xxxi) wherein $R_1$ is 3',3'-dimethylsuccinyl, n is 2, and $NR_2R_3$ is

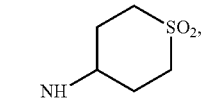

$R_6$ is isopropenyl;

(xxxii) wherein $R_1$ is 3',3'-dimethylsuccinyl, n is 2, and $NR_2R_3$ is

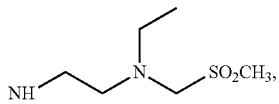

$R_6$ is isopropenyl;
(xxxiii) wherein $R_1$ is 3',3'-dimethylglutaryl, n is 2, and $NR_2R_3$ is

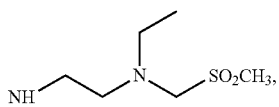

$R_6$ is isopropenyl;
(xxxiv) wherein $R_1$ is 3',3'-dimethylsuccinyl, n is 2, and $NR_2R_3$ is

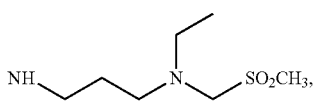

$R_6$ is isopropenyl;
(xxxv) wherein $R_1$ is 3',3'-dimethylsuccinyl, n is 2, and $NR_2R_3$ is

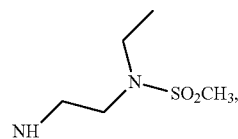

$R_6$ is isopropenyl; and
(xxxvi) wherein $R_1$ is 3',3'-dimethylsuccinyl, n is 2, and $NR_2R_3$ is

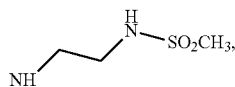

$R_6$ is isopropenyl.

In some embodiments, the disclosure provides a compound of Formula I,
(1) wherein $R_1$ is 3',3'-dimethylsuccinyl, n is 1, and $NR_2R_3$ is

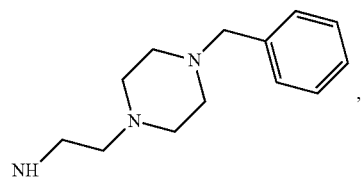 [SMILES: NCCN1CCN(Cc2ccccc2)CC1]

$R_6$ is isopropenyl;

(ii) wherein $R_1$ is 3',3'-dimethylsuccinyl, n is 1, and $NR_2R_3$ is

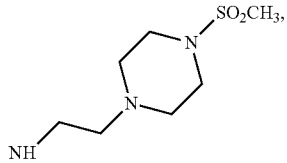 [SMILES: CS(=O)(=O)N1CCN(CCN)CC1]

$R_6$ is isopropenyl;
(iii) wherein $R_1$ is 3',3'-dimethylsuccinyl, n is 1, and $NR_2R_3$ is

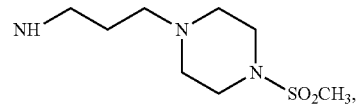 [SMILES: CS(=O)(=O)N1CCN(CCCN)CC1]

$R_6$ is isopropenyl;
(iv) wherein $R_1$ is 3',3'-dimethylglutaryl, n is 1, and $NR_2R_3$ is

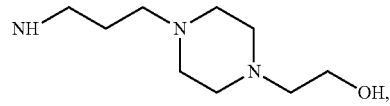 [SMILES: NCCCN1CCN(CCO)CC1]

$R_6$ is isopropenyl;
(v) wherein $R_1$ is 3',3'-dimethylglutaryl, n is 1, and $NR_2R_3$ is

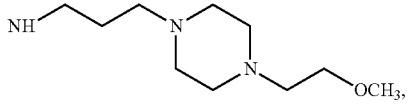

$R_6$ is isopropenyl;
(vi) wherein $R_1$ is 3',3'-dimethylsuccinyl, n is 1, and $NR_2R_3$ is

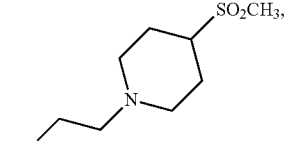

$R_6$ is isopropenyl;
(vii) wherein $R_1$ is 3',3'-dimethylsuccinyl, n is 1, and $NR_2R_3$ is $R_6$ is isopropenyl;

(viii) wherein $R_1$ is 3',3'-dimethylglutaryl, n is 1, and $NR_2R_3$ is

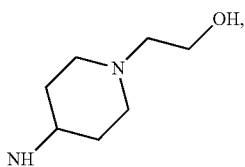

$R_6$ is 1-methyl-1-clyclopropyl;
(ix) wherein $R_1$ is 3',3'-dimethylglutaryl, n is 1, and $NR_2R_3$

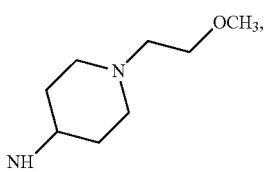 [SMILES: COCCN1CCC(N)CC1]

$R_6$ is 1-methyl-1-clyclopropyl;
(x) wherein $R_1$ is 3',3'-dimethylglutaryl, n is 1, and $NR_2R_3$ is

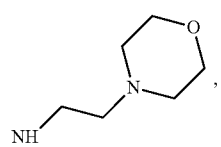

$R_6$ is isopropenyl;
(xi) wherein $R_1$ is 3',3'-dimethylsuccinyl, n is 1, and $NR_2R_3$ is

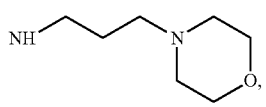

$R_6$ is isopropenyl;
(xii) wherein $R_1$ is 3',3'-dimethylglutaryl, n is 1, and $NR_2R_3$ is

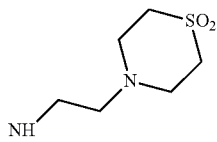

$R_6$ is isopropenyl; and
(xiii) wherein $R_1$ is 3',3'-dimethylsuccinyl, n is 1, and $NR_2R_3$ is

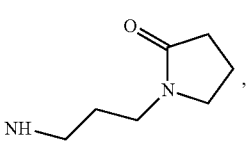

$R_6$ is isopropenyl.

In some embodiments, the disclosure provides a compound of Formula I,
(i) wherein $R_1$ is 3',3'-dimethylglutaryl, n is 1, and $NR_2R_3$ is

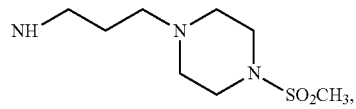

$R_6$ is isopropenyl;
(ii) wherein $R_1$ is 3',3'-dimethylsuccinyl, n is 1, and $NR_2R_3$ is

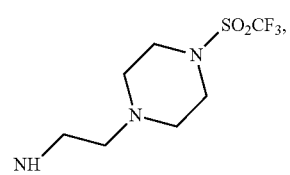

$R_6$ is isopropenyl;
(iii) wherein $R_1$ is 3',3'-dimethylsuccinyl, n is 1, and $NR_2R_3$ is

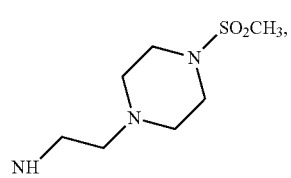 [SMILES: CS(=O)(=O)N1CCN(CCN)CC1]

$R_6$ is isopropenyl;
(iv) wherein $R_1$ is 3',3'-dimethylsuccinyl, n is 1, and $NR_2R_3$ is

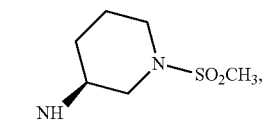

$R_6$ is isopropenyl;
(v) wherein $R_1$ is 3',3'-dimethylsuccinyl, n is 1, and $NR_2R_3$ is

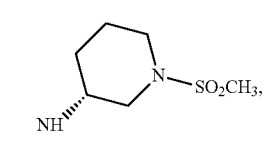

$R_6$ is isopropenyl;

(vi) wherein R₁ is 3',3'-dimethylsuccinyl, n is 1, and NR₂R₃ is

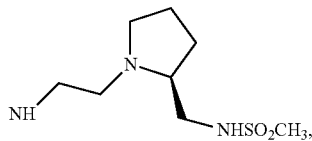

R₆ is isopropenyl;

(vii) wherein R₁ is 3',3'-dimethylsuccinyl, n is 1, and NR₂R₃ is

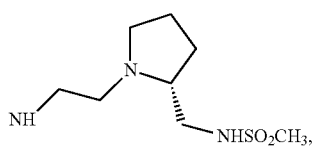

R₆ is isopropenyl;

(viii) wherein R₁ is 3',3'-dimethylsuccinyl, n is 1, and NR₂R₃ is

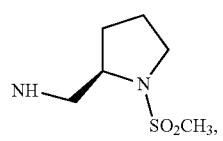

R₆ is isopropenyl;

(ix) wherein R₁ is 3',3'-dimethylsuccinyl, n is 1, and NR₂R₃ is

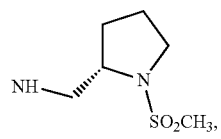

R₆ is isopropenyl;

(x) wherein R₁ is 3',3'-dimethylsuccinyl, n is 1, and NR₂R₃ is

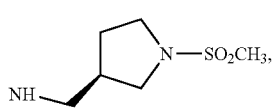 [SMILES: CS(=O)(=O)N1CC[C@H](CN)C1]

R₆ is isopropenyl;

(xi) wherein R₁ is 3',3'-dimethylsuccinyl, n is 1, and NR₂R₃ is

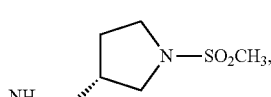

R₆ is isopropenyl;

(xii) wherein R₁ is 3',3'-dimethylglutaryl, n is 1, and NR₂R₃ is

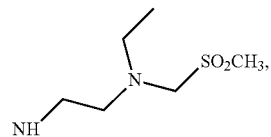

R₆ is isopropenyl;

(xiii) wherein R₁ is 3',3'-dimethylsuccinyl, n is 1, and NR₂R₃ is

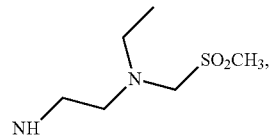

R₆ is isopropenyl;

(xiv) wherein R₁ is 3',3'-dimethylsuccinyl, n is 1, and NR₂R₃ is

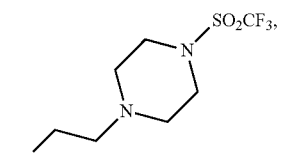

R₆ is isopropenyl;

(xv) wherein R₁ is 3',3'-dimethylsuccinyl, n is 1, and NR₂R₃ is

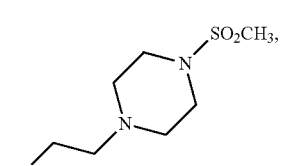

R₆ is isopropenyl;

(xvi) wherein R₁ is 3',3'-dimethylsuccinyl, n is 1, and NR₂R₃ is

R₆ is isopropenyl;

(xvii) wherein R₁ is 3',3'-dimethylsuccinyl, n is 1, and NR₂R₃ is

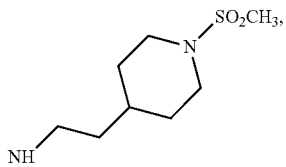 [SMILES: CS(=O)(=O)N1CCC(CCN)CC1]

R₆ is isopropenyl;

(xviii) wherein R₁ is 3',3'-dimethylsuccinyl, n is 1, and NR₂R₃ is

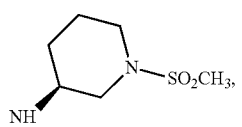 [SMILES: CS(=O)(=O)N1CCC[C@H](N)C1]

R₆ is isopropenyl;

(xix) wherein R₁ is 3',3'-dimethylsuccinyl, n is 1, and NR₂R₃ is

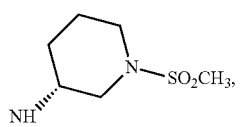

R₆ is isopropenyl;

(xx) wherein R₁ is 3',3'-dimethylsuccinyl, n is 1, and NR₂R₃ is

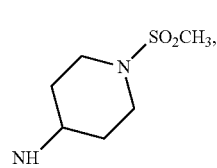 [SMILES: CS(=O)(=O)N1CCC(N)CC1]

R₆ is isopropenyl;

(xxi) wherein R₁ is 3',3'-dimethylglutaryl, n is 1, and NR₂R₃ is

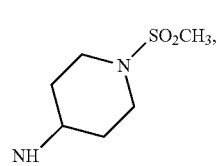 [SMILES: CS(=O)(=O)N1CCC(N)CC1]

R₆ is isopropenyl;

(xxii) wherein R₁ is 3',3'-dimethylsuccinyl, n is 1, and NR₂R₃ is

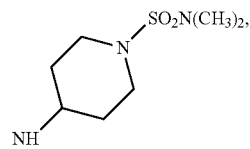

R₆ is isopropenyl;

(xxiii) wherein R₁ is 3',3'-dimethylsuccinyl, n is 1, and NR₂R₃ is

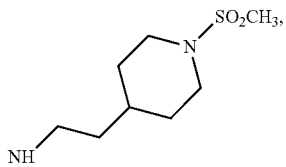 [SMILES: CS(=O)(=O)N1CCC(CCN)CC1]

R₆ is isopropenyl;

(xxiv) wherein R₁ is 3',3'-dimethylsuccinyl, n is 1, and NR₂R₃ is

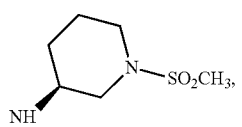 [SMILES: CS(=O)(=O)N1CCC[C@H](N)C1]

R₆ is isopropenyl;

(xxv) wherein R₁ is 3',3'-dimethylsuccinyl, n is 1, and NR₂R₃ is

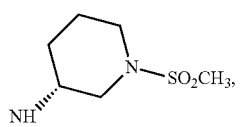

R₆ is isopropenyl;

(xxvi) wherein R₁ is 3',3'-dimethylsuccinyl, n is 1, and NR₂R₃ is

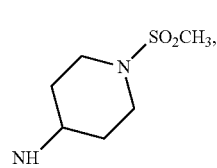 [SMILES: CS(=O)(=O)N1CCC(N)CC1]

R₆ is isopropenyl;

(xxvii) wherein R₁ is 3',3'-dimethylsuccinyl, n is 1, and NR₂R₃ is

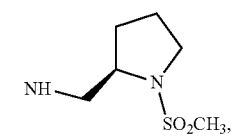 [SMILES: CS(=O)(=O)N1CCC[C@@H]1CN]

R₆ is isopropenyl;

(xxviii) wherein R₁ is 3',3'-dimethylsuccinyl, n is 1, and NR₂R₃ is

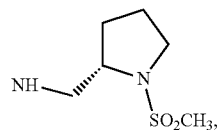 [SMILES: CS(=O)(=O)N1CCC[C@H]1CN]

R₆ is isopropenyl;

(xxix) wherein R₁ is 3',3'-dimethylsuccinyl, n is 1, and NR₂R₃ is

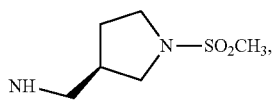 [SMILES: CS(=O)(=O)N1CC[C@H](CN)C1]

R₆ is isopropenyl;

(xxx) wherein R₁ is 3',3'-dimethylsuccinyl, n is 1, and NR₂R₃ is

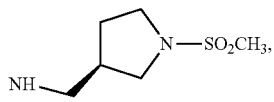

R₆ is isopropenyl;

(xxxi) wherein R₁ is 3',3'-dimethylsuccinyl, n is 1, and NR₂R₃ is

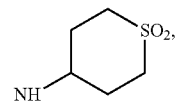

R₆ is isopropenyl;

(xxxii) wherein R₁ is 3',3'-dimethylsuccinyl, n is 1, and NR₂R₃ is

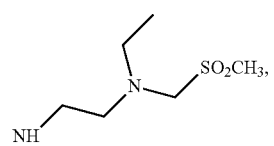

R₆ is isopropenyl;

(xxxiii) wherein R₁ is 3',3'-dimethylglutaryl, n is 1, and NR₂R₃ is

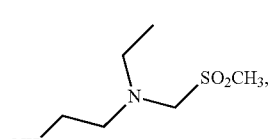

R₆ is isopropenyl;

(xxxiv) wherein R₁ is 3',3'-dimethylsuccinyl, n is 1, and NR₂R₃ is

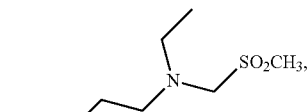

R₆ is isopropenyl;

(xxxv) wherein R₁ is 3',3'-dimethylsuccinyl, n is 1, and NR₂R₃ is

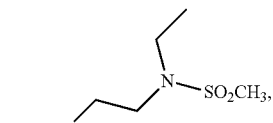

R₆ is isopropenyl; and (xxxvi) wherein R₁ is 3',3'-dimethylsuccinyl, n is 1, and NR₂R₃ is

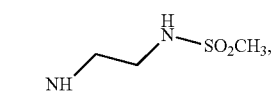

R₆ is isopropenyl.

In some embodiments, the compounds of the present invention are selected from the group consisting of those found in Formula V as described in Table 1.

Formula V

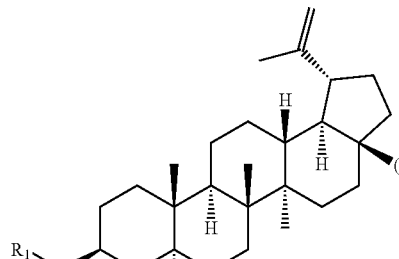

TABLE 1

| Entry | R₁O | n | NR₂R₃ |
|---|---|---|---|
| 1 | (S)-2,2-dimethylsuccinic acid monoester | 2 | 1-benzyl-4-(2-aminoethyl)piperazine |
| 2 | 3-methylglutaric acid monoester | 2 | 1-benzyl-4-(2-aminoethyl)piperazine |
| 3 | (S)-2-methylsuccinic acid monoester | 2 | 1-benzyl-4-(2-aminoethyl)piperazine |
| 4 | (R)-2-methylsuccinic acid monoester | 2 | 1-benzyl-4-(2-aminoethyl)piperazine |
| 5 | (S)-2,2-dimethylsuccinic acid monoester | 2 | 1-(naphthalen-1-ylmethyl)-4-(2-aminoethyl)piperazine |
| 6 | (S)-2,2-dimethylsuccinic acid monoester | 2 | 1-(naphthalen-2-ylmethyl)-4-(2-aminoethyl)piperazine |
| 7 | (S)-2,2-dimethylsuccinic acid monoester | 2 | 1-(pyridin-2-ylmethyl)-4-(2-aminoethyl)piperazine |
| 8 | (S)-2,2-dimethylsuccinic acid monoester | 2 | 1-(pyridin-3-ylmethyl)-4-(2-aminoethyl)piperazine |

TABLE 1-continued

| Entry | R₁O | n | NR₂R₃ |
|---|---|---|---|
| 9 | (2S)-2-methyl-2-carboxy-succinate | 2 | 1-(pyridin-4-ylmethyl)-4-(2-aminoethyl)piperazine |
| 10 | (2S)-2-methyl-2-carboxy-succinate | 2 | 4-benzyl-1-(2-aminoethyl)piperazin-2-one |
| 11 | (2S)-2-methyl-2-carboxy-succinate | 2 | 1-(4-benzylpiperazin-1-yl)-2-aminoethan-1-one |
| 12 | (2S)-2-methyl-2-carboxy-succinate | 2 | 1-benzoyl-4-(2-aminoethyl)piperazine |
| 13 | (2S)-2-methyl-2-carboxy-succinate | 2 | 2-(4-benzylpiperazin-1-yl)acetamide |
| 14 | (2S)-2-methyl-2-carboxy-succinate | 2 | 1-(2-fluorobenzyl)-4-(2-aminoethyl)piperazine |
| 15 | (2S)-2-methyl-2-carboxy-succinate | 2 | 1-(2-chlorobenzyl)-4-(2-aminoethyl)piperazine |

TABLE 1-continued
| Entry | R₁O | n | NR₂R₃ |
|---|---|---|---|
| 16 | 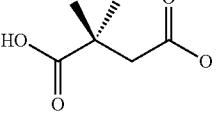 | 2 | 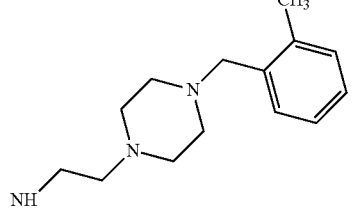 |
| 17 | 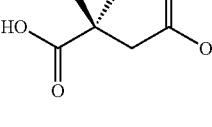 | 2 | 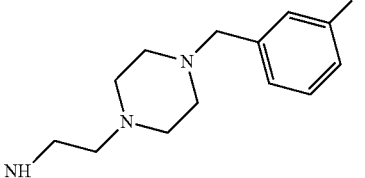 |
| 18 | 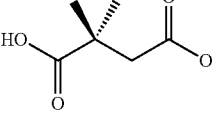 | 2 | 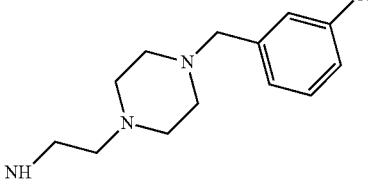 |
| 19 | 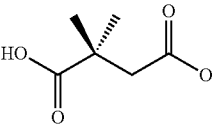 | 2 | 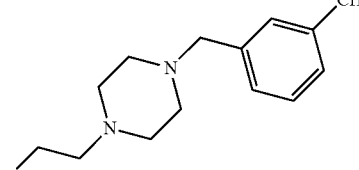 |
| 20 | 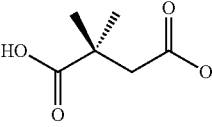 | 2 | 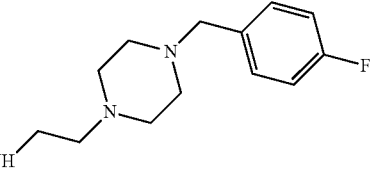 |
| 21 | 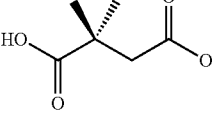 | 2 | 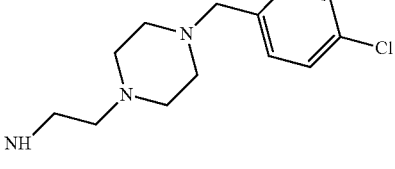 |
| 22 | 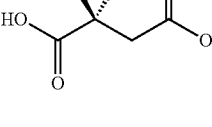 | 2 | 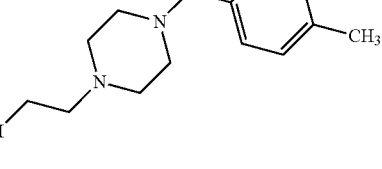 |
| 23 | 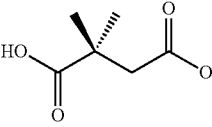 | 2 | 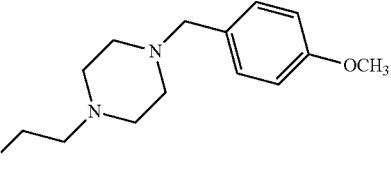 |

TABLE 1-continued

| Entry | R₁O | n | NR₂R₃ |
|---|---|---|---|
| 24 | (2S)-2-methyl-2-hydroxy succinate ester | 2 | 4-(4-hydroxybenzyl)piperazin-1-yl ethylamine |
| 25 | (2S)-2-methyl-2-hydroxy succinate ester | 2 | 4-(4-acetamidobenzyl)piperazin-1-yl ethylamine (NHCOCH₃) |
| 26 | (2S)-2-methyl-2-hydroxy succinate ester | 2 | 4-(4-methanesulfonamidobenzyl)piperazin-1-yl ethylamine (NHSO₂CH₃) |
| 27 | (2S)-2-methyl-2-hydroxy succinate ester | 2 | 4-(4-methanesulfonylbenzyl)piperazin-1-yl ethylamine (SO₂CH₃) |
| 28 | (2S)-2-methyl-2-hydroxy succinate ester | 2 | 4-(4-dimethylaminobenzyl)piperazin-1-yl ethylamine (N(CH₃)₂) |
| 29 | (2S)-2-methyl-2-hydroxy succinate ester | 2 | 4-(4-cyanobenzyl)piperazin-1-yl ethylamine (CN) |
| 30 | (2S)-2-methyl-2-hydroxy succinate ester | 2 | 4-(4-trifluoromethylbenzyl)piperazin-1-yl ethylamine (CF₃) |
| 31 | (2S)-2-methyl-2-hydroxy succinate ester | 2 | 4-(2-fluoro-4-chlorobenzyl)piperazin-1-yl ethylamine |

TABLE 1-continued

| Entry | R₁O | n | NR₂R₃ |
|---|---|---|---|
| 32 | (S)-2-methyl-2-carboxy-succinate | 2 | 4-(2,4-dichlorobenzyl)piperazin-1-yl ethylamine |
| 33 | (S)-2-methyl-2-carboxy-succinate | 2 | 4-(quinolin-4-ylmethyl)piperazin-1-yl ethylamine |
| 34 | (S)-2-methyl-2-carboxy-succinate | 2 | 4-(quinolin-8-ylmethyl)piperazin-1-yl ethylamine |
| 35 | (S)-2-methyl-2-carboxy-succinate | 2 | 4-(naphthalen-2-ylmethyl)piperazin-1-yl ethylamine |
| 36 | (S)-2-methyl-2-carboxy-succinate | 2 | 4-benzoylpiperazin-1-yl ethylamine |
| 37 | (S)-2-methyl-2-carboxy-succinate | 2 | 4-(4-methylbenzoyl)piperazin-1-yl ethylamine |
| 38 | (S)-2-methyl-2-carboxy-succinate | 2 | 4-(4-chlorobenzoyl)piperazin-1-yl ethylamine |

TABLE 1-continued

| Entry | R₁O | n | NR₂R₃ |
|---|---|---|---|
| 39 | (S)-3-methyl-3-carboxy-glutarate half-ester | 2 | 4-(4-fluorobenzoyl)piperazin-1-yl ethylamine |
| 40 | (S)-3-methyl-3-carboxy-glutarate half-ester | 2 | 4-(4-methoxybenzoyl)piperazin-1-yl ethylamine |
| 41 | (S)-3-methyl-3-carboxy-glutarate half-ester | 2 | 4-(4-dimethylaminobenzoyl)piperazin-1-yl ethylamine |
| 42 | (S)-3-methyl-3-carboxy-glutarate half-ester | 2 | 4-(4-cyanobenzoyl)piperazin-1-yl ethylamine |
| 43 | (S)-3-methyl-3-carboxy-glutarate half-ester | 2 | 4-(3-chlorobenzoyl)piperazin-1-yl ethylamine |
| 44 | (S)-3-methyl-3-carboxy-glutarate half-ester | 2 | 4-(2-chlorobenzoyl)piperazin-1-yl ethylamine |
| 45 | (S)-3-methyl-3-carboxy-glutarate half-ester | 2 | 4-(quinoline-8-carbonyl)piperazin-1-yl ethylamine |

TABLE 1-continued
| Entry | R₁O | n | NR₂R₃ |
|---|---|---|---|
| 46 | 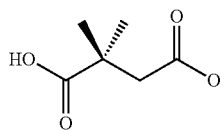 | 2 | 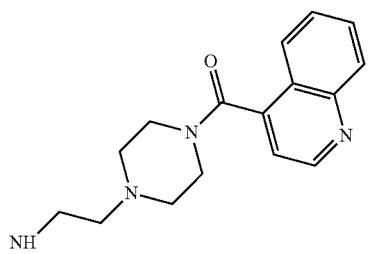 |
| 47 | 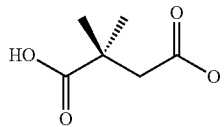 | 2 | 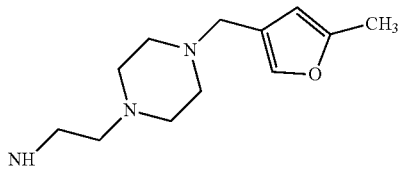 |
| 48 | 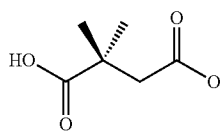 | 2 | 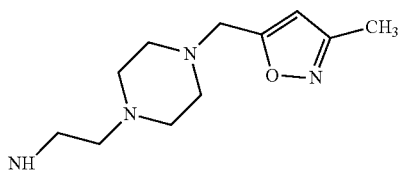 |
| 49 | 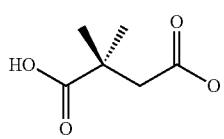 | 2 | 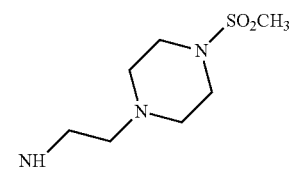 |
| 50 | 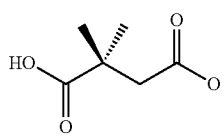 | 2 | 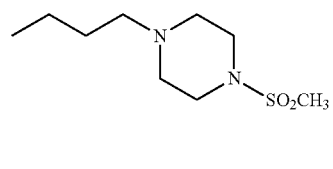 |
| 51 | 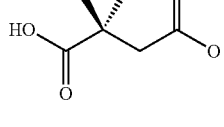 | 2 | 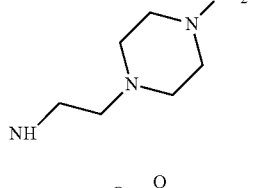 |
| 52 | 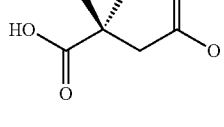 | 2 | 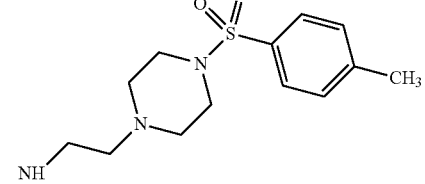 |
| 53 | 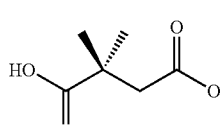 | 2 | 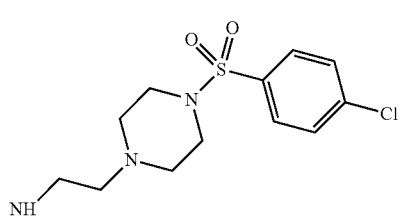 |

TABLE 1-continued

| Entry | R₁O | n | NR₂R₃ |
|---|---|---|---|
| 54 | | 2 | |
| 55 | | 2 | |
| 56 | | 2 | |
| 57 | | 2 | |
| 58 | | 2 | |
| 59 | | 2 | |
| 60 | | 2 | |
| 61 | | 2 | |

TABLE 1-continued

| Entry | R₁O | n | NR₂R₃ |
|---|---|---|---|
| 62 | (3-carboxy-3-methylbutanoate, HO-C(=O)-C(CH₃)(CH₃)-CH₂-C(=O)-O-) | 2 | 4-(2-aminoethyl)piperazine-1-carboxamide N,N-dimethyl (CON(CH₃)₂) |
| 63 | (same) | 2 | piperazine N-COCH₂OCH₃, 4-(2-aminoethyl)- |
| 64 | (same) | 2 | piperazine N-COCH₂OH, 4-(2-aminoethyl)- |
| 65 | (same) | 2 | piperazine N-COCH₂N(CH₃)₂, 4-(2-aminoethyl)- |
| 66 | (same) | 2 | piperazine N-CH₂CN, 4-(2-aminoethyl)- |
| 67 | (same) | 2 | piperazine N-CH₂CO₂Et, 4-(2-aminoethyl)- |
| 68 | (same) | 2 | piperazine N-CH₂CON(CH₃)₂, 4-(2-aminoethyl)- |
| 69 | (same) | 2 | piperazine N-CH₂-cyclopropyl, 4-(2-aminoethyl)- |
| 70 | (same) | 2 | piperazine N-CH₂-cyclohexyl, 4-(2-aminoethyl)- |

TABLE 1-continued

| Entry | R₁O | n | NR₂R₃ |
|---|---|---|---|
| 71 | (2-methyl-2-carboxy-succinate) | 2 | 4-(cyclopropyl)piperazin-1-yl ethylamine |
| 72 | (2-methyl-2-carboxy-succinate) | 2 | 4-phenylpiperazin-1-yl ethylamine |
| 73 | (2-methyl-2-carboxy-succinate) | 2 | 4-(pyridin-4-yl)piperazin-1-yl ethylamine |
| 74 | (2-methyl-2-carboxy-succinate) | 2 | 4-(pyridin-2-yl)piperazin-1-yl ethylamine |
| 75 | (2-methyl-2-carboxy-succinate) | 2 | 4-(cyclohexylmethyl)piperazin-1-yl ethylamine |
| 76 | (2-methyl-2-carboxy-succinate) | 2 | 4-(2-hydroxyethyl)piperazin-1-yl ethylamine |
| 77 | (3-methyl-3-carboxy-glutarate) | 2 | 4-(2-hydroxyethyl)piperazin-1-yl propylamine |
| 78 | (2-methyl-2-carboxy-succinate) | 2 | 4-(2-methoxyethyl)piperazin-1-yl ethylamine |

TABLE 1-continued

| Entry | R₁O | n | NR₂R₃ |
|---|---|---|---|
| 79 | | 2 | |
| 80 | | 2 | |
| 82 | | 2 | |
| 83 | | 2 | |
| 84 | | 2 | |
| 85 | | 2 | |
| 86 | | 2 | |
| 87 | | 2 | |

TABLE 1-continued

| Entry | R₁O | n | NR₂R₃ |
|---|---|---|---|
| 88 | (2-methyl-2-carboxylate succinate) | 2 | 4-(2-aminoethyl)piperazine-1-sulfonyl N(CH₃)₂ |
| 89 | (2-methyl-2-carboxylate succinate) | 2 | 4-(2-aminoethyl)piperazin-1-yl-CH₂-CO₂H |
| 90 | (2-methyl-2-carboxylate succinate) | 2 | 4-(2-aminoethyl)piperazin-1-yl-CH₂CH₂-NHCOCH₃ |
| 91 | (2-methyl-2-carboxylate succinate) | 2 | 4-(2-aminoethyl)piperazin-1-yl-CH₂CH₂-NHSO₂CH₃ |
| 92 | (2-methyl-2-carboxylate succinate) | 2 | 4-(2-aminoethyl)piperazin-1-yl-SO₂-(4-pyridyl) |
| 93 | (2-methyl-2-carboxylate succinate) | 2 | 4-(2-aminoethyl)piperazin-1-yl-SO₂-morpholine |
| 94 | (2-methyl-2-carboxylate succinate) | 2 | 4-(2-aminoethyl)piperazin-1-yl-SO₂-CH₂-N(CH₃)₂ |
| 95 | (2-methyl-2-carboxylate succinate) | 1 | 4-(2-aminoethyl)-1-benzylpiperazine |

TABLE 1-continued

| Entry | R₁O | n | NR₂R₃ |
|---|---|---|---|
| 96 | (2-methyl-2-carboxy-succinate, R config) | 3 | 4-benzylpiperazin-1-yl-ethylamine |
| 97 | (2-methyl-2-carboxy-succinate) | 2 | 4-benzylpiperazin-1-yl-butyl |
| 98 | (2-methyl-2-carboxy-succinate) | 1 | 4-(methylsulfonyl)piperazin-1-yl-ethylamine |
| 99 | (2-methyl-2-carboxy-succinate) | 3 | 4-(methylsulfonyl)piperazin-1-yl-ethylamine |
| 100 | (2-methyl-2-carboxy-succinate) | 2 | 4-(methylsulfonyl)piperazin-1-yl-propylamine |
| 101 | (2-methyl-2-carboxy-succinate) | 2 | 4-benzylpiperidin-1-yl-ethylamine |
| 102 | (2-methyl-2-carboxy-succinate) | 2 | 1-benzylpiperidin-4-yl-ethylamine |
| 103 | (2-methyl-2-carboxy-succinate) | 1 | 4-(methylsulfonyl)piperidin-1-yl-ethylamine |
| 104 | (2-methyl-2-carboxy-succinate) | 2 | 4-(methylsulfonyl)piperidin-1-yl-ethylamine |

TABLE 1-continued

| Entry | R₁O | n | NR₂R₃ |
|---|---|---|---|
| 105 | (2-methyl-2-carboxy-succinate) | 1 | 4-(2-aminoethyl)-1-(methylsulfonyl)piperidine |
| 106 | (2-methyl-2-carboxy-succinate) | 2 | 4-(2-aminoethyl)-1-(methylsulfonyl)piperidine |
| 107 | (2-methyl-2-carboxy-succinate) | 1 | 1-(2-aminoethyl)-4-hydroxypiperidine |
| 108 | (2-methyl-2-carboxy-succinate) | 2 | 1-(2-aminoethyl)-4-hydroxypiperidine |
| 109 | (2-methyl-2-carboxy-succinate) | 1 | 1-benzyl-4-aminopiperidine |
| 110 | (2-methyl-2-carboxy-succinate) | 2 | 1-benzyl-4-aminopiperidine |
| 111 | (2-methyl-2-carboxy-succinate) | 1 | 1-(4-fluorobenzyl)-4-aminopiperidine |
| 112 | (2-methyl-2-carboxy-succinate) | 2 | 1-(4-fluorobenzyl)-4-aminopiperidine |
| 113 | (2-methyl-2-carboxy-succinate) | 2 | 1-(4-chlorobenzyl)-4-aminopiperidine |

TABLE 1-continued

| Entry | R₁O | n | NR₂R₃ |
|---|---|---|---|
| 114 | (2-methyl-2-carboxy-succinate ester) | 2 | 4-(4-methylbenzyl)piperidin-4-ylamine |
| 115 | (2-methyl-2-carboxy-succinate ester) | 2 | 4-(4-trifluoromethylbenzyl)piperidin-4-ylamine |
| 116 | (2-methyl-2-carboxy-succinate ester) | 2 | 4-(4-cyanobenzyl)piperidin-4-ylamine |
| 117 | (2-methyl-2-carboxy-succinate ester) | 2 | 4-(4-methoxybenzyl)piperidin-4-ylamine |
| 118 | (2-methyl-2-carboxy-succinate ester) | 2 | 4-(4-acetamidobenzyl)piperidin-4-ylamine |
| 119 | (2-methyl-2-carboxy-succinate ester) | 2 | 4-(4-methanesulfonamidobenzyl)piperidin-4-ylamine |
| 120 | (2-methyl-2-carboxy-succinate ester) | 2 | 4-(4-(2-hydroxyethoxy)benzyl)piperidin-4-ylamine |
| 121 | (2-methyl-2-carboxy-succinate ester) | 2 | 4-(4-(2-methoxyethoxy)benzyl)piperidin-4-ylamine |
| 122 | (2-methyl-2-carboxy-succinate ester) | 2 | 4-(4-hydroxybenzyl)piperidin-4-ylamine |

TABLE 1-continued

| Entry | R₁O | n | NR₂R₃ |
|---|---|---|---|
| 123 | (2-methyl-2-carboxy-succinate ester) | 2 | 1-(4-(methylsulfonyl)benzyl)piperidin-4-ylamine |
| 124 | (2-methyl-2-carboxy-succinate ester) | 2 | 1-(3-fluorobenzyl)piperidin-4-ylamine |
| 125 | (2-methyl-2-carboxy-succinate ester) | 2 | 1-(2-fluorobenzyl)piperidin-4-ylamine |
| 126 | (2-methyl-2-carboxy-succinate ester) | 2 | 1-(2-fluoro-4-methylbenzyl)piperidin-4-ylamine |
| 127 | (2-methyl-2-carboxy-succinate ester) | 2 | 1-(3-chloro-4-methylbenzyl)piperidin-4-ylamine |
| 128 | (2-methyl-2-carboxy-succinate ester) | 2 | 1-(2,3-difluorobenzyl)piperidin-4-ylamine |
| 129 | (2-methyl-2-carboxy-succinate ester) | 2 | 1-(4-morpholinobenzyl)piperidin-4-ylamine |
| 130 | (2-methyl-2-carboxy-succinate ester) | 2 | 1-(4-(dimethylamino)benzyl)piperidin-4-ylamine |

TABLE 1-continued

| Entry | R₁O | n | NR₂R₃ |
|---|---|---|---|
| 131 | (S)-HOOC-C(CH₃)₂-CH₂-C(=O)O- | 2 | 4-amino-1-(4-nitrobenzyl)piperidine |
| 132 | (S)-HOOC-C(CH₃)₂-CH₂-C(=O)O- | 2 | 4-amino-1-[4-(N,N-dimethylsulfamoyl)benzyl]piperidine |
| 133 | (S)-HOOC-C(CH₃)₂-CH₂-C(=O)O- | 2 | (R)-4-amino-2-benzylpiperidine |
| 134 | (S)-HOOC-C(CH₃)₂-CH₂-C(=O)O- | 2 | (S)-4-amino-2-benzylpiperidine |
| 135 | (S)-HOOC-C(CH₃)₂-CH₂-C(=O)O- | 2 | (R)-3-amino-1-methanesulfonylpiperidine |
| 136 | (S)-HOOC-C(CH₃)₂-CH₂-C(=O)O- | 2 | (S)-3-amino-1-methanesulfonylpiperidine |
| 137 | (S)-HOOC-C(CH₃)₂-CH₂-C(=O)O- | 2 | 4-amino-1-methanesulfonylpiperidine |
| 138 | (S)-HOOC-C(CH₃)₂-CH₂-C(=O)O- | 2 | 4-amino-1-(ethoxycarbonylmethyl)piperidine |
| 139 | (S)-HOOC-C(CH₃)₂-CH₂-C(=O)O- | 2 | 4-amino-1-[2-(N,N-dimethylamino)ethyl]piperidine |
| 140 | (S)-HOOC-C(CH₃)₂-CH₂-C(=O)O- | 2 | 4-amino-1-acetylpiperidine |

TABLE 1-continued
| Entry | R₁O | n | NR₂R₃ |
|---|---|---|---|
| 141 | 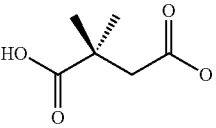 | 2 | 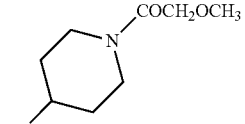 |
| 142 | 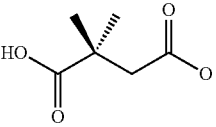 | 2 | 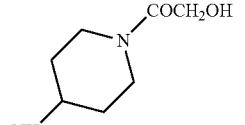 |
| 143 | 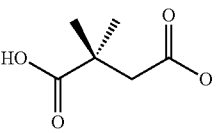 | 2 | 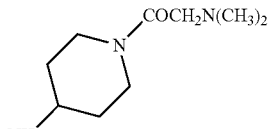 |
| 144 | 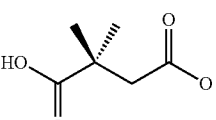 | 2 | 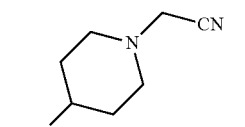 |
| 145 | 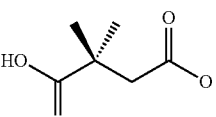 | 2 | 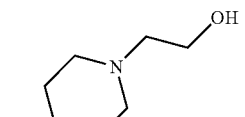 |
| 146 | 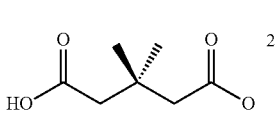 | 2 | 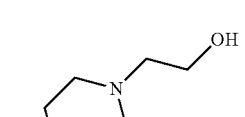 |
| 147 | 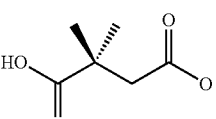 | 2 | 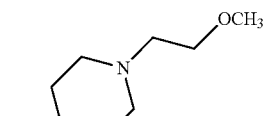 |
| 148 | 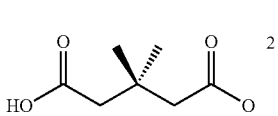 | 2 | 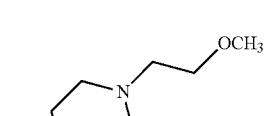 |
| 149 | 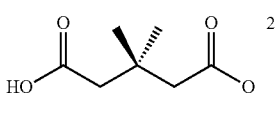 | 2 | 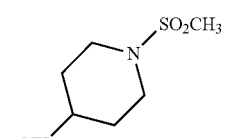 |

TABLE 1-continued
| Entry | R₁O | n | NR₂R₃ |
|---|---|---|---|
| 150 | 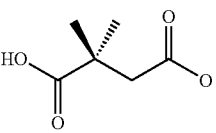 | 1 | 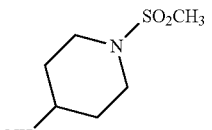 |
| 151 | 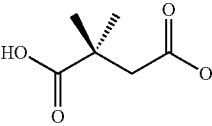 | 3 | 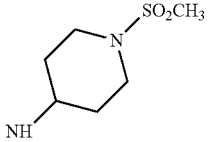 |
| 152 | 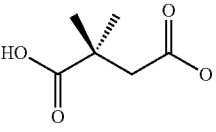 | 2 | 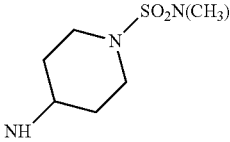 |
| 153 | 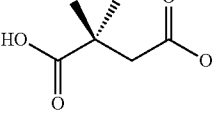 | 2 | 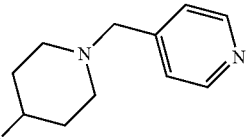 |
| 154 | 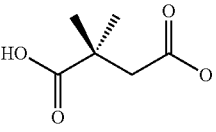 | 2 | 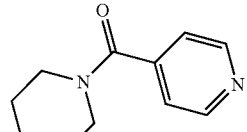 |
| 155 | 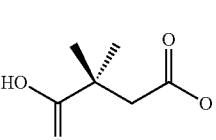 | 2 | 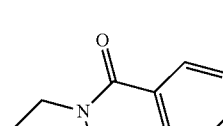 |
| 156 | 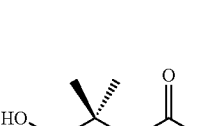 | 2 | 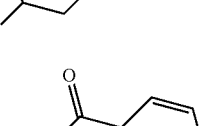 |
| 157 | 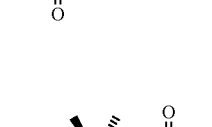 | 2 | 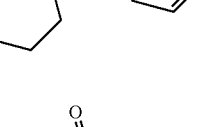 |
| 158 | 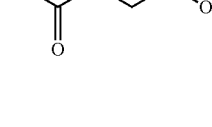 | 2 | 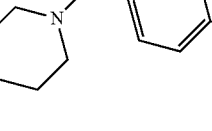 |

TABLE 1-continued
| Entry | R₁O | n | NR₂R₃ |
|---|---|---|---|
| 159 | 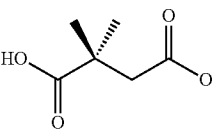 | 2 | 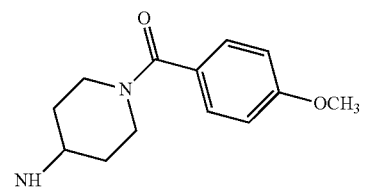 |
| 160 | 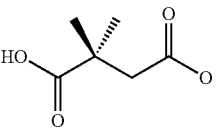 | 2 | 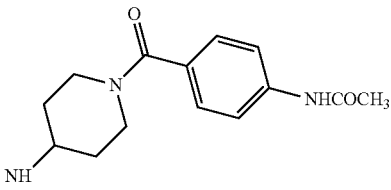 |
| 161 | 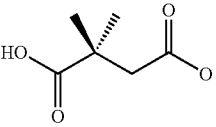 | 2 | 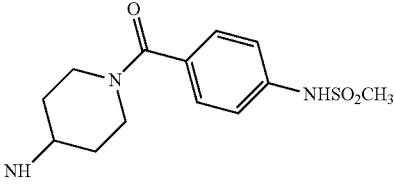 |
| 162 | 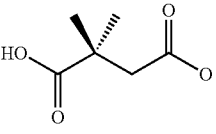 | 2 | 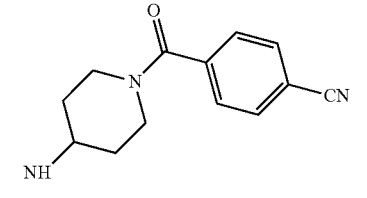 |
| 163 | 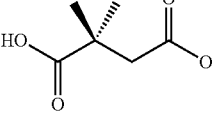 | 2 | 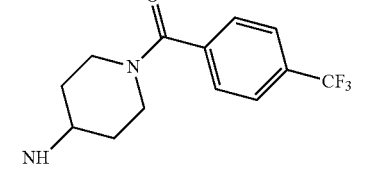 |
| 164 | 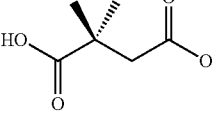 | 2 | 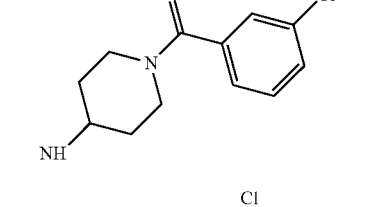 |
| 165 | 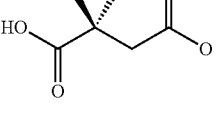 | 2 | 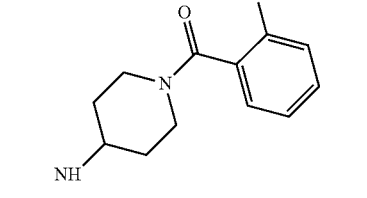 |
| 166 | 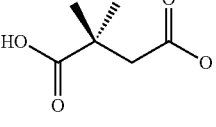 | 2 | 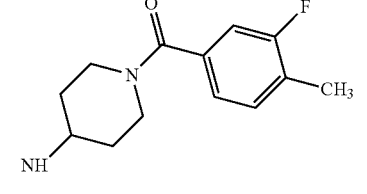 |

TABLE 1-continued

| Entry | R₁O | n | NR₂R₃ |
|---|---|---|---|
| 167 | (2-methylsuccinate, HO-C(=O)-C(CH₃)(wedge)-CH₂-C(=O)-O-) | 2 | 1-(2-fluoro-4-methylbenzoyl)-4-aminopiperidine |
| 168 | (2-methylsuccinate) | 1 | 8-(methylsulfonyl)-8-azabicyclo[3.2.1]octan-3-amine |
| 169 | (2-methylsuccinate) | 2 | 8-(methylsulfonyl)-8-azabicyclo[3.2.1]octan-3-amine |
| 170 | (2-methylsuccinate) | 1 | 8-(methylsulfonyl)-8-azabicyclo[3.2.1]octan-3-amine (other stereo) |
| 171 | (2-methylsuccinate) | 2 | 8-(methylsulfonyl)-8-azabicyclo[3.2.1]octan-3-amine (other stereo) |
| 172 | (2-methylsuccinate) | 2 | 2-(tetrahydro-2H-pyran-4-yl)ethan-1-amine |
| 173 | (2-methylsuccinate) | 2 | 2-morpholinoethan-1-amine |
| 174 | (3-methylglutarate) | 2 | 3-morpholinopropan-1-amine |
| 175 | (2-methylsuccinate) | 1 | 2-(thiomorpholine-S-oxide-4-yl)ethan-1-amine |

TABLE 1-continued

| Entry | R₁O | n | NR₂R₃ |
|---|---|---|---|
| 176 | (2-methyl-2-carboxy-succinate) | 2 | 2-(thiomorpholine-S-oxide-4-yl)ethylamine |
| 177 | (2-methyl-2-carboxy-succinate) | 1 | 2-(thiomorpholine-1,1-dioxide-4-yl)ethylamine |
| 178 | (2-methyl-2-carboxy-succinate) | 2 | 2-(thiomorpholine-1,1-dioxide-4-yl)ethylamine |
| 179 | (2-methyl-2-carboxy-succinate) | 3 | 2-(thiomorpholine-1,1-dioxide-4-yl)ethylamine |
| 180 | (3-methyl-3-carboxy-glutarate) | 2 | 3-(2-oxopyrrolidin-1-yl)propylamine |
| 181 | (2-methyl-2-carboxy-succinate) | 2 | 2-[(2S)-2-(methoxycarbonyl)pyrrolidin-1-yl]ethylamine |
| 182 | (2-methyl-2-carboxy-succinate) | 2 | 2-[(2R)-2-(methoxycarbonyl)pyrrolidin-1-yl]ethylamine |
| 183 | (2-methyl-2-carboxy-succinate) | 2 | 2-[(2S)-2-(hydroxymethyl)pyrrolidin-1-yl]ethylamine |
| 184 | (2-methyl-2-carboxy-succinate) | 2 | 2-[(2R)-2-(hydroxymethyl)pyrrolidin-1-yl]ethylamine |
| 185 | (2-methyl-2-carboxy-succinate) | 1 | 2-[2-(methanesulfonamidomethyl)pyrrolidin-1-yl]ethylamine |

TABLE 1-continued

| Entry | R₁O | n | NR₂R₃ |
|---|---|---|---|
| 186 | | 2 | |
| 187 | | 1 | |
| 188 | | 2 | |
| 189 | | 1 | |
| 190 | | 2 | |
| 191 | | 1 | |
| 192 | | 2 | |
| 193 | | 1 | |
| 194 | | 2 | |
| 195 | | 1 | |
| 196 | | 2 | |

TABLE 1-continued

| Entry | R₁O | n | NR₂R₃ |
|---|---|---|---|
| 197 | | 2 | tetrahydropyran-4-yl-NH— |
| 198 | | 2 | 1,1-dioxo-tetrahydrothiopyran-4-yl-NH— |
| 199 | | 2 | —NH—CH₂CH₂—N(Et)(CH₂CN) |
| 200 | | 2 | —NH—CH₂CH₂—N(Et)(CH₂CO₂Et) |
| 201 | | 2 | —NH—CH₂CH₂—N(Et)(CH₂SO₂CH₃) |
| 202 | | 2 | —NH—CH₂CH₂—N(Et)(CH₂CON(CH₃)₂) |
| 203 | | 2 | —NH—CH₂CH₂—N(Et)(CH₂CH₂OH) |
| 204 | | 2 | —NH—CH₂CH₂—N(Et)(CH₂CH₂OCH₃) |
| 205 | | 1 | —NH—CH₂CH₂—N(Et)(CH₂SO₂CH₃) |
| 206 | | 3 | —NH—CH₂CH₂—N(Et)(CH₂SO₂CH₃) |
| 207 | | 2 | —NH—CH₂CH₂—N(Et)(CH₂SO₂CH₃) |

TABLE 1-continued
| Entry | R₁O | n | NR₂R₃ |
|---|---|---|---|
| 208 | 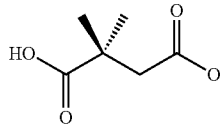 | 2 | 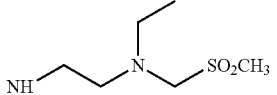 |
| 209 | 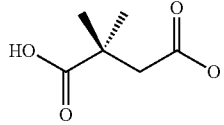 | 2 | 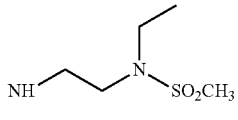 |
| 210 | 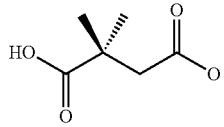 | 2 | 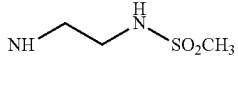 |
| 211 | 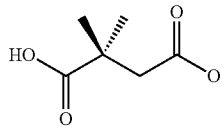 | 1 | 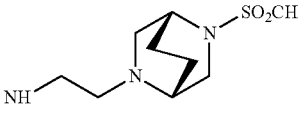 |
| 212 | 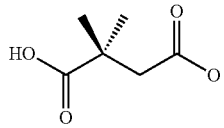 | 2 | 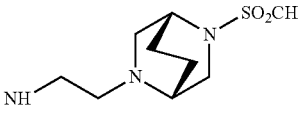 |
| 213 | 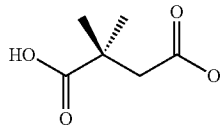 | 1 | 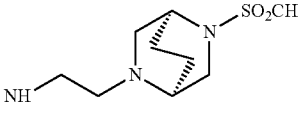 |
| 214 | 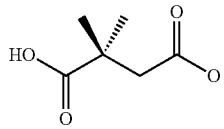 | 2 | 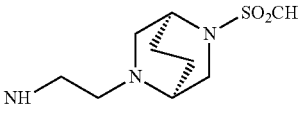 |
| 215 | 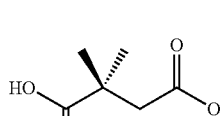 | 2 | 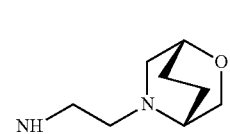 |
| 216 |  | 2 |  |

In some embodiments, the compounds of the present invention are selected from the group consisting of those found in Formula VI as described in Table 2.

In some embodiments, the compounds of the invention are selected from the group consisting of those found in Formula I, wherein $R_6$ is 1-methyl-1-cyclopropyl, and as described in Table 3.

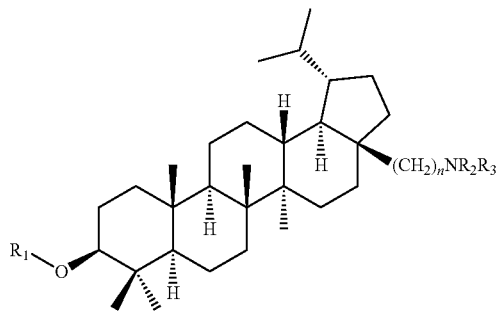

Formula VI

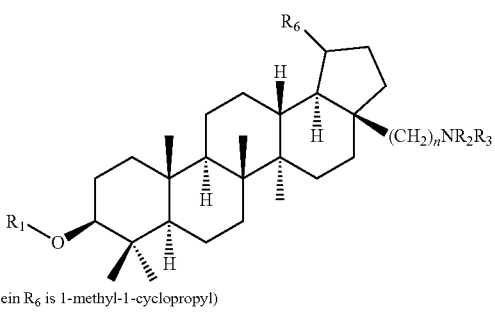

Formula I (wherein $R_6$ is 1-methyl-1-cyclopropyl)

TABLE 2

| Entry | $R_1O$ | n | $NR_2R_3$ |
|---|---|---|---|
| 217 | -C(CH3)-CH2-C(=O)-O-) | 2 | N-CH2-Ph) |
| 218 | -CH2-C(CH3)-CH2-C(=O)-O-) | 2 | N-CH2-Ph) |
| 219 | -C(CH3)-CH2-C(=O)-O-) | 1 | N-SO2CH3) |
| 220 | -C(CH3)-CH2-C(=O)-O-) | 3 | N-SO2CH3) |
| 221 | -C(CH3)-CH2-C(=O)-O-) | 2 | N-SO2CH3) |
| 222 | -C(CH3)-CH2-C(=O)-O-) | 2 | -CH2-SO2CH3) |

TABLE 3

| Entry | R₁O | n | NR₂R₃ |
|---|---|---|---|
| 223 | (S)-3-methyl-3-carboxy succinate | 2 | 4-benzylpiperazinyl ethylamine |
| 224 | 3-methyl-3-carboxy glutarate | 2 | 4-benzylpiperazinyl ethylamine |
| 225 | (S)-2-methyl-succinate with carboxyl | 2 | 4-benzylpiperazinyl ethylamine |
| 226 | (R)-2-methyl succinate | 2 | 4-benzylpiperazinyl ethylamine |
| 227 | (S)-3-methyl-3-carboxy succinate | 2 | 4-(naphthalen-1-ylmethyl)piperazinyl ethylamine |
| 228 | (S)-3-methyl-3-carboxy succinate | 2 | 4-(naphthalen-2-ylmethyl)piperazinyl ethylamine |
| 229 | (S)-3-methyl-3-carboxy succinate | 2 | 4-(pyridin-2-ylmethyl)piperazinyl ethylamine |
| 230 | (S)-3-methyl-3-carboxy succinate | 2 | 4-(pyridin-3-ylmethyl)piperazinyl ethylamine |
| 231 | (S)-3-methyl-3-carboxy succinate | 2 | 4-(pyridin-4-ylmethyl)piperazinyl ethylamine |
| 232 | (S)-3-methyl-3-carboxy succinate | 2 | 4-benzyl-3-oxopiperazinyl ethylamine |

TABLE 3-continued

| Entry | R₁O | n | NR₂R₃ |
|---|---|---|---|
| 233 | (S)-2-methyl-2-hydroxy-succinate | 2 | glycyl-4-benzylpiperazine |
| 234 | (S)-2-methyl-2-hydroxy-succinate | 2 | 1-(2-aminoethyl)-4-benzoylpiperazine |
| 235 | (S)-2-methyl-2-hydroxy-succinate | 2 | 2-(4-benzylpiperazin-1-yl)acetamide |
| 236 | (S)-2-methyl-2-hydroxy-succinate | 2 | 1-(2-aminoethyl)-4-(2-fluorobenzyl)piperazine |
| 237 | (S)-2-methyl-2-hydroxy-succinate | 2 | 1-(2-aminoethyl)-4-(2-chlorobenzyl)piperazine |
| 238 | (S)-2-methyl-2-hydroxy-succinate | 2 | 1-(2-aminoethyl)-4-(2-methylbenzyl)piperazine |
| 239 | (S)-2-methyl-2-hydroxy-succinate | 2 | 1-(2-aminoethyl)-4-(3-fluorobenzyl)piperazine |
| 240 | (S)-2-methyl-2-hydroxy-succinate | 2 | 1-(2-aminoethyl)-4-(3-chlorobenzyl)piperazine |
| 241 | (S)-2-methyl-2-hydroxy-succinate | 2 | 1-(2-aminoethyl)-4-(3-methylbenzyl)piperazine |

TABLE 3-continued

| Entry | R₁O | n | NR₂R₃ |
|---|---|---|---|
| 242 | (2-methyl-succinate, HO-C(=O)-C(CH₃)-CH₂-C(=O)-O-) | 2 | NH-CH₂CH₂-piperazine-CH₂-C₆H₄-4-F |
| 243 | (same) | 2 | NH-CH₂CH₂-piperazine-CH₂-C₆H₄-4-Cl |
| 244 | (same) | 2 | NH-CH₂CH₂-piperazine-CH₂-C₆H₄-4-CH₃ |
| 245 | (same) | 2 | NH-CH₂CH₂-piperazine-CH₂-C₆H₄-4-OCH₃ |
| 246 | (same) | 2 | NH-CH₂CH₂-piperazine-CH₂-C₆H₄-4-OH |
| 247 | (same) | 2 | NH-CH₂CH₂-piperazine-CH₂-C₆H₄-4-NHCOCH₃ |
| 248 | (same) | 2 | NH-CH₂CH₂-piperazine-CH₂-C₆H₄-4-NHSO₂CH₃ |
| 249 | (same) | 2 | NH-CH₂CH₂-piperazine-CH₂-C₆H₄-4-SO₂CH₃ |
| 250 | (same) | 2 | NH-CH₂CH₂-piperazine-CH₂-C₆H₄-4-N(CH₃)₂ |
| 251 | (same) | 2 | NH-CH₂CH₂-piperazine-CH₂-C₆H₄-4-CN |

TABLE 3-continued
| Entry | R₁O | n | NR₂R₃ |
|---|---|---|---|
| 252 | 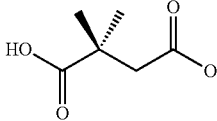 | 2 | 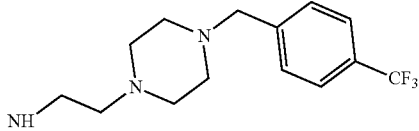 |
| 253 | 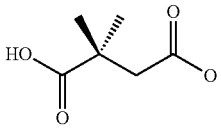 | 2 | 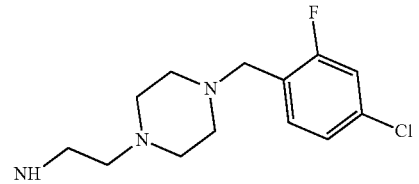 |
| 254 | 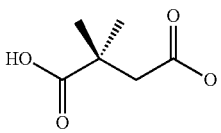 | 2 | 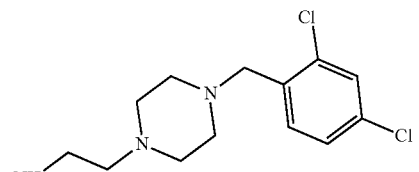 |
| 255 | 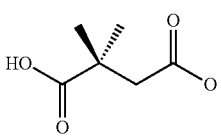 | 2 | 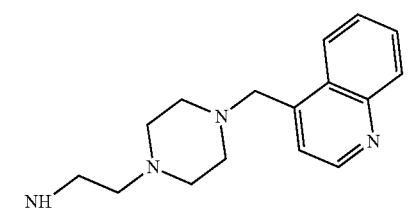 |
| 256 | 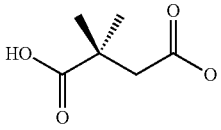 | 2 | 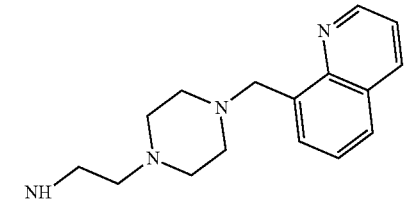 |
| 257 | 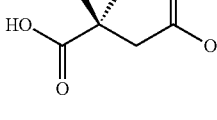 | 2 | 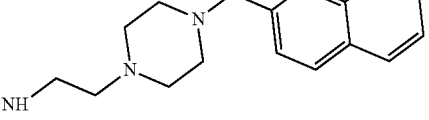 |
| 258 | 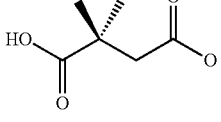 | 2 | 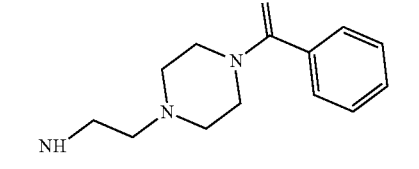 |
| 259 | 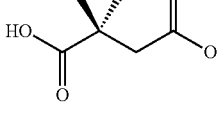 | 2 | 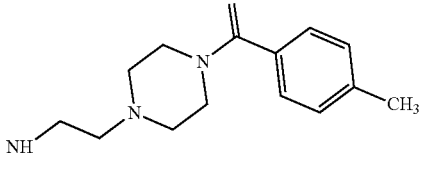 |

TABLE 3-continued

| Entry | R₁O | n | NR₂R₃ |
|---|---|---|---|
| 260 | (methyl-substituted succinate half-ester, HO-C(=O)-C(CH₃)-CH₂-C(=O)-O-) | 2 | piperazine-N-CH₂CH₂-NH, other N acylated with 4-chlorobenzoyl |
| 261 | (same R₁O) | 2 | piperazine-N-CH₂CH₂-NH, other N acylated with 4-fluorobenzoyl |
| 262 | (same R₁O) | 2 | piperazine-N-CH₂CH₂-NH, other N acylated with 4-methoxybenzoyl (OCH₃) |
| 263 | (same R₁O) | 2 | piperazine-N-CH₂CH₂-NH, other N acylated with 4-(dimethylamino)benzoyl, N(CH₃)₂ |
| 264 | (same R₁O) | 2 | piperazine-N-CH₂CH₂-NH, other N acylated with 4-cyanobenzoyl (CN) |
| 265 | (same R₁O) | 2 | piperazine-N-CH₂CH₂-NH, other N acylated with 3-chlorobenzoyl |
| 266 | (same R₁O) | 2 | piperazine-N-CH₂CH₂-NH, other N acylated with 2-chlorobenzoyl |
| 267 | (same R₁O) | 2 | piperazine-N-CH₂CH₂-NH, other N acylated with quinoline-8-carbonyl |

TABLE 3-continued

| Entry | R₁O | n | NR₂R₃ |
|---|---|---|---|
| 268 | (S)-2-methyl-2-carboxysuccinate | 2 | 4-(quinoline-4-carbonyl)piperazin-1-yl ethylamine |
| 269 | (S)-2-methyl-2-carboxysuccinate | 2 | 4-((5-methylisoxazol-3-yl)methyl)piperazin-1-yl ethylamine |
| 270 | (S)-2-methyl-2-carboxysuccinate | 2 | 4-((3-methylisoxazol-5-yl)methyl)piperazin-1-yl ethylamine |
| 271 | (S)-2-methyl-2-carboxysuccinate | 2 | 4-(methylsulfonyl)piperazin-1-yl ethylamine |
| 272 | 3-methyl-3-carboxyglutarate | 2 | 4-(methylsulfonyl)piperazin-1-yl propylamine |
| 273 | (S)-2-methyl-2-carboxysuccinate | 2 | 4-(phenylsulfonyl)piperazin-1-yl ethylamine |
| 274 | (S)-2-methyl-2-carboxysuccinate | 2 | 4-(p-tolylsulfonyl)piperazin-1-yl ethylamine |
| 275 | (S)-2-methyl-2-carboxysuccinate | 2 | 4-((4-chlorophenyl)sulfonyl)piperazin-1-yl ethylamine |
| 276 | (S)-2-methyl-2-carboxysuccinate | 2 | 4-((4-methoxyphenyl)sulfonyl)piperazin-1-yl ethylamine |

TABLE 3-continued

| Entry | R₁O | n | NR₂R₃ |
|---|---|---|---|
| 277 | (S)-2-methyl-2-methylsuccinate | 2 | 4-(2-aminoethyl)piperazin-1-yl 4-acetamidophenyl sulfone |
| 278 | (S)-2-methyl-2-methylsuccinate | 2 | 4-(2-aminoethyl)piperazin-1-yl 4-(trifluoromethyl)phenyl sulfone |
| 279 | (S)-2-methyl-2-methylsuccinate | 2 | 1-(4-benzylpiperazin-1-yl)-2-methylpropan-2-amine |
| 280 | (S)-2-methyl-2-methylsuccinate | 2 | (S)-1-(4-benzylpiperazin-1-yl)propan-2-amine |
| 281 | (S)-2-methyl-2-methylsuccinate | 2 | (R)-1-(4-benzylpiperazin-1-yl)propan-2-amine |
| 282 | (S)-2-methyl-2-methylsuccinate | 2 | (S)-2-(4-benzylpiperazin-1-yl)-1-phenylethan-1-amine |
| 283 | (S)-2-methyl-2-methylsuccinate | 2 | (R)-2-(4-benzylpiperazin-1-yl)-1-phenylethan-1-amine |
| 284 | (S)-2-methyl-2-methylsuccinate | 2 | 4-(2-aminoethyl)-N,N-dimethylpiperazine-1-carboxamide |
| 285 | (S)-2-methyl-2-methylsuccinate | 2 | 1-(4-(2-aminoethyl)piperazin-1-yl)-2-methoxyethan-1-one |
| 286 | (S)-2-methyl-2-methylsuccinate | 2 | 1-(4-(2-aminoethyl)piperazin-1-yl)-2-hydroxyethan-1-one |

TABLE 3-continued

| Entry | R₁O | n | NR₂R₃ |
|---|---|---|---|
| 287 | (2S)-2-methyl-succinate monoester | 2 | 4-(COCH₂N(CH₃)₂)-piperazin-1-yl-ethylamine |
| 288 | (2S)-2-methyl-succinate monoester | 2 | 4-(CH₂CN)-piperazin-1-yl-ethylamine |
| 289 | (2S)-2-methyl-succinate monoester | 2 | 4-(CH₂CO₂Et)-piperazin-1-yl-ethylamine |
| 290 | (2S)-2-methyl-succinate monoester | 2 | 4-(CH₂CON(CH₃)₂)-piperazin-1-yl-ethylamine |
| 291 | (2S)-2-methyl-succinate monoester | 2 | 4-(cyclopropylmethyl)-piperazin-1-yl-ethylamine |
| 292 | (2S)-2-methyl-succinate monoester | 2 | 4-(cyclohexylmethyl)-piperazin-1-yl-ethylamine |
| 293 | (2S)-2-methyl-succinate monoester | 2 | 4-cyclopropyl-piperazin-1-yl-ethylamine |
| 294 | (2S)-2-methyl-succinate monoester | 2 | 4-phenyl-piperazin-1-yl-ethylamine |
| 295 | (2S)-2-methyl-succinate monoester | 2 | 4-(pyridin-4-yl)-piperazin-1-yl-ethylamine |

TABLE 3-continued

| Entry | R₁O | n | NR₂R₃ |
|---|---|---|---|
| 296 | | 2 | |
| 297 | | 2 | |
| 298 | | 2 | |
| 299 | | 2 | |
| 300 | | 2 | |
| 301 | | 2 | |
| 302 | | 2 | |
| 303 | | 2 | |
| 304 | | 2 | |
| 305 | | 2 | |

TABLE 3-continued

| Entry | R₁O | n | NR₂R₃ |
|---|---|---|---|
| 306 | | 2 | piperazine-N-C(O)-(4-pyridyl), N-CH₂CH₂NH- |
| 307 | | 2 | piperazine-N-C(O)-morpholine, N-CH₂CH₂NH- |
| 308 | | 2 | piperazine-N-SO₂CF₃, N-CH₂CH₂NH- |
| 309 | | 2 | piperazine-N-SO₂N(CH₃)₂, N-CH₂CH₂NH- |
| 310 | | 2 | piperazine-N-CH₂CO₂H, N-CH₂CH₂NH- |
| 311 | | 2 | piperazine-N-CH₂CH₂NHCOCH₃, N-CH₂CH₂NH- |
| 312 | | 2 | piperazine-N-CH₂CH₂NHSO₂CH₃, N-CH₂CH₂NH- |
| 313 | | 2 | piperazine-N-SO₂-(4-pyridyl), N-CH₂CH₂NH- |
| 314 | | 2 | piperazine-N-SO₂-morpholine, N-CH₂CH₂NH- |

TABLE 3-continued

| Entry | R₁O | n | NR₂R₃ |
|---|---|---|---|
| 315 | (2-methyl-2-carboxy-succinate) | 2 | piperazine-N-SO₂-CH₂-N(CH₃)₂ with NH-ethyl linker |
| 316 | (2-methyl-2-carboxy-succinate) | 1 | 4-benzylpiperazine with NH-ethyl linker |
| 317 | (2-methyl-2-carboxy-succinate) | 3 | 4-benzylpiperazine with NH-ethyl linker |
| 318 | (2-methyl-2-carboxy-succinate) | 2 | 4-benzylpiperazine with NH-propyl linker |
| 319 | (2-methyl-2-carboxy-succinate) | 1 | 4-(SO₂CH₃)piperazine with NH-ethyl linker |
| 320 | (2-methyl-2-carboxy-succinate) | 3 | 4-(SO₂CH₃)piperazine with NH-ethyl linker |
| 321 | (2-methyl-2-carboxy-succinate) | 2 | 4-(SO₂CH₃)piperazine with NH-propyl linker |
| 322 | (2-methyl-2-carboxy-succinate) | 2 | 4-benzylpiperidine with NH-ethyl linker |
| 323 | (2-methyl-2-carboxy-succinate) | 2 | 1-benzyl-4-piperidyl with NH-ethyl linker |
| 324 | (2-methyl-2-carboxy-succinate) | 2 | 4-(SO₂CH₃)piperidine with NH-ethyl linker |

TABLE 3-continued

| Entry | R₁O | n | NR₂R₃ |
|---|---|---|---|
| 325 | (2S)-2-methyl-succinate mono-acid | 1 | 2-(1-methanesulfonyl-piperidin-4-yl)-ethylamine |
| 326 | (2S)-2-methyl-succinate mono-acid | 2 | 2-(1-methanesulfonyl-piperidin-4-yl)-ethylamine |
| 327 | (2S)-2-methyl-succinate mono-acid | 2 | 2-(4-hydroxy-piperidin-1-yl)-ethylamine |
| 328 | (2S)-2-methyl-succinate mono-acid | 2 | 1-benzyl-piperidin-4-ylamine |
| 329 | (2S)-2-methyl-succinate mono-acid | 2 | 1-(4-fluorobenzyl)-piperidin-4-ylamine |
| 330 | (2S)-2-methyl-succinate mono-acid | 2 | 1-(4-chlorobenzyl)-piperidin-4-ylamine |
| 331 | (2S)-2-methyl-succinate mono-acid | 2 | 1-(4-methylbenzyl)-piperidin-4-ylamine |
| 332 | (2S)-2-methyl-succinate mono-acid | 2 | 1-(4-trifluoromethylbenzyl)-piperidin-4-ylamine |
| 333 | (2S)-2-methyl-succinate mono-acid | 2 | 1-(4-cyanobenzyl)-piperidin-4-ylamine |
| 334 | (2S)-2-methyl-succinate mono-acid | 2 | 1-(4-methoxybenzyl)-piperidin-4-ylamine |
| 335 | (2S)-2-methyl-succinate mono-acid | 2 | 1-(4-acetamidobenzyl)-piperidin-4-ylamine |

TABLE 3-continued

| Entry | R₁O | n | NR₂R₃ |
|---|---|---|---|
| 336 | (2-methyl-2-carboxy-succinate) | 2 | 1-(4-(NHSO₂CH₃)benzyl)-4-aminopiperidine |
| 337 | (2-methyl-2-carboxy-succinate) | 2 | 1-(4-(OCH₂CH₂OH)benzyl)-4-aminopiperidine |
| 338 | (2-methyl-2-carboxy-succinate) | 2 | 1-(4-(OCH₂CH₂OCH₃)benzyl)-4-aminopiperidine |
| 339 | (2-methyl-2-carboxy-succinate) | 2 | 1-(4-OH-benzyl)-4-aminopiperidine |
| 340 | (2-methyl-2-carboxy-succinate) | 2 | 1-(4-SO₂CH₃-benzyl)-4-aminopiperidine |
| 341 | (2-methyl-2-carboxy-succinate) | 2 | 1-(3-F-benzyl)-4-aminopiperidine |
| 342 | (2-methyl-2-carboxy-succinate) | 2 | 1-(2-F-benzyl)-4-aminopiperidine |
| 343 | (2-methyl-2-carboxy-succinate) | 2 | 1-(2-F-4-CH₃-benzyl)-4-aminopiperidine |
| 344 | (2-methyl-2-carboxy-succinate) | 2 | 1-(3-Cl-4-CH₃-benzyl)-4-aminopiperidine |
| 345 | (2-methyl-2-carboxy-succinate) | 2 | 1-(2,3-diF-benzyl)-4-aminopiperidine |

TABLE 3-continued

| Entry | R₁O | n | NR₂R₃ |
|---|---|---|---|
| 346 | 2-methyl-2-(carboxy)succinate | 2 | 4-[(4-morpholinophenyl)methyl]piperidin-1-yl-amine |
| 347 | 2-methyl-2-(carboxy)succinate | 2 | 4-[(4-(dimethylamino)phenyl)methyl]piperidin-4-ylamine |
| 348 | 2-methyl-2-(carboxy)succinate | 2 | 4-[(4-nitrophenyl)methyl]piperidin-4-ylamine |
| 349 | 2-methyl-2-(carboxy)succinate | 2 | 4-[(4-(N,N-dimethylsulfamoyl)phenyl)methyl]piperidin-4-ylamine |
| 350 | 2-methyl-2-(carboxy)succinate | 2 | 1-benzylpiperidin-3-ylamine |
| 351 | 2-methyl-2-(carboxy)succinate | 2 | 1-benzylpiperidin-3-ylamine |
| 352 | 2-methyl-2-(carboxy)succinate | 2 | 1-(methylsulfonyl)piperidin-3-ylamine |
| 353 | 2-methyl-2-(carboxy)succinate | 2 | 1-(methylsulfonyl)piperidin-3-ylamine |
| 354 | 2-methyl-2-(carboxy)succinate | 2 | 1-(methylsulfonyl)piperidin-4-ylamine |
| 355 | 2-methyl-2-(carboxy)succinate | 2 | 1-(ethoxycarbonylmethyl)piperidin-4-ylamine |
| 356 | 2-methyl-2-(carboxy)succinate | 2 | 1-(2-(dimethylamino)ethyl)piperidin-4-ylamine |

TABLE 3-continued

| Entry | R₁O | n | NR₂R₃ |
|---|---|---|---|
| 357 | (2-methyl-succinate, HO-C(=O)-C(CH₃)(⃫)-CH₂-C(=O)-O-) | 2 | 4-amino-1-(acetyl)piperidine (NH-piperidine-N-COCH₃) |
| 358 | (2-methyl-succinate) | 2 | 4-amino-1-(methoxyacetyl)piperidine (NH-piperidine-N-COCH₂OCH₃) |
| 359 | (2-methyl-succinate) | 2 | 4-amino-1-(hydroxyacetyl)piperidine (NH-piperidine-N-COCH₂OH) |
| 360 | (2-methyl-succinate) | 2 | 4-amino-1-(N,N-dimethylglycyl)piperidine (NH-piperidine-N-COCH₂N(CH₃)₂) |
| 361 | (2-methyl-succinate) | 2 | 4-amino-1-(cyanomethyl)piperidine (NH-piperidine-N-CH₂CN) |
| 362 | (2-methyl-succinate) | 2 | 4-amino-1-(2-hydroxyethyl)piperidine (NH-piperidine-N-CH₂CH₂OH) |
| 363 | (3-methyl-glutarate, HO-C(=O)-CH₂-C(CH₃)(⃫)-CH₂-C(=O)-O-) | 2 | 4-amino-1-(2-hydroxyethyl)piperidine |
| 364 | (2-methyl-succinate) | 2 | 4-amino-1-(2-methoxyethyl)piperidine (NH-piperidine-N-CH₂CH₂OCH₃) |
| 365 | (3-methyl-glutarate) | 2 | 4-amino-1-(2-methoxyethyl)piperidine |
| 366 | (3-methyl-glutarate) | 2 | 4-amino-1-(methanesulfonyl)piperidine (NH-piperidine-N-SO₂CH₃) |
| 367 | (2-methyl-succinate) | 1 | 4-amino-1-(methanesulfonyl)piperidine |

TABLE 3-continued

| Entry | R₁O | n | NR₂R₃ |
|---|---|---|---|
| 368 | (2S)-2-methyl-2-carboxy-succinate | 3 | 4-amino-1-(methylsulfonyl)piperidine |
| 369 | (2S)-2-methyl-2-carboxy-succinate | 2 | 4-amino-1-(N,N-dimethylsulfamoyl)piperidine |
| 370 | (2S)-2-methyl-2-carboxy-succinate | 2 | 4-amino-1-(pyridin-4-ylmethyl)piperidine |
| 371 | (2S)-2-methyl-2-carboxy-succinate | 2 | 4-amino-1-(pyridine-4-carbonyl)piperidine |
| 372 | (2S)-2-methyl-2-carboxy-succinate | 2 | 4-amino-1-benzoylpiperidine |
| 373 | (2S)-2-methyl-2-carboxy-succinate | 2 | 4-amino-1-(4-methylbenzoyl)piperidine |
| 374 | (2S)-2-methyl-2-carboxy-succinate | 2 | 4-amino-1-(4-chlorobenzoyl)piperidine |
| 375 | (2S)-2-methyl-2-carboxy-succinate | 2 | 4-amino-1-(4-hydroxybenzoyl)piperidine |
| 376 | (2S)-2-methyl-2-carboxy-succinate | 2 | 4-amino-1-(4-methoxybenzoyl)piperidine |

TABLE 3-continued
| Entry | R₁O | n | NR₂R₃ |
|---|---|---|---|
| 377 | 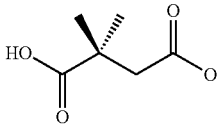 | 2 | 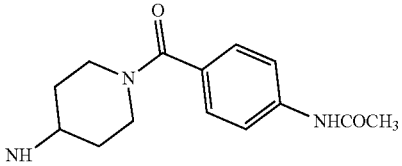 |
| 378 | 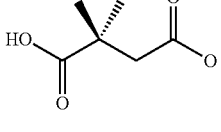 | 2 | 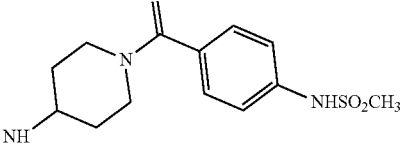 |
| 379 | 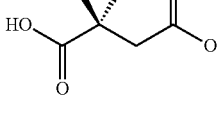 | 2 | 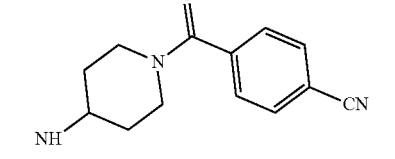 |
| 380 | 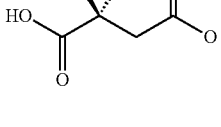 | 2 | 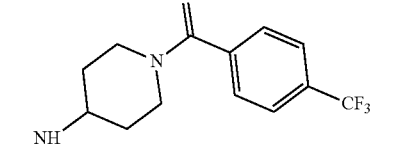 |
| 381 | 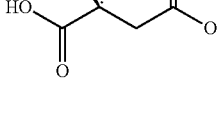 | 2 | 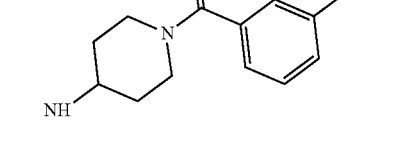 |
| 382 | 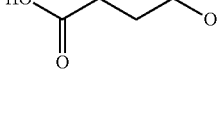 | 2 | 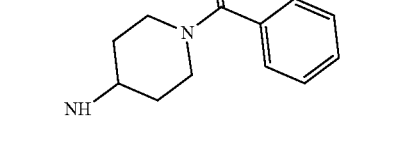 |
| 383 | 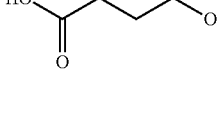 | 2 | 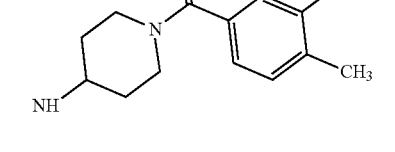 |
| 384 | 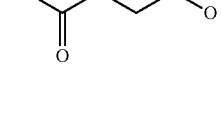 | 2 | 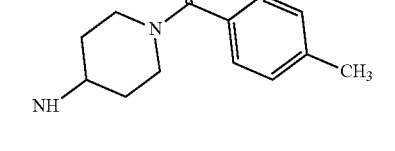 |

TABLE 3-continued

| Entry | R₁O | n | NR₂R₃ |
|---|---|---|---|
| 385 | (2-methyl succinate, HO on left) | 2 | 8-(methylsulfonyl)-8-azabicyclo[3.2.1]octan-3-amine (exo) |
| 386 | (2-methyl succinate, HO on left) | 2 | 8-(methylsulfonyl)-8-azabicyclo[3.2.1]octan-3-amine (endo) |
| 387 | (2-methyl succinate, HO on left) | 2 | 2-(tetrahydro-2H-pyran-4-yl)ethan-1-amine |
| 388 | (2-methyl succinate, HO on left) | 2 | 2-morpholinoethan-1-amine |
| 389 | (3-methyl glutarate) | 2 | 3-morpholinopropan-1-amine |
| 390 | (2-methyl succinate, HO on left) | 2 | 2-thiomorpholinoethan-1-amine |
| 391 | (2-methyl succinate, HO on left) | 2 | 2-(1-oxidothiomorpholino)ethan-1-amine |
| 392 | (2-methyl succinate, HO on left) | 1 | 2-(1,1-dioxidothiomorpholino)ethan-1-amine |
| 393 | (2-methyl succinate, HO on left) | 2 | 2-(1,1-dioxidothiomorpholino)ethan-1-amine |
| 394 | (3-methyl glutarate) | 2 | 3-(2-oxopyrrolidin-1-yl)propan-1-amine |

TABLE 3-continued

| Entry | R₁O | n | NR₂R₃ |
|---|---|---|---|
| 395 | (2-methyl succinate, R) | 2 | NH-CH₂CH₂-N-pyrrolidine-CO₂CH₃ |
| 396 | (2-methyl succinate, S) | 2 | NH-CH₂CH₂-N-pyrrolidine-CO₂CH₃ |
| 397 | (2-methyl succinate) | 2 | NH-CH₂CH₂-N-pyrrolidine-CH₂OH |
| 398 | (2-methyl succinate) | 2 | NH-CH₂CH₂-N-pyrrolidine-CH₂OH |
| 399 | (2-methyl succinate) | 1 | NH-CH₂CH₂-N-pyrrolidine-CH₂NHSO₂CH₃ |
| 400 | (2-methyl succinate) | 2 | NH-CH₂CH₂-N-pyrrolidine-CH₂NHSO₂CH₃ |
| 401 | (2-methyl succinate) | 1 | NH-CH₂CH₂-N-pyrrolidine-CH₂NHSO₂CH₃ |
| 402 | (2-methyl succinate) | 2 | NH-CH₂CH₂-N-pyrrolidine-CH₂NHSO₂CH₃ |
| 403 | (2-methyl succinate) | 1 | NH-CH₂-pyrrolidine-N-SO₂CH₃ |
| 404 | (2-methyl succinate) | 2 | NH-CH₂-pyrrolidine-N-SO₂CH₃ |

TABLE 3-continued

| Entry | R₁O | n | NR₂R₃ |
|---|---|---|---|
| 405 | (2-methyl-succinate, HO-C(=O)-C(CH₃)(methyl wedge)-CH₂-C(=O)-O-) | 1 | NH-CH₂-[(2S)-pyrrolidin-2-yl]-N-SO₂CH₃ |
| 406 | (same as 405) | 2 | NH-CH₂-[(2S)-pyrrolidin-2-yl]-N-SO₂CH₃ |
| 407 | (same) | 1 | NH-CH₂-[(3R)-pyrrolidin-3-yl]-N-SO₂CH₃ |
| 408 | (same) | 2 | NH-CH₂-[(3R)-pyrrolidin-3-yl]-N-SO₂CH₃ |
| 409 | (same) | 1 | NH-CH₂-[(3S)-pyrrolidin-3-yl]-N-SO₂CH₃ |
| 410 | (same) | 2 | NH-CH₂-[(3S)-pyrrolidin-3-yl]-N-SO₂CH₃ |
| 411 | (same) | 2 | 4-aminotetrahydropyran (NH-tetrahydropyran-4-yl) |
| 412 | (same) | 2 | 4-aminotetrahydrothiopyran-1,1-dioxide (NH-tetrahydrothiopyran-4-yl, SO₂) |
| 413 | (same) | 2 | NH-CH₂CH₂-N(Et)-CH₂-CN |
| 414 | (same) | 2 | NH-CH₂CH₂-N(Et)-CH₂-CO₂Et |
| 415 | (same) | 2 | NH-CH₂CH₂-N(Et)-CH₂-SO₂CH₃ |

TABLE 3-continued

| Entry | R₁O | n | NR₂R₃ |
|---|---|---|---|
| 416 | (2-methyl-2-carboxy-succinate) | 2 | NH₂-CH₂CH₂-N(Et)-CH₂-CON(CH₃)₂ |
| 417 | (2-methyl-2-carboxy-succinate) | 2 | NH₂-CH₂CH₂-N(Et)-CH₂CH₂-OH |
| 418 | (2-methyl-2-carboxy-succinate) | 2 | NH₂-CH₂CH₂-N(Et)-CH₂CH₂-OCH₃ |
| 419 | (2-methyl-2-carboxy-succinate) | 1 | NH₂-CH₂CH₂-N(Et)-CH₂-SO₂CH₃ |
| 420 | (2-methyl-2-carboxy-succinate) | 3 | NH₂-CH₂CH₂-N(Et)-CH₂-SO₂CH₃ |
| 421 | (3-methyl-3-carboxy-glutarate) | 2 | NH₂-CH₂CH₂-N(Et)-CH₂-SO₂CH₃ |
| 422 | (2-methyl-2-carboxy-succinate) | 2 | NH₂-CH₂CH₂CH₂-N(Et)-CH₂-SO₂CH₃ |
| 423 | (2-methyl-2-carboxy-succinate) | 2 | NH₂-CH₂CH₂-N(Et)-SO₂CH₃ |
| 424 | (2-methyl-2-carboxy-succinate) | 2 | NH₂-CH₂CH₂-NH-SO₂CH₃ |
| 425 | (2-methyl-2-carboxy-succinate) | 1 | NH₂-CH₂CH₂-(diazabicyclic)-N-SO₂CH₃ |
| 426 | (2-methyl-2-carboxy-succinate) | 2 | NH₂-CH₂CH₂-(diazabicyclic)-N-SO₂CH₃ |

TABLE 3-continued
| Entry | R₁O | n | NR₂R₃ |
|---|---|---|---|
| 427 | | 1 | |
| 428 | | 2 | |
| 429 | | 2 | |
| 430 | | 2 | |
In some embodiments, the disclosure provides compounds of Formula 1
Formula 1
wherein R₁O is
n is 2;
NR₂R₃ is selected from the group consisting of:
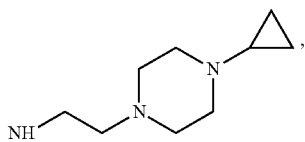
-continued
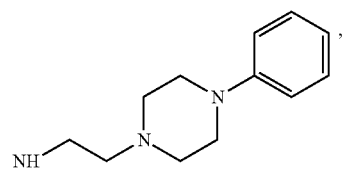
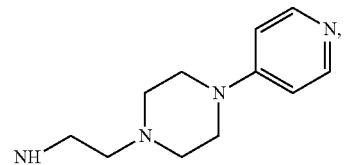
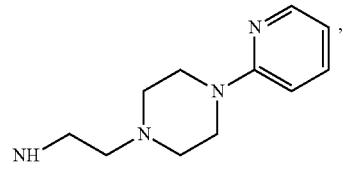
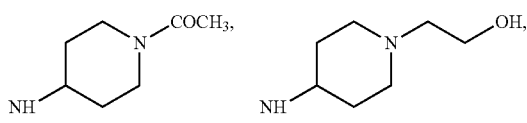
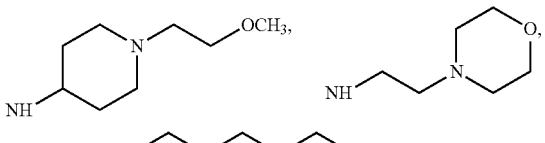
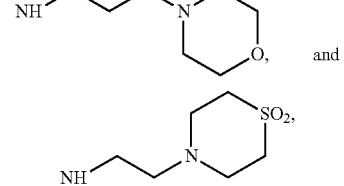
and or $R_3$ and/or $R_2$ is $R_4R_5N(CR_aR_b)_m$—, wherein $R_4$ and $R_5$ are independently selected from the group consisting of hydrido and alkyl; and $R_6$ is 1-methyl-1-cyclohexyl.

Compounds of the present invention include all regioisomers (e.g., cis and trans isomers) and stereoisomers (e.g. R and S enantiomers) of the compound of Formula I as well as racemic and diastereomeric forms of such isomers. The optical isomers can be obtained by resolution of the racemic mixtures according to conventional processes, for example by formation of diastereoisomeric salts by treatment with an optically active base and then separation of the mixture of diastereoisomers by crystallization, followed by liberation of the optically active bases from such salts. Alternatively, diastereoisomeric salts may be treated with an optically active acid and then separation of the mixture of diastereoisomers by crystallization, followed by liberation of the optically active acids from such salts. Examples of appropriate bases are brucine, dehydroabietylamine, quinine, cinchonidine, ephedrine, α-methylbenzylamine, deoxyephedrine, 2-amino-1-butanol, and 1-(1-naphthyl)ethylamine. A different process for separation of optical isomers involves the use of a chiral chromatography column optimally chosen to maximize the separation of the enantiomers. Still another available method involves synthesis of covalent diastereoisomeric molecules. The synthesized diastereoisomers can be separated by conventional means such as chromatography, distillation, crystallization or sublimation, and then hydrolyzed to deliver the enantiomerically pure compound. The optically active compounds of the present invention can likewise be obtained by utilizing an optically active starting material or reagent. These isomers may be in the form of a free acid, a free base, an ester, a salt, an amide or a prodrug.

Some compounds of Formula I and their respective prodrugs can exist in several tautomeric forms, including the keto-enol form and enamine-imine form and geometric isomers and mixtures thereof. Even though one tautomer may be described, the present invention includes all tautomers of the present compounds.

When any variable (e.g. $R_a$, $R_b$, heteroatom, etc.) occurs more than one time in any moiety, the choice of a variable is independently selected in each occurrence. For example, with regard to Formula I, $R_a$ and $R_b$ can be variable moieties bonded to a carbon which is part of a carbon chain of m subunits; when n>1, there are successive carbons each attached to a $R_a$ and $R_b$ variable moiety, however despite repetition of the $R_a$ and $R_b$ alphanumerical designations, each $R_a$ may be selected independently from other $R_a$ moieties, similarly each $R_b$ may be selected independently from other $R_b$ moieties.

Unit Dosages

Dosages described in this application refer to mass of the parent form of the relevant compound.

Illustrative dosage unit forms of the pharmaceutical compositions can typically contain about, 100, 200, 250, 300, 350, 400, 450, or 500 mg of a compound as described herein. In some embodiments, the dosage unit form contains about 200, 300, 400, or 500 mg of a compound described herein. The dosage unit form can be selected to accommodate the desired frequency of administration used to achieve the specified daily dosage. The amount of the unit dosage form of the pharmaceutical composition that is administered and the dosage regimen for treating the condition or disorder depends on a variety of factors, including the age, weight, sex and medical condition of the subject, the severity of the condition or disorder, the route and frequency of administration, and thus can vary widely, as is well known.

Where it is desired to formulate dosage units in which each unit consists of less than a therapeutically effective amount of a compound of the present invention, multiple dosage units, each containing smaller amounts of a compound of the present invention, can be administered to constitute the daily dose. It will be understood, however, that the specific dose level for any particular patient will depend upon a variety of factors including the activity of the specific compound employed, the age, body weight, general health, sex, diet, time of administration, route of administration, rate of excretion, drug combination, and the stage of disease progression of a particular patient undergoing therapy.

Prodrugs

The present invention further provides pharmaceutical compositions and methods of treatment comprising prodrugs of a compound of Formula I. Prodrugs of this invention may be called single, double, or triple, depending on the number of biotransformation steps required to release the active parent drug, and indicating the number of functionalities present in a precursor-type form. Prodrug forms often offer advantages of solubility, tissue compatibility, or delayed release in the mammalian organism. Prodrugs commonly known in the art include acid derivatives well known to practitioners of the art, such as, for example, esters prepared by reaction of a parent acid with a suitable alcohol, or an amides prepared by reaction of the parent acid compound with an amine, or basic groups reacted to form an acylated base derivative. Moreover, the prodrug derivatives of this invention may be combined with other features herein taught to enhance bioavailability. For example, a compound of Formula I having one or more free amino, amido, hydroxy or carboxylic groups can be converted into prodrugs. Prodrugs include compounds comprising an amino acid residue, or a polypeptide chain of two or more amino acid residues which are covalently joined through peptide bonds to a free amino, hydroxy or carboxylic acid groups of compounds of the invention. Amino acid residues useful in accordance with the present invention include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, 4-hydroxyproline, hydroxylysine, desmosine, isodesmosine, 3-methylhistidine, norvaline, β-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain.

Salts

The present invention further provides a pharmaceutically acceptable salt of a compound of the present invention composition.

The term "pharmaceutically acceptable salt" refers to a salt prepared from pharmaceutically acceptable non-toxic acids, including inorganic acids and organic acids. Suitable non-toxic acids include alkali or organic salts of acidic residues such as carboxylic acids wherein the carboxylate counterion is selected from the group consisting of formate, acetate, propionate, trifluoroacetate, succinate, salicylate, DL-aspartate, D-aspartate, L-aspartate, DL-glutamate, D-glutamate, L-glutamate, glycerate, succinate, steric, DL-tartarate, D-tartarate, L-tartarate, (±)-mandelate, (R)-(−)-mandelate, (S)-(+)-mandelate, citrate, mucate, maleate, malonate, benzoate, DL-malate, D-malate, L-malate, hemi-malate, 1-adamantaneacetate, 1-adamantanecarboxylate, flavianate, sulfonoacetate, (±)-lactate, L-(+)-lactate, D-(−)-lactate, pamoate, D-α-galacturonate, glycerate, DL-ascorbate, D-ascorbate, L-ascorbate, DL-cystate, D-cystate, L-cystate, DL-homocystate, D-homocystate, L-homocystate, DL-cysteate, D-cysteate, L-cysteate, (4S)-hydroxy-L-proline, cyclopropane-1,1-dicarboxylate, 2,2-dimethylmalonate, squarate, tyrosine anion, proline anion, fumarate, 1-hydroxy-2-naphthoate, phosphonoacetate, carbonate, bicarbonate, 3-phosphonopropionate, DL-pyroglutamate, D-pyroglutamate, and L-pyroglutamate. In another embodiment of the present invention, the anionic counterion is a sulfonate; for example the sulfonate counterion can be methanesulfonate, toluenesulfonate, benzenesulfonate, trifluoromethanesulfonate, ethanesulfonate, (±)-camphorsulfonate, naphthalenesulfonate, (1R)-(−)-camphorsulfonate, (1S)-(+)-camphorsulfonate, 2-mesitylenesulfonate, 1,5-naphthalenedisulfonate, 1,2-ethanedisulfonate, 1,3-propanedisulfonate, 3-(4-morpholinyl)propanesulfonate, biphenyl sulfonate, isethionate, or 1-hydroxy-2-naphthalenesulfonate. In another embodiment of the present invention, the anionic counterion is a sulfate; for example sulfate, monopotassium sulfate, monosodium sulfate, and hydrogen sulfate. In another embodiment of the present invention, the anionic counterion is a sulfamate. In another embodiment of the present invention, the anionic counterion is a phosphate; for example phosphate, dihydrogen phosphate, potassium hydrogen phosphate, dipotassium phosphate, potassium phosphate, sodium hydrogen phosphate, disodium phosphate, sodium phosphate, calcium dihydrogen phosphate, calcium phosphate, calcium hydrogen phosphate, calcium phosphate tribasic, or hexafluorophosphate. In another embodiment of the present invention, the anionic counterion is a phosphonate; for example, vinylphosphonate, 2-carboxymethylphosphonate or phenylphosphonate. In another embodiment of the present invention, the anionic counterion is a nitrate. In another embodiment of the present invention, the salt results from the addition of a compound with an oxide such as zinc oxide. In some embodiments of the present invention, salts such as choline, N-methylglucamine, potassium, sodium, (+)-arginine, diethanolamine, diethylamine, and triethanolamine are preferred. Pharmaceutically acceptable salts of the compounds of the invention can be prepared by contacting the free acid or base forms of these compounds with a stoichiometric amount of the appropriate base or acid in water or in an organic solvent, or in a mixture of water and an organic solvent. In some embodiments of the present invention, nonaqueous media such as ether, ethyl acetate, ethanol, isopropanol, or acetonitrile are preferred. In another embodiment of the present invention, the pharmaceutically acceptable salt of the compound of Formula I can be one in which the present inventive compound is in an anionic form with at least one cationic counterion. The cationic counterion can be, for example, an ammonium cation, an alkali metal cation, an alkaline earth metal cation, a transition metal cation, or a resin-bound cation. In another embodiment of the present invention, the anionic counterion is an ammonium cation, it can be substituted or unsubstituted; for example, the ammonium cation can be an alkylammonium cation, or a di-, tri-, or tetra-alkylammonium cation. In another embodiment of the present invention, the ammonium cation can be an acylammonium or a di-, tri-, or tetra-acylammonium cation. In another embodiment of the present invention, the ammonium cation contains both alkyl and aryl groups. The ammonium cation can be aromatic, for example, a pyridinium cation. Other functional groups can also be present in the ammonium cation. The ammonium cation can be, for example, ammonium, methylammonium, dimethylammonium, trimethylammonium, tetramethylammonium, hydroxyethylammonium, dicyclohexylammonium, guanidinium, or ethylenediammonium dication.

In some embodiments, the counterion is a halide. In some embodiments the counterion is fluoride. In some embodiments the counterion is chloride. In some embodiments the counterion is bromide.

Multiple salts forms are included within the scope of the present invention where a chemical of the present invention contains more than one group capable of forming such a salt. In some embodiments, disalts are preferred. Examples of typical multiple salt forms include, but are not limited to bis(choline), bis(N-methylglucamine), dipotassium, disodium, bis((+)-arginine), bis(diethanolamine), bis(diethylamine), and bis(triethanolamine).

For therapeutic uses, a salt of a compound of Formula I comprise a pharmaceutically acceptable counterion. However, non-pharmaceutically acceptable salts useful in the synthesis-preparation, or purification of a pharmaceutically acceptable compound are also embraced by the present invention.

The present invention further provides a pharmaceutical composition comprising a therapeutically effective amount of a compound of the present invention and one, two, three, four, five or six agents selected from the group consisting of a HIV protease inhibitor, a HIV reverse transcriptase inhibitor, an HIV entry/fusion inhibitor, an HIV integrase inhibitor and an HIV maturation inhibitor, and a pharmaceutically acceptable carrier.

The present invention further provides a pharmaceutical composition comprising a therapeutically effective amount of a compound of the present invention and a pharmaceutically acceptable carrier.

The present invention comprises a pharmaceutical composition for the treatment of retroviral disorders, such as HIV, comprising a therapeutically effective amount of a compound of the present invention in association with at least one pharmaceutically acceptable carrier, adjuvant or diluent.

The pharmaceutical compositions of the present invention comprise a compound of Formula I in association with one or more non-toxic, pharmaceutically acceptable excipient. The excipients are acceptable in the sense of being compatible with the other ingredients of the composition and are not deleterious to the recipient. The pharmaceutical compositions of the present invention can be adapted for administration by any suitable route by selection of appropriate carrier materials and a dosage of a compound of the present invention effective for the treatment intended. For example, these compositions can be prepared in a form suitable for administration orally, intravascularly, intraperitoneally, subcutaneously, intramuscularly (IM) or rectally. Accordingly, the carrier material employed can be a solid or a liquid, or both, and is preferably formulated with the compound as a unit-dose composition, for example, a tablet, which can contain from about 1% to about 95%, preferably about 10% to about 75%, more preferably about 20% to about 60%, and still more preferably about 20% to about 40%, by weight of a compound of the present invention.

The compounds of the present invention may be administered orally, parenterally, sublingually, rectovaginally, topically, transmucosally, transdermally, or through liposomes in dosage unit formulations optionally comprising conventional nontoxic pharmaceutically acceptable carriers, adjuvants, or vehicles as desired.

"Formulations suitable for systemic administration" means formulations which are in a form suitable to be administered systemically to a patient. Systematic administration can be achieved by oral delivery, parenteral delivery, transmucosal delivery, transdermal delivery, rectovaginal delivery or liposomal delivery.

"Formulations suitable for oral administration" means formulations which are in a form suitable to be administered orally to a patient. In some embodiments, the oral formulation is intended to be absorbed in the gastric or intestinal cavities. The formulations may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Solid dosage forms for oral administration may include capsules, tablets, pills, powders, and granules. In such solid dosage forms, the active compound may be admixed with at least one inert diluent such as sucrose, lactose or starch. Such dosage forms may also comprise, as is normal practice, additional substances other than inert, diluents, e.g., lubricating agents such as magnesium stearate. In the case of capsules, tablets, and pills, the dosage forms may also comprise buffering agents. Tablets and pills can additionally be prepared with enteric coating. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents. In some embodiments, the oral formulation is intended to be absorbed at least in part in the oral cavity including the lips, the inside lining of the lips and cheeks (buccal mucosa), the teeth, the gums (gingivae), the tongue, the floor of the mouth below the tongue, the bony roof of the mouth (hard palate), the area behind the wisdom teeth (retromolar trigone), and the salivary glands. Formulations suitable for topical administration in the mouth include lozenges comprising the active ingredient in a flavored basis, for example sucrose and acacia or tragacanth; pastilles comprising the active ingredient in an inert basis such as gelatin and glycerin, or sucrose and acacia; and mouthwashes comprising the active ingredient in a suitable liquid carrier.

"Formulations suitable for parenteral administration" means formulations which are in a form suitable to be administered parenterally to a patient. The term "parenteral" as used herein includes subcutaneous delivery, intravenous delivery, and intramuscular delivery. In some embodiments of the present invention, the formulations comprise emulsions, suspensions, aqueous or non-aqueous injection solutions. Injectable formulations, for example sterile injectable aqueous or oleaginous suspensions, may be formulated according to the known art using suitable dispersing or wetting agents and suspending agents, thickening agents, anti-oxidants, buffers, bacteriostats, and solutes which render the formulation isotonic. In preferred embodiments formulations suitable for parenteral administration have a pH adjusted to be compatible with the blood of the intended recipient. The sterile injectable formulation may also be a sterile injectable solution or suspension in a nontoxic parenterally acceptable diluent or solvent, for example, as a solution in 1,3-propanediol. Among the acceptable vehicles and solvents that may be employed are physiologically compatible buffers such as water, Hank's solution, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Some embodiments of the present invention comprise lyophilized formulations. In some embodiments of the present invention, the compounds are formulated in solid form and redissolved or suspended immediately prior to use.

"Formulations suitable for topical administration" means formulations which are in a form suitable to be administered topically to a patient. The formulation may be presented as a topical ointment, salve, powder, alcohol based gel, water based gel, or cream, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. In some embodiments, the transmucosal or transdermal formulation comprises a penetrant appropriate to the barrier to be permeated by at least one active ingredient of the formulation. Such penetrants are generally known in the art, and include, for example, bile salts and fusidic acid derivatives for transmucosal administration. In addition, detergents may be used to facilitate permeation.

"Formulations suitable for rectovaginal administration" means formulations which are in a form suitable to be administered to the rectum or vagina of a patient.

"Formulations suitable for rectal administration" means formulations which are in a form suitable to be administered rectally to a patient. The rectal formulation is preferably administered in the form of suppositories which can be prepared by mixing the compounds useful according to this invention with suitable non-irritating excipients or carriers such as cocoa butter, a polyethylene glycol or a suppository wax, which are solid at ordinary temperatures but liquid at body temperature and therefore, melt in the rectum or vaginal cavity and release the active component.

"Formulations suitable for vaginal administration" means formulations which are in a form suitable to be administered vaginally to a patient. The formulation may be presented as pessaries, tampons, creams, gels, pastes, foams or spray formulations containing in addition to the active ingredient such carriers as are known in the art to be appropriate.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can contain, in addition to the compound of the present invention, at least one additional compound selected from the group consisting of stabilizers, preservatives, and excipients. The preferred lipids are the phospholipids and phosphatidylcholines (lecithins), both natural and synthetic.

Form of Pharmaceutical Compositions

The pharmaceutical compositions of the present invention comprise a compound of the present invention in association with one or more non-toxic, pharmaceutically-acceptable carriers, excipients or adjuvants (collectively referred to herein as "earner materials"). The earner materials are acceptable in the sense of being compatible with the other ingredients of the composition and are not deleterious to the recipient. The pharmaceutical compositions of the present invention can be adapted for administration by any suitable route by selection of appropriate carrier materials and a dosage of a compound of the present invention effective for the treatment intended. For example, these compositions can be prepared in a form suitable for administration orally, intravascularly, intraperitoneally, subcutaneously, intramuscularly or rectally. Accordingly, the carrier material employed can be a solid or a liquid, or both, and is preferably formulated with the compound as a unit-dose composition, for example, a tablet, which can contain from about 1% to about 95%, preferably about 25% to about 70%, more preferably about 40% are to about 60%, and still more preferably about 20%, by weight of a compound of the present invention. Such pharmaceutical compositions of the invention can be prepared by any of the well-known techniques of pharmacy, consisting essentially of admixing the components.

Oral Administration

For oral administration, the pharmaceutical composition can contain a desired amount of a compound of the present invention and be in the form of, for example, a tablet, a hard or soft capsule, a lozenge, a sachet, a dispensable powder, granules, a suspension, an elixir, a liquid, or any other form reasonably adapted for oral administration. Such a pharmaceutical composition is preferably made in the form of a discrete dosage unit containing a predetermined amount of a compound of the present invention, such as tablets or capsules. Such oral dosage forms can further comprise, for example, buffering agents. In some embodiments of the present invention, tablets, pills, or other solid dosage forms are prepared with enteric coatings. Unit dosage tablets or capsules are preferred.

Pharmaceutical compositions suitable for buccal or sublingual administration include, for example, lozenges comprising a compound of the present invention in a flavored base, such as sucrose, and acacia or tragacanth, and pastilles comprising a compound of the present invention in an inert, base such as gelatin and glycerin or sucrose and acacia.

Liquid dosage forms for oral administration can include pharmaceutically acceptable emulsions, solutions, suspensions, syrups, and elixirs containing inert diluents commonly used in the art, such as water or a cyclodextrin. Such compositions can also comprise, for example, wetting agents, emulsifying and suspending agents, and sweetening, flavoring, and perfuming agents. Examples of suitable liquid dosage forms include, but are not limited, aqueous solutions comprising a compound of the present invention and β-cyclodextrin or a water soluble derivative of β-cyclodextrin such as sulfobutyl ether β-cyclodextrin, heptakis-2,6-di-O-methyl-β-cyclodextrin, hydroxypropyl-β-cyclodextrin, or dimethyl-β-cyclodextrin.

Parenteral Administration

The pharmaceutical compositions of the present invention can also be administered parenterally (via subcutaneous, intravenous, or intramuscular injection). Such injectable compositions can employ, for example, saline, dextrose, or water as a suitable carrier material. The pH value of the composition can be adjusted, if necessary, with suitable acid, base, or buffer. Suitable bulking, dispersing, wetting or suspending agents, including mannitol and poly(ethylene glycol)s, for example PEG 400, can also be included in the composition. A suitable parenteral composition can also include a compound of the present invention in injection vials. Aqueous solutions can be added to dissolve the composition prior to injection.

Rectovaginal Administration

The pharmaceutical compositions can be rectally or vaginally. Illustrative pharmaceutical compositions are administered in the form of a suppository or a pessary. In some embodiments, the rectovaginal formulations comprise a compound of the present invention in a total amount of, for example, 0.075 to 30% w/w, preferably 0.2 to 20% w/w and most preferably 0.4 to 15% w/w. Carrier materials such as cocoa butter, *theobroma* oil, and other oil and poly(ethylene glycol) suppository bases can be used in such compositions. Other carrier materials such as coatings, for example, hydroxypropyl methylcellulose film coating, and disintegrants, for example, croscarmellose sodium and cross-linked povidone are also contemplated as part, of the present invention.

As indicated above, these pharmaceutical compositions can be prepared by any suitable method of pharmacy which includes the step of bringing into association a compound of the present invention and at least one carrier material. In general, the compositions are prepared by uniformly and intimately admixing the active compound with a liquid or finely divided solid carrier, or both, and then, optionally coating the admixture, and then, optionally shaping the product. For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binding agent, lubricant, inert diluent or surface active/dispersing agent. Molded tablets can be made by molding, in a suitable machine, the powdered compound moistened with an inert liquid diluent.

Carrier Materials

As noted above, for therapeutic purposes, the pharmaceutical compositions of the present invention comprise a compound of the present invention in a desired amount in combination with at least one pharmaceutically acceptable carrier material appropriate to the indicated route of administration. It is understood in the art that certain carrier materials may provide a plurality of functions, for example hydroxypropyl methylcellulose may function as both a water retention agent and as an emulsifier; as such the inclusion of any particular excipient as a member of one class is not intended to limit other classes to its exclusion.

Oral dosage forms of the pharmaceutical compositions of the present invention preferably comprise a compound of the present invention in a desired amount admixed with one or more carrier materials selected from the group consisting of diluents, disintegrants, binding agents and adhesives, wetting agents, lubricants, and anti-adherents. More preferably, such compositions are tableted or encapsulated for convenient administration.

Injectable dosage forms preferably are adapted for parenteral injection. Preferably, these dosage forms comprise a compound of the present invention in aqueous or non-aqueous isotonic sterile injection solutions or suspensions, such as a of a compound of the present invention suspended or dissolved in water, poly(ethylene glycol), propylene glycol, ethanol, corn oil, cottonseed oil, peanut oil, sesame oil, benzyl alcohol, sodium chloride, or other pharmaceutically acceptable buffers. These solutions and suspensions can be prepared from sterile powders or granules having one or more of the carriers or diluents mentioned for use in the formulations for oral administration.

The selection and combination of carrier materials used in the pharmaceutical compositions of the present invention provides compositions exhibiting improved performance with respect to, among other properties, safety, efficacy, dissolution profile, disintegration profile, bioavailability, clearance times, stability, pharmacokinetic properties and pharmacodynamic properties. The carrier materials preferably are water soluble or water dispersible and have wetting properties to increase the aqueous solubility and decrease the hydrophobicity of pharmaceutical compositions of the present invention. Where the composition is formulated as a tablet the combination of carrier materials selected provides tablets that can exhibit, among other properties, improved dissolution and disintegration profiles, hardness, crushing strength, or friability properties.

Diluents

The pharmaceutical compositions of the present invention optionally can comprise one or more diluents as a carrier material. Suitable diluents can include, either individually or in combination, such diluents as lactose USP; lactose USP, anhydrous; lactose USP, spray dried; starch USP; directly compressible starch; mannitol USP; sorbitol; dextrose monohydrate; microcrystalline cellulose NF; dibasic calcium phosphate dihydrate NF; sucrose-based diluents; confectioner's sugar; monobasic calcium sulfate monohydrate; calcium sulfate dihydrate NF; calcium lactate trihydrate granular NF; dextrates NF, for example EMDEX™ and CELUTAB™; dextroses, for example CERELOSE™; inositol; hydrolyzed cereal solids such as the MALTRONS™ and MOR-REX™; amylose; REXCEL™ (cellulose); powdered celluloses, for example ELCEMA™; calcium carbonate; glycine; bentonite; and polyvinylpyrrolidone. The present pharmaceutical compositions comprise one or more diluents in the range of about 5% to about 99%, preferably about 25% to about 90%, and more preferably about 40% to about 80%, of the total weight of the composition. The selected diluent or diluents preferably exhibit suitable compressibility and pre-compression flow properties. Microcrystalline celluloses, for example AVICEL™PH 101 and lactose, either individually or in combination are preferred diluents. The use of extragranular microcrystalline cellulose, for example microcrystal line cellulose added to a wet granulated composition after the drying step, in addition to intergranular microcrystalline cellulose, for example microcrystalline cellulose added to the composition during or before the wet granulation step, can be used to improve tablet hardness or disintegration time. Lactose, especially lactose monohydrate, is particularly preferred. Lactose typically provides pharmaceutical compositions having suitable release rates, stability, pre-compression flowability, and drying properties at a relatively low diluent cost.

Disintegrants

The pharmaceutical compositions of the present invention optionally can comprise one or more disintegrants as a carrier material, particularly for tablet formulations. Suitable disintegrants can include, either individually or in combination, such disintegrants as starches; sodium starch glycolate; clays, for example VEEGUM™ HV; celluloses, for example purified cellulose, methylcellulose, sodium carboxymethyl cellulose, or carboxymethyl cellulose; alginates; pregelatinized corn starches, for example NATIONAL™ 1551, or NATIONAL™1550; crospovidone USP NF; gums, for example agar, guar, locust bean, KARAYA™ (vegetable gum), pectin, or tragacanth. Disintegrants can be added at any suitable step during the preparation of the pharmaceutical composition, particularly prior to granulation or during the lubrication step prior to compression. The present pharmaceutical compositions comprise one or more disintegrants in the range of about 0.5% to about 30%, preferably about 1% to about 10%, and more preferably about 2% to about 6%, of the total weight of the composition. Croscarmellose sodium is a preferred disintegrant for tablet formulations, preferably in the range of about 1% to about 10%, preferably about 2% to about 6%, and more preferably about 5%, by weight of the composition.

Binding Agents and Adhesives

The pharmaceutical compositions of the present invention optionally can comprise one or more binding agents or adhesives as a carrier material. Such binding agents and adhesives preferably impart sufficient cohesion to the powders to permit normal processing such as sizing; lubrication, compression and packaging, but still permit the tablet to disintegrate and the composition to dissolve upon ingestion. Suitable binding agents and adhesives include, either individually or in combination, such binding agents and adhesives as acacia; tragacanth; sucrose; gelatin; glucose; starch; cellulose materials such as, but not limited to, methylcellulose, or sodium carboxymethyl cellulose, for example TYLOSE™; alginic acid; salts of alginic acid; magnesium aluminum silicate; poly(ethylene glycol); guar gum; polysaccharide acids; bentonites; polyvinylpyrrolidone(povidone); polymethacrylates; hydroxypropyl methylcellulose (HPMC); hydroxypropyl cellulose, for example KLUCEL™; ethyl cellulose, for example ETHOCEL™; pregelatinized starch, for example NATIONAL™ 1511 or Starch 1500. In some embodiments, pharmaceutical compositions of the present invention comprise one or more binding agents or adhesives in the range of about 0.5% to about 25%, preferably about 0.75% to about 15%, and more preferably about 1% to about 10%, of the total weight of the composition.

Wetting Agents

Where it is desired to increase the aqueous solubility of a compound of the present invention, the pharmaceutical compositions can optionally can comprise one or more wetting agents as a carrier material, particularly for tablet formulations. Such wetting agents preferably maintain the compound in solution and improve the bioavailability of the pharmaceutical composition. Suitable wetting agents include, either individually or in combination, such wetting agents as oleic acid; glyceryl monostearate; sorbitan monooleate; sorbitan monolaurate; triethanolamine oleate; polyoxyethylene sorbitan monooleate; polyoxyethylene sorbitan monolaurate; sodium oleate; and sodium lauryl sulfate. In some embodiments, wetting agents that are surfactants are preferred. In some embodiments, wetting agents that are anionic surfactants are preferred. The present pharmaceutical compositions comprise one or more wetting agents present at about 0.1% to about 15%, preferably about 0.25% to about 10%, and more preferably about 0.5% to about 5%, of the total weight of the composition. Sodium lauryl sulfate is a preferred wetting agent for tablet formulations. The compositions of the present invention preferably comprise sodium lauryl sulfate as the wetting agent at about 0.25% to about 7%, more preferably about 0.4% to about 4%, and still more preferably about 0.5 to about 2%, of the total weight of the composition.

Lubricants

The pharmaceutical compositions of the present invention optionally comprise one or more lubricants as a carrier material. Suitable lubricants include, either individually or in combination, glyceryl behenate, for example COMPRITOL™ 888; metallic stearates, for example magnesium, calcium and sodium stearates; stearic acid; hydrogenated vegetable oils, for example STEROTEX™; talc; waxes; STEAR-O-WET™ (magnesium stearate and sodium lauryl sulfate); boric acid; sodium benzoate and sodium acetate;

sodium chloride; DL-leucine; poly(ethylene glycol)s, for example CARBOWAX™ 4000 and CARBOWAX™ 6000; sodium oleate; sodium benzoate; sodium acetate; sodium lauryl sulfate; sodium stearyl fumarate, for example PRUV™; and magnesium lauryl sulfate. The present pharmaceutical compositions comprise one or more lubricants at about 0.1% to about 10%, preferably about 0.2% to about 8%, and more preferably about 0.25% to about 5%, of the total weight of the composition. In some embodiments magnesium stearate is a lubricant used to reduce friction between the equipment and granulation during compression.

Anti-Adherents or Glidants

The pharmaceutical compositions of the present invention optionally can comprise one or more anti-adherent agents or glidants as a carrier material. Suitable anti-adherents or glidants include, either individually or in combination, such anti-adherents as talc, cornstarch, CAB-O-SIL™ (fumed silica), SYLOID™ (silica), DL-leucine, sodium lauryl sulfate, and metallic stearates. The present pharmaceutical compositions comprise one or more anti adherents or glidants at about 0.1% to about 15%, preferably about 0.25% to about 10%, and more preferably about 0.5% to about 5%, of the total weight of the composition. Talc is a preferred anti-adherent or glidants agent used to reduce formulation sticking to equipment surfaces and also to reduce static in the blend. The compositions preferably comprise talc at about 0.1% to about 10%, more preferably about 0.25% to about 5%, and still more preferably about 0.5% to about 2%, of the total weight of the composition.

Other carrier materials, for example colorants, flavors and sweeteners can be used in the preparation of the pharmaceutical compositions of the present invention.

Oral dosage forms, including tablets, can be coated or uncoated.

The individual pharmaceutically acceptable carrier materials described in the above embodiment optionally can be replaced with other suitable carrier materials if desired. Acceptable substitute carrier materials are chemically compatible both with the compound of the present invention and with the other carrier materials.

Compounds of the present invention can be used in the treatment of HIV in patients who are not adequately treated by other HIV-1 therapies. Accordingly, the invention is also drawn to a method of treating a patient in need of therapy, wherein the HIV-1 infecting said cells does not respond to at least one other HIV-1 therapy. In some embodiments, methods of the invention are administered to a patient infected with an HIV that is resistant to at least one class of drugs approved to treat HIV infection. In various applications, the HIV is resistant to one or more protease inhibitors, reverse transcriptase inhibitors, for example, nucleotide or non-nucleotide reverse transcriptase inhibitors; entry inhibitors, nucleoside analogs, vaccines, fusion inhibitors, attachment inhibitors, CCR5 inhibitors, and immunomodulators. In some embodiments, methods of the invention are administered to a patient infected with an HIV that is resistant to at least one drug approved to treat HIV infection. In some embodiments, the compositions and methods of the invention are practiced on a subject infected with an HIV that is resistant to one or more drugs used to treat HIV infections, for example, but not limited to, zidovudine, lamivudine, didanosine, zalcitabine, stavudine, abacavir, nevirapine, delavirdine, emtricitabine, efavirenz, saquinavir, ritonavir, lopinavir, indinavir, nelfinavir, tenofovir, amprenavir, adefovir, atazanavir, darunavir, raltegravir, maraviroc, vicriviroc, fosamprenavir, enfuvirtide, tipranavir, hydroxyurea, AL-721, AMPLIGEN™ (rintatolimod) ampligen, butylated hydroxytoluene, polymannoacetate, castanospermine, Contra-Can, PHARMATEX™ (non-hormonal, locally applied benzalkonium chloride spermicide), penciclovir, famciclovir, acyclovir, cidofovir, ganciclovir, dextran sulfate, D-penicillamine, trisodium phosphonoformate, fusidic acid, HPA-23, eflornithine, nonoxynol-9, pentamidine isethionate, peptide T, phenytoin, isoniazid, ribavirin, rifabutin, ansamycin, trimetrexate, SK-818, suramin, UA001, and combinations thereof.

In addition, a compound of the present invention can be used as a prophylactic to prevent transmission of HIV infection between individuals. For example, a compound of the present invention can be administered orally or by injection to an HIV infected pregnant woman or her fetus during pregnancy, immediately prior to, at, or subsequent to birth, to reduce the probability that the newborn infant becomes infected. Also, a compound of the present invention can be used can be administered vaginally immediately prior to childbirth to prevent infection of the infant during passage through the birth canal. Further, a compound of the present invention can be used can be used during sexual intercourse to prevent transmission of HIV by applying a retroviral inhibiting effective amount of a topical composition comprising a compound of the present invention to vaginal or other mucosa prior to sexual intercourse.

Various dosage amounts of the composition of the invention can be administered to provide various plasma levels of a compound of the present invention. In some embodiments, a preferred dosage amount is one which provides a trough concentration of a compound of the present invention in the patient's plasma of about 1 micromolar ($\mu$M) to about 1 millimolar (mM). In some embodiments, the dosage amount is one which provides a trough concentration of a compound of the present invention in the patient's plasma of about 4 $\mu$M to about 1000 $\mu$M, about 40 $\mu$M to about 1000 $\mu$M, or about 400 $\mu$M to about 1000 $\mu$M. In some embodiments, the dosage amount is one which provides a trough concentration of a compound of the present invention in the patient's plasma of about 4 $\mu$M to about 200 $\mu$M, about 10 $\mu$M to about 200 $\mu$M, or about 40 $\mu$M to about 200 $\mu$M, In some embodiments, the dosage amount is one which provides a trough concentration of a compound of the present invention in the patient's plasma of at least about 4 $\mu$M or greater, at least about 10 $\mu$M or greater, at least about 40 $\mu$M or greater, at least about 100 $\mu$M or greater, or at least 200 $\mu$M or greater. In some embodiments, the dosage amount is one which provides a trough concentration of a compound of the present invention in the patient's plasma of about 400 $\mu$M. The "trough concentration" is the concentration of a compound of the present invention in the patient's plasma just prior to subsequent dosing of the patient.

Therapeutic administration can also include prior, concurrent, subsequent or adjunctive administration of at least one compound of the present invention according to the present invention or other therapeutic agent, such as an anti-viral or immune stimulating agent. In such an approach, the dosage of the second drug can be the same as or different from the dosage of the first therapeutic agent. In one embodiment of the present invention, the drugs are administered on alternate days in the recommended amounts of each drug.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. In one embodiment, the preparations, particularly those preparations which can be administered orally, such as tablets, dragees, and capsules, and also preparations winch can be administered rectally, such as suppositories, as well as suitable solutions for administration by injection or orally, contain from about 0.01 to 99 percent of the active ingredient together with the excipient. In another embodiment, the preparation can include from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

The present invention also provides all pharmaceutically-acceptable isotopically labeled compounds of the present invention wherein one or more atoms are replaced by atoms having the same atomic number, but an atomic mass or mass number different from the atomic mass or mass number predominantly found in nature.

Examples of isotopes suitable for inclusion in the compounds of the present invention include isotopes of hydrogen, for example $^2H$ or $^3H$, carbon, for example $^{11}C$, $^{13}C$, or $^{14}C$, chlorine, for example $^{36}Cl$, fluorine, for example $^{18}F$, iodine, for example $^{123}I$ or $^{123}I$, nitrogen, for example $^{13}N$ or $^{15}N$, oxygen, for example $^{15}O$, $^{17}O$, or $^{18}O$, phosphorus, for example $^{32}P$, and sulfur, for example $^{35}S$.

Certain isotopically labeled compounds of the present invention are useful in drug or substrate tissue studies. The radioactive isotopes tritium ($^3H$) and carbon-14 ($^{14}C$) are particularly useful for this purpose in view of their ease of incorporation and ready means of detection.

Substitution with heavier isotopes, for example deuterium ($^2H$) may afford certain therapeutic advantages resulting from greater metabolic stability, for example, increased in vivo half-life or reduced dosage requirements.

Substitution with positron emitting isotopes, for example $^{11}C$, $^{18}F$, $^{13}O$, or $^{13}N$, may be useful in positron emission topography (PET) studies for examining substrate-receptor occupancy.

The present invention also provides pharmaceutically acceptable solvates where the solvent of crystallization may be isotopically substituted, for example $D_2O$, acetone-$d_6$, or DMSO-$d_6$.

Isotopically labeled compounds of the present invention can be prepared by conventional techniques known to those skilled in the art or by synthetic processes analogous to those described in the present application using appropriate isotopically labeled reagents in place of the non-labeled reagent mentioned therein.

The present compounds may also be used in co-therapies, partially or completely, in place of other conventional antiviral therapies, such as in a combination comprising a first compound of the present invention and a second pharmaceutical agent selected from a second compound of the present invention or another anti-infective agent.

In some embodiments of the present invention, combinations comprising a compound of the present invention in combination with another anti-infective agent will produce a synergistic effect or reduce the toxic side effects associated with another anti-infective by reducing the therapeutic dose of the side effect-causing agent needed for therapeutic efficacy or by directly reducing symptoms of toxic side effects caused by the side effect causing agent.

Some embodiments of the present invention comprise a combination of a compound of the present invention and a secondary pharmaceutical agent selected from the group consisting of entry inhibitors, reverse transcriptase inhibitors, integrase inhibitors, protease inhibitors, assembly inhibitors, budding inhibitors, and maturation inhibitors in amounts effective for treatment of HIV when used in a combination therapy.

Some embodiments of the present invention comprise a compound of the present invention and in combination with an antiretroviral agent selected from the group consisting of vaccines, gene therapy treatments, cytokines, TAT inhibitors, and immunomodulators in amounts effective for treatment of HIV when used in a combination therapy.

Some embodiments of the present invention comprise a compound of the present invention and an anti-infective agent selected from the group consisting of antifungals, antibacterials, anti-neoplastics, anti-protozoals, DNA polymerase inhibitors, DNA synthesis inhibitors, anti-HIV antibodies, HIV antisense drugs, IL-2 agonists, α-glucosidase inhibitors, purine nucleoside phosphorylase inhibitors, apoptosis agonists, apoptosis inhibitors, and cholinesterase inhibitors, where the compounds are present in amounts effective for treatment of HIV when used in a combination therapy.

Some embodiments of the present invention comprise a compound of the present invention and a protease inhibitor selected from the group consisting of ritonavir, lopinavir, saquinavir, amprenavir, fosamprenavir, nelfinavir, tipranavir, indinavir, atazanavir, TMC-126, darunavir, mozenavir (DMP-450), JE-2147 (AG1776), L-756423, KNI-272, DPC-681, DPC-684, telinavir (SC-52151), BMS 186318, droxinavir (SC-55389a), DMP-323, KNI-227, 1-[(2-hydroxyethoxy)methyl]-6-(phenylthio)thymine, AG-1859, RO-033-4649, R-944, DMP-850, DMP-851, and brecanavir (GW640385). Preferred protease inhibitors for use in combination with a compound of the present invention include saquinavir, ritonavir, indinavir, nelfinavir, amprenavir, lopinavir, atazanavir, darunavir, brecanavir, fosamprenavir, and tipranavir.

Some embodiments of the present invention comprise a compound of the present invention and a reverse transcriptase inhibitor selected from the group consisting of emtricitabine, capravirine, tenofovir, lamivudine, zalcitabine, delavirdine, nevirapine, didanosine, stavudine, abacavir, alovudine, zidovudine, racemic emtricitabine, apricitabine (AVX754), emivirine, elvucitabine, TMC278 (also known as rilpivirine), DPC-083, amdoxovir, (−)-β-D-2,6-diaminopurine dioxolane (also known as amdoxovir), MIV-210 (FLG), dexelvucitabine (DFC), dioxolane thymine, calanolide A, etravirine (TMC125), L-697639, atevirdine (U87201E), MIV-150, GSK-695634, GSK-678248, KP-1461, KP-1212, lodenosine (FddA), 5-[(3,5-dichlorophenyl)thio]-4-isopropyl-1-(4-pyridylmethyl)imidazole-2-methanol carbamic acid, BCH-13520, BMS-56190 ((4S)-6-chloro-4-[(1E)-cyclopropylethenyl]-3,4-dihydro-4-trifluoromethyl-2(1H)-quinazolinone), TMC120 (also known as dapivirine), and L697639, where the compounds are present in amounts effective for treatment of HIV when used in a combination therapy.

Some embodiments of the present invention comprise a compound of the present invention and a viral entry inhibitor in amounts effective for treatment of HIV when used in a combination therapy. In some embodiments, the viral entry inhibitor is an attachment inhibitor. In some embodiments, the viral entry inhibitor is a fusion inhibitor. In some embodiments, the viral entry inhibitor is a CD4 receptor binding inhibitor. In some embodiments, the viral entry inhibitor is a CD4 mimic. In some embodiments, the viral entry inhibitor is a gp120 mimic. In some embodiments, the viral entry inhibitor is a gp41 antagonist. In some embodiments, the viral entry inhibitor is a CD4 monoclonal antibody. In some embodiments, the viral entry inhibitor is a CCR5 antagonist. In some embodiments, the viral entry inhibitor comprises a sub-class of CCR5 antagonists, for example a zinc finger inhibitor. In some embodiments, the viral entry inhibitor is a CXCR4 co-receptor antagonist.

Some embodiments of the present invention comprise a compound of the present invention and an immunomodulator is selected from the group consisting of pentamidine isethionate, autologous CD8+ infusion, α-interferon immunoglobulins, thymic peptides, IGF-1, anti-Leu3A, autovaccination, biostimulation, extracorporeal photophoresis, cyclosporin, rapamycin, FK-565, FK-506, GCSF, GM-CSF, hyperthermia, isoprinosine, IVIG, HIVIG, passive immunotherapy and polio vaccine hyperimmunization, where the compounds are present in amounts effective for treatment of HIV when used in a combination therapy.

Some embodiments of the present invention comprise a compound of the present invention and a secondary pharmaceutical agent selected from the group consisting of antifungals, antibacterials, anti-neoplastics, anti-protozoals, ceragenins, DNA polymerase inhibitors, DNA synthesis inhibitors, anti-HIV antibodies, HIV antisense drugs, IL-2 agonists, α-glucosidase inhibitors, purine nucleoside phosphorylase inhibitors, apoptosis agonists, apoptosis inhibitors, and cholinesterase inhibitors in amounts effective for treatment of HIV when used in a combination therapy.

Synthetic Processes

Generally, C-28 amine triterpene compounds of the present invention that exhibit superior anti-retroviral properties are derived from compounds of the structure:

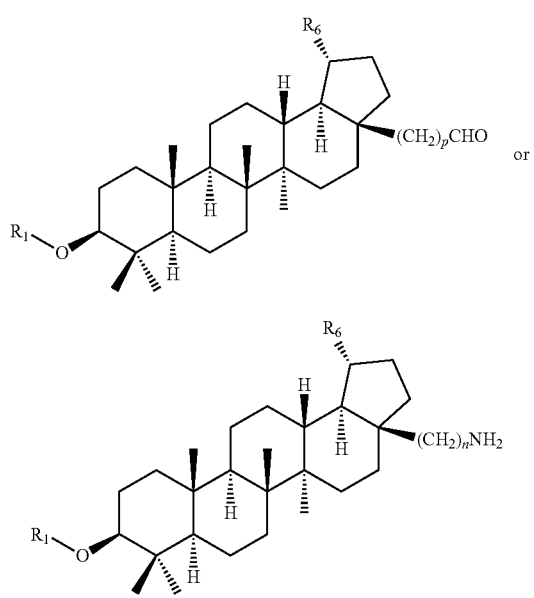

In some embodiments of the present invention the C-28 amine triterpene precursor is betulin. In some embodiments of the present invention the C-28 amine triterpene precursor is betulinic acid.

One process for synthesizing some compounds of the present invention includes providing a triterpene comprising a C-28 aldehyde or C-28 homologated aldehyde; and reductive animation of the triterpene comprising the C-28 aldehyde or the C-28 homologated aldehyde with an amine of the formula —NR$_2$R$_3$ to yield a C-28 amine triterpene. In some embodiments, the C-28 amine triterpene is a compound of Formula I. In some embodiments, the reductive animation is performed using sodium cyanoborohydride in an alcoholic solvent, for example, methanol or ethanol. In some embodiments, the reductive amination is performed using sodium triacetoxyborohydride in a mixed solvent system, for example, acetic acid in 1,2-dichloroethane or tetrahydrofuran. In some embodiments, the triterpene comprising a C-28 aldehyde or C-28 homologated aldehyde further comprises a C-3 alcohol. In some embodiments, the triterpene comprising a C-28 aldehyde or C-28 homologated aldehyde further comprises a substituted or unsubstituted $C_3$-$C_{20}$ alkanoyl, carboxyalkanoyl, carboxyalkenoyl, carboxylalkynoyl, carboxycyloalkylalkanoyl, carboxyalkylcycloalkylalkanoyl, carboxycyloalkylcarbonyl, carboxyalkylcycloalkylcarbonyl at the C-3 position. In some embodiments, the triterpene comprising a C-28 aldehyde or C-28 homologated aldehyde further composes a protecting group at the C-3 position, and the protecting group is removed after the reductive amination of the C-28 aldehyde or homologated aldehyde.

Another process for synthesizing some compounds of the present invention includes providing a triterpene comprising a C-28 primary amine or C-28 homologated primary amine; and reductive amination of the triterpene comprising the C-28 primary amine or the C-28 homologated primary amine with an aldehyde or a ketone of the formula R$_2$'COR$_3$', or an aldehyde acetal or ketone ketal of the formula R$_2$'C(OR$_x$)$_2$R$_3$' or R$_2$'C[O(CH$_2$)$_y$O]R$_3$' to yield a C-28 amine triterpene. R$_2$' is equal to R$_2$ with one less carbon if applicable; R$_3$' is equal to R$_3$ with one less carbon if applicable. R$_x$ is lower alkyl, e.g., $C_1$-$C_4$, and y is 2 or 3. In some embodiments, the C-28 amine triterpene is a compound of Formula I. In some embodiments, the reductive animation is performed using sodium cyanoborohydride in an alcoholic solvent, for example, methanol or ethanol. In some embodiments, the reductive amination is performed using sodium triacetoxyborohydride in a mixed solvent system, for example, acetic acid in 1,2-dichloroethane or tetrahydrofuran. In some embodiments, the triterpene comprising a C-28 primary amine or C-28 homologated primary amine further comprises a C-3 alcohol. In some embodiments, the triterpene comprising a C-28 primary amine or C-28 homologated primary amine further comprises a substituted or unsubstituted $C_3$-$C_{20}$ alkanoyl, carboxyalkanoyl, carboxyalkenoyl, carboxylalkynoyl, carboxycyloalkylalkanoyl, carboxyalkylcycloalkylalkanoyl, carboxycyloalkylcarbonyl, carboxyalkylcycloalkylcarbonyl at the C-3 position. In some embodiments, the triterpene comprising a C-28 primary amine or C-28 homologated primary amine further comprises a protecting group at the C-3 position, and the protecting group is removed after the reductive amination of the C-28 primary amine or homologated primary amine.

In some embodiments, a process for providing the triterpene comprising a C-28 aldehyde includes the steps of providing a triterpene comprising a C-3 alcohol and a C-28 alcohol; oxidizing the C-28 alcohol to a C-28 aldehyde; and acylating or alkylating the C-3 alcohol to yield a triterpene comprising a C-3 ester or ether and a C-28 aldehyde. The C-28 aldehyde can be homologated to yield the C-28 homologated aldehyde. In some embodiments, the homologation is repeated in succession to yield a C-28 aldehyde with the desired carbon chain length. In some embodiments, the triterpene comprising a C-3 alcohol and a C-28 alcohol is betulin.

In some embodiments, the oxidizing step comprises dissolving the triterpene in an organic solvent, for example, tetrahydrofuran (THF) or dimethylsulfoxide (DMSO); and contacting the triterpene with an oxidant, for example, 2-iodoxybenzoic acid (IBX), oxoammonium salts like 2,2,6,6-tetramethylpiperidine-1-oxyl (TEMPO) when used in combination with an N-halosuccinimide like TV-chlorosuccinimide (NCS), or by using DMSO in the presence of a suitable an activating agent, i.e., a Pfitzner-Moffat like oxidation wherein DMSO is activated by a carbodiimide like N,N-dicyclohexylcarbodiimide (DCC). In some embodiments, the acylating or alkylating the C-3 alcohol uses anhydrides, mixed anhydrides, acid halides, silyl halides, or a combination thereof.

In some embodiments, the homologation is performed by a Wittig reaction, wherein the C-28 aldehyde is converted into a C-28 enol ether, which is then hydrolyzed to yield a C-28 homologated aldehyde. Exemplary conditions for the Wittig reactions detailed herein include reactions wherein the triterpene is first dissolved in an organic solvent, for example, THE or DMSO; contacted with an oxidant, for example, IBX; poured into an aqueous solution, for example, water; extracted with an organic solvent; contacted with an ylide derived from either a phosphonium salt, for example a triarylalkylphosphonium salt, such as (methoxymethyl)triphenylphosphonium bromide, and a base, such as the sodium salt of dimethylsulfoxide in DMSO or potassium r-butoxide in THE or base like lithium diisopropylamide (EDA) or sodium hexamethyldisilazide (NaHMDS) in a solvent like THE and, then isolating the resultant product. Alternatively, arsonium salts may be used in Wittig-type reactions.

In some embodiments, the homologation is performed by a Henry reaction, wherein triterpenals are reacted with an anion derived from a nitroalkane in the presence of a suitable base. In some embodiments, the homologation is performed by a Knoevenagel condensation with, for example, malonic acid and malonic esters and diesters and malonic amides, cyanoacetic esters, and cyanoacetamides. Appropriate functional group manipulation then provides the triterpene precursors II or III, wherein p in II is an integer from 0 to 5.

In some embodiments, a process for providing the triterpene comprising a C-28 aldehyde includes the steps of providing a triterpene comprising a C-3 alcohol and a C-28 alcohol; diacylating the triterpene to yield a triterpene comprising a C-3 ester and a C-28 ester; selectively transesterifying the C-28 ester to a C-28 alcohol; and oxidizing the C-28 alcohol to a C-28 aldehyde to yield a triterpene comprising a C-3 ester and a C-28 aldehyde. The C-28 aldehyde can be homologated to yield a C-28 homologated aldehyde. In some embodiments, the homologation and hydrolysis are repeated in succession to yield a C-28 aldehyde with the desired carbon chain length. In some embodiments, the triterpene comprising a C-3 alcohol and a C-28 alcohol is betulin. In some embodiments, the homologation is performed using the Wittig reaction.

In some embodiments, a process for providing the triterpene comprising a C-28 aldehyde includes the steps of providing a triterpene comprising a C-3 alcohol and a C-28 carboxylic acid; protecting the C-3 alcohol: activating the C-28 carboxylic acid to generate a C-28 acid halide or mixed anhydride; amidating the activated C-28 acid halide or mixed anhydride to form a C-28 Weinreb amide; and reducing the C-28 amide to yield a triterpene comprising a protected C-3 alcohol and a C-28 aldehyde. In some embodiments, the protected C-3 alcohol is reduced concurrently with the C-28 amide to yield a triterpene comprising a C-3 alcohol and a C-28 aldehyde. The C-28 aldehyde can be homologated to yield a C-28 homologated aldehyde. In some embodiments, the homologation is repeated in succession to yield a C-28 aldehyde with the desired carbon chain length. In some embodiments, the triterpene comprising the C-3 alcohol and the C-28 carboxylic acid is derived from betulin or betulinic-acid.

In some embodiments, the C-3 alcohol is protected as an ester, for example, an acetate or benzoate. In some embodiments, the C-28 acid halide is formed using oxalyl chloride, oxalyl bromide, thionyl chloride, thionyl bromide, phosphorus oxychloride, phosphorus oxybromide, phosphorus trichloride, phosphorus tribromide, phosphorus pentachloride, or phosphorus pentabromide and the like. In some embodiments, the C-28 acid halide is formed in an inert solvent for example, benzene or dichloromethane, or without added solvent. In some embodiments, the C-28 mixed anhydride is formed using alkyl chloroformates, for example, ethyl chloroformate, in an inert solvent such as, for example, DCM or THF in the presence of a base such as TEA or N-methylmorpholine. In some embodiments, the C-28 Weinreb amide is formed when the C-28 acid halide or mixed anhydride is treated with N,O-dimethylhydroxylamine or N,O-dimethylhydroxylamine hydrochloride in a suitable solvent like DCM or THF in the presence of added base like TEA, DIPEA, or pyridine. In some embodiments, the C-28 amide is reduced using reducing agents such as, for example, lithium aluminum hydride or diisobutylaluminum hydride or combinations of lithium aluminum hydride and diisobutylaluminum hydride.

In some embodiments, a process for providing the triterpene comprising a C-28 primary amine includes the steps of providing a triterpene comprising a C-3 alcohol and a C-28 carboxylic acid; protecting the C-3 alcohol; activating the C-28 carboxylic acid to generate a C-28 acid halide; amidating the C-28 acid halide to form a C-28 amide; and reducing the C-28 amide to yield a C-28 primary amine. In some embodiments, the protected C-3 alcohol is reduced concurrently with the C-28 amide to yield a triterpene comprising a C-3 alcohol and a C-28 primary amine. In some embodiments, the process further includes the steps of protecting the C-28 primary amine; acylating the C-3 alcohol to generate a C-3 ester; and deprotecting the C-28 primary amine to yield a triterpene comprising a C-3 ester and a C-28 primary amine. In some embodiments, the triterpene comprising the C-3 alcohol and the C-28 carboxylic acid is derived from betulin or betulinic acid.

In some embodiments, a process for providing the triterpene comprising a C-28 homologated primary amine includes the steps of providing a triterpene comprising a C-3 alcohol and a C-28 aldehyde; performing a Henry reaction with the C-28 aldehyde to generate a C-28 nitro-olefin; optionally acylating the C-3 alcohol to generate a C-3 ester; and reducing the C-28 nitro-olefin to yield a triterpene comprising a C-3 ester and a C-28 homologated primary amine. In some embodiments, the triterpene comprising the C-3 alcohol and the C-28 aldehyde is derived from betulin. In some embodiments, the Henry reaction is performed by reacting the C-28 aldehyde with nitromethane employing a base such as, for example, ammonium acetate or piperidine in an appropriate solvent, for example, nitromethane, dichloromethane, toluene, and the like, to generate a Henry product intermediate nitro-alcohol, which further undergoes elimination to yield a C-28 nitro-olefin. In some embodiments, the C-28 nitro-olefin is reduced in a single step using, for example, nickel hydride prepared in situ from nickel II chloride and sodium borohydride in a mixed solvent like THF and methanol, or using sodium cyanoborohydride in conjunction with titanium chloride in an acidic alcoholic solvent such as, for example, ethanol containing 1 N HCl. In some embodiments, the C-28 nitro-olefin is reduced in a two-step process, wherein the intro-olefin is reduced to a intro-alkane using a borohydride reducing agent, for example, sodium borohydride, followed by reduction of the nitro group using a combination of iron and iron II chloride in ethanol and aqueous HCl.

In some embodiments, an alternative process for providing the triterpene comprising a C-3 ester or ether and a C-28 homologated primary amine includes the steps of providing a triterpene comprising a C-3 alcohol and a C-28 nitro-olefin; reducing the C-28 nitro-olefin to generate a C-28 homologated primary amine; protecting the C-28 homologated primary amine; acylating or alkylating the C-3 alcohol to generate a C-3 ester or ether; and de-protecting the protected C-28 homologated primary amine to yield a triterpene comprising a C-3 ester or ether and a C-28 homologated primary amine. In some embodiments, the triterpene comprising the C-3 alcohol and the C-28 nitro-olefin is derived from betulin using the Henry reaction.

In some embodiments, a process for providing a C-19 1-methyl-1-cyclopropyl triterpene aldehyde includes the steps of providing a triterpene comprising a C-19 2-isopropenyl and a C-28 aldehyde; and cyclopropanating the C-19 2-isopropenyl to yield a triterpene comprising a C-19 1-methyl-1-cyclopropyl and a C-28 aldehyde. In some embodiments, the C-28 aldehyde is homologated to yield a C-28 homologated aldehyde. In some embodiments, the homologation is repeated in succession to yield a C-28 aldehyde with the desired carbon chain length. In some embodiments, the triterpene comprising a C-19 2-isoprepenyl and a C-28 aldehyde is derived from betulin. In some embodiments, cyclopropanation of the C-19 2-isopropenyl is performed using addition of a Simmons-Smith reagent, generated from a dihalomethane like diiodomethane or dibromomethane and metal or metal couple like zinc or zinc-copper couple, or an alkylmetal halide or dialkyl metal like ethylzinc iodide of diethylzinc in an appropriate solvent like dichloromethane.

In some embodiments, the compound as described herein is an intermediate useful in the synthesis of the C-28 amine triterpene derivatives of Formula I.

The present invention has been described by way of example only, and it is to be recognized that modifications thereto which fall within the scope and spirit of the appended claims, and which would be obvious to a skilled person based upon the disclosure herein, are also considered to be included within the invention.

EXAMPLES

Example 1. General Method for the Syntheses of Compounds of Formula I by Reductive Animation of Triterpene C-28 Aldehydes and Homologated Aldehydes One process for preparing some compounds of Formula I can be achieved by reductive animation of triterpene C-28 aldehydes or C-28 homologated aldehydes II with the appropriate amine, $HNR_2R_3$ as shown in Scheme 1. Appropriate reductive amination conditions include but are not limited to reductants like sodium cyanoborohydride in an alcoholic solvent like methanol or ethanol, or sodium triacetoxyborohydride in a mixed solvent system composed of acetic acid in 1,2-dichloroethane or tetrahydrofuran. Compounds of Formula I can be directly obtained when Rr is a substituted or unsubstituted $C_3$-$C_{20}$ alkanoyl, carboxyalkanoyl, carboxyalkenoyl, carboxylalkynoyl, carhoxycyloalkylalkanoyl, carboxyalkylcycloalkylalkanoyl, carboxycyloalkylcarbonyl, carboxyalkylcycloalkylcarbonyl. When $R_1$ has a protected carboxyl ester protecting group like alkoxycarbonylalkanoyl, arylalkyloxycarbonylalkanoyl, trimethylsilylalkoxycarbonylalkanoyl, alkoxycarbonylalkenoyl, arylalkyloxycarbonylalkenoyl, trimethylsilylalkoxycarbonylalkenoyl alkoxycarbonylalkynoyl, arylalkyloxycarbonylalkynoyl, trimethylsilylalkoxycarbonylalkynoyl alkoxycarbonylcyloalkylalkanoyl, arylalkyloxycarbonylcyloalkylalkanoyl, trimethylsilylalkoxycarbonylcyloalkylalkanoyl, alkoxycarbonylalkylcycloalkylalkanoyl, arylalkyloxycarbonylalkylcycloalkylalkanoyl, trimethylsilylalkoxycarbonylalkylcycloalkylalkanoyl, alkoxycarbonyicyloalkylcarbonyl, arylalkyloxycarbonylcyloalkylcarbonyl, trimethylsilylalkoxycarbonylcyloalkylcarbonyl, alkoxycarbonylalkylcycloalkylcarbonyl, arylalkyloxycarbonylalkylcycloalkylcarbonyl, or trimethylsilylalkoxycarbonylalkylcycloalkylcarbonyl, the protecting group can be removed using standard methods as described in P. G. M. Wuts and T. W, Greene, *Greene's Protective Groups in Organic Synthesis,* 4th Edition, John Wiley & Sons, Inc., New York, 2007) providing compounds of Formula I.

Scheme 1. General Method for the Syntheses of Compounds of Formula I by Reductive Amination of Triterpene C-28 Aldehydes and Homologated Aldehydes

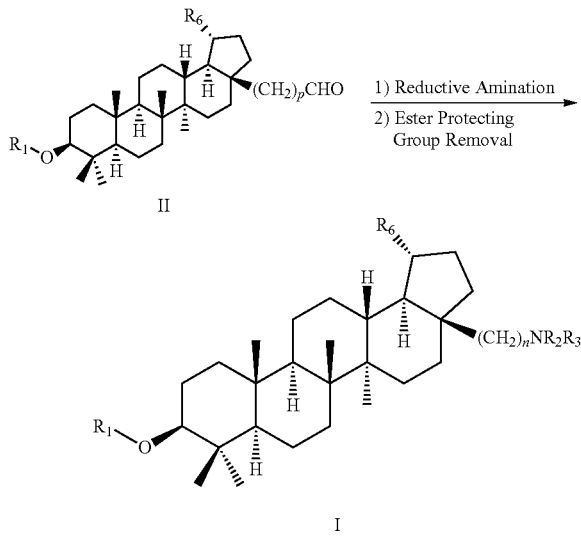

Example 2. General Method for the Syntheses of Compounds of Formula I by Reductive Animation of Triterpene C-28 Amines and Homologated Amines Another process for preparing compounds of Formula I can be achieved by reductive amination of triterpene C-28 amines or C-28 homologated amines III with the appropriate aldehyde or aldehyde acetal as shown in Scheme 2. Appropriate reductive amination conditions include but are not limited to reductants like sodium cyanoborohydride in an alcoholic solvent like methanol or ethanol, or sodium triacetoxyborohydride in a mixed solvent system composed of acetic acid in 1,2-dichloroethane or tetrahydrofuran. Compounds of Formula I are directly obtained when $R_1$ is a substituted or unsubstituted $C_3$-$C_{20}$ alkanoyl, carboxyalkanoyl, carboxyalkenoyl, carboxyalkynoyl, carboxycyloalkylalkanoyl, carboxyalkylcycloalkylalkanoyl, carboxycyloalkylcarbonyl, carboxyalkylcycloalkylcarbonyl. When $R_1$ has a protected carboxyl ester protecting group like alkoxycarbonylalkanoyl, arylalkyloxycarbonylalkanoyl, trimetliylsilylalkoxycarbonylalkanoyl, alkoxycarbonylalkenoyl, arylalkyloxycarbonylalkenoyl, trimethylsilylalkoxycarbonylalkenoyl alkoxycarbonylalkynoyl, arylalkyloxycarbonylalkynoyl, trimethylsilylalkoxycarbonylalkynoyl alkoxycarbonylcyloalkylalkanoyl, arylalkyloxycarbonylcyloalkylalkanoyl, trimethylsilylalkoxycarbonylcyloalkylalkanoyl, alkoxycarbonylalkylcycloalkylalkanoyl, arylalkyloxycarbonylalkylcycloalkylalkanoyl, trimethylsilylalkoxycarbonylalkylcycloalkylalkanoyl, alkoxycarbonylcyloalkylcarbonyl, arylalkyloxycarbonylcyloalkylcarbonyl, trimethylsilylalkoxycarbonylcyloalkylcarbonyl, alkoxycarbonylalkylcycloalkylcarbonyl, arylalkyloxycarbonylalkylcycloalkylcarbonyl, or trimethylsilylalkoxycarbonylalkylcycloalkylcarbonyl, the protecting group can be removed using standard methods as described in P. G. M. Wuts and T. W. Greene, *Greene's Protective Groups in Organic Synthesis*, 4th Edition, John Wiley & Sons, Inc., New York, 2007 providing compounds of Formula I.

Scheme 2. General Method for the Syntheses of Compounds of Formula I by Reductive Amination of Triterpene C-28 Amines and Homologated Amines

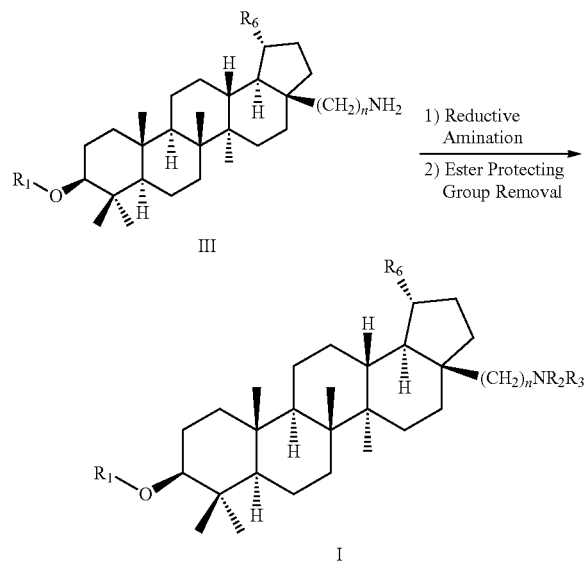

Example 3. General Syntheses of Triterpene C-28 Aldehyde and C-28 Homologated Aldehyde Intermediates from C-3, C-28 Triterpenediols One process for the general syntheses of the triterpene 028 aldehydes and 028 homologated aldehydes II is shown in Scheme 3. Reduction of the C-19, 20 double bond of triterpenes like betulin ($R_6$=2-propenyl) can be achieved with hydrogen and a catalyst derived from metals like nickel, palladium, platinum, or rhodium, or a hydride transfer reduction using 1,4-cyclohexadienes, formic acid, or ammonium formate in a solvent like dioxane or aqueous alcohols using a palladium catalyst like 10% palladium on carbon provides the dihydro-triterpenes ($R_6$=2-propyl). The syntheses of C-19 1-methyl-1-cyclopropyl triterpenes are described in accompanying schemes. The C-28 aldehydes V can be made available via oxidation of a C-3, C-28 triterpene diols IV. Oxidative conditions include but are not limited to reactions where a triterpene like betulin is first dissolved in an organic solvent, for example tetrahydrofuran (THF) and dimethylsulfoxide (DMSO); contacted with an oxidant, for example 2-iodoxybenzoic acid (IBX), oxoammonium salts like 2,2,6,6-tetramethylpiperidine-1-oxyl (TEMPO) when used in combination with an N-halosuccinimide like N-chlorosuccinimide (NCS), or by using DMSO in the presence of a suitable an activating agent, i.e., a Pfitzner-Moffat like oxidation wherein DMSO is activated by a carbodiimide like N,N-dicyclohexylcarbodiimide (DCC). Introduction of the $R_1$ grouping can be effected using standard acylation or alkylation conditions employing anhydrides, mixed anhydrides, acid halides, silyl halides, and the like, providing C-3 acylated or alkylated aldehydes IIa. Homologated aldehydes can be made available by Wittig reaction providing enoi ethers VIb, hydrolysis of which then provides the homologated aldehydes lib. Exemplary conditions for the Wittig reactions include but are not limited to reaction of II with an ylide derived from either a phosphonium halide salt, for example a triarylalkylphosphonium salt, such as (methoxymethyl)triphenylphosphonium bromide, and a base, such as the sodium salt of dimethylsulfoxide in DMSO or potassium t-butoxide in THF or base like lithium diisopropylamide (LDA) or sodium hexamethyldisilazide (NaHMDS) in a solvent like THF and, then isolating the resultant product. Alternatively, arsonium salts may be used in Wittig-type reactions. Repetition of the Wittig reaction/hydrolysis provides the aldehydes IIIc. Aldehydes of increasing chain length can be made available by the same or similar sequences. Alternative methods to affect homologation include a Peterson olefination of a suitably protected triterpenal II with a trialkylsilyl organometallic reagent like the organolithium reagents derived from (methoxymethyl)trimethylsilane, (phenylthiomethyl)trimethylsilane, (trimethylsilyl)acetonitrile, 2-trimethylsilyl-1,3-dithiane, or ethyl trimethylsilylacetate, provides for an additional method of homologation. Homologation at C-28 can also achieved via a Henry reaction wherein triterpenals II or V are reacted with an anion derived from a nitroalkane like nitromethane in the presence of a suitable base like pentylamine, piperidine, or ammonium acetate. Other methods suitable for homologation of triterpenals II or V include Knoevenagel condensations with malonic acid and malonic esters and diesters and malonic amides, cyanoacetic esters, and cyanoacetamides. Additional conditions useful for the homologation of triterpenals II or V are reported in standard organic textbooks like, for example, M. B. Smith and J. March, *March's Advanced Organic Chemistry: Reactions, Mechanisms, and Structure*, 5th Edition, John Wiley and Sons, Inc., New York, 2001, F. A. Carey and R. J. Sundherg, *Advanced Organic Chemistry Part B: Reactions and Synthesis*, 4th Edition, Kluwar Academic/Plenum Publishers, New York, 2001, or R. C. Larock, *Comprehensive Organic Transformations: A Guide to Functional Group Preparations*, 2nd Edition, John Wiley and Sons, Inc., New York, 1999.

Scheme 3. General Syntheses of Triterpene C-28 Aldehyde and C-28 Homologated Aldehyde Intermediates from C-3, C-28 Triterpenediols

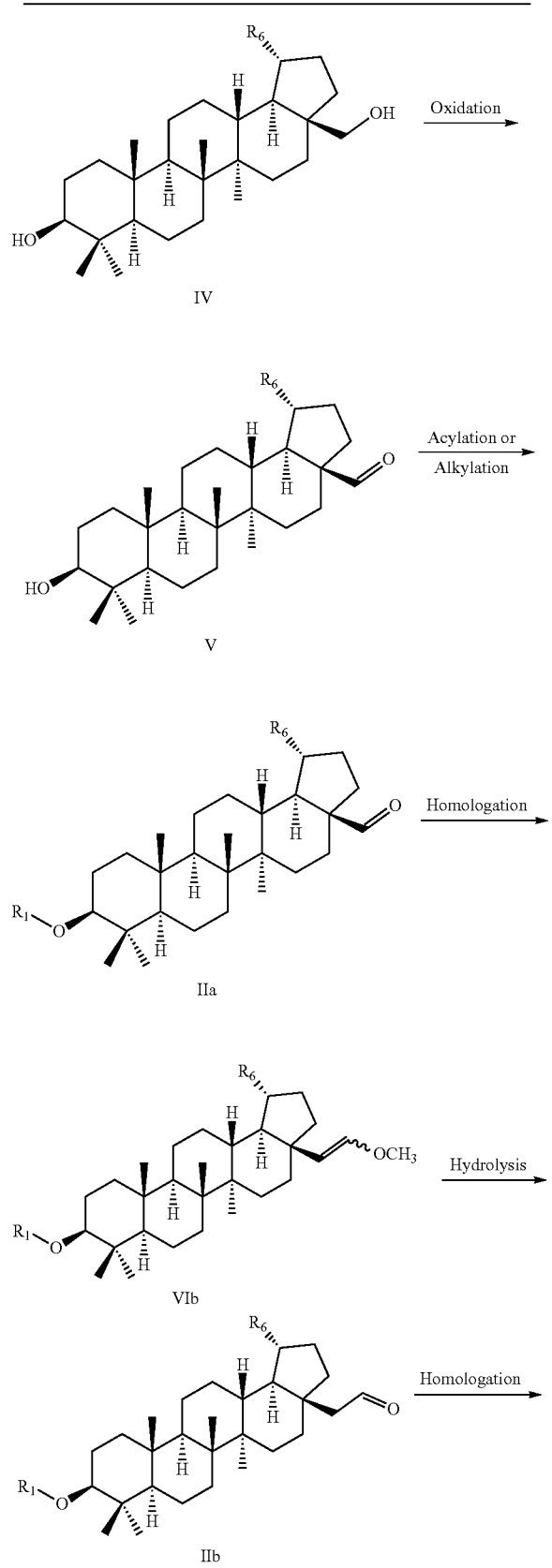

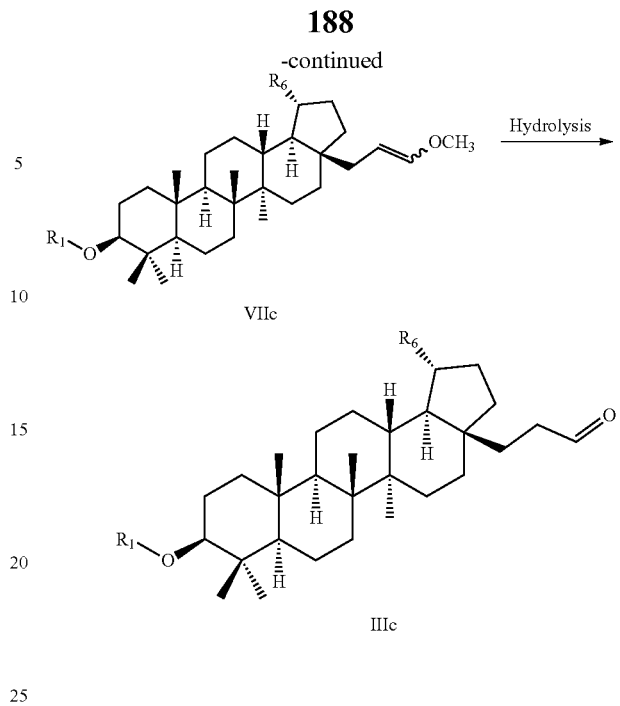

Example 4. General Reaction Scheme for Preparing C-28 Aldehyde and Homologated Aldehyde Intermediates from Triterpenediols IV Via the Selective Transesterification of a C-28 Ester to a C-28 Alcohol, Oxidation to a C-28 Aldehyde, and Homologation An alternate route to C-28 aldehyde and homologated intermediates is shown in Scheme 4. Triterpendiols IV can be converted to the C-3, C-28 diesters VII wherein RE is lower alkyl, e.g., methyl, or aryl, e.g., phenyl. Reagents suitable for diester formation include acid halides or acid anhydrides like acetyl chloride, acetic anhydride, or monoester acid halides or anhydrides derived from cyclic anhydrides like methyl 3,3-dimethylglutaryl chloride in the presence of a base like triethylamine (TEA) or pyridine in an inert solvent like dichloromethane (DCM) or tetrahydrofuran (THE) with or without addition of a catalyst like 4-(dimethylamino)pyridine (DMAP). Alternatively, a mixed anhydride can be prepared from the desired carboxylic acid and an acid chloride like pivaloyl chloride or 2,6-dichlorobenzoyl chloride in an inert solvent like DCM or THE in the presence of a base like TEA, N,N-diisopropylethylamine (DIPEA), or pyridine with or without addition of a catalyst like DMAP. Selective transesterification can be achieved with metal alkoxides in alcohol like magnesium methoxide in methanol or aluminum isopropoxide in isopropanol to form C-28 alcohols IX, Oxidation of IX to aldehydes X can be accomplished with the oxidants described in Example 3. Alternate oxidants include Swern type conditions using oxalyl chloride, dimethylsulfoxide, and a base like triethylamine in a solvent like dichloromethane, or chromium based oxidants like chromium trioxide in pyridine, pyridinium dichromate, or Jones' Reagent. Homologation of X to XI is achieved by a Wittig reaction of X with ylides derived from phosphonium salts as described in Example 3.

Scheme 4: General Reaction Scheme for Preparing C-28 Aldehyde and Homologated Aldehyde Intermediates from Triterpenediols IV via the Selective Transesterification of a C-28 Ester to a C-28 Alcohol, Oxidation to a C-28 Aldehyde, and Homologation

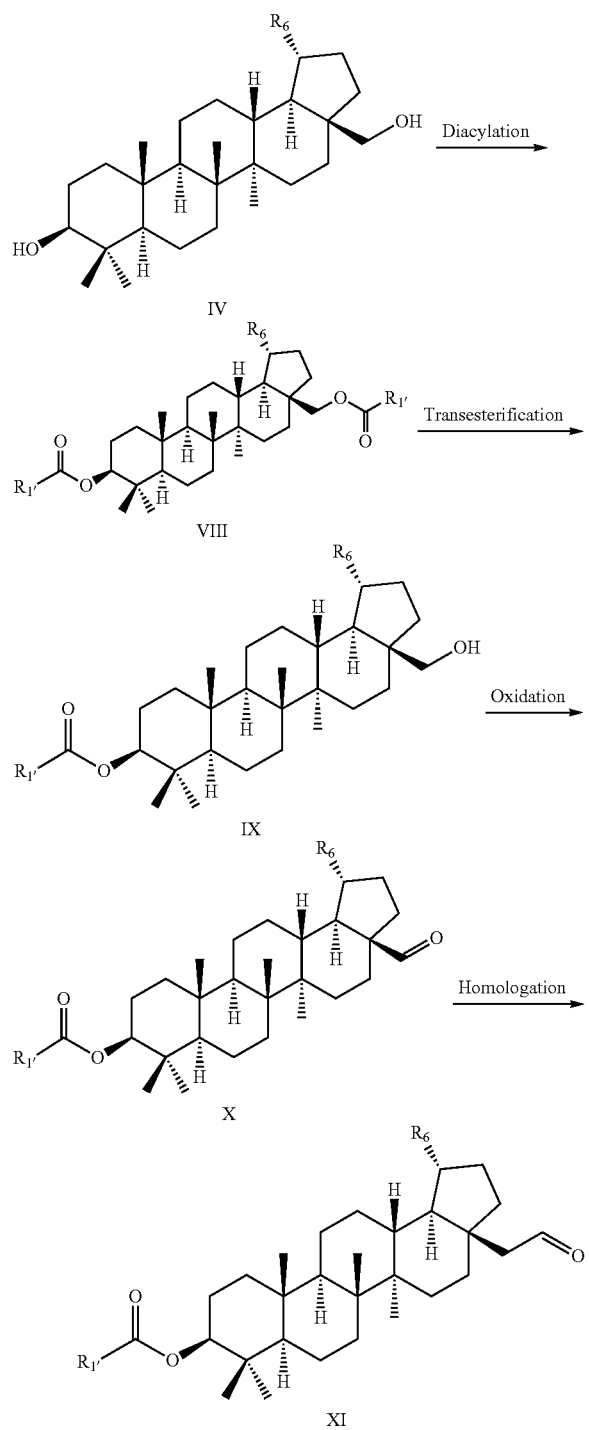

Example 5. Alternative Route to C-28 Aldehyde and Homologated Aldehyde Intermediates Via C-28 Triterpene Carboxylic Acids Example 5 describes an alternate route to C-28 aldehyde and homologated intermediates starting from C-28 triterpene carboxylic acids as shown in Scheme 5. Reduction of the C-19,20 double bond of triterpenes like betulin ($R_6$=2-propenyl) can be achieved with hydrogen and a catalysts derived from metals like nickel, palladium, platinum, or rhodium, or a hydride transfer reduction using 1,4-cyclohexadiene, formic acid, or ammonium formate in a solvent like dioxane or aqueous alcohols using a palladium catalyst like 10/palladium on carbon provides the dihydrotriterpenes ($R_6$=2-propyl). The C-3 alcohol group of a triterpene carboxylic acid XII can be protected as an ester like acetate or benzoate using conditions reported in P. G. M. Wuts and T. W. Greene, *Greene's Protective Groups in Organic Synthesis,* 4th Edition, John Wiley & Sons, Inc., New York, 2007 providing XIII. The C-28 carboxylic acid group can be activated as an acid halide or mixed anhydride XIV. Reagents suitable for formation of an acid halide include oxalyl chloride, oxalyl bromide, thionyl chloride, thionyl bromide, phosphorus oxychloride, phosphorus oxybromide, phosphorus trichloride, phosphorus tribromide, phosphorus pentachloride, or phosphorus pentabromide and the like. Formation of the acid halide can be performed in an inert solvent like benzene or DCM or without added solvent. Reagents suitable for formation of mixed anhydrides include alkyl chloroformates like ethyl chloroformate in an inert solvent like DCM or THF in the presence of a base like TEA or N-methylmorpholine. The Weinreb amides XV are formed when the acid halides or mixed anhydrides XIV are treated with N,O-dimethylhydroxylamine or N,O-dimethylhydroxylamine hydrochloride in a suitable solvent like DCM or THF in the presence of added base like TEA, DIPEA, or pyridine. The mixed anhydrides are generally formed in situ and treated with the N,O-dimethylhydroxylamine or N,O-dimethylhydroxylamine hydrochloride without prior isolation of the mixed anhydride. Reduction of XV to triterpene C-28 aldehydes V can be achieved with reducing agents like lithium aluminum hydride or diisobutylaluminum hydride or combinations of lithium aluminum hydride and diisobutylaluminum hydride. The C-3 ester group can also be reduced concurrent with the reduction of the C-28 Weinreb amide. The triterpene C-28 aldehydes V obtained are protected and homologated as described in Examples 3 and 4.

Scheme 5. Alternative Route to C-28 Aldehyde and Homologated Aldehyde Intermediates via C-28 Triterpene Carboxylic Acids

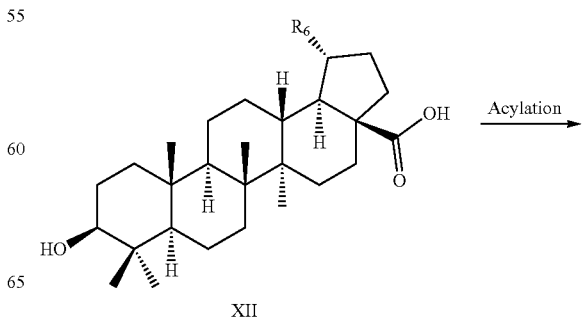

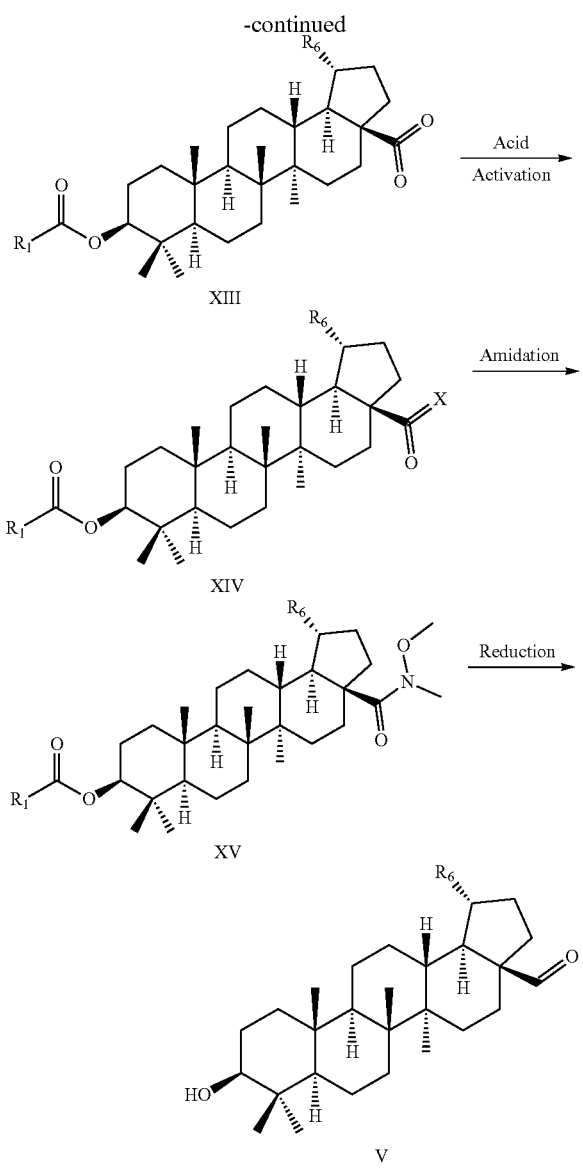

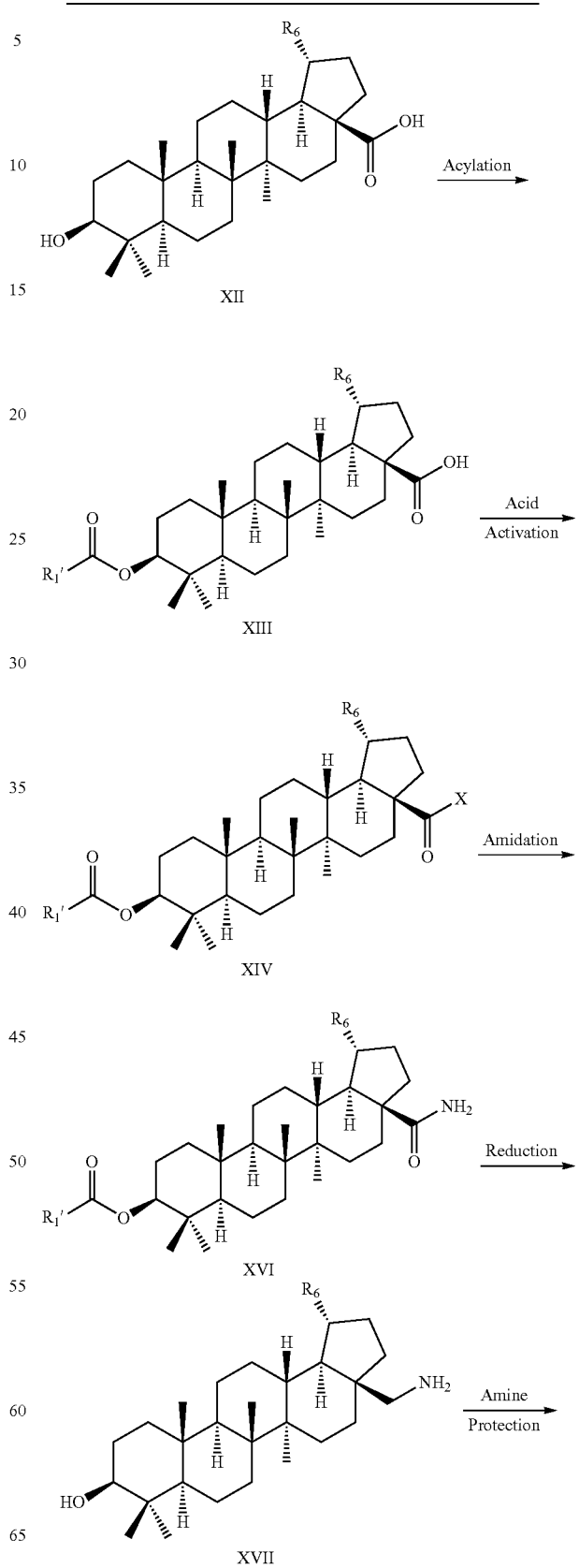

Scheme 6. General Procedure for Preparing C-28 Triterpenamines via C-28 Triterpene Carboxylic Acids Example 6. General Procedure for Preparing C-28 Triterpenamines Via C-28 Triterpene Carboxylic Acids A general method for preparing C-28 triterpenamines from C-28 triterpene carboxylic acids is shown in Scheme 6. Addition of ammonia to acid halides prepared as described in Example 5 provides C-28 triterpenecarboxamides XVI. Reduction as described in Example 5 provides the C-28 triterpenamines XVII which are protected using methods that are described in P. G. M. Wuts and T. W. Greene, *Greene's Protective Groups in Organic Synthesis,* 4th Edition, John Wiley & Sons, Inc., New York, 2007 providing protected amines XVIII. Introduction of the C-3$R_1$ esters can be achieved using methods described in Example 3 providing XIX. Removal of the amine-protecting group using standard methods provides the triterpenamines XX. $R_z$ can be lower alkyl, arylalkyl, t-butyl, allyl, trialykylsilyl, trialkylsilylalkyl, aryldialkylsilyl, triarlysilyl, aryldialkylsilylalkyl, or triarlysilylalkyl.

-continued

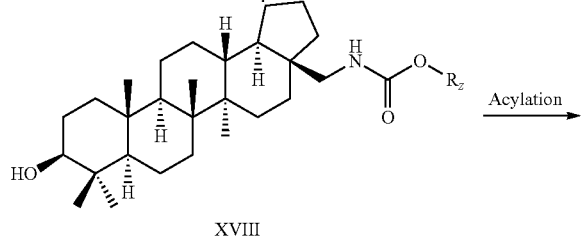

XVIII

XIX

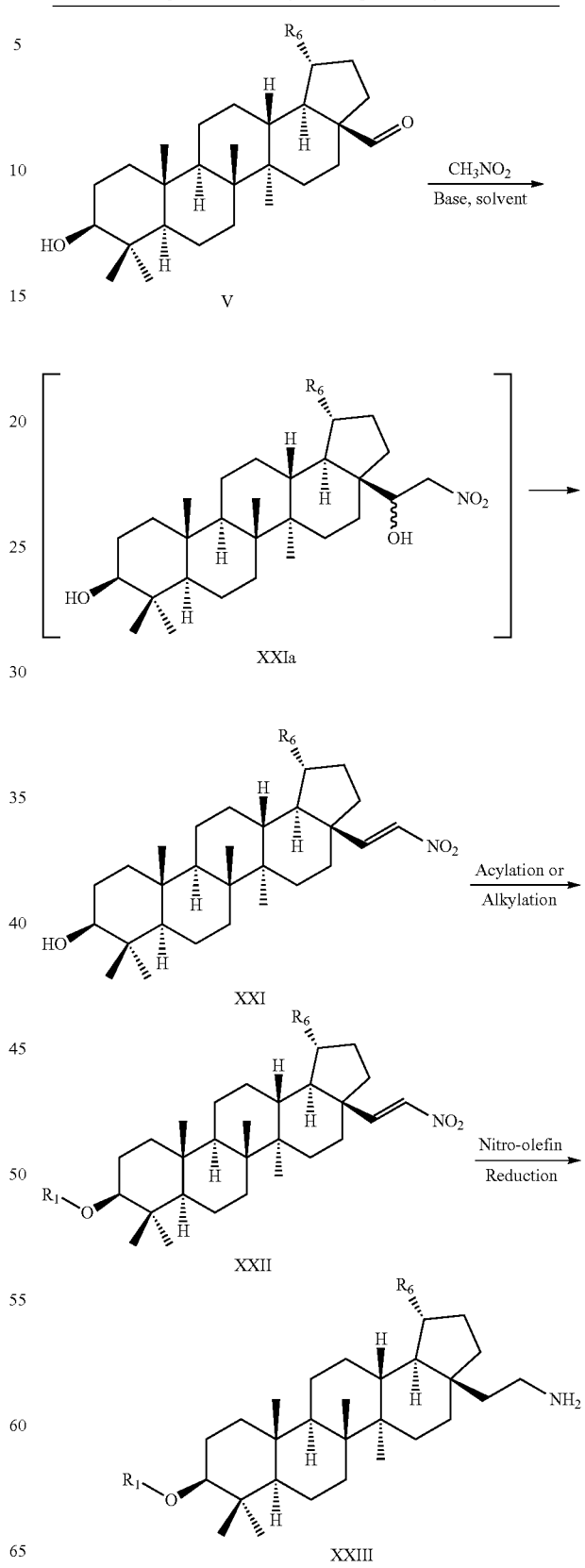

Scheme 7. General Preparation of C-28 Homologated Triterpenamines via Triterpene C-28 Aldehydes Using the Henry Reaction

Example 7. General Preparation of C-28 Homologated Triterpenamines Via Triterpene C-28 Aldehydes Using the Henry Reaction A general procedure for preparing C-28 homologated triterpenamines is shown in Scheme 7. Reaction of triterpenals V with nitromethane employing a base like ammonium acetate or piperidine in an appropriate solvent like nitromethane, dichloromethane, toluene, and the like provides the intermediate Henry product XXIa that undergoes elimination under the reaction conditions providing the nitro-olefins XXI. Introduction of the $R_1$ grouping can be achieved via methods described above providing the acylated or alkylated C-3 triterpene nitro-olefins XXII. Reduction of the nitro-olefin can be achieved in a single step using nickel hydride, prepared in situ from nickel II chloride and sodium borohydride in a mixed solvent like THF and methanol (MeOH), or using sodium cyanoborohydride in conjunction with titanium chloride in an acidic alcoholic solvent like ethanol containing 1 N HCl providing the amines XXI. Alternatively, a two-step process can be used wherein the olefin is reduced to the nitro-alkane using a borohydride reducing agent like sodium borohydride followed by reduction of the nitro group using a combination of iron and iron II chloride in ethanol and aqueous HCl providing XXIII.

Example 8. Alternative General Preparation of C-28 Homologated Triterpenamines Via Triterpene C-28 Aldehydes Using the Henry Reaction An alternative approach to C-28 homologated triterpenamines XXIII is shown in Scheme 8. Reduction of the nitro-olefin XXI can be achieved using hydride reducing agents like LAH providing XXIV. The amine of XXIV can be protected using carbamate protecting groups like t-butoxycarbonyl, allyloxycarbonyl, and the like as described in P. G. M. Wuts and T. W. Greene, *Greene's Protective Groups in Organic Synthesis*, 4th Edition, John Wiley & Sons, Inc., New York, 2007. The C-3 alcohol of XXV can be alkylated or acylated as described in the above examples providing XXVI. The C-28 homologated triterpenamines XXII can be obtained using standard amine deprotection methods as described in P. G. M. Wuts and T. W. Greene.

Scheme 8. Alternative General Preparation of C-28 Homologated Triterpenamines via Triterpene C-28 Aldehydes Using the Henry Reaction

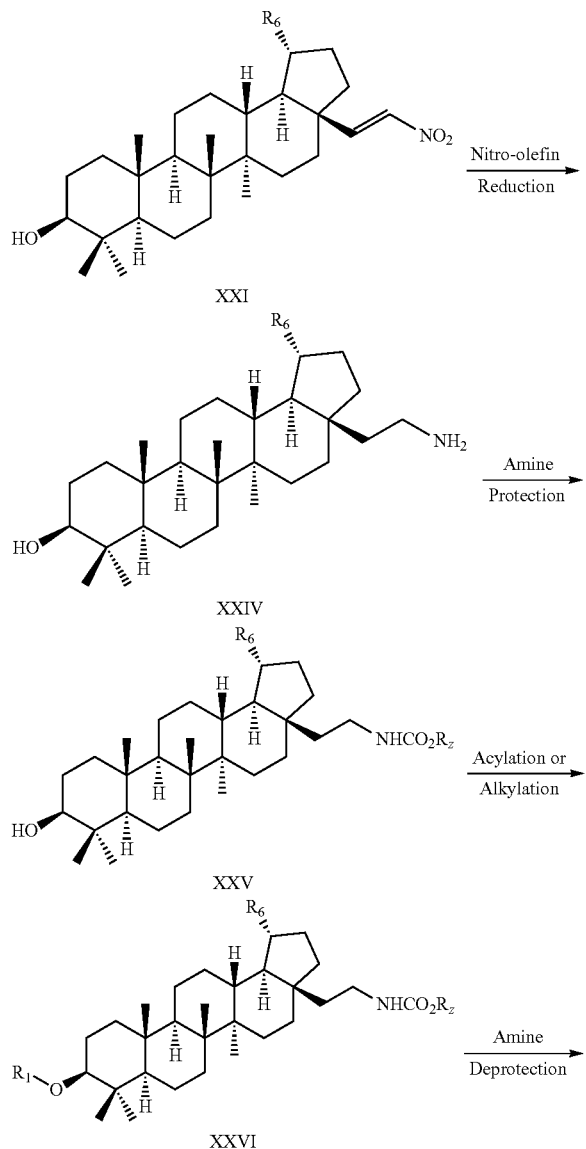

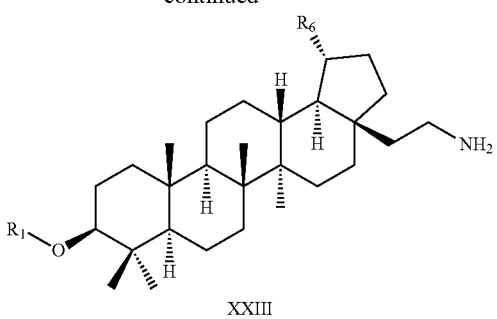

Example 9. General Procedure for the Preparation of C-19 1-Methyl-1-cyclopropyl Triterpene Aldehydes and Homologated Aldehydes Scheme 9 outlines a general route to C-19 1-methyl-1-cyclopropyl triterpene aldehydes and homologated aldehydes. Cyclopropanation of C-19 2-isopropenyl triterpenals IIa can be achieved via addition of a Simmons-Smith reagent, generated from a dihalomethane like diiodomethane or dibromomethane and metal or metal couple like zinc or zinc-copper couple, or an alkylmetal halide or dialkylmetal like ethylzinc iodide of diethylzinc in an appropriate solvent like dichloromethane providing the 1-methyl-1-cyclopropyl triterpene aldehydes XXVII. Additional conditions useful for the preparation of 1-methyl-1-cyclopropyl triterpene derivatives are reported in standard organic textbooks like, for example, M. B. Smith and J. March, *March's Advanced Organic Chemistry: Reactions, Mechanisms, and Structure*, $5^{th}$ Edition, John Wiley and Sons, Inc., New York, 2001, F. A. Carey and R. J. Sundberg, *Advanced Organic Chemistry Part B: Reactions and Synthesis*, $4^{th}$ Edition, Kluwar Academic/Plenum Publishers, New York, 2001, or R. C. Larock, *Comprehensive Organic Transformations: A Guide to Functional Group Preparations*, $2^{nd}$ Edition, John Wiley and Sons, Inc., New York, 1999. Homologated C-19 1-methyl-1-cyclopropyl triterpene aldehydes XXIX can be obtained using the methods described in the above examples.

Scheme 9. General procedure for the Preparation of C-19 1-Methyl-1-cyclopropyl Triterpene Aldehydes and Homologated Aldehydes.

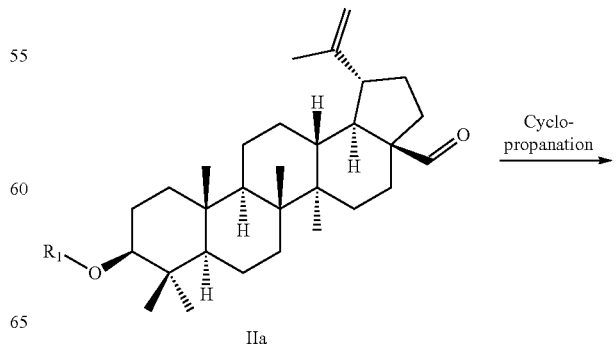

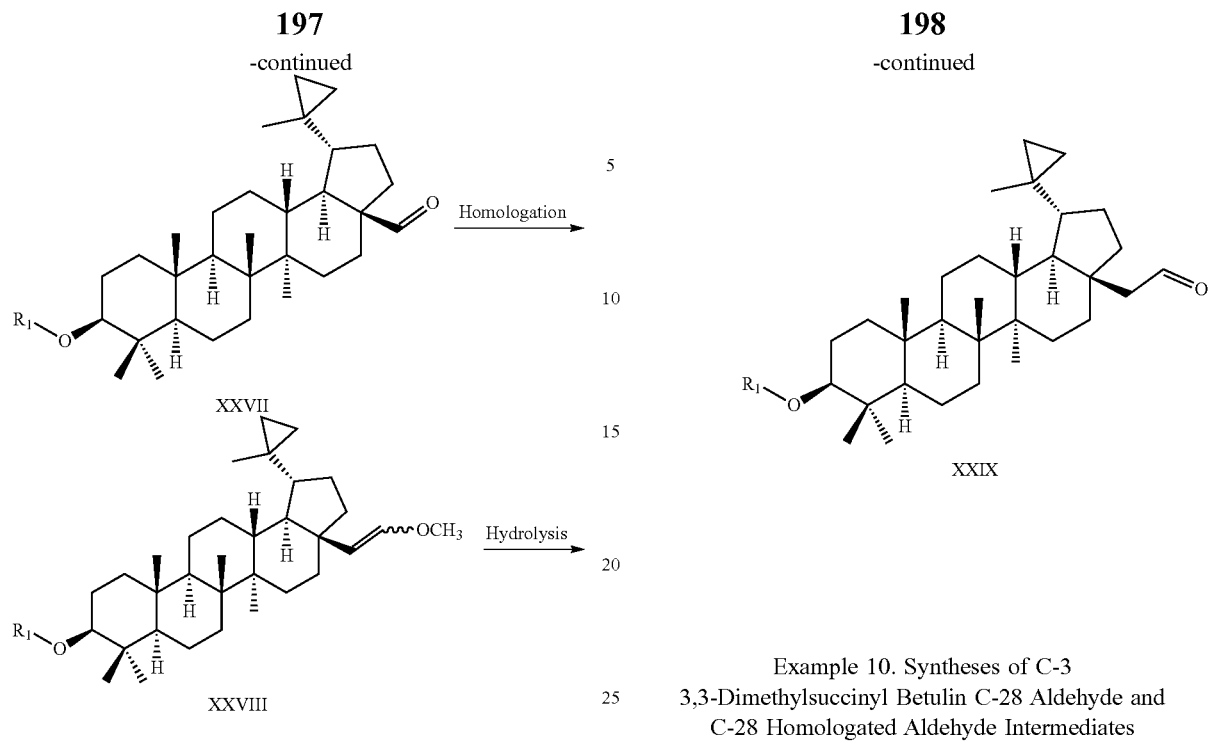
Example 10. Syntheses of C-3 3,3-Dimethylsuccinyl Betulin C-28 Aldehyde and C-28 Homologated Aldehyde Intermediates
Scheme 10. Syntheses of C-3 Benzyl 3,3-Dimethylsuccinyl Betulin C-28 Aldehyde (4), 3,3-Dimethylsuccinyl Betulin C-28 Aldehyde (3), and C-28 Homologated Aldehyde Intermediates 6a, 6b, and 7b
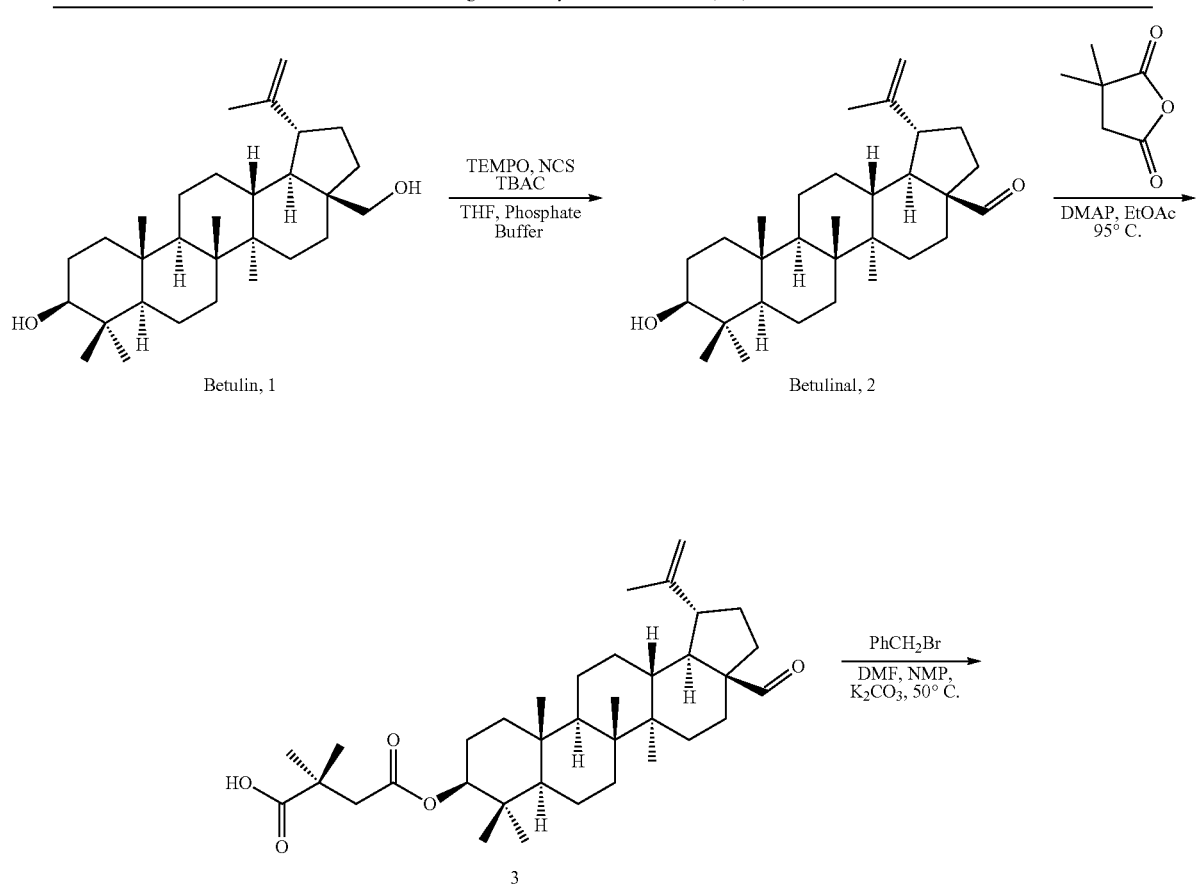

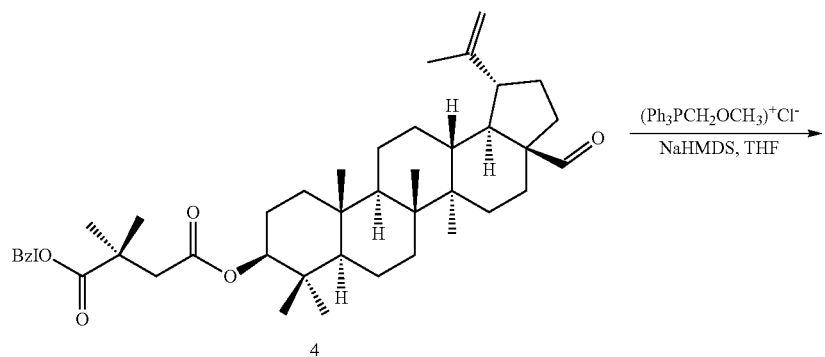
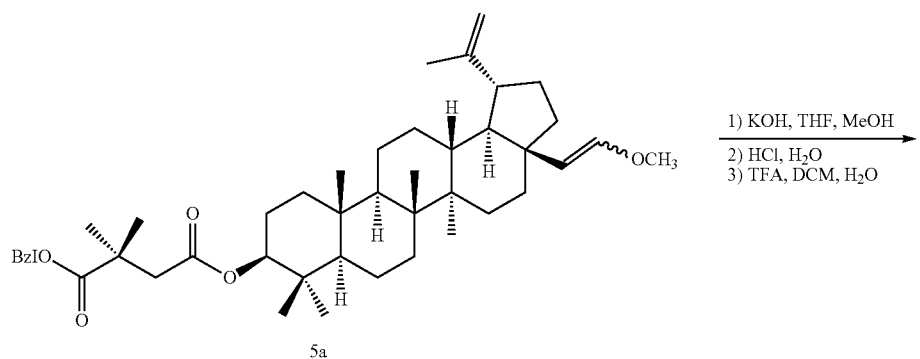
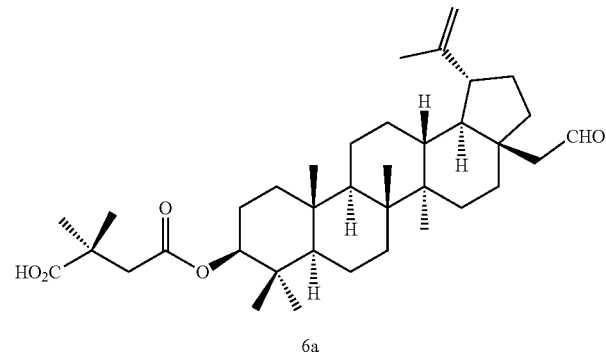
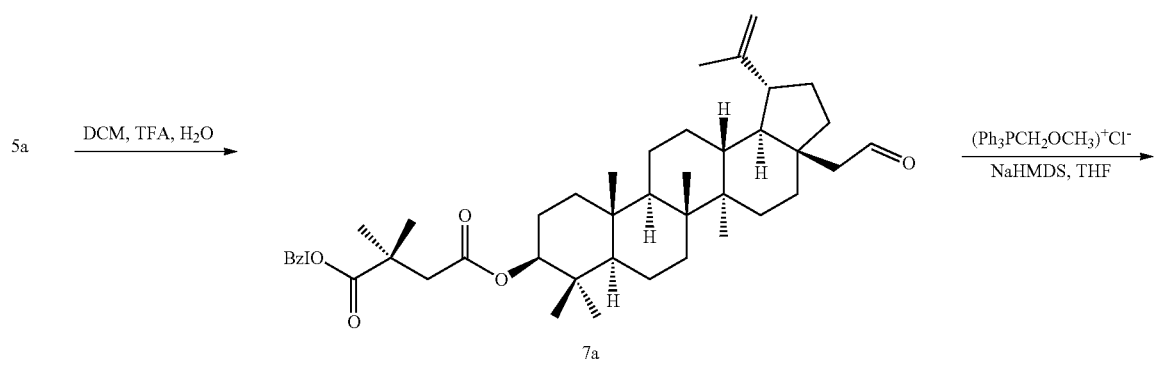

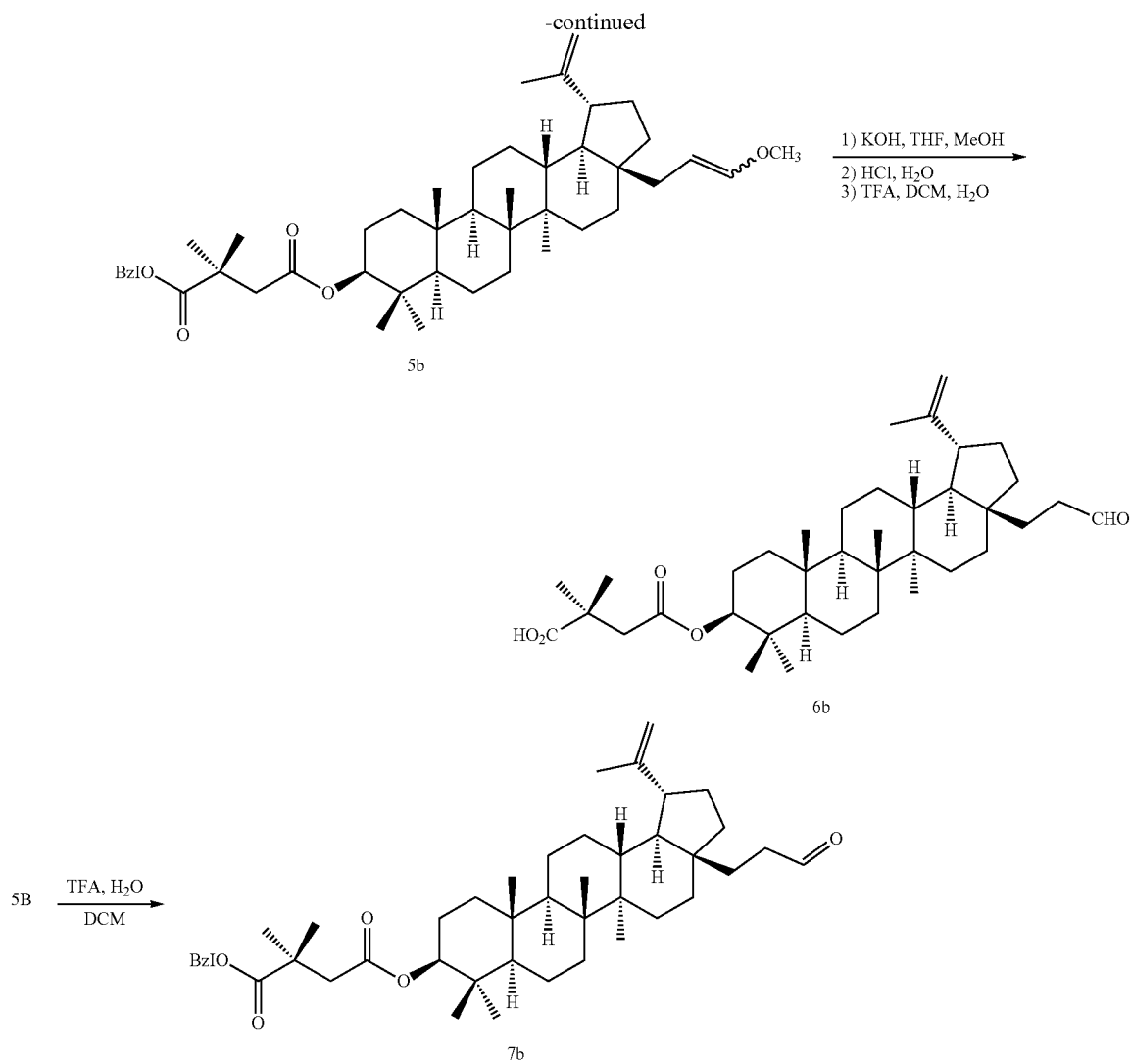

Preparation of (3β)-3-Hydroxylup-20(29)-en-28-al, Betulinal (2) Via TEMPO/NCS. To a rapidly stirred mixture of betulin (1) (50.0 g, 113 mmol) in THF (1 L) and 0.5 M NaHCO$_3$/0.05 M K$_2$CO$_3$ (1 L) was added sequentially TBAC (3.12 g, 11.2 mmol, TEMPO (6.50 g, 41.6 mmol), NCS (63.0 g, 472 mmol). After stirring at rt for 16 h, EtOAc (400 mL) was added. The organic phase was removed and the aqueous phase extracted with EtOAc (600 mL and 250 mL). The combined organic phases are washed with 10% Na$_2$S$_2$O$_3$ (2×300 mL), dried (Na$_2$SO$_4$), filtered, and coned in vacuo to provide a yellow-orange solid that was dry-loaded onto silica gel (70 g) and purified by silica gel (1.3 kg) FCC (1-10% EtOAc/hexane gradient) providing 2 (36.9 g, 74%) as a colorless solid: mp 155-156° C.; IR (solid ATR) ν (OH) 3399 (br), ν (C:O) 1701 cm$^{-1}$; H NMR (360 MHz, CDCl$_3$) δ 9.65 (s, 1H), 4.73 (s, 1H), 4.60 (s, 1H), 3.16 (dd, J=10.9 and 5.3 Hz, 1H), 2.85 (dt, J=11.2 and 5.7 Hz, 1H), 2.07-0.64 (m, 43H); $^{13}$C NMR (62.9 MHz, CDCl$_3$) δ 207.7, 149.7, 110.2, 78.9, 59.2, 55.2, 50.4, 48.0, 47.4, 42.5, 40.7, 38.77, 38.67, 38.61, 37.1, 34.2, 33.1, 29.8, 29.2, 28.7, 27.9, 27.3, 25.4, 20.7, 18.9, 18.2, 16.1, 15.8, 15.3, 14.2.

Alternative Preparation of (3β)-3-Hydroxylup-20(29)-en-28-al, Betulinal (2) Via TEMPO/NCS. To a mixture of betulin (1) (6.0 g, 13.6 mmol) in THF (120 mL) and 0.5 M NaHCO$_3$/0.5 M K$_2$CO$_3$ buffer (120 mL) at rt were added successively tetra-n-butylammonium bisulfate (0.6 g, 1.13 mmol), TEMPO (0.78 g, 5.0 mmol), and NCS (7.56 g, 56.6 mmol). After stirring at rt for 18 h, the mixture was extracted with EtOAc (3×250 mL) and the combined organic extracts washed with 10% Na$_2$S$_2$O$_3$ (150 mL), brine (100 mL), dried (Na$_2$S$_{O4}$), filtered, and coned in vacuo. The crude product was purified by column chromatography using 0-20% EtOAc in hexanes as eluent to provide 2 (4.7 g, 78.7%) as a white solid with spectral properties consistent with 2 obtained above.

Preparation of Betulinal (2) Via IBX. Under an inert atmosphere, IBX (23.73 g, 84.7 mmol, 1.5 equivalents) was added to a solution of betulin (1) (25.0 g, 56.5 mmol) dissolved in THF (500 mL) and DMSO (500 mL) and stirred for 16 h at rt. Evaporation in vacuo of the THF yielded a clear solution that was poured into water (5 L) and stirred. The resulting suspension was extracted with TBME (3×1.5 L). The TBME extracts are combined, dried (Na$_2$SO$_4$), filtered, and coned in vacuo to yield a colorless foam. The foam was re-dissolved in DCM (250 mL) and dry-loaded onto silica gel (100 g). Purification by FCC using 1-10% EtOAc/hexane gradient provided the desired aldehyde 2 isolated as a colorless solid with spectral data consistent with that obtained above.

Preparation of Betulinal (2) via Pfitzner-Moffat Oxidation. DCC (1.38 g, 6.78 mmol) and phosphoric acid (0.11 g 1.13 mmol) are added to a solution of betulin (1) (1.00 g, 2.26 mmol) in THF/DMSO 1:1 (20 mL) under an inert atmosphere. The resulting solution was stirred at rt for 120 h under nitrogen. Evaporation of THF in vacuo yielded a clear solution that was poured into EtOAc (100 mL) to induce precipitation. The resultant precipitate was removed by filtration under vacuum. The filtrate was washed with water (2×200 mL), dried (MgSO$_4$), filtered, and coned in vacuo to yield a solid. The solid was dry-loaded onto silica gel (5 g) and purified by dry-flash chromatography using 2-12% EtOAc/hexane gradient. The desired aldehyde 2 was isolated as a colorless solid with spectral data consistent with that obtained above.

Preparation of (3β)-3-Hydroxylup-20(29)-en-28-al, 3-(1-Hydrogen 2,2-Dimethylbutanedioate) (3): To a solution of betulinal (2) (4.41 g, 10.00 mmol) in EtOAc (50 mL) under an inert atmosphere was introduced 2,2-dimethylsuccinic anhydride (1.41 g, 11.00 mmol) and DMAP (1.34 g, 11.00 mmol). The reaction mixture was heated at 95° C. for 72 h; additional 2,2-dimethylsuccinic anhydride (0.64 g, 5.00 mmol) was added after 24 and 48 h at this temperature. After cooling to rt, the reaction mixture was diluted with EtOAc (50 mL), washed with 1 M citric acid (20 mL), and deionized water (20 mL). The organic phase was dried (Na$_2$SO$_4$), filtered, and coned in vacuo to furnish carboxylic acid 3 (5.12 g, 9.01 mmol, 90%) as a colorless amorphous solid: TLC $R_f$ 0.71 (1:1 heptane/EtOAc), 0.22 (4:1 heptane/EtOAc); IR (solid, ATR golden-gate) 2939, 1726, 1701, 1641, 1450, 1369, 1320, 1266, 1199, 1132, 1002, 978 cm$^{-1}$; $^1$H NMR (400 MHz, CDCl$_3$) δ 9.66 (d, J=1.5 Hz, 1H), 4.75 (d, J=1.8 Hz, 1H), 4.62 (s, 1H), 4.51-4.44 (m, 1H), 2.91-2.81 (m, 1H), 2.67 (d, J=15.7 Hz, 1H), 2.55 (d, J=15.7 Hz, 1H), 2.10-1.95 (m, 2H), 1.93-1.80 (m, 1H), 1.79-0.69 (m, 46H); $^{13}$C NMR (100.6 MHz, CDCl$_3$) δ 207.16, 183.25, 170.87, 149.62, 110.17, 81.44, 59.27, 55.35, 50.28, 47.97, 47.48, 44.66, 42.48, 40.77, 40.44, 38.61, 38.35, 37.65, 37.00, 34.17, 33.16, 29.77, 29.16, 28.72, 27.84, 25.55, 25.40, 24.93, 23.52, 20.69, 18.92, 18.07, 16.42, 16.11, 15.84, 14.19; LCMS, 99% ELS, m/z 591 [M+Na]$^+$ 5%, m/z 423 [M+H−HO$_2$CCMe$_2$CH$_2$CO$_2$H]$^+$ 100%.

Preparation of (3β)-3-Hydroxylup-20(29)-en-28-al, 3-(1-Phenylmethyl 2,2-Dimethylbutanedioate) (4): To a solution of carboxylic acid 3 (4.14 g, 7.28 mmol) in 2:1 NMP/DMF (35 mL) under an inert atmosphere was added benzyl bromide (1.0 mL, 8.73 mmol) and K$_2$CO$_3$ (4.01 g, 29.1 mmol). The reaction mixture was stirred at 50° C. for 4 h. After cooling to rt, the reaction mixture was diluted with water (40 mL) and EtOAc (150 mL). The organic phase was washed with brine (50%, 20 mL), dried (Na$_2$SO$_4$), filtered, and concd in vacuo furnishing a colorless oil. Purification by silica gel FCC (1-7% EtOAc/heptane gradient) furnished ester 4 (4.28 g, 6.50 mmol, 89%) as a colorless solid: TLC $R_f$ 0.24 (9:1 heptane % EtOAc); IR (film, ATR) 2942, 1729, 456, 1375, 1302, 1260, 1220, 1174, 1141, 1126, 1002, 978, 881 cm$^{-1}$; $^1$H NMR (400 MHz, CDCl$_3$) δ 9.68 (s, 1H), 7.37-7.30 (m, 5H), 5.13 (s, 2H), 4.77 (s, 1H), 4.64 (s, 1H), 4.48 (dd, J=10.5 and 5.6 Hz, 1H), 2.95 (dt, J=11.3 and 5.9 Hz, 1H), 2.67 (d, J=16.1 Hz, 1H), 2.60 (d, J=16.1 Hz, 1H), 2.12-1.97 (m, 2H), 1.95-1.82 (m, 1H), 1.79-1.32 (m, 18H), 1.30 (s, 6H), 1.27-1.07 (m, 6H), 0.97 (s, 3H), 0.96-0.92 (m, 1H), 0.91 (s, 3H), 0.91-0.84 (m, 1H), 0.83 (s, 6H), 0.80 (s, 3H), 0.77 (br d, J=9.8 Hz, 1H); $^{13}$C NMR (100.6 MHz, CDCl$_3$) δ 206.59, 176.40, 170.97, 149.62, 139.10, 128.43, 127.86, 127.81, 110.16, 81.16, 66.37, 59.25, 55.33, 50.26, 47.94, 47.47, 44.65, 42.47, 40.75, 40.56, 38.58, 38.32, 37.64, 36.98, 34.15, 33.14, 29.76, 29.14, 28.72, 27.85, 25.53, 25.40, 25.26, 23.58, 20.67, 18.91, 18.06, 16.50, 16.12, 15.82, 14.18; LCMS, 98% ELS, m/z 659 [M+H]$^+$ 5%, n/z 423 [M+H−BnO$_2$CCMe$_2$CH$_2$CO$_2$H]$^+$ 5%, m/z 237 [BnO$_2$CCMe$_2$CH$_2$CO$_2$H+H]$^+$ 100%.

Preparation of (3β)-28-(Methoxymethylene)lup-20(29)-en-3-ol, 3-(1-Phenylmethyl 2,2-Dimethylbutanedioate) (5a): A stirred suspension of (methoxymethyl)triphenylphosphonium chloride (10.0 g, 29.2 mmol) in THF (188 mL) under an inert atmosphere was cooled to 0° C. A solution of NaHMDS (30.7 mL, 30.7 mmol as 1 M in THF) was added, the reaction mixture allowed to warm to rt, then was cooled again to 0° C. Compound 4 (8.80 g, 14.7 mmol was added as a solid, the mixture stirred for thirty minutes then quenched with the addition of satd NH$_4$Cl (176 mL). The layers were separated, and the aqueous portion extracted with EtOAc (3×220 mL). The combined organics were washed with brine (88 mL), dried (Na$_2$SO$_4$), filtered, and coned in vacuo to an oily solid (~19 g). The material was purified by column chromatography (500 g SiO$_2$, 0-6% EtOAc/hexane gradient). Appropriate fractions were pooled and concd in vacuo to produce a white foam that was dried at 30° C. to give 6.80 g (74.0%) of 5a as a white solid: mixture of E- and Z-isomers: $^1$H NMR (400 MHz, CDCl$_3$) δ 7.28-7.38 (m, 5H), 6.28 (d, J=12.8 Hz, 0.4H), 5.79 (d, J=7 Hz, 0.6H), 5.13 (s, 2H), 4.97 (d, J=13.0, 0.4H), 4.70 (s, 1H), 4.58 (s, 1H), 4.47 (m, 1H), 4.28 (d, J=7 Hz, 0.6H), 2.85 (m, 3H), 2.63 (dd, 2H), 2.48-0.72 (m, 49H).

Alternative Preparation of (3β)-28-(Methoxymethylene) lup-20(29)-en-3-ol, 3-(1-Phenylmethyl 2,2-Dimethylbutanedioate) (5a): (Methoxymethyl)triphenylphosphonium chloride (1.98 g, 5.77 mmol) was weighed in glove box under argon and suspended in anhydrous THF (50 mL). The reaction mixture was cooled to −10° C. To this suspension NaHMDS (4.90 mL, 1 M in THF) was added and the mixture allowed to warm to rt over a period of 10 min and cooled back to −10° C. Aldehyde 4 (1.90 g, 2.88 mmol), that was co-evaporated with toluene two times, was added as a solution in THF (5 mL) to the dark red solution. The reaction mixture turns yellow over a period of 15 min. The mixture was quenched with satd NH$_4$Cl and extracted with EtOAc (3×100 mL). The organic layer was separated, washed with brine (50 mL), dried (Na$_2$SO$_4$), filtered, and coned in vacuo. The crude mixture was purified by column chromatography using 0-5% EtOAc in hexanes as eluent providing 5a (1.15 g, 58%) as a white solid: mixture of E- and Z-isomers, $^1$H NMR (400 MHz, CDCl$_3$) δ 7.38-7.28 (m, 5H), 6.28 (d, J=12.8 Hz, 0.4H), 5.79 (d, J=7 Hz, 0.6H), 5.13 (s, 2H), 4.97 (d, J=13.0 Hz, 0.4H), 4.70 (s, 1H), 4.58 (s, 1H), 4.47 (m, 1H), 4.28 (d, J=7 Hz, 0.6H), 2.85 (m, 3H), 2.63 (dd, 2H), 2.48-0.72 (m, 49H).

Alternative Preparation of (3β)-28-(Methoxymethylene) lup-20(29)-en-3-ol, 3-(1-Phenylmethyl 2,2-Dimethylbutanedioate) (5a). To a suspension of (methoxymethyl)triphenylphosphonium chloride (2.056 g, 6.00 mmol) in anhydrous THF (20 mL) at 5° C. under an atmosphere of nitrogen was added n-butyllithium (3.12 mL of a 1.6 M solution in hexanes, 5.0 mmol). In a separate flask, a solution of aldehyde 4 (1.318 g, 2.0 mmol) in anhydrous THF (20 mL) was chilled to −10° C. under an atmosphere of nitrogen. After 60 min, the ylide solution was transferred to the aldehyde solution via a cannula and the reaction mixture warmed to 20° C. After 5 h, the reaction was quenched with satd NH$_4$Cl (20 mL) and the organic phase separated. The aqueous phase was extracted with EtOAc (3×30 mL). The combined organic phases and extracts were dried (Na$_2$SO$_4$), filtered, and concd in vacuo. The residual gum was purified by silica gel FCC (1-7% EtOAc/heptane gradient) providing the enol ether 5a (0.765 g, 1.11 mmol, 56%) as a colorless foam: TLC $R_f$ 0.41 (9:1 heptane/EtOAc); IR (film, ATR) 2937, 1723, 1641, 1456, 1372, 1298, 1253, 1211, 11123, 1102, 981 cm; $^1$H NMR (400 MHz, CDCl$_3$) Z-isomer 7.18-7.28 (m, 5H), 6.20 (d, J=13.0 Hz, 1H), 5.04 (s, 2H), 4.88 (d, J=13.0 Hz, 1H), 4.62 (d, J=2.4 Hz, 1H), 4.49 (br s, 1H), 4.38-4.42 (m, 1H), 3.46 (s, 3H), 2.58 (d, J=15.9 Hz, 1H), 2.51 (d, J=15.9 Hz, 1H), 2.31 (sept, J=5.5 Hz, 1H), 2.15 (dt, J=9.5 and 3.3 Hz, 1H), 1.91 (dd, J=10.8 and 8.2 Hz, 1H), 0.67-1.75 (m, 45H); E-isomer 7.18-7.28 (m, 5H), 5.70 (d, J=6.9 Hz, 1H), 5.04 (s, 2H), 4.61 (d, J=2.4 Hz, 1H), 4.48 (br s, 1H), 4.38-4.42 (m, 1H), 4.20 (d, J=6.9 Hz, 1H), 3.47 (s, 3H), 2.58 (d, J=15.9 Hz, 1H), 2.51 (d, J=15.9 Hz, 1H), 2.31 (sept, J=5.5 Hz, 1H), 2.15 (dt, J=9.5 and 3.3 Hz, 1H), 1.91 (dd, J=10.8 and 8.2 Hz, 1H), 0.67-1.75 (m, 45H); LCMS, 92% ELS, m/z 709 [M+Na]$^+$ 5%, m/z 451 [M+H–BnO$_2$CCMe$_2$CH$_2$CO$_2$H]$^+$ 30%.

Preparation of (3β)-17-[(3-Carboxy-3-methyl-2-oxobutoxy)-28-norlup-20(29)-enyl]acetaldehyde (6a): To a solution of enol ether 5a (297 mg, 0.43 mmol) in a 1:1 mixture of THF (5 mL) and MeOH (5 mL) was added 2.5 M KOH (1.5 mL, 3.9 mmol). The mixture was stirred at rt for 48 h. The mixture was concd in vacuo, water (7.5 mL) was added, the pH adjusted to 1 with 2 M HCl, and extracted with DCM (2×10 mL). To the DCM extract was added TFA (0.1 mL) and water (0.1 mL) and stirred for 24 h. Additional TFA (0.1 mL) was added and stirred an additional 8 h. The reaction mixture was dried (Na$_2$SO$_4$), filtered, and concd in vacuo. The crude mixture was purified by column chromatography using 0-25% EtOAc in hexanes to furnish 220 mg of 6a admixed with benzyl alcohol as a foamy white solid. Trituration with pentane (5 mL) followed by filtration and drying gave 6a (170 mg, 65.9%) as a white solid: $^1$H NMR (400 MHz, CDCl$_3$) δ 9.83 (t, 1H), 4.70 (s, 1H), 4.60 (s, 1H), 4.49 (m, 1H), 2.62 (dd, 2H), 2.41-0.76 (m, 51H).

Preparation of (3β)-17-[(3-Phenylmethoxycarbonyl-3-methyl-1-oxobutoxy)-28-norlup-20(29)-enyl]acetaldehyde (7a). To a solution of enol ether 5a (0.765 g, 1.11 mmol) in wet DCM (10.0 mL) at 20° C. was added TFA (0.016 mL, 0.22 mmol). After 16 h at rt, silica gel (2.0 g) was introduced and the slurry concd to dryness in vacuo. The dry-loaded material was purified by silica gel FCC (1-8% EtOAc/heptane gradient) to furnish aldehyde 7a (0.640 g, 0.952 mmol, 85%) as a colorless foam: TLC $R_f$ 0.65 (1:1 heptane/ethyl acetate), 0.34 (9:1 heptane/ethyl acetate); IR (film, ATR) 2940, 1717, 1454, 1299, 1222, 1174, 1127, 1011, 981, 907, 726 cm$^{-1}$; $^1$H NMR (400 MHz, CDCl$_3$) δ 9.83 (t, J=3.1 Hz, 1H), 7.28-7.38 (m, 5H), 5.12 (s, 2H), 4.70 (d, J=1.8 Hz, 1H), 4.60 (s, 1H), 4.45-4.50 (m, 1H), 2.66 (d, J=15.9 Hz, 1H), 2.59 (d, J=15.9 Hz, 1H), 2.54 (br d, J=14.6 Hz, 1H), 2.34 (dt, J=11.0 and 5.9 Hz, 1H), 2.06 (br d, J=15.0 Hz, 1H), 1.92-2.03 (m, 1H), 1.83-1.91 (m, 2H), 1.37-1.77 (m, 20H), 1.29 (s, 6H), 1.06-1.27 (m, 8H), 1.04 (s, 3H), 0.98-1.03 (m, 1H), 0.97 (s, 3H), 0.85-0.95 (m, 4H), 0.83 (s, 3H), 0.82 (s, 3H), 0.81 (s, 3H), 0.76 (br d, J=10.3 Hz, 1H); $^{13}$C NMR (400 MHz, CDCl$_3$) δ 203.99, 176.37, 170.94, 149.73, 136.09, 128.37, 127.92, 127.79, 110.02, 81.18, 66.36, 55.29, 50.15, 49.97, 47.42, 45.60, 44.78, 42.40, 42.13, 40.77, 40.55, 38.27, 37.63, 37.39, 36.95, 36.25, 34.02, 31.99, 29.44, 27.84, 26.85, 25.51, 25.24, 24.85, 23.57, 20.74, 19.25, 18.06, 16.49, 16.07, 15.93, 14.84; LCMS, 89% ELS, m, 673 [M+H]$^+$ 10%, ml 695 [M+Na]$^+$ 20%, m/z 437 [M+H–BnO$_2$CCMe$_2$CH$_2$CO$_2$H]$^+$ 10%, m/z 237 [BnO$_2$CCMe$_2$CH$_2$CO$_2$H+H]$^+$ 100%.

Alternative Preparation of (3β)-17-[(3-Phenylmethoxycarbonyl-3-methyl-1-oxobutoxy)-28-norlup-20(29)-enyl] acetaldehyde (7a): To a solution of enol ether 5a (1.75 g, 2.55 mmol) in a DCM (50 mL) were added TFA (1 drop) and water (1 drop). After 24 h at rt, the reaction mixture was dried (Na$_2$S$_{O4}$), filtered, and coned in vacuo. The crude product was purified by silica gel column chromatography using 0-5% EtOAc in hexanes to furnish 7a (1.25 g, 73.6%) as foamy white solid with spectral data consistent with that obtained above.

Preparation of (3β)-17-(3-Methoxy-2-propenyl)-28-norlup-20(29)-en-3-ol, 3-(1-Phenylmethyl 2,2-Dimethylbutanedioate) (5b). (Methoxymethyl)triphenylphosphonium chloride (1.63 g, 4.7 mmol) was suspended in anhydrous THF (35 mL) and cooled to 0° C. To this suspension was added NaHMDS (4.75 mL, 1 M THF) and the mixture allowed to warm to rt over a period of 10 min and cooled back to 0° C. The aldehyde 7a (1.6 g, 2.4 mmol) was added as a solid to the dark red solution that turns yellow over a period of 15 min. The mixture was stirred for 1 h and was quenched with satd NH$_4$Cl and extracted with EtOAc (3×50 mL). The combined organic phases were washed with brine (50 mL), dried (Na$_2$SO$_4$), filtered, and coned in vacuo. The crude product was purified by silica gel column chromatography using 0-5% EtOAc in hexanes as eluent to provide 5b (0.86 g, 52%) as a foamy white solid (mixture of E- and Z-isomers): $^1$H NMR (200 MHz, CDCl$_3$) δ 7.33 (s, 5H), 6.25 (d, J=11.0 Hz, 0.45H), 5.98 (d, J=6.2 Hz, 0.55H), 5.12 (s, 2H), 4.67 (s, 1H), 4.56 (s, 1H), 4.51-4.43 (m, 1H), 4.30-4.20 (m, 1H), 3.56 (s, 2H), 3.52 (s, 1H), 2.63-2.61 (m, 2H), 2.53-2.20 (m, 2H), 2.20-1.05 (m, 29H), 1.05-0.9 (m, 10H), 0.95-0.85 (m, 10H).

Preparation of (3β)-17-[(3-Carboxy-3-methyl-2-oxobutoxy)-28-norlup-20(29)-enyl]propanal (6b): To a solution of enol ether 5b (350 g, 0.47 mmol) in 1:1 mixture of THF/MeOH (12 mL) was added 2.5 M KOH (2 mL). The mixture was stirred at rt for 24 h. The volatiles were removed in vacuo, water (7.5 mL) was added, pH adjusted to 1 with 2 M HCl and extracted with DCM (2×15 mL). To the DCM extract TFA (0.15 mL) and water (0.15 mL) were added and stirred at rt for 24 h. The reaction mixture was dried (Na$_2$SO$_4$), filtered, and concd in vacuo. The crude product was purified by column chromatography using 0-25% EtOAc in hexanes to furnish 140 mg (40.0%) of 6b: $^1$H NMR (200 MHz, CDCl$_3$) δ 9.83 (s, 1H), 8.95-8.35 (bs, 3H), 7.35 (m, 3H), 4.68 (m, 5H), 4.48-4.04 (m, 10H), 3.33 (d, 1H), 2.71-0.80 (m, 37H).

Preparation of (3β)-17-[(3-Phenylmethoxycarbonyl-3-methyl-1-oxobutoxy)-28-norlup-20(29)-enyl]propanal (7b): To a solution of enol ether 5b (0.51 g, 0.7 mmol) in DCM (10 mL) were added TFA (0.05 mL) and water (0.05 mL). After 4 days at, the reaction mixture was coned in vacuo and the residue obtained purified by column chromatography using 0-10% EtOAc in hexanes to furnish 460 mg (92% %) of 7b: $^1$H NMR (200 MHz, CDCl$_3$) δ 9.83 (s, 1H), 7.36-7.28 (m, 5H), 5.12 (s, 2H), 4.68 (s, 1H), 4.58 (s, 1H), 4.51-4.43 (m, 1H), 2.63-2.61 (m, 1.5H), 2.61-2.25 (m, 2.8H), 1.95-1.85 (m, 2H), 1.85-1.05 (m, 28H), 1.05-0.95 (m, 10H), 0.95-0.85 (m, 10H).

Example 11. Preparation of (3β)-3-Hydroxylup-20(29)-en-28-al, Betulinal (2) Via Betulin (1) Using Betulin C-3,28 Diacetate (8)

Scheme 11. Alternative Preparation of (3β)-3-Hydroxylup-20(29)-en-28-al, Betulinal (2) Via Betulin (1) Using Betulin C-3,28 Diacetate (8)

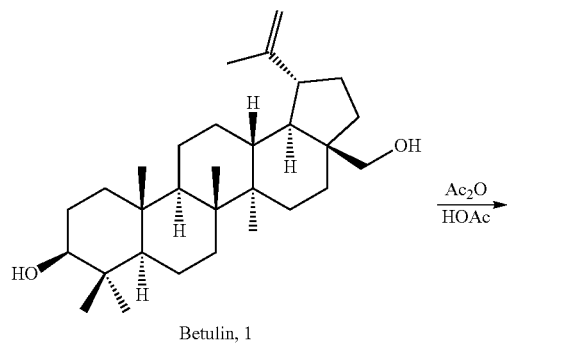

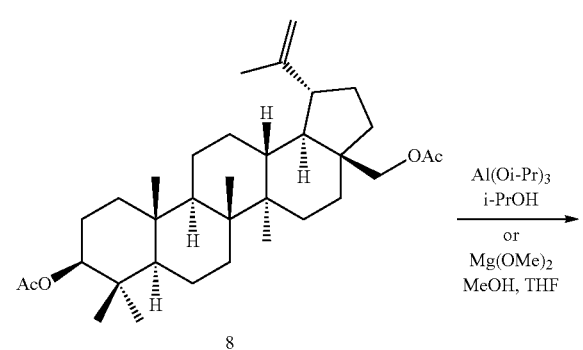

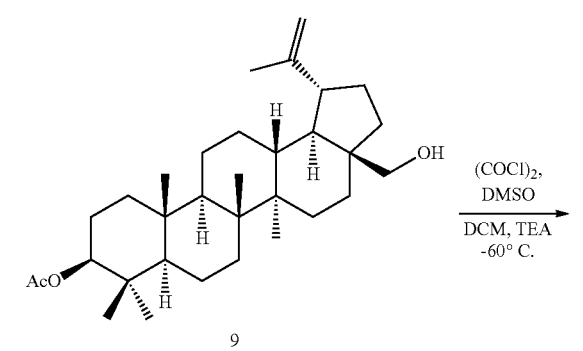

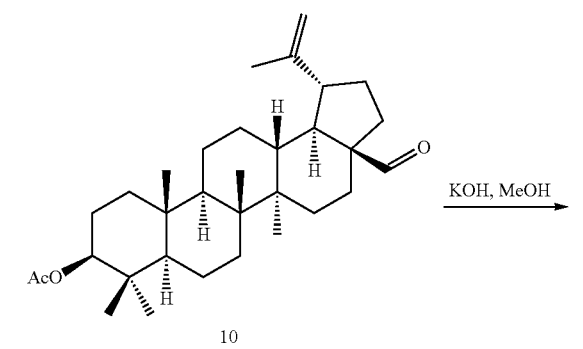

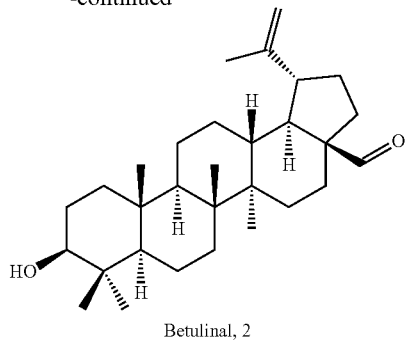

Betulinal, 2

Preparation of Betulin C-3,28 Diacetate (8) using Acetic Anhydride in Acetic Acid: Betulin (1) (9.55 g, 22.6 mmol) was added to a solution of Ac$_2$O (90 mmol) and HOAc (80 mL) under an inert atmosphere and heated overnight at 110° C. The reaction mixture was allowed to cool to rt and concd in vacuo. The residual oil was purified using an ISCO Teledyne (ELSD) with 0-10% EtOAc/hexanes to afford 81% of 9: $^1$H NMR (400 MHz, CDCl$_3$) δ 4.65 (d, J=2.3 Hz, 1H), 4.55 (dd, J=2.5 and 1.4 Hz, 1H), 4.48-4.38 (m, 1H), 4.26-4.17 (m, 1H), 3.81 (dd, J=11.1 and 1.2 Hz, 1H), 2.41 (td, J=11.0 and 5.8 Hz, 1H), 2.02 (d, J=11.8 Hz, 7H), 1.99-1.86 (m, 1H), 1.87-1.31 (m, 14H), 1.35-1.10 (m, 4H), 1.15-0.95 (m, 3H), 1.00 (s, 3H), 0.94 (s, 3H), 0.98-0.87 (m, 1H), 0.82-0.69 (m, 11H).

Preparation of Betulin C-3,28 Diacetate (8) using Acetic Anhydride, TEA, and DMAP in 1,4-Dioxane: To a solution of betulin (1) (6.34 g, 14 mmol) in 1,4-dioxane (70 mL) under nitrogen was added Ac$_2$O (3.4 mL, 36 mmol), TEA (5.0 mL, 36 mmol), and DMAP (1.71 g, 14.0 mmol). After stirring for 24 h at 80° C., the reaction mixture was concd in vacuo to dryness, re-dissolved in EtOAc (200 mL), and washed with 1 M KHSO$_4$ (3×100 mL), water (100 mL), and brine (100 mL). The organic phase was dried (MgSO$_4$), filtered, and concd in vacuo to furnish the product 8 as an off-white, amorphous solid (5.55 g, 10.6 mmol, 75%) that was used without further purification: TLC R$_f$ 0.43 (4:1 hexane/EtOAc); mp 219-220° C.; $^1$H NMR (400 MHz, CDCl$_3$) δ 4.69 (d, J=1.8 Hz, 1H), 4.60 (br s, 1H), 4.49-4.45 (m, 1H), 4.26 (d, J=11.0 Hz, 1H), 3.86 (d, J=11.0 Hz, 1H), 2.45 (dt, J=10.9 and 5.8 Hz, 1H), 2.08 (s, 3H), 2.05 (s, 3H), 2.02-0.78 (m, 42H); LCMS, 100% (ELS), m/z 549 [M+Na]$^+$ 100%.

Preparation of Betulin C-3 Acetate (9) using Mg(OCH$_3$)$_2$: To a solution of 8 (5.55 g, 10.6 mmol) in a mixture of THF (130 mL) and MeOH (400 mL) under an inert atmosphere was added Mg(OCH$_3$)$_2$ (60 mL of an ~8% solution in methanol, ~56 mmol), heated at 50° C. for 48 h, and then concd in vacuo to dryness. The residue was partitioned between 2 M HCl (200 mL) and EtOAc (150 mL). The aqueous phase was extracted with EtOAc (150 mL). The combined EtOAc extracts were washed with satd brine (100 mL), dried (MgSO$_4$), filtered, and concd in vacuo. The residue was dry-loaded onto 40 g of silica gel and purified by FCC using an EtOAc/hexane gradient. The desired monoacetate 9 (3.69 g, 7.4 mmol, 70%) was isolated as a colorless amorphous solid: mp 252-253° C.; IR (solid, ATR) 3370, 2938, 1730, 1450, 1369, 1240, 1018, 972, 884, 645 cm$^{-1}$; $^1$H NMR (400 MHz, CDCl$_3$) δ 4.68 (d, J=2.4 Hz, 1H), 4.59 (dd, J=2.2 and 1.3 Hz, 1H), 4.51-4.44 (m, 1H), 3.80 (d, J=10.6 Hz, 1H), 3.34 (d, J=10.6 Hz, 1H), 2.45-2.34 (m, 1H), 2.05 (s, 3H), 1.98 (m, 43H); $^{13}$C NMR (100.6 MHz, CDCl$_3$)

δ 171.0, 150.4, 109.7, 80.9, 60.4, 55.3, 50.2, 48.7, 47.81, 47.78, 42.7, 40.9, 38.3, 37.7, 37.2, 37.0, 34.1, 33.9, 29.7, 29.1, 27.9, 27.0, 25.1, 23.6, 21.3, 20.8, 19.0, 18.1, 16.5, 16.1, 15.9, 14.7.

Preparation of Betulin C-3 Acetate (9) using Al(Oi-Pr)$_3$: To the solution of 8 (5.00 g, 9.49 mmol) in i-PrOH (100 mL) under an inert atmosphere was added powered Al(Oi-Pr)$_3$ (1.94 g, 9.49 mmol). The reaction mixture was refluxed for 1.5 h, cooled to rt, and concd in vacuo. The solid obtained was dissolved in DCM (50 mL) and water (3 mL) was added. After stirring (10-15 min), the precipitated material was filtered, extracted with DCM, dried (Na$_2$SO$_4$), and coned in vacuo. The residue obtained was purified using an ISCO Teledyne (ELSD) with 0-20% EtOAc/hexanes providing 80% of 9: $^1$H NMR (400 MHz, CDCl$_3$) δ 4.69-4.63 (m, 1H), 4.56 (dt, J=2.3 and 1.3 Hz, 1H), 4.49-4.40 (m, 1H), 3.81-3.72 (m, 1H), 3.30 (d, J=10.8 Hz, 1H), 2.36 (td, J=10.8 and 5.8 Hz, 1H), 2.02-1.79 (m, 3H), 1.75-1.50 (m, 10H), 1.47-1.13 (m, 10H), 1.17-0.90 (m, 10H), 0.86-0.73 (m, 12H), 1.64 (s, 1H).

Preparation of Betulinal C-3 Acetate (10): To a solution of oxalyl chloride (0.27 mL, 3.1 mmol) in DCM (12.5 mL) cooled −50° C. under an inert atmosphere was added dropwise with efficient stirring a solution of DMSO (0.29 mL, 4.1 mmol) in DCM (12.5 mL) over 5-10 min. The mixture was stirred for an additional 5-10 min until gas evolution stops. Alcohol 9 (999 mg, 2.06 mmol) was then added. After 45 min, TEA (1.44 mL, 10.3 mmol) was added, the cooling bath was removed, and the mixture was allowed to warm to 10° C., after which cold water (20 mL) was added. The organic phase was separated and the aqueous phase extracted with DCM (50 mL). The combined organic layers were washed with water (20 mL), dried (Na$_2$SO$_4$), and coned in vacuo. The residue obtained was purified using an ISCO Teledyne (ELSD) using 0-10% EtOAc/hexanes as solvent to afford 935 mg (94.0%) of 10: $^1$H NMR (400 MHz, CDCl$_3$) 9.64 (d, J=1.6 Hz, 1H), 4.73 (dt, J=2.3 and 0.7 Hz, 1H), 4.60 (dd, J=2.3 and 1.4 Hz, 1H), 4.49-4.39 (m, 1H), 2.84 (td, J=11.1 and 5.8 Hz, 1H), 2.09-1.93 (m, 2H), 2.01 (s, 3H), 1.94-1.79 (m, 1H), 1.84-1.60 (m, 6H), 1.65-1.54 (m, 2H), 1.50-0.86 (m, 20H), 0.85-0.69 (m, 11H).

Preparation of Betulinal (2): To a solution of 10 (801 mg, 1.66 mmol) in THF (10 mL) was added dropwise a solution of KOH (0.32 g, 6.6 mmol) in MeOH (10 mL). After stirring overnight at rt, the mixture was coned in vacuo and the residue obtained partitioned between DCM (20 mL) and water (10 mL). The organic phase was dried (Na$_2$SO$_4$), coned in vacuo, and purified using an ISCO Teledyne with ELSD using 0-15% EtOAc/hexanes as solvents to afford 651 mg (89%) of 2: $^1$H NMR (400 MHz, CDCl$_3$) δ 9.66 (d, J=1.6 Hz, 1H), 4.74 (dt, J=2.3 and 0.7 Hz, 1H), 4.61 (dd, J=2.3 and 1.4 Hz, 1H), 3.47 (s, 1H), 3.17 (dd, J=10.8 and 5.1 Hz, 1H), 2.85 (td, J=11.1 and 5.8 Hz, 1H), 2.11-1.94 (m, 2H), 1.86 (dtd, J=13.5, 10.5, and 8.7 Hz, 1H), 1.82-1.71 (m, 1H), 1.76-1.61 (m, 6H), 1.66-1.56 (m, 1H), 1.61-1.50 (m, 1H), 1.50 (dt, J=9.1 and 2.8 Hz, 1H), 1.49-1.40 (m, 2H), 1.44-1.30 (m, 4H), 1.35-1.11 (m, 4H), 1.11-0.98 (m, 1H), 1.03-0.87 (m, 10H), 0.92-0.82 (m, 1H), 0.80 (d, J=0.9 Hz, 3H), 0.74 (s, 3H), 0.70-0.62 (m, 1H).

Scale-up Preparation of Betulinal (2) from Betulin (1) Using Betulin C-3,28 Diacetate (8) Route Synthesis of Betulin C-3,28 Diacetate (8): A stirred suspension of betulin (1) (50.2 g, 0.113 mol) in Ac$_2$O (42.5 mL, 0.450 mol) and glacial acetic acid (400 mL) was heated to reflux, resulting in solution formation. The reaction mixture was stirred at reflux for 3 h. TLC (EtOAc/hexanes 1:4, p-anisaldehyde stain) indicated complete consumption of starting material. The mixture was allowed to cool to 40° C., and the volatiles were removed in vacuo at 40° C. The residue was dried under high vacuum to constant weight to give 59.2 g of 9 (99.4% yield) as an off-white solid that was used in the following step without further purification.

Synthesis of Betulin C-3 Acetate (9): A stirred suspension of 8 (59.2 g, 0.112 mol) and aluminum isopropoxide (49.7 g, 0.243 mol) in 2-propanol (1.25 L) was heated to reflux, resulting in formation of a solution. The reaction mixture was stirred at reflux for 2.5 h. The mixture was allowed to cool to rt and the volatiles were removed in vacuo at 40° C. to give a foam. The material was stirred suspended for 15 min in DCM (500 mL) containing water (50 mL). The gel-like insoluble material was collected on a filter, thoroughly rinsed by re-suspension in DCM (4×100 mL), and discarded. The combined filtrates were dried (Na$_2$SO$_4$), filtered, and coned in vacuo at 40° C. to give an off-white solid. The material was dried under high vacuum to constant weight to give 51.6 g of 9 (95.0% yield) that was used in the following step without further purification.

Synthesis of Betulinal C-3 Acetate (10): A vigorously stirred argon-blanketed solution of oxalyl chloride (20.4 g, 0.161 mol) in DCM (650 mL, anhydrous) was cooled to −65° C. A solution of DMSO (16.7 g, 0.214 mL) in DCM (650 mL) was added dropwise over 1 h while maintaining the temperature between −60° C. and −65° C. The mixture was vigorously stirred an additional 15 min before the addition of solid 9 (51.5 g, 0.106 mol). After 45 min at −60° C. TEA (53.6 g, 0.530 mol) was added dropwise over 20 min while maintaining the temperature between −60° C. and −65° C. The cooling bath was removed, and the reaction mixture was allowed to warm to 12° C. before the dropwise addition of water (260 mL) over 15 min. The reaction was stirred for a final 15 min and layers were separated. The aqueous phase was extracted with DCM (3×130 mL), the organic layers were combined and washed with water (5×130 mL), 5% HCl (2×130 mL), dried (Na$_2$SO$_4$), filtered, and coned in vacuo at 40° C. to give a cream-colored solid. The material was dried under high vacuum at 40° C. to constant weight to give 57.1 g of 10 admixed with residual DMSO. TLC (EtOAc/hexanes 1:4, p-anisaldehyde stain) indicated pure betulinal 3-acetate 10 as a single spot. This material was used in the following step without further purification.

Synthesis of Betulinal (2): A stirred suspension of 10 (~0.121 moles) in methanolic KOH (3% solution made from 175 g of +85% KOH, ~2.65 moles, and 5.8 L MeOH) was heated to reflux. The reaction mixture slowly became a solution. After 3 h at reflux, TLC (EtOAc/hexanes 1:4, p-anisaldehyde stain) indicated complete consumption of starting material. The mixture was allowed to cool to 40° C. and coned in vacuo at 40° C. to a final volume of ~2.5 L. This solution was treated with cold water (3.8 L), and the resulting suspension was stirred for 15 min before extracting with diethyl ether (2.5 L followed by 2×1 L). The combined ether extracts were dried (Na$_2$SO$_4$), filtered, and coned in vacuo at 40° C. to give a cream-colored solid. The material was dried under high vacuum at 40° C. to constant weight to give 51.8 g (97.1%) of 2 with analytical and spectral data consistent with 2 obtained in Example 10.

Example 12. Preparation of (3β)-3-hydroxylup-20(29)-en-28-al, Betulinal (2), from Betulinic Acid (11)

Scheme 12. Preparation of (3β)-3-hydroxylup-20(29)-en-28-al, Betulinal (2), from Betulinic Acid (11)

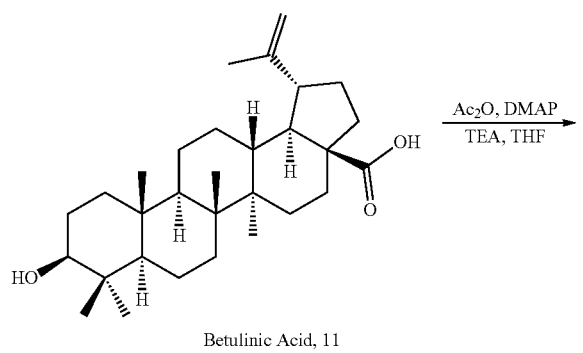

Betulinic Acid, 11

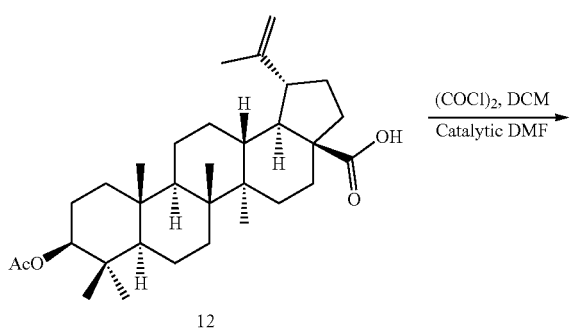

12

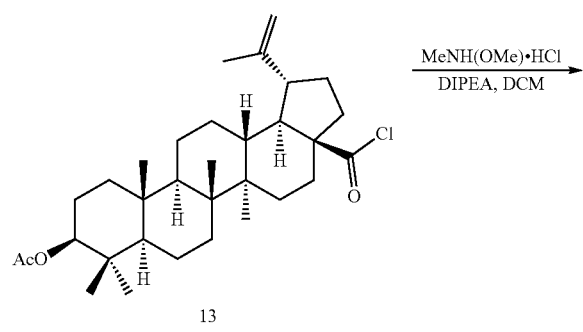

13

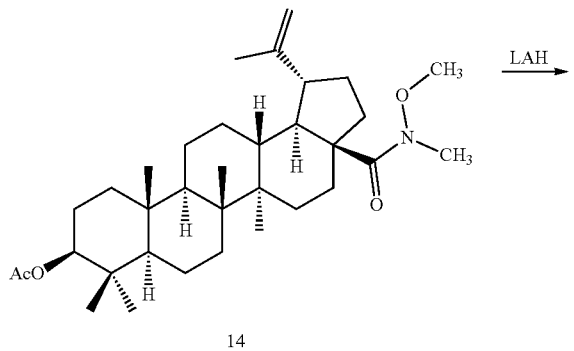

14

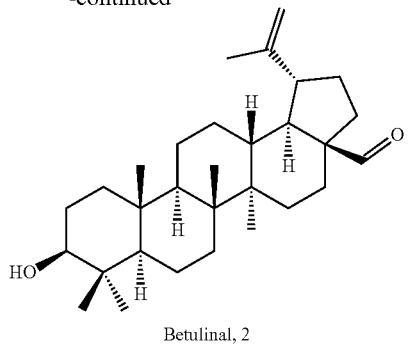

Betulinal, 2

Preparation of 3-O-Acetylbetulinic Acid (12). To a solution of betulinic acid (11) (1.0 g, 2.2 mmol), DIPEA (1 mL), and DMAP (0.034 g, 0.27 mmol) in anhydrous THF (10 mL) under an inert atmosphere was added $Ac_2O$ (0.3 mL, 3.1 mmol). The mixture was heated at 65° C. for 2 h and monitored until TLC demonstrated complete consumption of the starting material with formation of 12 and a small amount of the C-28 mixed anhydride. The mixture was concd in vacuo to dryness to yield a white solid. To hydrolyze the mixed anhydride, this solid was suspended into 0.6 M HCl solution (20 mL) and heated at 100° C. for 30 min. The suspension was cooled to rt and filtered, the filter cake washed with water (20 mL), and dried at 50° C. in vacuo yielding 3-O-acetylbetulinic acid (12), 1.06 g (97%), as a white free-flowing powder: TLC $R_f$ 0.65 (DCM/EtOAc 95:5); $^1$H NMR (250 MHz, $CDCl_3$); δ 4.74 (d, J=1.3 Hz, 1H), 4.61 (s, 1H), 4.53-4.41 (m, 1H), 3.09-2.92 (m, 1H), 2.34-2.10 (m, 2H), 2.09-1.92 (m, 5H), 1.83-0.69 (m, 38H).

Preparation of 3-O-Acetylbetulinic Acid Chloride (13). To a chilled (0° C.) solution of 3-O-acetylbetulinic acid (12) (10.0 g, 20.0 mmol) in DCM (100 mL) under an inert atmosphere was added oxalyl chloride (12 mL, 70 mmol) and 2 drops of DMF as catalyst. The reaction was allowed to reach rt and stirred at rt for 6 h. Excess oxalyl chloride and DCM are removed in vacuo providing a yellow solid that was re-dissolved into DCM (20 mL). The solution was concd in vacuo providing 13: IR (solid, ATR golden-gate) ν (C:O) 1794 and 1724 $cm^{-1}$.

Preparation of (3β)-N-Methyl-N-methoxy-3-acetoxylup-20(29)-en-28-amide (14). To a chilled (0° C.) suspension of N,O-dimethylhydroxylamine hydrochloride (11.8 g, 120 mmol) in DCM (100 mL) under an inert atmosphere was added DIPEA (24.7 mL, 150 mmol). A solution of acid chloride 13 (10.3 g, 20.0 mmol) in DCM (20 mL) was added and the mixture allowed to warm to rt and stirred at rt for 3 d. The solution was poured into brine (200 mL), the organic phase separated and the aqueous phase extracted with diethyl ether (100 mL) and DCM/diethyl ether 1:1 (2×200 mL). The combined organic layers were washed with brine (100 mL), dried ($Na_2SO_4$), and concd in vacuo to give a pale yellow solid that was purified by dry flash chromatography (2-10% EtOAc in heptane) providing 8.50 g (78%) of 14 as a white solid: $^1$H NMR (400 MHz, $CDCl_3$) δ 4.72 (d, J=2.2 Hz, 1H), 4.58 (s, 1H), 4.51-4.45 (m, 1H), 3.66 (s, 3H), 3.16 (s, 3H), 3.04-2.94 (m, 1H), 2.77-2.67 (m, 1H), 2.37-2.29 (m, 1H), 2.13-2.06 (m, 1H), 2.03 (s, 3H), 1.85-1.76 (m, 1H), 1.75-0.73 (m, 44H).

Preparation of (3β)-3-Hydroxylup-20(29)-en-28-al, Betulinal (2). To a chilled (−10° C.) solution of Weinreb amide 14 (5.41 g, 10.0 mmol) in anhydrous THF (100 mL) under an inert atmosphere was added dropwise 1 M LAH in THF (31 mL, 31 mmol). The solution was allowed to warm to rt and stirred at rt for 72 h. The reaction mixture was chilled (0° C.), water (1.5 mL) was cautiously added dropwise followed by the dropwise addition of 15% NaOH (1.5 mL) and water (4.5 mL) providing a white gel that was filtered through Celite®. The filter cake was washed with brine (100 mL) and the brine filtrate extracted with EtOAc (2×100 mL). The THF filtrate and EtOAc extracts were combined and washed with brine (100 mL), dried ($Na_2SO_4$), and concd in vacuo providing 4.46 g (~100%) of 2 as a white solid with spectral and analytical data ($^1$H NMR and TLC) consistent with aldehyde 2 obtained in Example 10.

Example 13. Syntheses of C-3 3,3-Dimethylglutaryl Betulin C-28 Aldehyde and C-28 Homologated Aldehyde Intermediates Scheme 13. Syntheses of C-3 3,3-Dimethylglutaryl Betulin C-28 Aldehydes and C-28 Homologated Aldehyde Intermediates 17a, 17b, 17d, 17e, 19, 20, 22, and 23

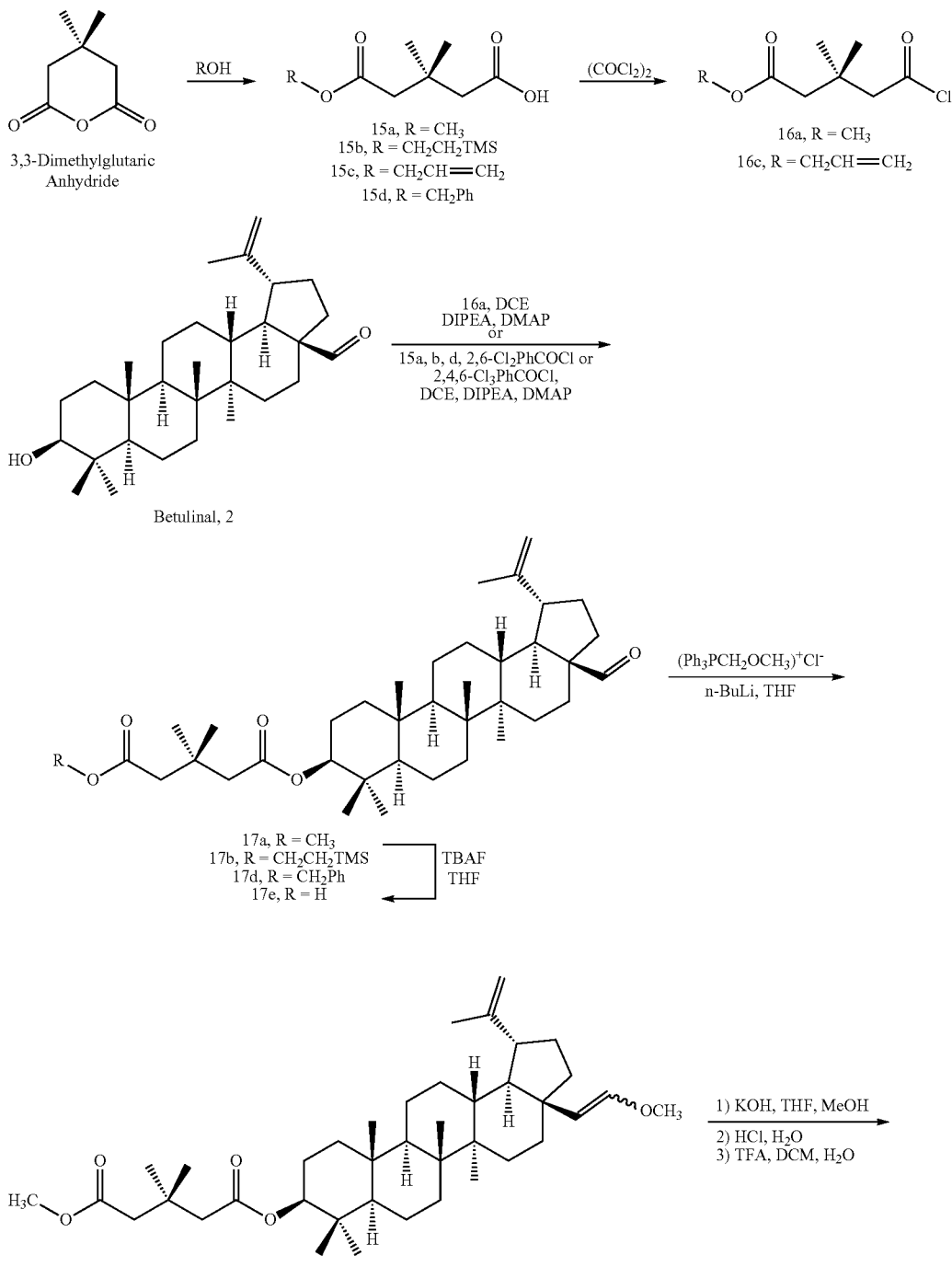

-continued
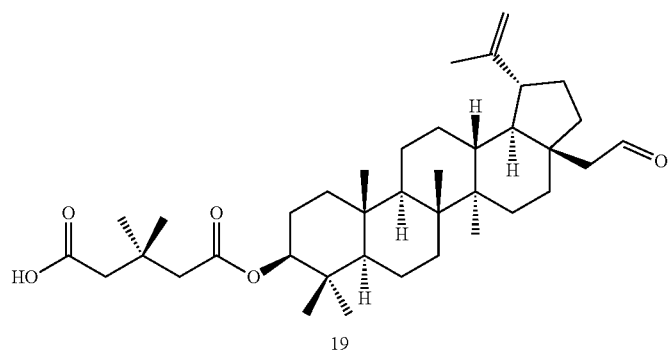
19
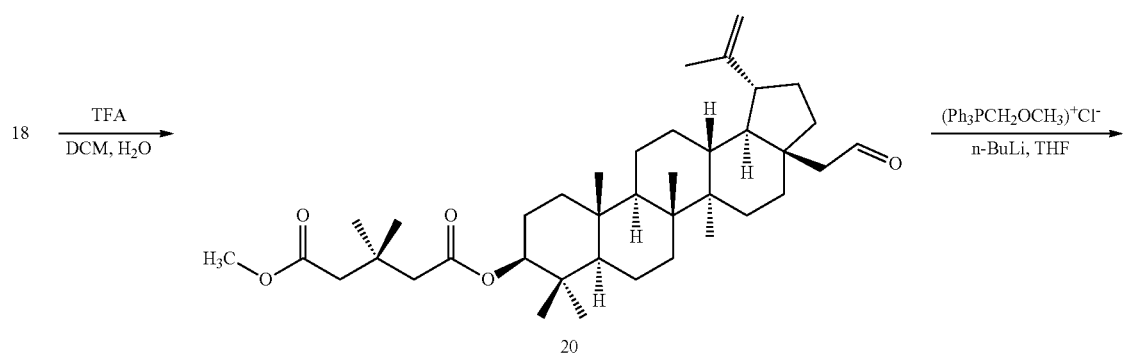
20
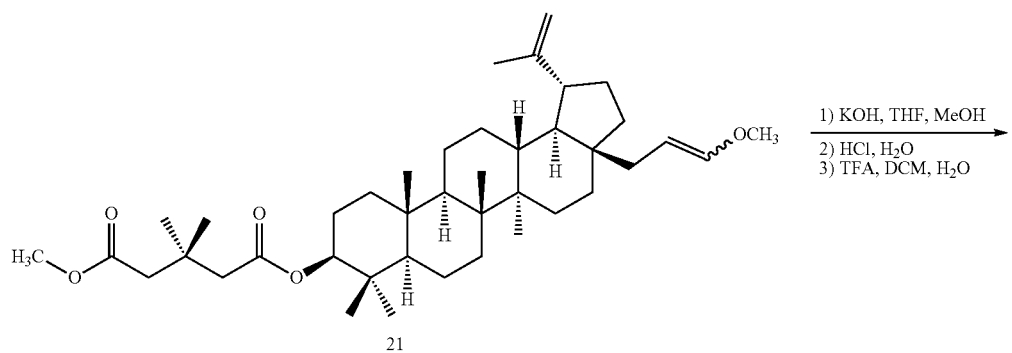
21
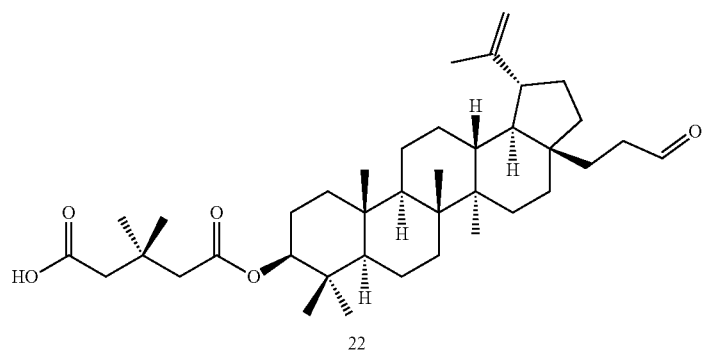
22

 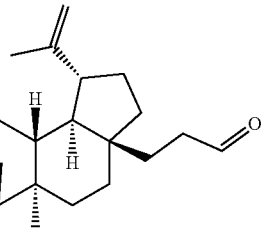

Preparation of Methyl 3,3-Dimethylglutarate (15a). Under an inert atmosphere, a suspension of 3,3-dimethylglutaric anhydride (9.00 g, 63.4 mmol) and DMAP (0.77 g, 6.3 mmol), TEA (8.8 mL, 63.4 mmol), and methanol (75 mL) was heated at reflux overnight. The volatiles were removed in vacuo, and the residue was dissolved in EtOAc (150 mL), washed successively with 1 M citric acid (3×100 mL), water, dried (MgSO$_4$), and concd in vacuo affording 15a (11.1 g, ~100%) as a colorless oil that was used in the next step without further purification: $^1$H NMR (400 MHz, CDCl$_3$) δ 10.9 (br s, 1H), 3.7 (s, 3H), 2.45 (d, 4H), 1.15 (s, 6H).

Preparation of Methyl 3,3-Dimethylglutaryl Chloride (16a). To a chilled (0° C.) solution of 15a (10.4 g, 60 mmol) in DCM (100 mL) under an inert atmosphere was added oxalyl chloride (7.7 mL, 90 mmol) and DMF (30 µL, 0.38 mmol). The reaction was allowed to reach rt and was stirred for 1 h. The volatiles were removed in vacuo. The resulting solid residue was dissolved in DCM (10 mL) and concd to dryness in vacuo. This operation was repeated twice more, providing acid chloride 16a (11.5 g, ~100%) that was used without further purification.

Preparation of Allyl 3,3-Dimethylglutarate (15c). A suspension of 3,3-dimethylglutaric anhydride (5.3 g, 38 mmol) and allyl alcohol (10.0 mL, 145 mmol) under an inert atmosphere was heated at reflux for 5 h (solution became clear). The volatiles were removed in vacuo, the residue was diluted in EtOAc (100 mL), washed successively twice with water, dried (Na$_2$S$_4$), and coned in vacuo to 15c (6.7 g, 99%) as a colorless oil that was used in the next step without further purification: $^1$H NMR (400 MHz, CDCl$_3$) δ 5.90 (m, 1H), 5.32 (dd, J=17.3 and 1.3 Hz, 1H), 5.25 (dd, J=10.4 and 1.3 Hz, 1H), 4.59 (d, J=5.8 Hz, 2H), 2.49 (s, 2H), 2.48 (s, 2H), 1.18-1.13 (s, 6H).

Preparation of Allyl 3,3-Dimethylglutaryl chloride (16c). DMF (30 µL, 0.38 mmol) was added to a chilled (0° C.) solution of oxalyl chloride (16.6 mL, 175 mmol) and 15c (3.5 g, 17.5 mmol) in DCM (60 mL) under an inert atmosphere. The reaction was allowed to reach rt and was stirred for 1 h. The volatiles were removed in vacuo. The resulting solid residue was dissolved in DCM (10 mL) and coned to dryness in vacuo. This operation was repeated twice more, providing acid chloride 16c (3.8 g, ~100%) as yellow oil, that was used without further purification.

Preparation of 2-(Trimethylsilyl)ethyl 3,3-Dimethylglutarate (15b). A mixture of 2-(trimethylsilyl)ethanol (3.7 g, 31 mmol) and 3,3-dimethylglutaric anhydride (4.26 g, 30 mmol) in toluene (1 mL) under an inert atmosphere was heated at 100° C. for 8 h (complete reaction by $^1$H NMR analysis). The mixture was coned in vacuo providing 15b (~100%) that was used without further purification: $^1$H NMR (400 MHz, CDCl$_3$) δ 4.23-4.13 (m, 2H), 2.49 (s, 2H), 2.42 (s, 2H), 1.15 (s, 6H), 1.04-0.96 (m, 2H), 0.00 (s, 9H).

Preparation of Benzyl 3,3-Dimethylglutarate (15d). To a suspension of 3,3-dimethylglutaric anhydride (10.0 g, 70.4 mmol) in toluene (10 mL) under an inert atmosphere was added benzyl alcohol (7.4 mL, 72 mmol). The mixture was stirred at 100° C. for 3 h. The mixture was concd in vacuo to yield 15d as a pale yellow oil: $^1$H NMR (360 MHz, CDCl$_3$) δ 10.03 (br s, 1H), 7.54-7.20 (m, 5H), 5.14 (s, 2H), 2.53 (s, 2H), 2.50 (s, 2H), 1.17 (s, 6H).

Preparation of (3β)-3-(4-Methoxycarbonyl-3,3-dimethyl-1-oxobutoxy)lup-20(29)-en-28-al (17a) via Acid Chloride Route. To a solution of aldehyde 2 (0.847 g, 1.92 mmol) in DCE (15 mL) under an inert atmosphere was added DIPEA (0.77 mL, 4.8 mmol) and DMAP (0.01 g). The solution was cooled to 0° C., and methyl 3,3-dimethylglutaryl chloride (16a) (0.737 g, 3.84 mmol) was added dropwise. The mixture was warmed to rt and stirred for an additional 16 h. DCM (50 mL) was added to the mixture to yield a solution that was washed with 2 M HCl (2×10 mL), water (10 mL), and brine (10 mL). The organic phase was dried (MgSO$_4$), filtered, and coned in vacuo to yield a solid that was dry-loaded onto silica gel (5 g) and purified by FCC using 1-10% EtOAc/hexane gradient. The desired ester 17a was isolated as a colorless solid: 0.493 g, 43%; mp 115-117° C.; IR (solid ATR) ν (C:O) 1719 cm$^{-1}$; $^1$H NMR (250 MHz, CDCl$_3$) δ 9.68 (s, 1H), 4.76 (s, 1H), 4.63 (s, 1H), 4.48 (dd, J=10.8 and 4.8 Hz, 1H), 3.66 (s, 3H), 2.86 (dt, J=10.6 and 4.7 Hz, 1H), 2.48-2.33 (m, 4H), 2.11-0.83 (m, 48H); $^{13}$C NMR (62.9 MHz, CDCl$_3$) δ 206.7, 172.3, 171.7, 149.7, 110.2, 80.9, 59.3, 55.4, 51.2, 50.3, 48.0, 47.5, 45.7, 45.1, 42.5, 40.8, 38.7, 38.4, 37.7, 37.1, 34.2, 33.2, 32.6, 29.8, 29.2, 28.8, 28.0, 27.7, 25.5, 23.8, 20.8, 19.0, 18.2, 16.6, 16.2, 15.9, 14.2.

Preparation of (3β)-3-(4-Methoxycarbonyl-3,3-dimethyl-1-oxobutoxy)lup-20(29)-en-28-al (17a) via Mixed Anhydride. To a chilled (0° C.) solution of methyl 3,3-dimethylglutarate (15a) (3.31 g, 19.0 mmol), aldehyde 2 (7.0 g, 15.9 mmol), and 2,6-dichlorobenzoyl chloride (4.0 g, 19.0 mmol) in DCM (300 mL) under an inert atmosphere were added DIPEA (5.7 mL, 31.8 mmol) and DMAP (0.97 g, 7.95 mmol). After 30 min, the reaction mixture was allowed to warm to rt and stirred for 18 h. The reaction mixture was poured into DCM (200 mL), washed with 2 M HCl (30 mL), 1 M NaOH (30 mL), water (30 mL), brine (30 mL), dried (Na$_2$SO$_4$) and coned in vacuo. The crude product was dissolved in DCM and purified by column chromatography using Florisil as adsorbent and DCM as eluent providing 17a (9.2 g, 97%) as pale orange solid: $^1$H NMR (200 MHz, CDCl$_3$) δ 9.67 (s, 1H), 4.75 (s, 1H), 4.63 (s, 1H), 4.62-4.43 (m, 1H), 3.66 (s, 3H), 2.95-2.79 (m, 1H), 2.50-2.35 (m, 4H), 2.11-0.75 (m, 48H).

Preparation of (3β)-3-[4-[(2-Trimethylsilyl)ethoxycarbonyl]-3,3-dimethyl-1-oxobutoxy)]lup-20(29)-en-28-al (17b). To a chilled (0° C.) solution of aldehyde 2 (3.96 g, 9.00 mmol), 2,4,6-trichlorobenzoyl chloride (2.43 g, 10.0 mmol), and 2-(trimethylsilyl)ethyl 3,3-dimethylglutarate (15b) (2.60 g, 10.0 mmol) in DCM (100 mL) under an inert atmosphere was added dropwise TEA (2.5 mL, 18 mmol) followed by DMAP (549 mg, 4.50 mmol). The reaction was allowed to warm to rt and stirred at rt for 5 h. The volatiles were removed in vacuo to yield a solid that was purified by SiO$_2$ dry-flash chromatography (heptane/EtOAc 9:1) providing 5.75 g (93%) 17b as a colorless solid: $^1$H NMR (400 MHz, CDCl$_3$) δ 9.67 (s, 1H), 4.75 (d, J=1.8 Hz, 1H), 4.63 (s, 1H), 4.47 (dd, J=11.3 and 4.7 Hz, 1H), 4.18-4.10 (m, 2H), 2.92-2.81 (m, 1H), 2.49-2.33 (m, 4H), 2.11-1.96 (m, 1H), 1.80-0.71 (m, 56H), 0.00 (s, 9H).

Preparation of (3β)-3-[4-(2-Phenylmethoxycarbonyl)-3,3-dimethyl-1-oxobutoxy)]lup-20(29)-en-28-al (17d). To a chilled solution of betulin-28-al (2) (23.50 g, 53.3 mmol) in DCM (160 mL) under an inert atmosphere was added benzyl 3,3-dimethylglutarate (15d) (15.80 g, 63.10 mmol), and 2,6-dichlorobenzoyl chloride (13.20 g, 63.1 mmol). After cooling to 5° C., DIPEA (13.20 mL, 80.00 mmol) and DMAP (4.60 g, 37.30 mmol) were added and stirred at 20° C. for 16 h. The volatiles were removed in vacuo; the residue was re-dissolved in EtOAc (300 mL) and washed with 1 M HCl (300 mL), 1 M NaOH (300 mL), and water (300 mL). The organic phase was dried (Na$_2$SO$_4$), filtered, and coned in vacuo. Purification of the residue by silica gel FCC (2-5% EtOAc/heptane gradient) furnished ester 17d (34.30 g, 50.96 mmol, 95%) as a colorless solid: TLC R$_f$ 0.53 (4:1 heptane/EtOAc), 0.35 (9:1 heptane/EtOAc); IR (solid, ATR goldengate) 2940, 1717, 1453, 1376, 1345, 1211, 1134, 1090, 1003, 974, 882, 735 cm$^{-1}$; $^1$H NMR (400 MHz, CDCl$_3$) δ 9.68 (d, J=1.5 Hz, 1H), 7.38-7.29 (m, 5H), 5.10 (s, 2H), 4.77 (d, J=1.8 Hz, 1H), 4.64 (m, 1H), 4.46 (m, 1H), 2.87 (dt, J=11.3 and 5.9 Hz, 1H), 2.52-2.41 (m, 1H), 2.48 (s, 2H), 2.46 (d, J=13.9 Hz, 1H), 2.37 (d, J=13.9 Hz, 1H), 2.10-2.06 (m, 1H), 2.02 (dt, J=12.1 and 3.3 Hz, 1H), 1.93-1.83 (m, 1H), 1.79-1.16 (m, 25H), 1.12 (s, 3H), 1.11 (s, 3H), 1.08-1.00 (m, 1H), 0.97 (s, 3H), 0.96-0.93 (m, 1H), 0.92 (s, 3H), 0.89-0.85 (m, 1H), 0.84 (s, 3H), 0.83 (s, 3H), 0.81 (s, 3H), 0.77 (br d, J=9.5 Hz, 1H); $^{13}$C NMR (100.6 Hz, CDCl$_3$) δ 171.64, 171.62, 149.66, 135.95, 128.48, 128.21, 128.11, 110.17, 80.81, 65.93, 59.28, 55.34, 50.29, 47.97, 47.49, 45.68, 45.21, 42.49, 40.78, 38.62, 38.33, 37.61, 37.02, 34.19, 33.16, 32.66, 29.79, 29.17, 28.74, 27.95, 27.68, 27.66, 25.42, 23.72, 20.70, 18.93, 18.10, 16.56, 16.11, 15.84, 14.20; LCMS, 99% ELS, m/z 673 [M+H]$^+$ 5%, m/z 695 [M+Na]$^+$ 5%, m, 251 [BnO$_2$CCH$_2$CMe$_2$CH$_2$CO$_2$H+H]$^+$ 100%.

Preparation of (3β)-3-[4-(Carboxy-3,3-dimethyl-1-oxobutoxy)]lup-20(29)-en-28-al (17e). To a solution of trimethylsilylethyl ester 17b (6.83 g, 10 mmol) in anhydrous THF (50 mL) at rt was added tetra-n-butylammonium fluoride (1 M in THF, 30 mL, 30 mmol) and stirred at rt for 20 h. The solvent was coned in vacuo, and crude product was dissolved in DCM/diethyl ether (1:1, 200 mL). The organic phase was washed with 1 M HCl (50 mL), satd NaHCO$_3$ (50 mL), satd NaCl (50 mL), dried (Na$_2$SO$_4$), and concd in vacuo to give 17e as a colorless solid that was used without further purification.

Preparation of (3β)-28-(Methoxymethylene)lup-20(29)-en-3-ol, 3-(Methyl 3,3-Dimethylpentanedioate) (18) Using Ylide Generated with n-Butyllithium. To a chilled (0° C.) suspension of (methoxymethyl)triphenylphosphonium chloride (0.396 g, 1.15 mmol) in anhydrous THF (10 mL) under an inert atmosphere was added dropwise a 1.6 M n-butyllithium solution in hexanes (0.72 mL, 1.15 mmol). After 15 min, the deep red solution was added dropwise over 20 min to a chilled (0° C.) solution of aldehyde 17a in anhydrous THF (10 mL). The solution was stirred for an additional 15 min at 5° C., the ice bath removed, and stirred at rt for 30 min. The solution was dry loaded directly onto silica gel (~4 g) and purified by FCC using 1-10% hexane/EtOAc gradient to yield the desired enol ether 18 (0.172 g, 0.28 mmol, 33%) as a mixture of E- and Z-isomers in the form of a colorless solid: E-isomer $^1$H NMR (360 MHz, CDCl$_3$) δ 5.79 (d, J=7.0 Hz, 1H), 4.69 (d, J=2.3 Hz, 1H), 4.57 (dd, J=2.4 and 1.3 Hz, 1H), 4.47 (dd, J=11.0 and 4.5 Hz, 1H), 4.28 (d, J=6.8 Hz, 1H), 3.66 (s, 3H), 3.56 (s, 3H), 2.35-2.47 (m, 5H), 2.20-2.24 (m, 1H), 1.96-2.01 (m, 1H), 0.75-1.90 (m, 41H); Z-isomer $^1$H NMR β 6.28 (d, J=13.2 Hz, 1H), 4.97 (d, J=13.4 Hz, 1H), 4.69 (d, J=2.3 Hz, 1H), 4.57 (dd, J=2.4 and 1.3 Hz, 1H), 4.47 (dd, J=11.0 and 4.5 Hz, 1H), 3.64 (s, 3H), 3.55 (s, 3H), 2.47-2.35 (m, 5H), 2.24-2.20 (m, 1H), 2.01-1.96 (m, 1H), 1.90-0.75 (m, 41H).

Preparation of (3β)-28-(Methoxymethylene)lup-20(29)-en-3-ol, 3-(Methyl 3,3-Dimethylpentanedioate) (18) Using Ylide Generated with Sodium Hexamethyldisilazide. Under an inert atmosphere, (methoxymethyl)triphenylphosphonium chloride (8.00 g, 23.4 mmol) was suspended in anhydrous THF (150 mL) and cooled to 0° C. To this suspension NaHMDS (22.3 mL, 1 M THF) was added and the mixture allowed to warm to rt over a period of 10 min and cooled back to 0° C. The aldehyde 17a (7.0 g, 11.7 mmol) was added as a solid to the dark red solution which turns yellow over a period of 15 min. The mixture was quenched with satd NH$_4$Cl and extracted with EtOAc (3×150 mL). The organic layer was separated, washed with brine (50 mL), dried (Na$_2$SO$_4$), filtered, and concd in vacuo. The residue obtained was purified by SiO$_2$ column chromatography using 0-8% EtOAc/hexanes gradient as eluent to provide 18 (5.0 g, 68.2%) as foamy white solid: mixture of E- and Z-isomers $^1$H NMR (200 MHz, CDCl$_3$) δ 6.28 (d, J=13.2 Hz, 0.4H), 5.78 (d, J=7 Hz, 0.6H), 4.96 (d, J=12.8 Hz, 0.4H), 4.69 (s, 1H), 4.57 (s, 1H), 4.51-4.43 (m, 1H), 4.27 (d, J=7 Hz, 0.6H), 3.65 (s, 1.2H), 3.55 (s, 1.8H), 2.50-2.19 (m, 6H), 2.01-0.75 (m, 24H).

Preparation of (30)-17-[3-(4-Carboxy-3,3-dimethyl-1-oxobutoxy)-28-norlup-20(29)-enyl]acetaldehyde (19). To a solution of enol ether 18 (1.25 g, 2.0 mmol) in THF/MeOH 1:1 (50 mL) under N$_2$ was added 2.5 M KOH (6.0 mL, 15 mmol). The resulting solution was heated at 50° C. for 72 h, then coned in vacuo. Water (50 mL) was added to the residue, the pH adjusted to 1 with 2 M HCl and extracted with DCM (50 mL). To the DCM extract was added TFA (0.1 mL) and water (0.1 mL) and the solution stirred at rt for 24 h. The reaction solution was dried (Na$_2$SO$_4$), filtered, and coned in vacuo to furnish aldehyde 11 as a pale yellow foam: mp 175-176° C.; TLC R$_f$ 0.26 (1:1 heptane/EtOAc); IR (film, ATR) 2944, 1707, 1451, 1229, 978, 907 cm$^1$; $^1$H NMR (250 MHz, CDCl$_3$) δ 9.83 (t, J=2.9 Hz, 1H), 4.70 (br d, J=2.3 Hz, 1H), 4.60 (br t, J=1.3 Hz, 1H), 4.49 (dd, J=9.4 and 4.6 Hz, 1H), 2.57-2.33 (m, 6H), 1.88-0.84 (m, 50H); $^{13}$C NMR (62.9 MHz, CDCl$_3$) δ 204.23, 177.04, 172.19, 149.78, 110.04, 81.23, 55.32, 50.18, 50.00, 47.46, 45.64, 45.50, 45.07, 42.44, 42.16, 40.80, 38.29, 37.62, 37.42, 37.00, 36.29, 34.05, 32.59, 31.84, 28.98, 27.95, 27.91, 27.86, 26.88, 24.86, 23.71, 20.78, 19.27, 18.11, 16.54, 16.10, 15.97, 14.86; LCMS, 98% (ELS), m/z 597 [M+H]⁺ 5%, 619 [M+Na]⁺ 20%.

Alternative Preparation of (30)-17-[3-(4-Carboxy-3,3-dimethyl-1-oxobutoxy)-28-norlup-20(29)-enyl]acetaldehyde (19). To a solution of enol ether 18 (3.25 g, 5.2 mmol) in a 1:1 mixture of THF (65 mL) and MeOH (65 mL) was added 2.5 M KOH (15 mL), 39 mmol). The mixture was stirred at rt for 48 h. The volatiles were removed in vacuo, water (75 mL) was added, the pH adjusted to 1 with 2 M HCl and extracted with DCM (2×50 mL). To the DCM extracts, TFA (0.1 mL) and water (0.1 mL) were added and let stir for 24 h. Additional TFA (0.1 mL) was added and let reaction continue for another 8 h for the reaction to complete. The reaction mixture was dried ($Na_2S_4$), filtered, and coned in vacuo to furnish 3.25 g of 19 as a foamy white solid with analytical data consistent with aldehyde 19 obtained above.

Preparation of (3β)-17-[3-(4-Methoxycarbonyl-3,3-dimethyl-1-oxobutoxy)-28-norlup-20(29)-enyl]acetaldehyde (20). Enol ether 18 (0.100 g, 0.16 mmol) was dissolved in DCM (4.0 mL) and stirred with 2 M HCl (4.0 mL) for 4 days under $N_2$, then extracted with DCM (20 mL). The organic phase was washed with water (10 mL), dried ($Na_2SO_4$), filtered, and concd in vacuo. Aldehyde 20 (0.096 g, 98%) was isolated as a colorless foam: ¹H NMR (360 MHz, $CDCl_3$) δ 9.84 (t, J=3.2 Hz, 1H), 4.70 (br s, 1H), 4.61 (m, 1H), 4.45-4.50 (m, 1H), 3.65 (s, 3H), 2.30-2.56 (m, 6H), 2.09-0.77 (m, 49H); ¹³C NMR (62.9 MHz, $CDCl_3$) δ 204.1, 172.3, 171.7, 149.8, 110.1, 80.8, 55.4, 51.2, 50.2, 50.0, 47.5, 45.7, 45.0, 42.5, 42.2, 40.8, 38.3, 37.6, 37.5, 37.0, 36.3, 34.1, 32.6, 32.1, 29.5, 28.0, 27.7, 26.9, 24.9, 23.7, 20.8, 19.3, 18.1, 16.6, 16.1, 16.0, 14.9; LCMS, 100% ELS, m/z 633 [M+Na]⁺ 10%, m/z 437 [M+H–$MeO_2CCH_2CMe_2CH_2CO_2H$]⁺ 5%, m/z 175 [$MeO_2CCH_2CMe_2CH_2CO_2H+H$]⁺ 100%.

Alternative Procedure for the Preparation of (3)-17-[3-(4-Methoxycarbonyl-3,3-dimethyl-1-oxobutoxy)-28-norlup-20(29)-enyl]acetaldehyde (20). Enol ether 18 (0.050 g, 0.08 mmol) was stirred in wet DCM (2.0 mL) containing TFA (0.0009 g, 0.008 mmol) for 48 h at rt under $N_2$. The reaction mixture was adsorbed onto silica (0.3 g) and purified by silica gel FCC to furnish the desired aldehyde 20 (0.049 g, ~100%) with ¹H NMR identical to aldehyde 20 prepared by DCM/2 M HCl hydrolysis described above. This procedure was performed on 2.2-7.2 mmol scale in 78-88%.

Preparation of (3β)-17-(3-Methoxy-2-propenyl)-28-norlup-20(29)-en-3-ol, 3-(Methyl 3,3-Dimethylpentanedioate) (21). The preparation of enol ether 21 was performed analogously to the method described in enol ether 18. Enol ether 21 was isolated as a colorless oil (1.98 g, 57%) as a 68:32 cis:trans isomers by ¹H NMR: TLC $R_f$ 0.52 (4:1 heptane/EtOAc), 0.35 (9:1 heptane/EtOAc); IR (film, ATR) 2938, 1729, 1649, 1451, 1366, 1214, 1146, 1104, 1007, 981, 935, 880 cm⁻¹; ¹H NMR (400 MHz, $CDCl_3$) δ 6.26 (d, J=12.5 Hz, 0.32$H_{trans}$), 5.98 (d, J=6.6 Hz, 0.68$H_{cis}$), 4.69 (d, J=2.2 Hz, 1H), 4.68-4.63 (m, 0.32$H_{trans}$), 4.59-4.56 (m, 1H), 4.50-4.46 (m, 1H), 4.31 (app q, J=6.8 Hz, 0.68$H_{cis}$), 3.66 (s, 3H), 3.58 (s, 2.04$H_{cis}$), 3.53 (s, 0.96$H_{trans}$), 2.35-2.50 (m, 5H), 2.28 (dd, J=13.5 and 7.7 Hz, 0.68$H_{cis}$), 2.10 (dd, J=13.6 and 7.3 Hz, 0.32$H_{trans}$), 2.00-1.17 (m, 32H), 1.13 (s, 3H), 1.12 (s, 3H), 1.05 (s, 3H), 1.04-0.96 (m, 4H), 0.95 (s, 3H), 0.85 (s, 6H), 0.84 (s, 3H), 0.79 (br d, J=8.8 Hz, 1H) LCMS, 33%+65% ELS, m/z 661 [M+Na]⁺ 5%, m/z 465 [M+H–$MeO_2CCH_2CMe_2CH_2CO_2H$]⁺.

Preparation of (3β)-17-[3-(4-Carboxy-3,3-dimethyl-1-oxobutoxy)-28-norlup-20(29)-enyl]propanaldehyde (22). To a solution of enol ether 21 (1.87 g of a 68:32 cis/trans mixture, 2.93 mmol) in a 1:1 THF/MeOH (80 mL) under $N_2$ was introduced 2.6 M KOH (12.0 mL, 29.3 mmol). After heating at 35° C. for 24 h, the solution was concd to dryness in vacuo at 20° C. and the residue partitioned between DCM (150 mL) and 2 M HCl (50 mL). The organic phase was washed with 2 M HCl (50 mL). To the rapidly stirred organic phase was added TFA (0.25 mL, 3.35 mmol) and water (0.25 mL, 13.90 mmol). After 16 h at 20° C., the organic phase was separated, dried ($Na_2SO_4$), filtered, silica gel (10.0 g) was added, and coned in vacuo. Purification of the dry loaded substrate by silica gel FCC (hexane/EtOAc) gradient of increasing polarity containing 0.5% acetic acid) furnished the carboxylic acid 22 (1.33 g, 74%) as a colorless foam: TLC & 0.09 (DCM); IR (solid, ATR golden gate) 2944, 2868, 1719, 1456, 1211, 1153, 1007, 978, 902, 878, 732 cm⁻¹; ¹H NMR (360 MHz, $CDCl_3$), δ 9.79 (t, J=1.6 Hz, 1H), 4.62 (d, J=2.2 Hz, 1H), 4.52 (dd, J=3.7 and 1.4 Hz, 1H), 4.45-4.40 (m, 1H), 2.44-2.24 (m, 7H), 1.86-1.69 (m, 4H), 1.62-1.13 (m, 29H), 1.07 (s, 6H), 1.02-0.98 (m, 2H), 0.96 (s, 3H), 0.89 (m, 3H), 0.78 (s, 6H), 0.77 (s, 3H), 0.71 (m, 1H): ¹³C NMR (100.6 MHz, $CDCl_3$) δ 203.18, 176.99, 172.25, 150.37, 109.67, 81.31, 55.32, 50.26, 49.51, 47.10, 45.51, 45.14, 45.07, 42.46, 40.81, 39.20, 38.29, 37.61, 36.99, 35.41, 34.07, 32.59, 30.85, 29.66, 27.94, 27.89, 27.84, 26.97, 24.96, 23.70, 20.86, 19.23, 19.20, 18.11, 16.52, 16.07, 16.00, 14.76; LCMS, 100% ELS, m/z 633 [M+Na]⁺ 30%, m/z 451 [M+H–$HO_2CCH_2CMe_2CH_2CO_2H$]⁺.

Preparation of (3β)-17-[3-(4-Methoxycarbonyl-3,3-dimethyl-1-oxobutoxy)-28-norlup-20(29)-enyl]propanaldehyde (23). To a solution of enol ether 21 (0.100 g of a cis/trans mixture, 0.16 mmol) in DCM (5.0 mL) under $N_2$ was introduced TFA (0.025 mL, 0.33 mmol) and water (0.025 mL, 1.4 mmol). After 24 h of rapid stirring at 20° C., silica gel (1.0 g) was added and the reaction mixture coned in vacuo. Purification of the dry-loaded substrate by silica-gel FCC (hexane/EtOAc, 1-10% gradient) furnished the aldehyde 23 (0.089 g, 88%) as a colorless foam: TLC $R_f$ 0.33 (4:1 heptane/EtOAc); ¹H NMR (400 MHz, $CDCl_3$) δ 9.84 (br s, 1H), 4.69 (d, J=1.9 Hz, 1H), 4.59 (s, 1H), 4.49-4.46 (m, 1H), 3.66 (s, 3H), 2.50-2.28 (m, 7H), 1.93-1.18 (m, 26H), 1.13 (s, 3H), 1.12 (s, 3H), 1.10-1.05 (m, 1H), 1.03 (s, 3H), 1.01-0.98 (m, 2H), 0.97 (s, 3H), 0.85 (s, 6H), 0.84 (s, 3H), 0.78 (m, 1H); ¹³C NMR (62.9 MHz, $CDCl_3$) δ 203.07, 172.31, 171.78, 150.32, 109.65, 80.92, 67.87, 55.32, 51.15, 50.25, 49.50, 47.08, 45.61, 45.12, 44.98, 42.44, 40.79, 39.17, 38.28, 37.59, 36.98, 35.39, 34.06, 32.52, 30.83, 29.65, 27.91, 27.65, 26.95, 24.94, 23.69, 20.84, 19.20, 18.09, 16.51, 16.05, 15.98, 14.73; LCMS, 98% ELS, m/z 647 [M+Na]⁺ 5%, m/z 451 [M+H–$MeO_2CCH_2CMe_2CH_2CO_2H$]⁺, m/z 175 [$MeO_2CCH_2CMe_2CH_2CO_2H+1$]⁺, m/z 157 [$MeO_2CCH_2CMe_2CH_2CO_2H+H–H_2O$]⁺ 100%.

Example 14. Syntheses of Betulin C-28 Aldehyde C-3 Esters Via C-3,28 Bis(esters)

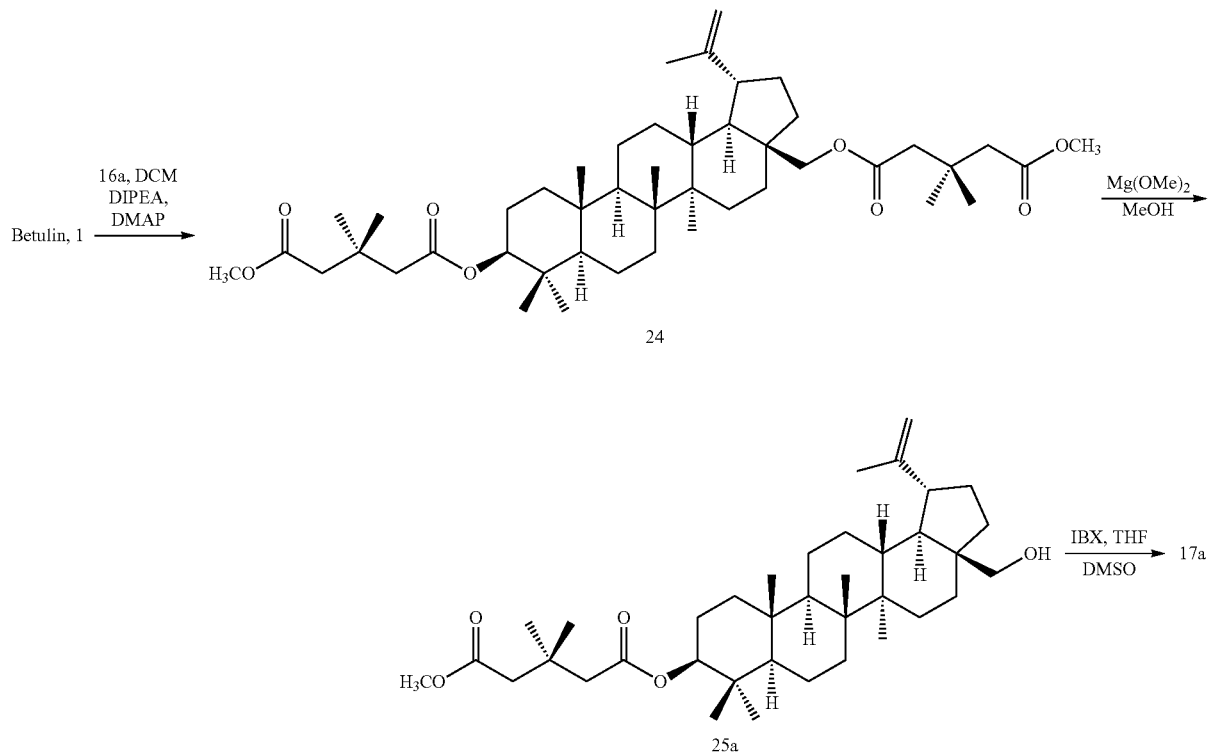

Preparation of (3β)-Lup-20(29)-en-3,28-diol, Bis(Methyl 3,3-Dimethylpentanedioate) (24). To a chilled (0° C.) solution of betulin (1) (0.500 g, 1.13 mmol), DIPEA (0.63 mL, 3.95 mmol), and DMAP (0.010 g) in DCM (10 mL) under $N_2$ was added methyl 3,3-dimethylglutaryl chloride (16a) (0.651 g, 3.39 mmol). The solution was allowed to warm to rt and stirred at rt for 16 h. The reaction mixture was diluted with DCM (50 mL) and washed with 2 M HCl (2×10 mL), water (10 mL), and brine (10 mL). The organic phase was dried ($MgSO_4$), filtered, and the filtrate dry-loaded onto silica gel. Purification by FCC using hexane with a 1-10% EtOAc gradient furnished the desired bis-ester 24 (0.611 g, 72%) as a colorless foam: $^1$H NMR (360 MHz, $CDCl_3$) δ 4.69 (m, 1H), 4.59 (m, 1H), 4.48 (dd, J=10.9, 4.7 Hz, 1H), 4.24 (d, J=10.8 Hz, 1H), 3.85 (d, J=10.8 Hz, 1H), 3.66 (s, 3H), 3.65 (s, 3H), 2.47-2.38 (m, 8H), 2.00-0.77 (m, 43H); IR (solid, ATR golden-gate) ν (C:O) 1719 $cm^{-1}$.

Preparation of (3β)-3-(4-Methoxycarbonyl-3,3-dimethyl-1-oxobutoxy)lup-20(29)-en-28-ol (25a). A 6% solution of $Mg(OMe)_2$ in MeOH (39 mL, 1.4 mmol) was added to a solution of bis-ester 24 (0.600 g, 0.795 mmol) in MeOH (200 mL) under $N_2$. The resulting suspension was heated at 100° C. for 96 h. Additional $Mg(OMe)_2$ solution (3×39 mL) was added during the course of the reaction. After cooling to rt, the mixture was filtered, concd in vacuo, and the residue partitioned between EtOAc (200 mL) and 2 M HCl (200 mL). The organic phase was dried ($Na_2SO_4$), filtered, and concd in vacuo onto silica gel (5 g). Purification by FCC using hexane with a 1-16% EtOAc gradient provided monoester 25a (0.178 g, 37%) as a colorless foam: $^1$H NMR (400 MHz, $CDCl_3$) δ 4.68 (d, J=2.1 Hz, 1H), 4.58 (t, J=1.8 Hz, 1H), 4.47 (dd, J=11.3 and 4.7 Hz, 1H), 3.79 (d, J=10.8 Hz, 1H), 3.65 (s, 3H), 3.33 (d, J=10.8 Hz, 1H), 2.46-2.35 (m, 5H), 1.95-0.76 (m, 49H); $^{13}$C NMR (90 MHz, $CDCl_3$) δ 172.1, 171.6, 150.3, 109.5, 80.7, 60.1, 55.2, 51.0, 50.1, 48.6, 47.7, 47.6, 45.5, 44.9, 42.5, 40.8, 38.2, 37.5, 37.1, 36.9, 34.0, 33.8, 32.4, 29.6, 29.0, 27.8, 27.6, 26.9, 25.0, 23.6, 20.7, 18.9, 18.0, 16.5, 16.0, 15.8, 14.6; IR (solid ATR golden-gate) ν (OH) 3560-3300 (br.) $cm^{-1}$, ν (C:O) 1724 $cm^{-1}$; LC/MS 100% (ELS), m/z 599 $[M+H]^+$ 5%.

Preparation of (3β)-3-(4-Methoxycarbonyl-3,3-dimethyl-1-oxobutoxy)lup-20(29)-en-28-al (17a). To a solution of alcohol 25 (0.059 g, 0.10 mmol) in 1:1 THF/DMSO (4.0 mL) under $N_2$ was added IBX (0.042 g, 0.15 mmol). The reaction mixture was stirred at rt for 3 h, the THF removed in vacuo, and the residual solution poured into water (40 mL) and extracted with diethyl ether (3×20 mL). The combined organic phases were dried ($MgSO_4$), filtered, and concd in vacuo to furnish aldehyde 17a (0.053 g, 90%) with analytical data consistent with that prepared according to Example 13 (TLC and $^1$H NMR analyses).

Example 15. Syntheses of Betulin C-28 Aldehyde C-3 Esters from C-3, 28 Diols Via Selective Protection of the C-28 Alcohol Scheme 15. Alternative Syntheses of Betulin C-28 Aldehyde C-3 Ester 17c from Betulin via Selective Protection of the C-28 Alcohol

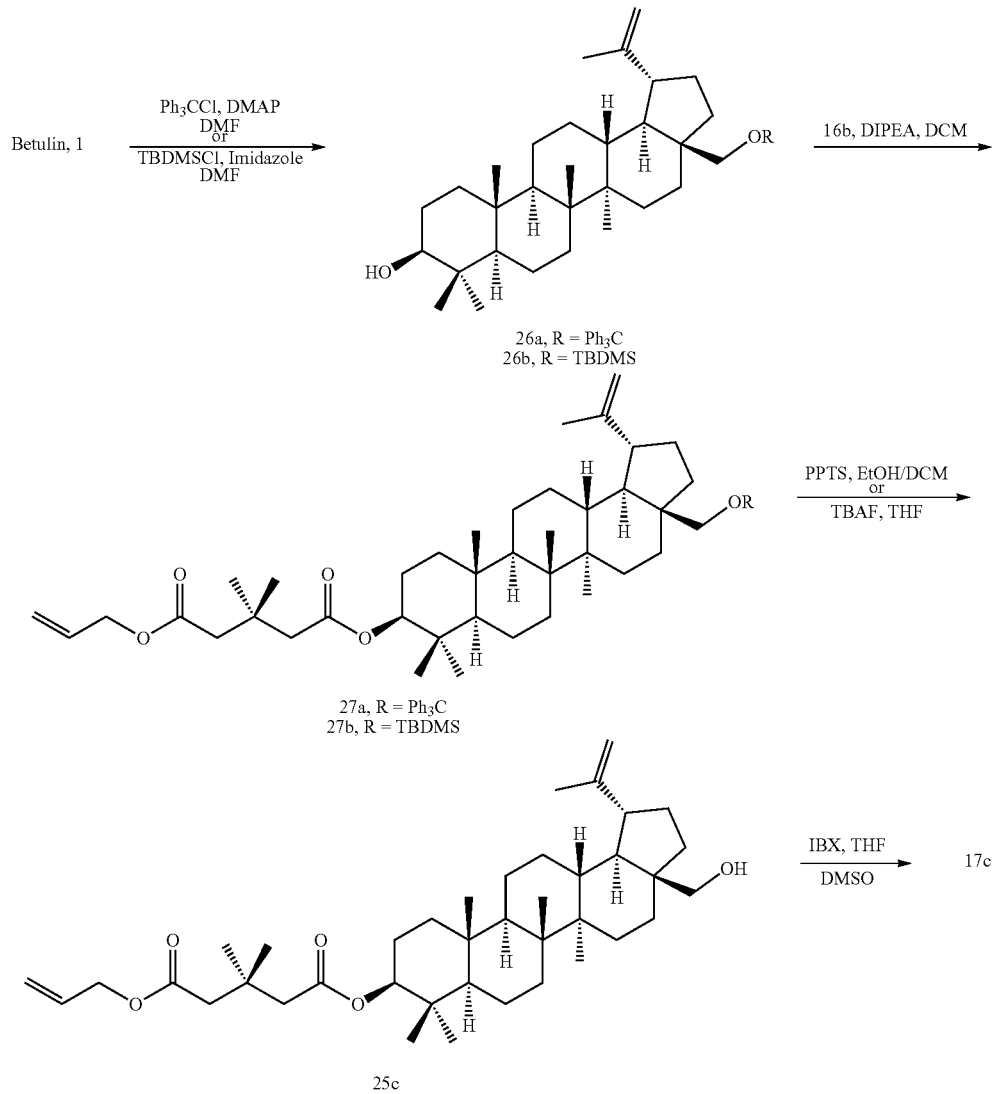

Preparation of (3β)-28-(Triphenylmethoxy)lup-20(29)-en-3-ol (26a). Trityl chloride (2.85 g, 10.0 mmol) and DMAP (0.97 g, 7.7 mmol) were added to a suspension of betulin 1 (3.1 g, 7.0 mmol) in DMF (20 mL) under $N_2$. The reaction mixture was heated to reflux for 5.5 h. The reaction mixture was diluted in EtOAc (200 mL), washed six times with water, dried ($Na_2SO_4$), and concd in vacuo to dryness. The resulting solid was purified by FCC on silica gel (0 to 20% EtOAc in heptane) to provide 26a as a white solid (2.0 g, 42%): $^1$H NMR (400 MHz, acetone-$d_6$) δ 7.81 (s, 3H), 7.47-7.29 (m, 6H), 7.28-7.04 (m, 6H), 4.48-4.34 (m, 2H), 3.10 (d, J=8.8 Hz, 1H), 2.96 (dd, J=10.2 and 5.5 Hz, 1H), 2.82 (d, J=8.8 Hz, 1H), 2.16-2.01 (m, 3H), 1.94-1.87 (m, 2H), 1.68-0.41 (m, 38H).

Preparation of (3β)-28-[(Dimethylethyl)dimethylsilyloxy]lup-20(29)-en-3-ol (26b). A solution of tert-butyldimethylsilyl chloride (0.79 g, 4.8 mmol) in dry DMF (10 mL) was added to a chilled (° C.) suspension of betulin (1) (2.0 g, 4.4 mmol) and imidazole (0.4 g, 5.8 mmol) in DMF (20 mL) under $N_2$. The reaction mixture was heated at 60° C. overnight (became a clear solution above 45° C.). The reaction mixture was diluted in EtOAc (300 mL), washed three times with sat $NaHCO_3$, four times with water, dried ($Na_2SO_4$), filtered, and concd in vacuo to dryness. The resulting solid was purified by FCC on silica gel (0 to 30% EtOAc in heptane) providing 26b as a white solid (1.8 g, 71%): TLC (30% EtOAc/heptane) $R_f$ 0.58; $^1$H NMR (400 MHz, $CDCl_3$) δ 4.63 (d, J=2.4 Hz, 1H), 4.53 (s, 1H), 3.63 (d, J=9.8 Hz, 1H), 3.25-3.10 (m, 2H), 2.42-2.30 (m, 1H), 1.96-1.80 (m, 4H), 1.72-0.58 (m, 56H).

Preparation of (3β)-[28-(Triphenylmethoxy)]lup-20(29)-en-3-ol, 3-[1-(2-Propenyl) 3,3-Dimethylpentanedioate] (27a). To a chilled (0°C) solution of allyl 3,3-dimethylglutaryl chloride (16b) (0.66 g, 3.1 mmol) and DIPEA (1.04 mL, 6.00 mmol) in dry DCM (20 mL) under $N_2$ was added trityl ether 26a (2.00 g, 2.92 mmol). The reaction mixture was stirred at 40° C. overnight, diluted with DCM (50 mL), washed three times with 1 M $Na_2CO_3$, water, dried ($MgSO_4$), and concd in vacuo to dryness. Purification by FCC on silica gel using 5:95 EtOAc/heptane provided 27a (1.0 g, 39%) as a pale oil: H NMR (400 MHz, acetone-$d_6$) δ 7.51-7.32 (m, J 7.0 Hz, 6H), 7.31-7.03 (m, 9H), 5.91-5.72 (m, 1H), 5.27-4.99 (m, 2H), 4.51-4.22 (m, 5H), 3.10 (d, J=9.5 Hz, 1H), 2.82 (d, J=9.1 Hz, 1H), 2.43-2.18 (m, 5H), 2.16-2.00 (m, 3H), 2.00-0.27 (m, 45H); $R_f$=5.30; m/z (relative intensity) 890 [M+Na]$^+$ 100%.

Preparation of (3)-28-[(Dimethylethyl)dimethylsilyloxy] lup-20(29)-en-3-ol, 3-[1-(2-Propenyl) 3,3-Dimethylpentanedioate] (27b). To a chilled (0° C.) solution of allyl 3,3-dimethylglutaryl chloride (16b) (0.98 g, 4.4 mmol) and DIPEA (1.5 mL, 9.0 mmol) in dry DCM (10 mL) under $N_2$ was added TBDMS ether 26b (1.8 g, 3.2 mmol). The reaction mixture was stirred at 40° C. overnight. The reaction was concd in vacuo to dryness and the solid obtained purified by FCC on silica gel using 5:95 EtOAc/heptane to give the desired compound (0.58 g, 25%) as a white solid: $^1$H NMR (400 MHz, CDCl$_3$) δ 6.01-5.72 (m, 1H), 5.28 (d, J 17.1 Hz, 1H), 5.19 (d, J=11.7 Hz, 1H), 4.68-4.49 (m, 4H), 4.48-4.33 (m, 1H), 3.63 (d, J=8.8 Hz, 1H), 3.21 (d, J=9.8 Hz, 1H) 2.50-2.26 (m, 5H), 1.99-1.73 (m, 3H), 1.70-0.66 (m, 54H), 0.06 to −0.06 (m, 6H).

Preparation of (3β)-Lup-20(29)-en-28-ol, 3-[1-(2-Propenyl) 3,3-Dimethylpentanedioate] (25c). Trityl ether 27a (0.98 g, 1.11 mmol) and PPTS (1.53 g, 6.62 mmol) were refluxed overnight in a 2:1 mixture EtOH/DCM (18 mL) under an inert atmosphere. The reaction mixture was concd in vacuo and the residue partitioned between water and EtOAc. The organic phase was washed twice with water, dried (Na$_2$SO$_4$), and concd in vacuo. Purification by FCC on silica gel using 0 to 20% EtOAc/heptane provided 25c (0.52 g, 75%) as a white solid: $^1$H NMR (400 MHz, CDCl$_3$) δ 6.00-5.82 (m, 1H), 5.38-5.17 (m, 2H), 4.68 (d, J=2.4 Hz, 1H), 4.61-4.52 (m, 3H), 4.50-4.42 (m, 1H), 3.80 (d, J=10.3 Hz, 1H), 3.33 (d, J=10.8 Hz, 1H), 2.56-0.57 (m, 53H).

Preparation of (3)-Lup-20(29)-en-28-ol, 3-[1-(2-Propenyl) 3,3-Dimethylpentanedioate] (25c). TBDMS ether 27b (0.578 g, 0.780 mmol) and TBAF (2.1 mL, 1 M in THF, 2.2 mmol) were stirred overnight in THF (2 mL) at rt under N$_2$. The reaction mixture was diluted with EtOAc, washed twice with water, dried (Na$_2$SO$_4$) and concd in vacuo. Purification by FCC on silica gel 0 to 10% EtOAc/heptane) provided 25c (0.402 g, 82%) as a white solid with analytical data consistent with that obtained above.

Preparation of (3)-Lup-20(29)-en-28-al, 3-[1-(2-Propenyl) 3,3-Dimethylpentanedioate] (17c). A solution of alcohol 25c (370 mg, 0.592 mmol) in DCM (4 mL) was added to a suspension of Dess-Martin periodinane (290 mg, 0.684 mmol) in DCM (3 mL) under N$_2$ and left stirring at rt for 3 h. The reaction mixture was washed three times with 1 M NaOH, dried (Na$_2$SO$_4$) and concd to yield 381 mg of aldehyde 17c. This compound was used without further purification.

Example 16. Syntheses of C-3 3,3-Dimethylsuccinyl C-19 1-Methyl-1-Cyclopropyl Betulin C-28 Aldehyde and C-28 Homologated Aldehyde Intermediates Scheme 16. Syntheses of C-3 3,3-Dimethylsuccinyl C-19 1-Methyl-1-Cyclopropyl Betulin C-28 Aldehyde and C-28 Homologated Aldehyde Intermediates 28 and 30

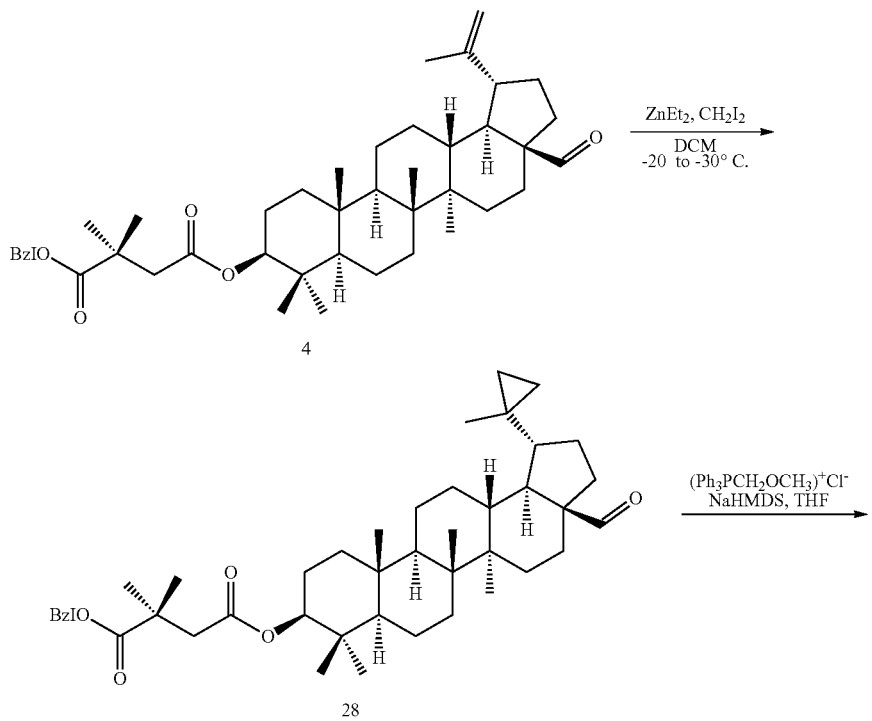

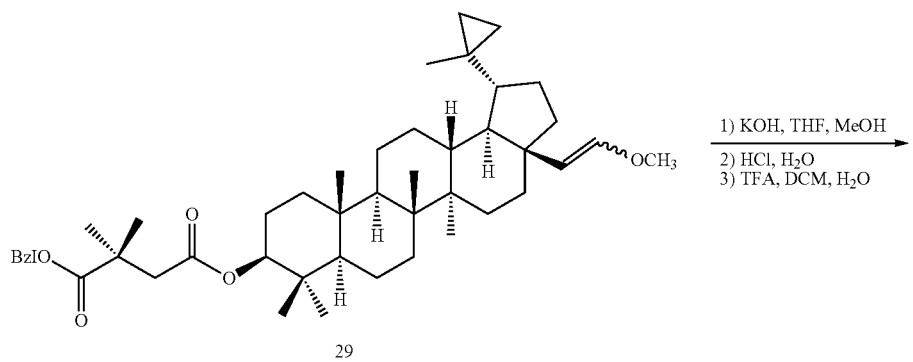

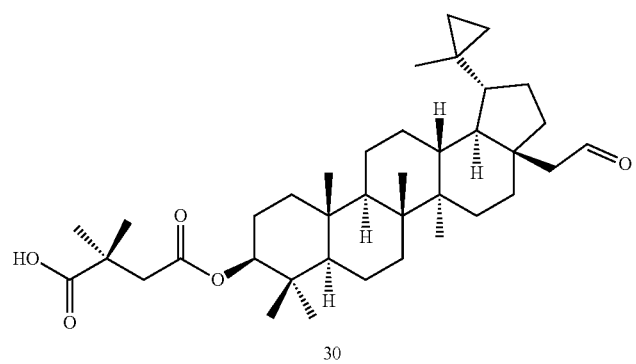

Preparation (3β)-3-[(1-Phenylmethoxycarbonyl)-3-methyl-2-oxobutoxy)]-20,29-methanolupan-28-al, (28): To a cold (−20° C.) solution of aldehyde 4 (1.40 g, 2.0 mmol) in DCM (60 mL) was added diethylzinc (10.0 mL, 1 M solution in hexanes). After 1 h diiodomethane (1.3 mL, 16 mmol) was added and the mixture was allowed to warm to rt and stirred for 16 h. The mixture was quenched with satd NH$_4$Cl and extracted with EtOAc (3×40 mL). The combined organic phases were washed with brine (20 mL), dried (Na$_2$SO$_4$), filtered, and coned in vacuo. The residue obtained was purified by silica gel column chromatography eluting with 1-10% EtOAc in hexanes furnishing 28 (760 mg, 53.1%) as a white solid: $^1$H NMR (400 MHz, CDCl$_3$) δ 9.61 (m, 1H), 7.30-7.40 (m, 5H), 5.13 (s, 2H), 4.48 (m, 1H), 2.62 (dd, 2H), 2.15-0.70 (m, 48H), 0.45-0.15 (m, 4H).

Preparation of (3β)-20,29-Methano-28-(methoxymethyl-ene)lupan-3-ol, 3-(1-(Phenylmethyl 2,2-Dimethylbutane-dioate) (29): (Methoxymethyl)triphenylphosphonium chloride (715 mg, 2.08 mmol) was suspended in anhydrous THF (15 mL) and cooled to 0° C. To this suspension NaHMDS (2.1 mL, 1 M/THF) was added and the mixture allowed to warm to rt over a period of 10 min and cooled back to 0° C. The aldehyde 28 (700 mg, 1.04 mmol) was added as a solid to the dark red solution which turns yellow over a period of 15 min. The mixture was quenched with satd NH$_4$Cl and extracted with EtOAc (3×50 mL). The organic layer was separated, washed with brine (20 mL), dried (Na$_2$SO$_4$), filtered, and coned in vacuo. The crude mixture was purified by column chromatography using 0 to 5% EtOAc in hexanes as eluent to provide 29 (mixture of E- and Z-isomers, 330 mg, 45.3%) as a foamy white solid: $^1$H NMR (200 MHz, CDCl$_3$) δ 7.37-7.9 (m, 5H), 6.22 (d, J=13.0 Hz, 0.4H), 5.73 (d, J=7 Hz, 0.6H), 5.13 (s, 2H), 5.05 (d, J=7 Hz, 0.6H), 4.88 (d, J=12.8, 0.4H), 4.49 (m, 1H), 3.52 (m, 3H), 2.63 (dd, 2H), 2.30-0.72 (m, 49H), 0.42-0.15 (m, 4H).

Preparation of (3β)-17-[3-(3-Carboxy-3-methyl-2-oxobu-toxy)-20,29-methano-28-norlupan]acetaldehyde (30): To a solution of enol ether 29 (330 g, 0.47 mmol) in a 1:1 mixture of THF (5 mL) and MeOH (5 mL) was added 2.5 M KOH (1.5 mL, 3.9 mmol). The mixture was stirred at rt for 48 h, then concd in vacuo. Water (7.5 mL) was added, the pH adjusted to 1 with 2 M HCl, and extracted with DCM (2×10 mL). To the DCM extract TFA (0.1 mL) and water (0.1 mL) were added and stirred for 24 h. Additional TFA (0.1 mL) was added and stirred for an additional 8 h. The reaction mixture was dried (Na$_2$SO$_4$), filtered, and concd in vacuo. The crude mixture was purified by column chromatography using 0-25% EtOAc in hexanes to furnish 120 mg of 30 as a foamy white solid: $^1$H NMR (200 MHz, CDCl$_3$) δ 9.78 (t, 1H), 4.49 (m, 1H), 2.62 (dd, 2H), 2.20-0.60 (m, 51H), 0.50-0.15 (m, 4H).

Example 17. Syntheses of C-3 3,3-Dimethylglutaryl 28-Lupaneamine Intermediates

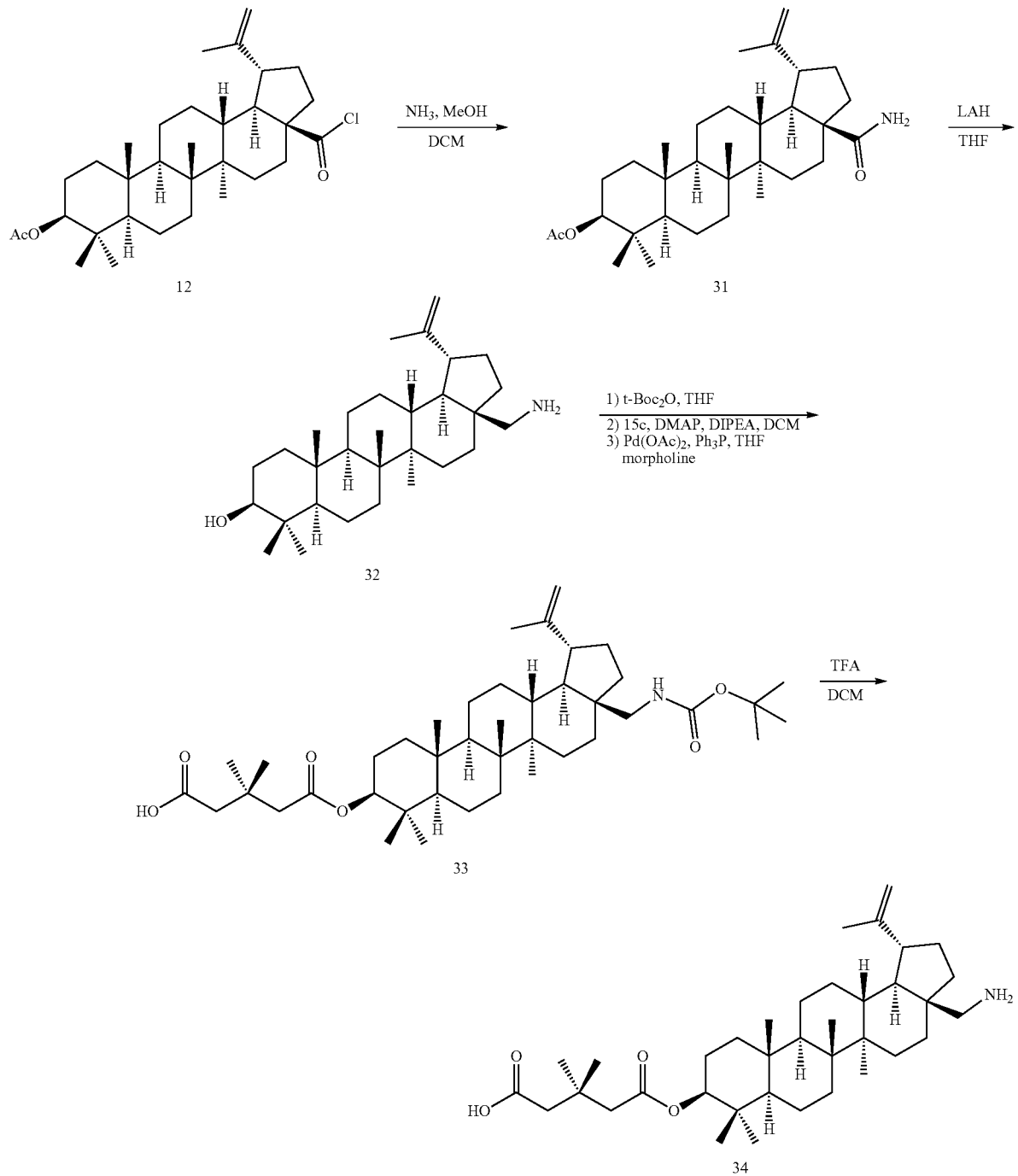

Preparation of (3β)-3-(Acetyloxy)lup-20(29)-en-28-amide (31). To a solution of 12 (556 mg, 1.08 mmol) DCM was added excess 7 M ammonia in methanol. The reaction was stirred at rt overnight. The volatiles were removed in vacuo. The residue was diluted with EtOAc and washed successively with 1 M HCl, water, dried ($Na_2SO_4$), and coned to dryness in vacuo. The resulting oil was purified by flash column chromatography on silica gel (hexane/EtOAc) to provide 230 mg (43%) 31: TLC $R_f$ 0.4 (EtOAc/Heptane 40:60).

Preparation of (3β)-28-Aminolup-20(29)-en-3-ol (32). A solution of LAH in THF (1 M, 2 mL) was added to a solution of 31 (230 mg, 0.46 mmol) in dry THF (3 mL) and the reaction was stirred at 45° C. for 16 h. The reaction was carefully quenched with 1 M $K_2CO_3$, and extracted several times with EtOAc. The organic phase was dried ($Na_2SO_4$) and coned in vacuo to give the desired crude 28-aminolup-20(29)-ene (32) (170 mg) which was used without further purification.

Preparation of N-[1-[(3)-3-(4-Carboxy-3,3-dimethyl-1-oxobutoxy)lup-20(29)-en-28-yl]]carbamic Acid, 1,1-Dimethylethyl Ester (33). Di-tert-butyl dicarbonate (1.1 equ) was added to a solution of 32 (1 equ) in dry THF (5 mL) and left stirring at rt for 3 h. The reaction mixture was then diluted with methanol and all organic solvents were removed in vacuo to yield a crude solid which was used without further purification. Using the method as described for 27a and 27b, the crude solid was acylated with 15c in dry DCM, followed by DMAP (1 equ) and DIPEA (4 equ). The reaction was heated at 40° C. overnight, diluted in EtOAc, washed successively with 1 M HCl, water, dried ($Na_2SO_4$), filtered, and concd to dryness in vacuo. The crude product was purified by FCC on silica gel (hexane/EtOAc) to provide the desired diprotected amino acid. Palladium (11) acetate (1.05 equ) and polymer bound triphenylphosphine (3.1 equ) were added to a degassed solution of the diprotected amino acid (1 equ) and morpholine (20 equ) in THF under a nitrogen atmosphere. The reaction was stirred overnight at 60° C., cooled to rt, and filtered. The filtrate was diluted with EtOAc, washed successively with 1 M $KHSO_4$, water, dried ($Na_2SO_4$), coned to dryness in vacuo and the resulting solid purified by FCC on silica gel (hexane/EtOAc) to provide the desired protected amino acid 33; $^1$H NMR (400 MHz, $CDCl_3$) δ 4.68 (m, 1H), 4.58 (m, 1H), 4.52-4.47 (dd, J=4.6 and 10.8 Hz, 1H), 4.41-4.34 (m, 1H), 3.32-3.27 (dd, J=5.4 and 13.4 Hz, 1H), 2.97-2.92 (dd, J=6.8 and 13.7 Hz, 1H), 2.49-2.38 (m, 4H), 2.07-1.97 (m, 1H), 1.75-0.77 (m, 48H); LCMS, 87% pure, $R_f$ 5.21, m/z (relative intensity) 707 $[M+Na]^+$ 55%.

Preparation of (3)-3-(4-Carboxy-3,3-dimethyl-1-oxobutoxy)lup-20(29)-en-28-amine (34). TFA (~10 equ) was added to a solution of 33 in DCM at 0° C. The ice bath was removed and the reaction mixture allowed to warm to rt over 2 h. The reaction mixture was coned to dryness in vacuo, dissolved in DCM and concd to dryness in vacuo. Dilution and evaporation was twice repeated. Purification by FCC on silica gel (hexane/EtOAc) provided 34: $^1$H NMR (250 MHz, $CD_3OD$) δ 4.66 (m, 1H), 4.59 (m, 1H), 4.40-4.34 (m, 2H), 3.08-3.02 (m, 1H), 2.68-2.62 (m, 1H), 2.42-2.28 (m, 4H), 2.04-1.85 (m, 1H), 1.74-0.75 (m, 50H); LCMS, 95% pure, $R_t$ 4.03, m/z (relative intensity) 585 $[M+H]^+$ 100%.

Example 18. Syntheses of C-3 3,3-Dimethylglutaryl Homologated 28-Lupaneamine Intermediates

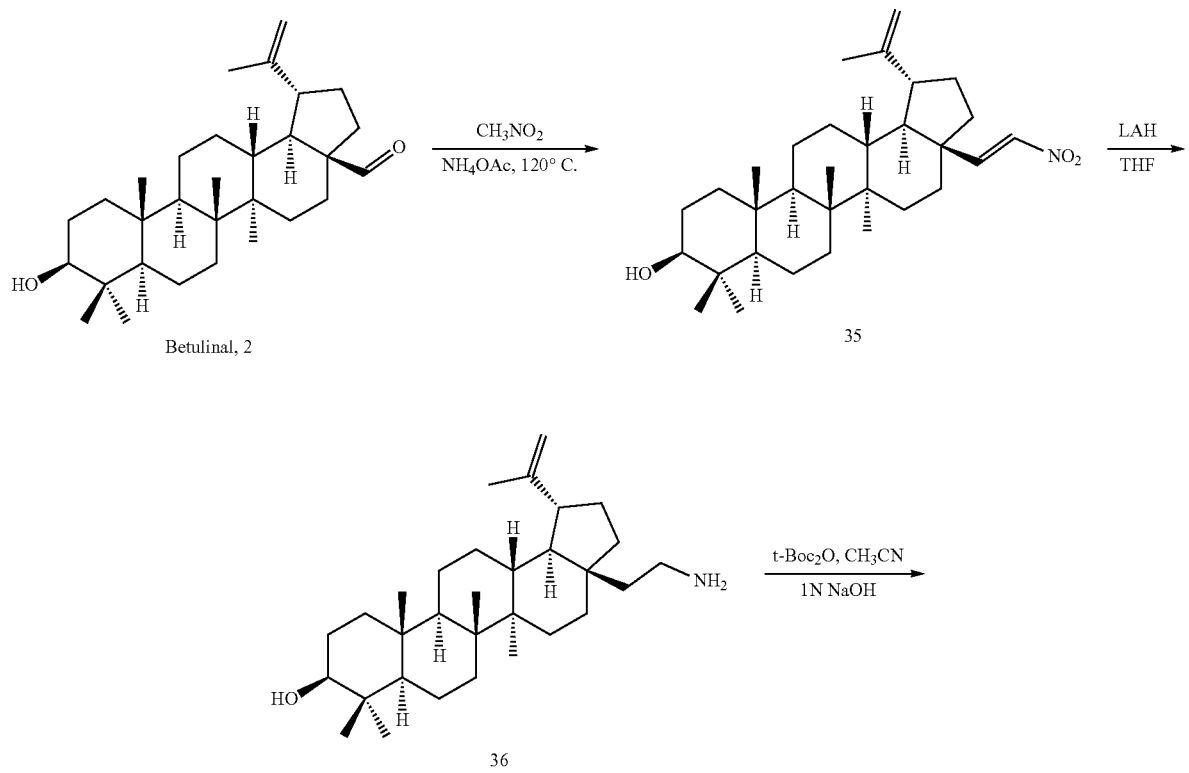

Scheme 18. Syntheses of C-3 3,3-Dimethylglutaryl Homologated 28-Lupaneamine 40

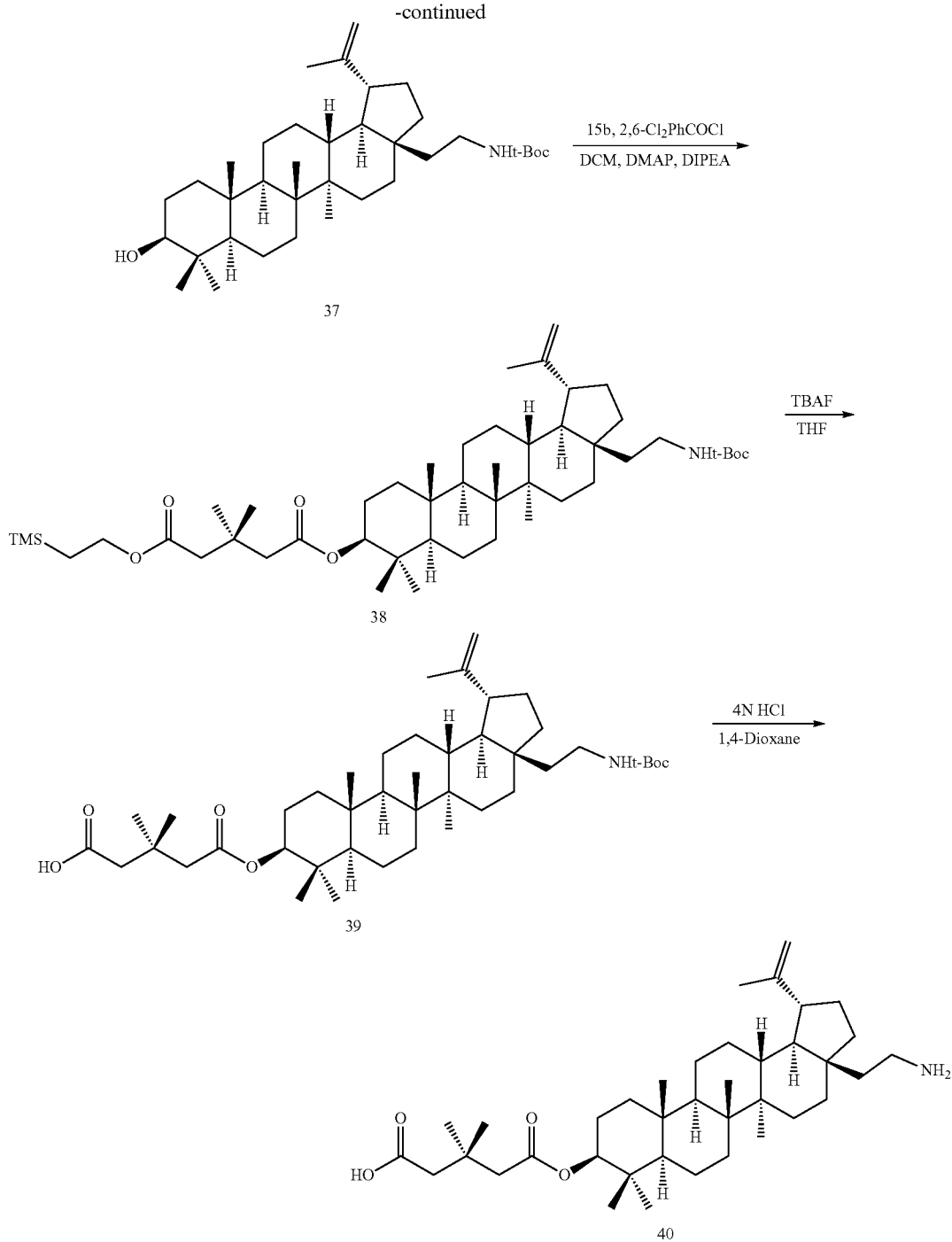

Preparation of (3β)-28-(Nitromethylene)lup-20(29)-en-3-ol (35). Into a thick glass walled pressure tube (Ace #15 tube) was introduced 2 (4.0 g, 9.08 mmol), ammonium acetate (3.49 g, 45.3 mmol), and nitromethane (20.0 mL). The tube was capped and heated to 120° C. for 3 h. After cooling, the reaction mixture was diluted with DCM (120 mL), washed with 1 M KHSO$_4$ (2×20 mL) and brine (2×20 mL), dried (Na$_2$SO$_4$), filtered, and coned in vacuo furnishing nitroalkane 35 (3.56 g, 7.37 mmol, 81%) as a pale yellow amorphous solid: IR (solid, ATR golden-gate) 3545, 2929, 1639, 1518, 1449, 1352, 1047, 978, 881, 724 cm$^{-1}$; $^1$H NMR (360 MHz, CDCl$_3$) 7.56 (d, J=13.6 Hz, 1H), 7.02 (d, J=13.6 Hz, 1H), 4.75 (d, J=1.8 Hz, 1H), 4.65 (br s, 1H), 3.16-3.21 (m, 1H), 2.45-2.53 (m, 1H), 1.80-1.92 (m, 2H), 1.04-1.73 (m, 24H), 1.00 (s, 3H), 0.97 (s, 3H), 0.96 (s, 3H), 0.83-0.95 (m, 2H), 0.82 (s, 3H), 0.76 (s, 3H), 0.67-0.69 (m, 1H); $^{13}$C NMR (CDCl$_3$, 62.9 MHz) δ 148.80, 147.14, 139.80, 110.58, 78.86, 55.21, 50.22, 49.87, 49.22, 47.63, 42.81, 40.72, 39.31, 38.78, 38.63, 38.48, 37.07, 34.21, 33.08, 29.37, 27.92, 27.66, 27.28, 25.07, 20.60, 19.17, 18.17, 16.02, 15.84, 15.31, 14.67; LCMS, 100% ELS, m/z 484 [M+H]$^+$ 5%, m/z 466 [M+H−H$_2$O]$^+$ 100%.

Preparation of (3β)-17-(2-Aminoethyl)-28-norlup-20 (29)-en-3-ol (36). To a chilled (5° C.) solution of nitroalkane 35 (0.150 g, 0.31 mmol) in anhydrous THF (17.0 mL) under an atmosphere of nitrogen was added LAH (3.10 mL of a 1.0 M solution in THF, 3.10 mmol). The cloudy solution was warmed to rt and stirred rapidly for 16 h. After careful addition of water until effervescence ceased, the reaction mixture was diluted with EtOAc (25 mL) and washed with 1 M NaOH (25 mL). The aqueous phase was extracted with EtOAc (3×5 mL). The combined organic phases were dried (MgSO$_4$), filtered, and concd in vacuo providing amine 36 (0.100 g) as a colorless solid. Purification by reverse-phase chromatography (Macherey-Nagel Chromabond C18-ec, 1.0 g cartridge, eluent: water/methanol 100:0 to 0:100 gradient) afforded amine 36 (0.026 g, 0.057 mmol, 18%) as a colorless, amorphous solid: IR (solid, ATR golden gate) 2933, 1453, 1371, 1264, 1190, 1036, 907, 872 cm$^{-1}$; $^1$H NMR (400 MHz, CDCl$_3$) δ 4.69 (d, J=2.4 Hz, 1H), 4.58 (s, 1H), 3.17-3.21 (m, 1H), 2.63-2.75 (m, 2H), 2.44 (dt, J=11.2 and 5.8 Hz, 1H), 0.90-1.99 (m, 28H), 1.05 (s, 3H), 0.97 (s, 6H), 0.96 (s, 3H), 0.83 (s, 3H), 0.77 (s, 3H), 0.69 (br d, J=8.8 Hz, 1H); $^{13}$C NMR (62.9 MHz, CDCl$_3$) δ 150.69, 109.50, 78.91, 55.27, 50.41, 49.92, 47.30, 45.06, 42.49, 40.33, 38.83, 38.67, 37.76, 37.12, 37.04, 35.96, 34.21, 31.32, 29.97, 27.96, 27.37, 27.28, 25.06, 20.90, 19.26, 18.28, 16.09, 15.35, 14.86; LCMS, 100% ELS, m/z 456 [M+H]$^+$ 100%.

Preparation of N-17-[2-[(3β)-3-Hydroxy-28-norlup-20 (29)-en]ethyl]carbamic Acid, 1,1-Dimethylethyl Ester (37). To a vigorously stirred suspension of amine 36 (3.65 g, 8.02 mmol) in acetonitrile (30 mL) was introduced di-tert-butyl dicarbonate (1.92 g, 8.8 mmol) and 1 M NaOH (12.0 mL, 12.0 mmol). After 16 h at rt, the reaction mixture was evaporated to dryness in vacuo and the residue re-dissolved in DCM (100 mL). After washing with brine (2×100 mL), the organic phase was dried (MgSO$_4$), filtered, and concd in vacuo providing 37 (4.26 g, 7.66 mmol, 96%) as an off-white solid: $^1$H NMR (250 MHz, CDCl$_3$) δ 4.66 (1H, d, J=2.0 Hz), 4.56 (2H, m), 3.12-3.22 (1H, m), 2.91-3.17 (2H, m), 2.38 (1H, dt, J=11.0 and 5.7 Hz), 0.75-1.72 (54H, m), 0.66 (1H, br d, J=8.6 Hz); LCMS, 87% ELS, m/z 500 [M+H−C(CH$_3$)$_3$]$^+$ 5%, m/z 482 [M+H−(CH$_3$)$_3$COH]$^+$ 100%.

Preparation of (3β)-17-[[2-[[(1,1-Dimethylethyl)oxy]carbonyl]amino]ethyl]-28-norlup-20(29)-en-3-ol; 3-[2-(Trimethylsilyl)ethyl 3,3-Dimethylpentanedioate] (38). To a solution of alcohol 37 (4.20 g, 7.55 mmol) in DCM (30 mL) was introduced DIPEA (2.0 mL, 11.30 mmol), DMAP (0.92 g, 7.55 mmol) and 3,3-dimethylglutarate 2-(trimethylsilyl) ethyl ester (15b) (2.16 g, 8.30 mmol). After 5 min, 2,6-dichlorobenzoyl chloride (1.20 mL, 8.30 mmol) was added and the reaction mixture stirred at rt for 16 h. The reaction mixture was washed with 1 M HCl (25 mL), 1 M NaOH (25 mL), brine (5 mL), dried (Na$_2$SO$_4$), filtered, and concd in vacuo to an oil that was purified by silica gel FCC (heptane/EtOAc, 0-25% gradient) to furnish ester 38 (5.02 g, 6.29 mmol, 83%) as a colorless oil: $^1$H NMR (250 MHz, CDCl$_3$) δ 4.68 (m, 1H), 4.58 (br m, 1H), 4.45-4.51 (m, 1H), 4.12-4.18 (m, 2H), 2.91-3.13 (br s, 2H), 2.42-2.53 (m, 1H), 2.47 (d, J=14.4 Hz), 2.40 (s, 2H), 2.38 (d, J=14.4 Hz and 1H), 0.90-1.71 (m, 32H), 1.46 (s, 6H), 1.13 (s, 9H), 1.03 (s, 3H), 0.96 (s, 3H), 0.86 (s, 6H), 0.84 (s, 3H), 0.79 (br d, J=6.7 Hz, 1H), 0.04 (s, 9H); LCMS, 97% ELS.

Preparation of (3β)-17-[[2-[[(1,1-Dimethylethyl)oxy]carbonyl]amino]ethyl]-28-norlup-20(29)-en-3-ol; 3-(Hydrogen 3,3-Dimethylpentanedioate) (39). To a solution of ester 38 (0.200 g, 0.27 mmol) in THF (3.0 mL) was added tetra-n-butylammonium fluoride (0.70 mL of a 1.0 M solution in THF, 0.70 mmol). After 64 h at rt, the reaction mixture was concd in vacuo, the residue re-dissolved in EtOAc (2.5 mL) and washed with 1 M HCl (2×2.5 mL). The organic phase was dried (Na$_2$SO$_4$), filtered, and concd in vacuo. The residue obtained was purified by silica gel FCC (DCM/EtOAc, 0-100% gradient) to furnish carboxylic acid 39 (0.105 g, 0.15 mmol, 55%) as a colorless amorphous solid: $^1$H NMR (360 MHz, CDCl$_3$) δ 4.63 (br s, 1H), 4.45 (br s, 1H), 4.39-4.48 (m, 2H), 2.87-3.12 (m, 2H), 2.42 (d, J=14.1 Hz, 1H), 2.41 (s, 2H), 2.35 (d, J=14.1 Hz, 1H), 2.29-2.35 (m, 1H), 1.79-1.86 (m, 2H), 0.87-1.71 (m, 41H), 1.40 (s, 9H), 1.09 (s, 6H), 0.98 (s, 3H), 0.90 (s, 3H), 0.81 (s, 6H), 0.80 (s, 3H), 0.73 (br d, J=8.2 Hz, 1H); LCMS, 95% ELS, m/z 698 [M+H]$^+$ 20%, m/z 720 [M+Na]$^+$, m/z 598 [M−t-Boc+H]$^+$ 50%, m/z 482 [M+H−HO$_2$CCH$_2$CMe$_2$CH$_2$CO$_2$H—CH$_2$CMe$_2$]$^+$ 100%.

Preparation of (3β)-17-(2-Aminoethyl)-28-norlup-20 (29)-en-3-ol; 3-(Hydrogen 3,3-Dimethylpentanedioate) (40) Hydrochloride Salt. To a solution of 39 (0.100 g, 0.14 mmol) in 1,4-dioxane (1.0 mL) was introduced a 4 M HCl in 1,4-dioxane solution (0.36 mL, 1.40 mmol). After 16 h at rt, the reaction mixture was concd in vacuo to furnish the hydrochloride salt of amine 40 (0.089 g, 0.14 mmol, 100%) as a glassy, colorless solid: $^1$H NMR (400 MHz, DMSO-d$_6$) δ 4.69 (br s, 1H), 4.57 (br s, 1H), 4.39-4.44 (m, 1H), 2.54-2.60 (m, 2H), 2.42 (d, J=14.4 Hz, 1H), 2.36-2.43 (m, 1H), 2.36 (d, J=14.4 Hz, 1H), 2.26 (s, 2H), 1.89-1.95 (m, 1H), 0.95-1.80 (s, 23H), 1.08 (s, 6H), 1.06 (s, 3H), 0.97 (s, 3H), 0.86 (s, 3H), 0.84 (s, 6H); LCMS, 94% ELS, m/z 598 [M+H]$^+$ 100%.

Example 19. Preparation of Aminoalkylamine Intermediates NHR$_2$R$_3$

Non-commercially available and new aminoalkylamine intermediates NHR$_2$R$_3$ were prepared according to the procedures shown in the following schemes. As shown in Scheme 19, reductive amination of t-Boc protected aminoaldehydes 41 with the appropriate amine NHR$_4$R$_5$ provided the protected aminoalkylamines 42 that were deprotected with TFA. The amines 43 were obtained as the TFA salt and generally used without further purification.

Scheme 19. Preparation of Aminoalkylamines 43

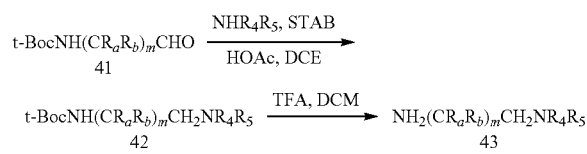

General Procedure for the Preparation of t-Boc Protected Aminoalkylamines 42: To a solution of amine NHR$_4$R$_5$ (4.0 mmol) and N-t-Boc-aminoaldehydes 41 (2.0 mmol) in DCE (3 mL) were added STAB (10 mmol) and a drop of acetic acid. The mixture was stirred at rt for 16 h, then acidified with 10% NaHSO$_4$ and concd to dryness in vacuo. The crude mixture was purified by column chromatography using 0-20% methanol in DCM providing the t-Boc protected aminoalkylamines 42.

General Procedure for Preparation of Aminoalkylamines 43: The t-Boc protected aminoalkylamines 42 were dissolved in DCM (2 mL) and TFA (1 mL) was added. The mixture was stirred for 16 h and solvent removed in vacuo.

The crude product was dried under vacuum providing the aminoalkylamines as the TFA salt that were used without any further purification.

Preparation of N-[2-[4-(1,1-Dioxothiomorpholinyl)]ethyl]carbamic Acid, 1,1-Dimethylethyl Ester (42a).

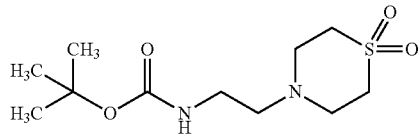

42a

Reductive amination of N-t-Boc-aminoacetaldehyde 41a with 1,1-dioxothiomorpholine provided 42a as a thick viscous oil (180 mg, 32.4%): $^1$H NMR (200 MHz, CDCl$_3$) δ 4.80 (br, 1H), 3.32-3.15 (m, 2H), 3.04 (s, 8H), 2.62 (t, 2H), 1.42 (s, 9H); LCMS, m/z calcd for $C_{11}H_{23}N_2O_4S^+$ [M+H]$^+$ 279.1, found 279.0.

Preparation of 2-[4-(1,1-Dioxothiomorpholinyl)]ethanamine (43a).

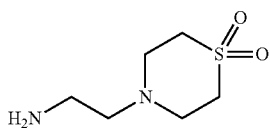

43a

Removal of the t-Boc group of 42a with TFA provided the TFA salt of 43a.

Preparation of N-[2-[4-(Methylsulfonyl)piperazinyl)]ethyl]carbamic Acid, 1,1-Dimethylethyl Ester (42b)

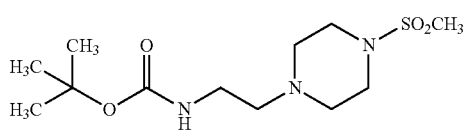

42b

Reductive amination of 41a with 1-(methylsulfonyl)piperazine provided 42b as a thick viscous oil (210 mg, 34.2%): H NMR (200 MHz, CDCl$_3$) δ 5.0 (br, 1H), 3.32-3.18 (m, 4H), 2.78 (s, 3H), 2.62-2.48 (m, 6H), 1.42 (s, 9H); LCMS, m/z calcd for $C_{12}H_{26}N_3O_4S^+$ [M+H]$^+$ 308.2, found 308.1.

Preparation of 2-[4-(Methylsulfonyl)piperazinyl)]ethanamine (43b).

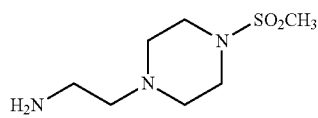

43b

Removal of the t-Boc group of 42b with TFA provided the TFA salt of 43b.

Preparation of N-[2-4-(Methylsulfonyl)piperidinyl)]ethyl]carbamic Acid, 1,1-Dimethylethyl Ester (42c).

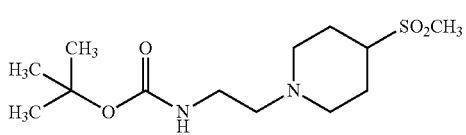

42c

Reductive amination of 41a with 4-(methylsulfonyl)piperidine provided 42c as a thick viscous oil (240 mg, 39.2%): $^1$H NMR (200 MHz, CDCl$_3$) δ 5.06 (br, 1H), 3.32-3.18 (m, 2H), 3.18-3.02 (m, 2H), 2.82 (s, 3H), 2.5 (t, 2H), 2.2-1.80 (m, 7H), 1.42 (s, 9H); LCMS, m/z calcd for $C_{13}H_{27}N_2O_4S^+$ [M+H]$^+$ 307.2, found 307.2.

Preparation of 2-[4-(Methylsulfonyl)piperidinyl)]ethanamine (43c).

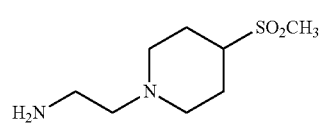

43c

Removal of the t-Boc group of 42c with TFA provided the TFA salt of 43c.

Preparation of N-[2-[4-(Phenylmethyl)piperazinyl]ethyl]carbamic Acid, 1,1-Dimethylethyl Ester (42d).

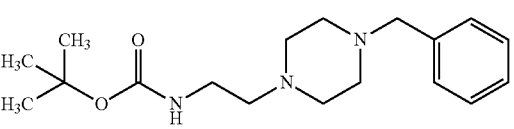

42d

Reductive amination of 41a with 1-(phenylmethyl)piperazine provided 42d as a thick viscous liquid (220 mg, 34.3%): $^1$H NMR (200 MHz, CDCl$_3$) 7.3 (m, 5H), 4.98 (br, 1H), 3.5 (s, 2H), 3.2 (m, 2H), 2.44 (m, 10H), 1.42 (s, 9H); LCMS, m/z calcd for $C_{18}H_{30}N_3O_2^+$ [M+H]$^+$ 320.2, found 320.0.

Preparation of 2-[4-(Phenylmethyl)piperazinyl]ethanamine (43d).

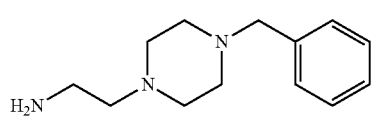

43d

Removal of the t-Boc group of 42d with TFA provided the TFA salt of 43d.

Preparation of N-[2-[4-(4-Fluorophenylmethyl)piperazinyl]ethyl]carbamic Acid, 1,1-Dimethylethyl Ester (42e).

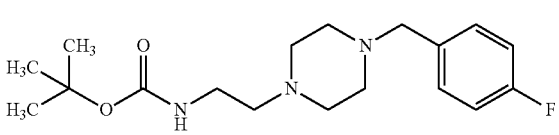

42e

Reductive amination of 41a with 1-(4-fluorophenylmethyl)piperazine provided 42e.

Preparation of 2-[4-(4-Fluorophenylmethyl)piperazinyl]ethanamine (43e).

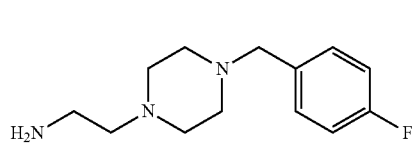
43e

Removal of the t-Boc group of 42e with TFA afforded the TFA salt of 43e: $^1$H NMR (400 MHz, CD$_3$OD) δ 7.56-7.44 (m, 2H), 7.24-7.13 (m, 2H), 4.18 (s, 2H), 3.19-3.07 (m, 4H), 3.10-3.00 (m, 2H), 2.74 (s, 4H), 2.72-2.61 (m, 2H); m/z MS calcd for C$_{13}$H$_{21}$FN$_3$$^+$ [M+H]$^+$ 238.2, found 238.0.

Preparation of N-[2-[4-(3-Fluorophenylmethyl)piperazinyl]ethyl]carbamic Acid, 1,1-Dimethylethyl Ester (42f).

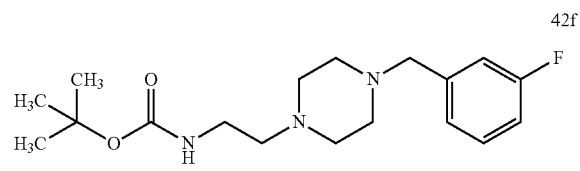 [SMILES: CC(C)(C)OC(=O)NCCN1CCN(Cc2cccc(F)c2)CC1]
42f

Reductive amination of 41a with 1-(3-fluorophenylmethyl)piperazine provided 42f.

Preparation of 2-[4-(3-Fluorophenylmethyl)piperazinyl]ethanamine (43f).

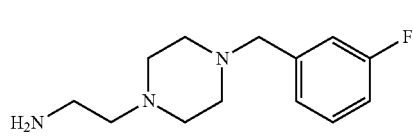
43f

Removal of the t-Boc group of 42f with TFA afforded the TFA salt of 43f: $^1$H NMR (400 MHz, CD$_3$OD) δ 7.46 (td, J=8.0 and 5.9 Hz, 2H), 7.32-7.12 (m, 3H), 4.12 (s, 2H), 3.34 (s, 2H), 3.07 (s, 2H), 3.13-2.99 (m, 2H), 2.72 (s, 4H), 2.71-2.63 (m, 2H); MS m/z calcd for C$_{13}$H$_{21}$FN$_3$$^+$ [M+H]$^+$ 238.2, found 238.0.

Preparation of N-[2-[4-(4-Chlorophenylmethyl)piperazinyl]ethyl]carbamic Acid, 1,1-Dimethylethyl Ester (42g).

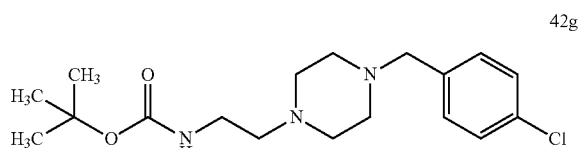
42g

Reductive amination of 41a with 1-(4-chorophenylmethyl)piperazine provided 42g.

Preparation of 2-[4-(4-Chlorophenylmethyl)piperazinyl]ethanamine (43g).

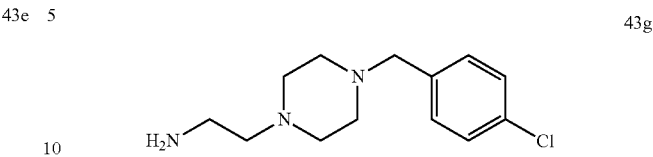
43g

Removal of the t-Boc group of 42g with TFA afforded the TFA salt of 43g: $^1$H NMR (400 MHz, CD$_3$OD) δ 7.55-7.37 (m, 2H), 7.45 (s, 2H), 4.11 (s, 2H), 3.78 (s, 1H), 3.34 (s, 1H), 3.14-3.00 (m, 6H), 2.72 (s, 2H), 2.76-2.63 (m, 2H); MS m/z calcd for C$_{13}$H$_{21}$ClN$_3$$^+$ [M+H]$^+$ 254.1, found 254.

Preparation of N-[2-[4-(3-Chlorophenylmethyl)piperazinyl]ethyl]carbamic Acid, 1,1-Dimethylethyl Ester (42h).

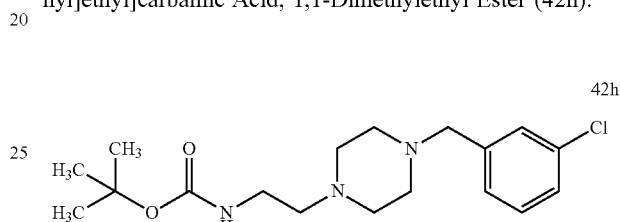
42h

Reductive amination of 41a with 1-(3-chlorophenylmethyl)piperazine provided 42h.

Preparation of 2-[4-(3-Chlorophenylmethyl)piperazinyl]ethanamine (43h).

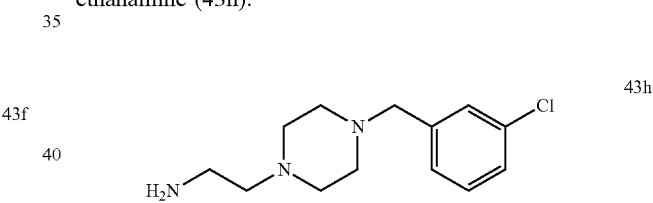
43h

Removal of the t-Boc group of 42h with TFA afforded the TFA salt of 43h: $^1$H NMR (400 MHz, CD$_3$OD) δ 7.53 (q, J=1.4 Hz, 1H), 7.42 (tdd, J=6.2, 5.0, and 3.0 Hz, 3H), 4.15 (s, 2H), 3.16-3.09 (m, 4H), 3.10-3.00 (m, 2H), 2.78 (s, 1H), 2.74 (s, 3H), 2.73-2.64 (m, 2H); MS m/z calcd for C$_{13}$H$_{21}$ClN$_3$$^+$ [M+H]$^+$ 254.1, found 254.

Preparation of N-[2-[4-(1-Naphthalenylmethyl)piperazinyl]ethyl]carbamic Acid, 1,1-Dimethylethyl Ester (42i).

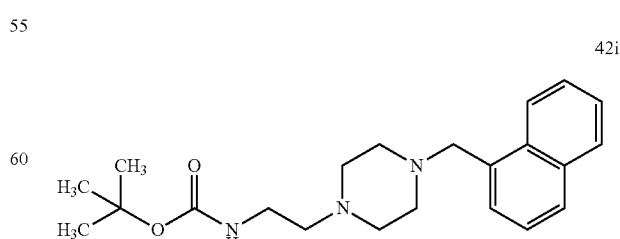
42i

Reductive amination of 41a with 1-(1-naphthalenylmethyl)piperazine provided 42i.

Preparation of 2-[4-(1-Naphthalenylmethyl)piperazinyl]ethanamine (43i).

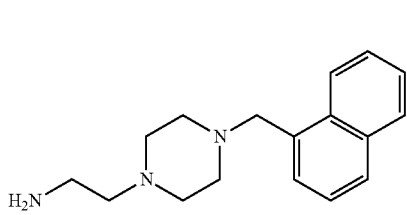

Removal of the t-Boc group of 42i with TFA afforded the TFA salt of 43i: $^1$H NMR (400 MHz, CD$_3$OD) δ 8.25 (dd, J=8.5 and 1.0 Hz, 1H), 8.06-7.94 (m, 2H), 7.74-7.61 (m, 2H), 7.64-7.51 (m, 2H), 4.73 (s, 2H), 3.31 (s, 2H), 3.24 (s, 1H), 3.09-2.99 (m, 2H), 2.82 (s, 5H), 2.71-2.61 (m, 2H); MS m/z calcd for C$_{17}$H$_{24}$N$_3$$^+$ [M+H]$^+$ 270.2, found 270.0.

Preparation of N-[2-[4-(2-Naphthalenylmethyl)piperazinyl]ethyl]carbamic Acid, 1,1-Dimethylethyl Ester (42j).

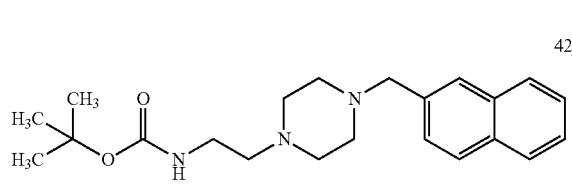 [SMILES: CC(C)(C)OC(=O)NCCN1CCN(Cc2ccc3ccccc3c2)CC1]

Reductive amination of 41a with 1-(2-naphthalenylmethyl)piperazine provided 42j.

Preparation of 2-[4-(2-Naphthalenylmethyl)piperazinyl]ethanamine (43j).

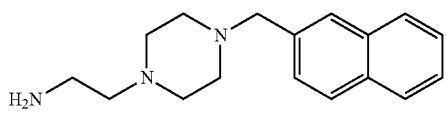

Removal of the t-Boc group of 42j with TFA afforded the TFA salt of 43j: $^1$H NMR (400 MHz, CD$_3$OD) δ 8.54 (ddd, J=4.9, 1.8, and 0.9 Hz, 1H), 7.84 (td, J=7.7 and 1.8 Hz, 2H), 7.52 (dt, J=7.8 and 1.1 Hz, 2H), 7.36 (ddd, J=7.6, 4.9, and 1.2 Hz, 2H), 3.96 (s, 2H), 3.09-3.00 (m, 3H), 2.87 (s, 5H), 2.69-2.60 (m, 4H); MS m/z calcd for C$_{17}$H$_{24}$N$_3$$^+$ [M+H]$^+$ 270.2, found 270.

Preparation of N-[2-[4-(2-Pyridinylmethyl)piperazinyl]ethyl]carbamic Acid, 1,1-Dimethylethyl Ester (42k).

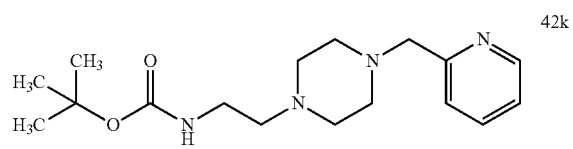 [SMILES: CC(C)(C)OC(=O)NCCN1CCN(Cc2ccccn2)CC1]

Reductive amination of 41a with 1-(2-pyridinylmethyl)piperazine provided 42k.

Preparation of 2-[4-(2-Pyridinylmethyl)piperazinyl]ethanamine (43k).

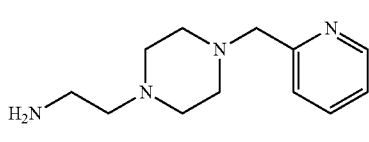

Removal of the t-Boc group of 42k with TFA afforded the TFA salt of 43k: $^1$H NMR (400 MHz, CD$_3$OD) δ 8.54 (ddd, J=4.9, 1.8, and 0.9 Hz, 1H), 7.84 (td, J=7.7 and 1.8 Hz, 1H), 7.52 (dt, J=7.8 and 1.1 Hz, 1H), 7.36 (ddd, J=7.6, 4.9, and 1.2 Hz, 1H), 3.96 (s, 2H), 3.09-3.00 (m, 4H), 2.87 (s, 5H), 2.69-2.60 (m, 3H); MS m/z calcd for C$_{12}$H$_{21}$N$_4$$^+$ [M+H]$^+$ 221.1, found 221.0.

Preparation of N-[2-[4-(2-Pyridinylmethyl)piperazinyl]ethyl]carbamic Acid, 1,1-Dimethylethyl Ester (42l).

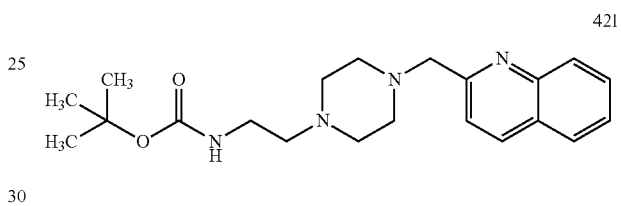

Reductive amination of 41a with 1-(2-quinolinylmethyl)piperazine provided 42l.

Preparation of 2-[4-(2-Quinolinylmethyl)piperazinyl]ethanamine (43).

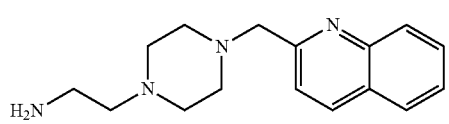

Removal of the t-Boc group of 42l with TFA afforded the TFA salt of 43l: $^1$H NMR (400 MHz, CD$_3$OD) δ 8.40 (dd, J=8.6 and 0.8 Hz, 1H), 8.13-8.04 (m, 1H), 7.97 (dd, J=8.1 and 1.4 Hz, 1H), 7.81 (ddd, J=8.5, 6.9, and 1.5 Hz, 1H), 7.69-7.56 (m, 2H), 3.29-3.21 (m, 4H), 3.12-3.04 (m, 2H), 2.80 (s, 5H), 2.76-2.67 (m, 3H); MS m, calcd for C6H$_{23}$N$_4$$^+$ [M+H]$^+$ 271.2, found 271.0.

Preparation of N-[2-[4-(Cyclohexylmethyl)piperazinyl]ethyl]carbamic Acid, 1,1-Dimethylethyl Ester (42m).

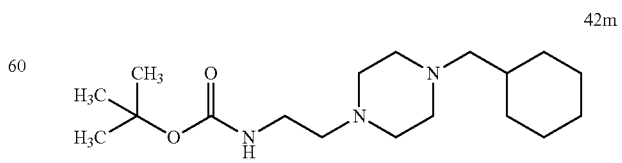

Reductive amination of 41a with 1-(cyclohexylmethyl)piperazine provided 42m.

Preparation of 2-[4-(Cyclohexylmethyl)piperazinyl]ethanamine (43m).

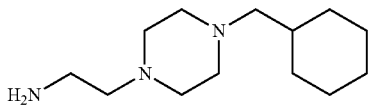

43m

Removal of the t-Boc group of 42m with TFA afforded the TFA salt of 43m: $^1$H NMR (400 MHz, CD$_3$OD) δ 3.21 (t, J=6.6 Hz, 2H), 2.78 (s, 3H), 2.70 (s, 4H), 2.55 (t, J=6.6 Hz, 2H), 2.46 (d, J=7.0 Hz, 2H), 1.94 (s, 2H), 1.83-1.68 (m, 4H), 1.67 (s, 2H), 1.37-1.15 (m, 2H), 1.03-0.87 (m, 2H); MS m/z calcd for C$_{13}$H$_{28}$N$_3^+$ [M+H]$^+$ 226.2, found 226.0.

Preparation of N-[2-(4-Phenylpiperazinyl)ethyl]carbamic Acid, 1,1-Dimethylethyl Ester (42n).

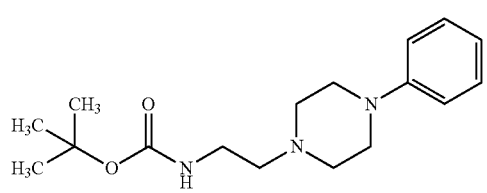

42n

Reductive amination of 41a with 1-phenylpiperazine provided 42n.

Preparation of 2-(4-Phenylpiperazinyl)ethanamine (43n).

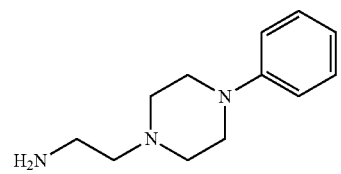

43n

Removal of the t-Boc group of 42n with TFA afforded the TFA salt of 43n: $^1$H NMR (400 MHz, CD$_3$OD) δ 7.31-7.19 (m, 2H), 7.00-6.91 (m, 2H), 6.87 (tt, J=7.3 and 1.0 Hz, 1H), 3.40-3.31 (m, 2H), 3.34-3.25 (m, 2H), 3.04 (d, J=10.3 Hz, 1H), 3.04 (s, 2H), 2.88 (t, J=6.5 Hz, 2H), 1.96 (s, 4H); MS n/z calcd for C$_{12}$H$_{20}$N$_3^+$ [M+H]$^+$ 206.2, found 206.0.

Example 20. Preparation of 3-Aminopropylamine Intermediates NHR$_2$R$_3$

Non-commercially available and new aminopropylamine intermediates NHR$_2$R$_3$ were prepared according to the procedure shown in Scheme 20. Michael addition of acrylonitrile to the appropriate amine NHR$_4$R$_5$ provided the 3-aminopropanenitriles 44. Catalytic hydrogenation of the nitrile using Raney nickel provided the 3-aminopropylamines 45.

Scheme 20. Preparation of Aminopropylamines 45

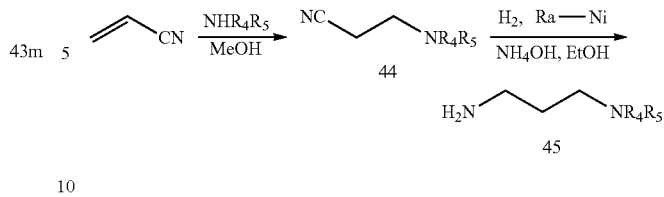

General Procedure for the Preparation of 3-Aminopropanenitriles 44: To a solution of amine NHR$_4$R$_5$ (10.0 mmol) in MeOH was added acrylonitrile (1.5 mL). After 18 h at rt, the mixture was dry loaded onto silica gel. Elution with EtOAc provided the pure 3-aminopropionitriles 44.

General Procedure for Nitrile Reduction: A solution of 44 (~8 mmol) in EtOH (20 mL) was added to a suspension of Raney nickel (4 g) in NH$_4$OH (20 mL) contained in a Parr bottle and hydrogenated at 40 psi for 18 h. The reaction mixture was filtered through celite. The filter cake was washed with EtOH. The combined filtrates were concd in vacuo providing the 3-aminopropylamines 45 in nearly quantitative yield. The amines were used without further purification.

Preparation of 3-[(4-Methylsulfonyl)piperazinyl]propanenitrile (44a):

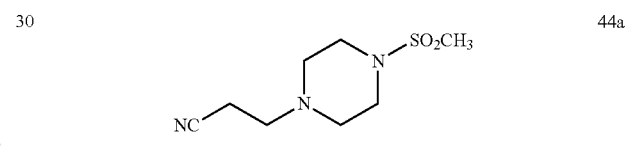

44a

Reaction of acrylonitrile with 1-(methylsulfonyl)piperazine provided 44a: $^1$H NMR (200 MHz, CDCl$_3$) 3.30-3.20 (m, 4H), 2.78 (s, 3H), 2.80-2.42 (m, 8H).

Preparation of 3-[(4-Methylsulfonyl)piperazinyl]propanamine (45a).

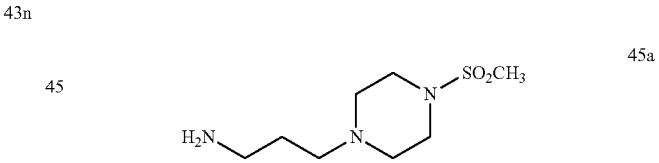

45a

The nitrile 44a was reduced as described above providing 45a: $^1$H NMR (200 MHz, CD$_3$OD) δ 3.30-3.15 (m, 4H), 2.90-2.70 (m, 5H), 2.68-2.40 (m, 6H), 1.84-1.40 (m, 2H).

Preparation of 3-[(4-Acetyl)piperazinyl]propanenitrile (44b).

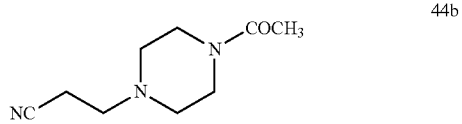 [SMILES: CC(=O)N1CCN(CCC#N)CC1]

44b

Reaction of acrylonitrile with 1-(acetyl)piperazine provided 1.40 g (77.7%) 44b as an oil: $^1$H NMR (200 MHz, CDCl$_3$) δ 3.65 (t, 2H), 3.46 (t, 2H), 2.78-2.64 (m, 2H), 2.60-2.40 (m, 6H), 2.06 (s, 3H).

Preparation of 3-[(4-Acetyl)piperazinyl]propanamine (45b).

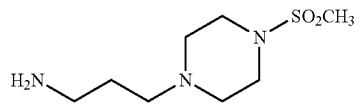
45b

The nitrile 44b was reduced as described above providing 45b: $^1$H NMR (200 MHz, CDCl$_3$) δ 3.70-3.50 (m, 2H), 3.50-3.35 (m, 2H), 2.82-2.70 (m, 2H), 2.52-2.30 (m, 6H), 2.08 (s, 3H), 1.75-1.50 (m, 2H), 1.50-1.30 (br m, 2H).

Example 21. Preparation of Aminoalkylamides Intermediates NHR$_2$R$_3$

Aminoalkylamides 47 were prepared by the general procedure shown in Scheme 21. Coupling of t-Boc aminoacid with the appropriate amine NHR$_4$R$_5$ using standard coupling techniques provided the t-Boc aminocarbamides 46 that were deprotected providing aminoalkylcarbamides 47 as shown in Scheme 21.

Scheme 21. Synthesis of Aminoalkylcarbamides 47

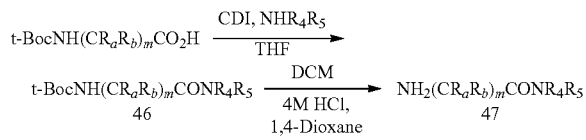

Preparation of N-[[3-(4-Methylpiperazin-1-yl)-3-oxo]propyl]carbamic Acid, 1,1-Dimethylethyl Ester (46a).

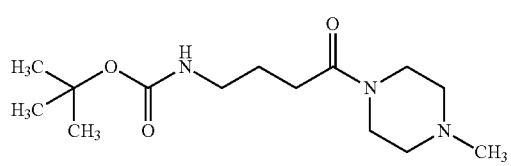
46a

To a solution of N-t-Boc-3-aminopropionic acid (0.95 g, 5.0 mmol) in THF (10 mL) was added 1,1-carbonyldiimidazole (0.82 g, 5.0 mmol). After 1 h, N-methylpiperazine (0.501 g, 5.0 mmol) was added and stirred for 18 h. Volatiles were removed in vacuo and the crude mixture was diluted with EtOAc (20 mL), washed with water (20 mL), and brine (10 mL). The EtOAc layer was dried (Na$_2$SO$_4$) and coned in vacuo providing 46a. The crude product was used without further purification: $^1$H NMR (200 MHz, CDCl$_3$) δ 5.32-5.20 (m, 1H), 3.68-3.59 (m, 2H), 3.50-3.35 (m, 4H), 2.55-2.42 (m, 2H), 2.42-2.30 (m, 4H), 2.30 (s, 3H), 1.42 (s, 9H).

Preparation of 1-(4-Methylpiperazinyl)(2-aminopropyl)methanone (47a).

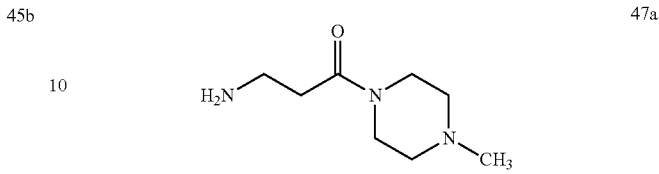
47a

To a solution of 46a (0.90 g, 3.0 mmol) in DCM (5 mL) was added 4 M HCl in 1,4-dioxane (2 mL, 8 mmol) was added and stirred at rt for 6 h. The reaction mixture was coned in vacuo, satd aqueous NaHCO$_3$ (10 mL) was added, and concd in vacuo to dryness. The residue was extracted with 5% MeOH in DCM, filtered, and the filtrate coned providing 47a (0.65 g) admixed with imidazole: $^1$H NMR (200 MHz, CDCl$_3$) δ 3.70-3.59 (m, 2H), 3.60-3.40 (m, 2H), 3.0 (t, 2H), 2.50-2.25 (m, 6H), 2.30 (s, 3H), 2.15-1.40 (br m, 2H).

Example 22. General Procedure for the Preparation of Aminoalkylamine Intermediates NHR$_2$R$_3$ via the Gabriel Amine Synthesis The Gabriel amine synthesis was employed for the general preparation of aminoalkylamines as shown in Scheme 22. The N-bromoalkylphthalimide 48 was treated with the appropriate amine NHR$_4$R$_5$ in refluxing acetonitrile containing a base like K$_2$CO$_3$ providing the N-aminoalkylphthalimides 49. Removal of the phthalimide with hydrazine in ethanol followed by filtration of the phthaloyl hydrazide byproduct and solvent removal provided the aminoalkylamines 50 that were used without further purification.

Scheme 22. Gabriel Synthesis of Aminoalkylamine Intermediates

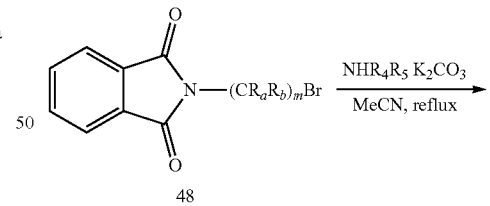
48

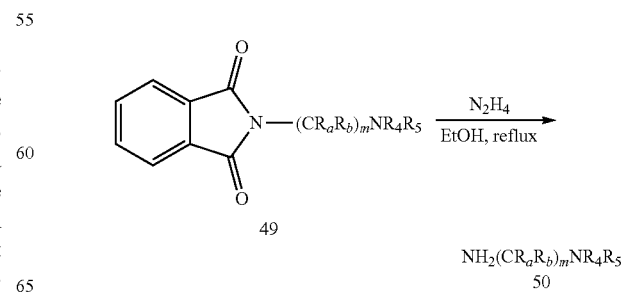
49

NH$_2$(CR$_a$R$_b$)$_m$NR$_4$R$_5$
50

Preparation of N-[3-[1-[4-(2-Methoxyethyl)piperazinyl] propyl]phthalimide (49a).

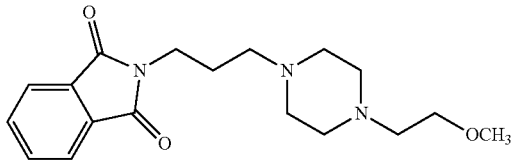
49a

Reaction of 1-(2-methoxyethyl)piperazine with N-(3-bromopropyl)phthalimide 48a provided aminopropylphthalimide 49a.

Preparation of 3-[1-[4-(2-Methoxyethyl)piperazine]propanamine (50a).

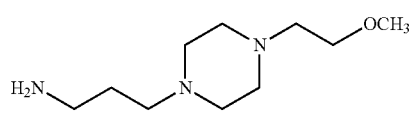
50a

Treatment of 49a with hydrazine providing amine 50a.

Preparation of N-[3-[1-[4-(2-Hydroxyethyl)piperazinyl] propyl]phthalimide (49b).

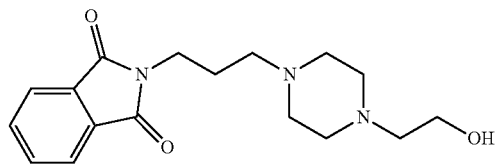
49b

Reaction of 2-(piperazine)ethanol with N-(3-bromopropyl)phthalimide 48a provided aminopropylphthalimide 49b.

Preparation of 2-[4-(3-Aminopropyl)piperazine]ethanol (50b).

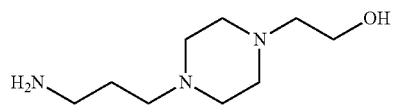
50b

Treatment of 49b with hydrazine providing amine 50b.

Example 23. Methods of the Syntheses of C-28 Alkylamines from C-28 Aldehyde and Homologated Aldehyde and C-28 Amine and Homologated Amine C-3 Acids

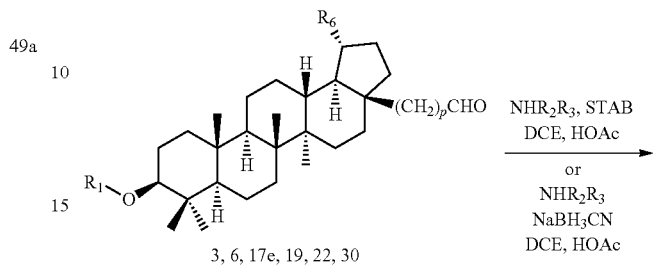

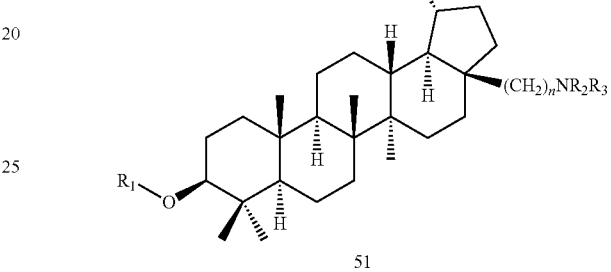
51

Scheme 23. Reductive Amination of Aldehydes and Homologated Aldehydes and C-28 Amine and Homologated Amine C-3 Acids

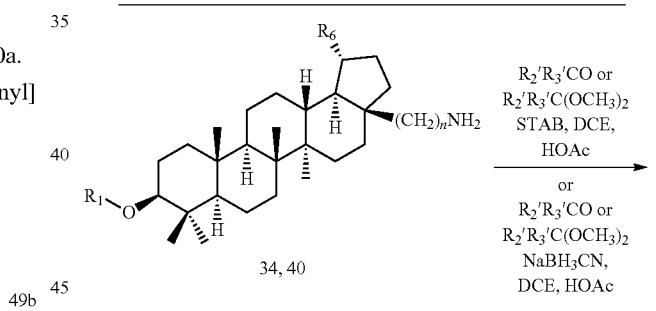

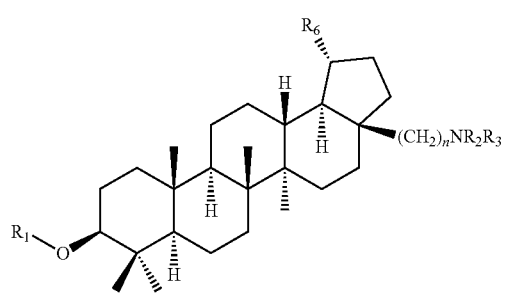
51

Method A1. General reductive amination procedure using sodium triacetoxyborohydride: To a solution of the appropriate triterpene aldehyde (0.05 mmol) in DCE (2 mL), appropriate amine $NHR_2R_3$ (0.25 mmol), or triterpene amine (0.05 mmol) and aldehyde or ketone $R_2'R_3'CO$, or aldehyde or ketone acetal or ketal, like $R_2'R_3'C(OCH_3)_2$, glacial acetic acid (15 μL, 0.25 mmol), and STAB (106 mg, 0.5 mmol) were added. R$_2$' is equal to R$_3$ with one less carbon if applicable; R$_3$' is equal to R$_3$ with one less carbon if applicable. The mixture was stirred for 18 h and solvent removed in vacuo. The residue was treated with 2 M KOH (0.2 mL) and stirred for 10 min, after which the pH (using pH paper) was adjusted to 1 with 2 M HCl and stirred for 10 min more. The solution was neutralized with 2 M KOH, and the pH was adjusted to 6.8 with phosphate buffer pH 6.8 phosphate buffer (0.13 M KH$_2$PO$_4$ and 0.13 M K$_2$HPO$_4$). The product was extracted with EtOAc (2×30 mL), and the organic layer was washed with water (30 mL), brine (20 mL), dried (Na$_2$SO$_4$), and concd in vacuo. The crude product was purified by silica gel chromatography with the solvent gradient of 0-20% (10% NH$_{40}$H in methanol) in DCM. The fractions containing the product were analyzed by LCMS for purity, pooled, and concd in vacuo providing the pure products 51 as off-white to white solids. Alternatively, the crude product was purified used reversed phase chromatography eluting with 0.1% TFA in water and acetonitrile in which case the product amines were obtained as the TFA salt. Alternatively, the crude product was purified using a Waters Preparatory HPLC with UV detector (254 nm) fitted with a SunFire C18 5 μm 4.6×150 mm column eluting with water/formic acid as mobile phase A and a 5-100% gradient of acetonitrile/formic acid as mobile phase B and a flow rate of 0.6 mL/min. This purification method provided purity data as well.

Method A2. Alternative reductive amination procedure using sodium triacetoxyborohydride: To a solution of the appropriate triterpene aldehyde (0.088 mmol) in DCE (3 mL), were added the appropriate amine (0.132 mmol), glacial acetic acid (5 μL, 0.088 mmol), and STAB (186 mg, 0.88 mmol). The mixture was stirred for 18 h. The reaction mixture was acidified to pH 2 with 10% NaHSO$_4$ (150 μL) and dry-loaded onto silica. The crude product was purified by silica gel chromatography with the solvent gradient of 0-10% gradient of 10% NH$_4$OH/MeOH in DCM. The fractions containing the product were analyzed by LCMS for purity, pooled, and concd in vacuo. The solids obtained were washed with 10% NaHSO$_4$ (1 mL), filtered, washed with water (1 mL), and dried in vacuo providing the pure products 51 as off-white to white sulfate salts.

Method B. General reductive amination procedure using sodium cyanoborohydride: A mixture of the appropriate aldehyde (1 equ, 0.2 mmol), appropriate amine (2.5 equ) and one drop of acetic acid in DCE (4 mL) was stirred at rt for 1 h, and then NaBH$_3$CN (25 mg, 0.4 mmol) was added. The reaction was stirred at rt for 2.5 d. Solvent was removed in vacuo, and then 1 M NaOH (1 mL) was added, and the solution was stirred for 1 h, after which 1 N HCl (1 mL) and phosphate buffer (0.13 M KH$_2$PO$_4$ and 0.13 M K$_2$HPO$_4$, 2 mL) were added. The aqueous phase was extracted with ethyl acetate (2×4 mL). The combined organic phases were dried (Na$_2$SO$_4$) and concd in vacuo. The product obtained was purified by silica gel FCC using a DCM/MeOH gradient (100:1-4:1), pure fractions pooled, and concd in vacuo providing the pure products 51 obtained as off-white to white solids.

LCMS Purity Methods

The following LCMS conditions were used to determine the purities:

Column, Kinetex, 2.6μ, XB-C18, 50×60 mm; Mobile Phase A, 0.1% aqueous TFA; Mobile Phase B 0.1% TFA in acetonitrile; Gradient 30-90% acetonitrile over a period of 4 min and held at 90% for another 4 min with a flow rate of 0.6 mL/min.

Column, Waters Xterra® MS C8 2.1×50 mm, 3.5 um; Mobile Phase 0.1% aqueous formic acid; Mobile Phase B 0.1% formic acid in acetonitrile; Gradient 5-100% acetonitrile over a period of 5 min and held at 100% for an additional 2 min with a flow rate of 0.6 mL/min.

Example 24. Preparation of (3β)-17-[2-[[3-(2-Oxopyrrolidin-1-yl)propyl]amino]ethyl]-28-norlup-20(29)-en-3-ol, 3-(Hydrogen 3,3-Dimethylpentanedioate) (51a)

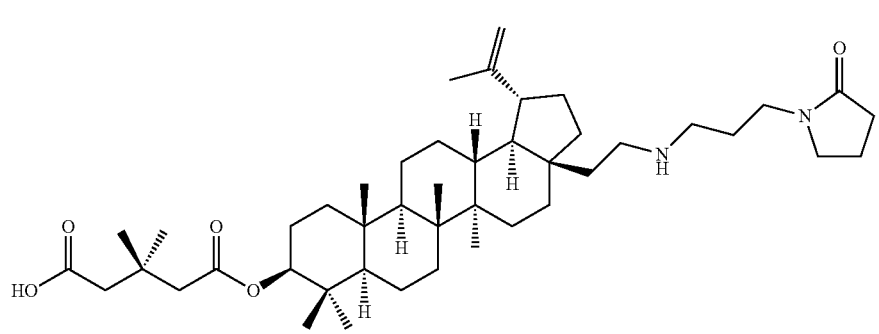

Amine 51a was obtained from aldehyde 19 and 3-(2-oxopyrrolidin-1-yl)propanamine as a white solid (15.2 mg, 42%) using Method A1: H NMR (200 MHz, CD$_3$OD) δ 4.70 (s, 1H), 4.60 (s, 1H), 4.50-4.39 (m, 1H), 3.55-3.35 (m, 4H), 3.02-2.85 (m, 4H), 2.55-2.34 (m, 4H), 2.52 (s, 2H), 2.16-0.8 (m, 55H); LCMS, purity 100% (based on total ion count), m/z calcd for C$_{45}$H$_{75}$N$_2$O$_5^+$ [M+H]$^+$ 723.6, found 723.9.

Example 25. Preparation of (3β)-17-[2-[[3-(4-Methylpiperazin-1-yl)-3-oxopropyl]amino]ethyl]-28-norlup-20(29)-en-3-ol, 3-(Hydrogen 3,3-Dimethylpentanedioate) (51b)

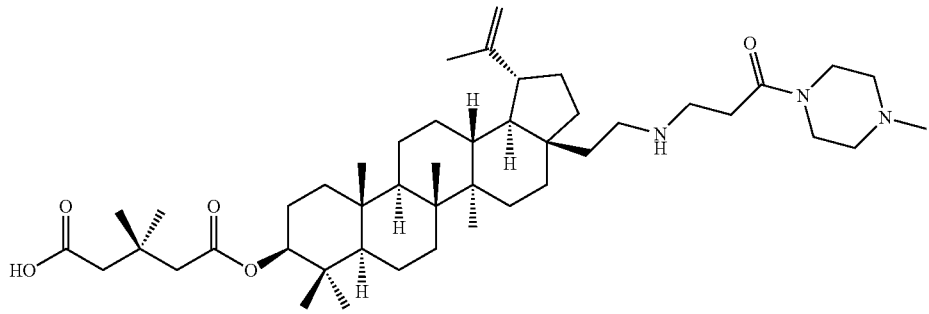

Amine 51b was obtained from aldehyde 19 and amine 47a as a white solid (24.7 mg, 65%) using Method A1: $^1$H NMR (200 MHz, CD$_3$OD) δ 4.70 (s, 1H), 4.60 (s, 1H), 4.50-4.40 (m, 1H), 3.68-3.58 (m, 2H), 3.58-3.48 (m, 2H), 3.3-3.20 (m, 2H), 3.05-2.75 (m, 2H), 2.52-2.38 (m, 6H), 2.32 (s, 3H), 2.25 (s, 2H), 2.1-0.88 (m, 51H); LCMS, purity 100% (based on total ion count), m/z calcd for $C_{46}H_{75}N_3O_5^+$ [M+H]$^+$ 752.6, found 752.8.

Example 26. Preparation of (3β)-17-[2-[[3-[4-(Methylsulfonyl)piperazin-1-yl]propyl]amino]ethyl]-28-norlup-20(29)-en-3-ol, 3-(Hydrogen 3,3-Dimethylpentanedioate) (51c)

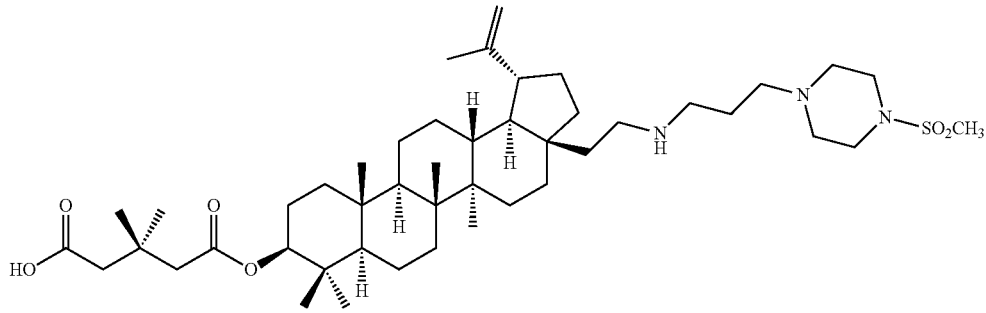

Amine 51c was obtained from aldehyde 19 and amine 45a as a white solid (22.9 mg, 57%) using Method A1: $^1$H NMR (200 MHz, CD$_3$OD) δ 4.70 (s, 1H), 4.60 (s, 1H), 4.50-4.39 (m, 1H), 3.40-3.15 (m, 2H), 3.15-2.85 (m, 6H), 2.85 (s, 3H), 2.60-2.40 (m, 8H), 2.23 (s, 2H), 2.1-0.80 (m, 53H); LCMS, purity 100% (based on total ion count), m/z calcd for $C_{46}H_{80}N_3O_6S$ [M+H]$^+$ 802.6, found 802.9.

Example 27. Preparation of (3β)-17-[2-[[3-[4-(2-Hydroxyethyl)piperazin-1-yl]propyl]amino]ethyl]-28-norlup-20(29)-en-3-ol, 3-(Hydrogen 3,3-Dimethylpentanedioate) (51d)

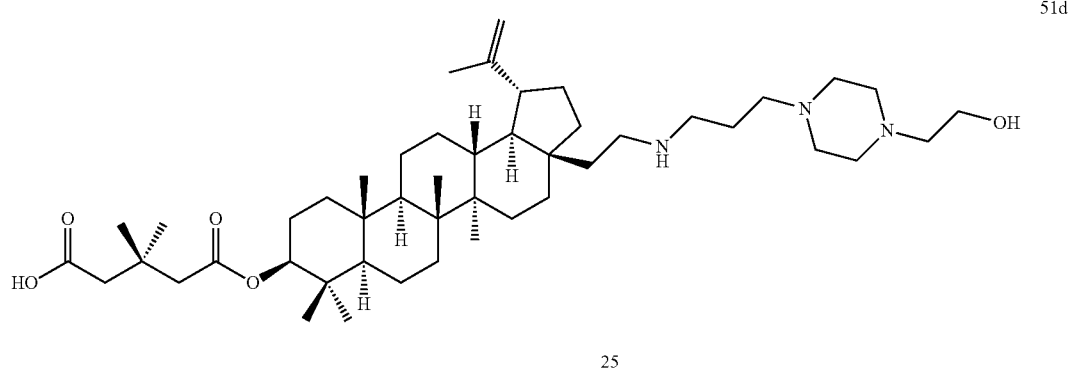

Amine 51d was obtained from aldehyde 19 and amine 50b as a white solid using Method A1: $^1$H NMR (400 MHz, CD$_3$OD) δ 4.74 (br s, 1H), 4.64 (br s, 1H), 4.48 (m, 1H), 3.74 (m, 2H), 3.34 (m, 2H), 3.14 (m, 2H), 3.08-2.90 (m, 3H), 2.88-2.40, (m, 16H), 2.34 (br s, 3H), 2.06-1.86 (5H, m), 1.75-1.60 (overlapping m, 6H; 1.74, s, 3H), 1.59-1.53 (4H), 1.52-1.36 (m, 6H), 1.35-1.24 (m, 2H), 1.20-1.06 (m, 3H), 1.18 (s, 6H), 1.03 (overlapping m, 1H, s, 3H), 0.90 (s, 3H), 0.87 (s, 6H), 0.85 (m, 1H).

Example 28. Preparation of (3β)-17-[2-[[3-[4-(2-Methoxyethyl)piperazin-1-yl]propyl]amino]ethyl]-28-norlup-20(29)-en-3-ol, 3-(Hydrogen 3,3-Dimethylpentanedioate) (51e)

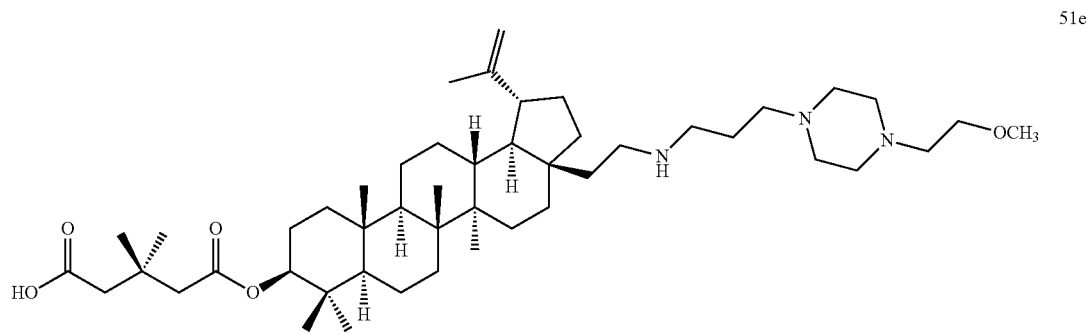

Amine 51e was obtained from aldehyde 19 and amine 50a as a white solid using Method A1: $^1$H NMR (400 MHz, CD$_3$OD) δ 4.74 (br s, 1H), 4.62 (br s, 1H), 4.47 (m, 1H), 3.58 (m, 2H), 3.36 (s, 3H), 3.34 (m, 2H), 3.12 (m, 2H), 3.07-2.87 (m, 3H), 2.86-2.57, (m, 12H), 2.56-2.38 (m, 2H), 2.50 (d, J=13.9 Hz, 1H), 2.39 (d, J=13.9 Hz, 1H), 2.28 (s, 3H), 2.06-1.86 (m, 5H), 1.75-1.60 (overlapping m, 6H; 1.74, s, 3H), 1.59-1.53 (4H), 1.52-1.36 (m, 6H), 1.35-1.24 (m, 2H), 1.20-1.06 (m, 3H), 1.18 (s, 6H), 1.03 (overlapping m, 1H, s, 3H), 0.90 (s, 3H), 0.87 (s, 6H), 0.85 (m, 1H).

Example 29. Preparation of (3β)-17-[2-[[1-(2-Hydroxyethyl)piperidin-4-yl]amino]ethyl]-28-norlup-20(29)-en-3-ol, 3-(Hydrogen 3,3-Dimethylpentanedioate), Bis(trifluoroacetate) Salt (51f)

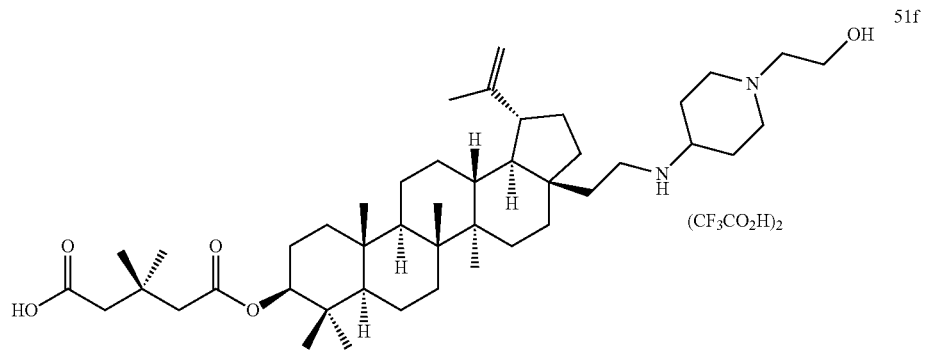

Amine 51f was obtained from aldehyde 19 and 2-(4-aminopiperidin-1-yl)ethanol as a white solid using Method A1: $^1$H NMR (400 MHz, CD$_3$OD) δ 4.70 (d, J=2.3 Hz, 1H), 4.60 (dd, J=2.4 and 1.4 Hz, 1H), 4.46 (dd, J=10.3 and 6.0 Hz, 1H), 3.89 (ddd, J=6.7, 5.1, and 3.5 Hz, 2H), 3.75 (br d, J=12.5 Hz, 2H), 3.47 (m, 1H), 3.29 (m, 2H), 3.23-3.13 (m, 2H), 3.12-2.97 (m, 2H), 2.48 (d, J=14.1 Hz, 1H), 2.39 (d, J=14.1 Hz, 1H), 2.38 (s, 3H), 2.48-2.38 (m, 2H), 2.10-1.93 (m, 4H), 1.79 (m, 1H), 1.75-1.60 (overlapping m, 6H; 1.71, s, 3H), 1.58-1.53 (4H), 1.50-1.38 (m, 6H), 1.34-1.23 (m, 2H), 1.20-1.06 (m, 3H), 1.12 (s, 3H), 1.11 (s, 6H), 1.03 (overlapping m, 1H, s, 3H), 0.90 (s, 3H), 0.87 (s, 6H), 0.83 (m, 1H); $^{13}$C NMR (400 MHz, CD$_3$OD) δ 175.41, 173.53, 151.38, 115.01, 110.57, 82.34, 56.80, 56.49, 53.65, 51.69, 51.05, 49.32, 49.28, 49.00, 48.60, 46.42, 46.30, 45.93, 43.73, 43.34, 42.11, 39.55, 38.78, 38.65, 38.25, 36.37, 35.33, 33.25, 31.72, 30.74, 28.57, 28.34, 28.12, 26.36, 25.31, 24.82, 22.01, 19.50, 19.28, 17.10, 16.69, 15.31; LCMS, purity 99.1% (based on total ion count) m/z calcd for C$_{45}$H$_{77}$N$_2$O$_5^+$ [M+H]$^+$ 725.5827, found 725.70.

Example 30. Preparation of (3β)-17-[2-[[1-(2-Methoxyethyl)piperadin-4-yl]amino]ethyl]-28-norlup-20(29)-en-3-ol, 3-(5-Hydrogen 3,3-Dimethylpentanedioate), Bis(trifluoroacetate) Salt (51g)

Amine 51g was obtained from aldehyde 19 and 1-(2-methoxyethyl)-4-piperidinamine as a white solid using Method A1: $^1$H NMR (400 MHz, CD$_3$OD) δ 4.71 (d, J=1.9 Hz, 1H), 4.60 (dd, J=2.3 and 1.4 Hz, 1H), 4.46 (dd, J=10.2 and 6.2 Hz, 1H), 3.78 (br s, H), 3.77 (overlapping br s, 1H, app t, J=5.1 and 4.9 Hz, 2H), 3.47 (m, 1H), 3.41 (s, 3H), 3.37 (m, 2H), 3.23-3.12 (m, 2H), 3.09-2.96 (m 2H), 2.48 (d, J=14.1 Hz, 1H), 2.39 (d, J=14.1 Hz, 1H), 2.38 (s, 3H), 2.48-2.38 (m, 2H), 2.10-1.88 (n, 4H), 1.80 (m, 1H), 1.75-1.60 (overlapping m, 6H; 1.70, s, 3H), 1.59-1.53 (4H), 1.52-1.36 (m, 6H), 1.35-1.24 (m, 2H), 1.20-1.06 (m, 3H), 1.12 (s, 3H), 1.11 (s, 6H), 1.03 (overlapping m, 1H, s, 3H), 0.90 (s, 3H), 0.87 (s, 6H), 0.85 (m, 1H); $^{13}$C NMR (400 MHz, CD$_3$OD) δ 175.41, 173.53, 151.39, 110.57, 82.35, 66.90, 59.27, 56.81, 54.48, 51.69, 51.06, 49.11, 48.95, 48.86, 48.39, 46.42, 46.31, 45.94, 43.73, 43.34, 42.11, 39.56, 38.78, 38.65, 38.25, 36.37, 35.33, 33.25, 31.72, 30.75, 28.57, 28.35, 28.12, 26.36, 25.31, 24.82, 22.01, 19.50, 19.28, 17.10, 16.75, 16.69, 15.32; LCMS, purity 99.3% (based on total ion count), m, calcd for C$_{46}$H$_{79}$N$_2$O$_5^+$ [M+H]$^+$ 739.5984, found 739.70.

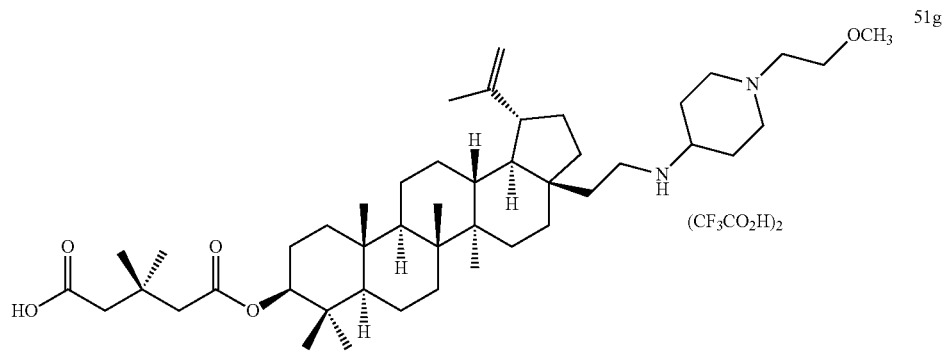

Example 31. Preparation of (3β)-17-[2-[[2-(1-Pyrrolidinyl)ethyl]amino]ethyl]-20,29-methano-28-norlupan-3-ol, 3-(1-Hydrogen 2,2-Dimethylbutanedioate) (51h)

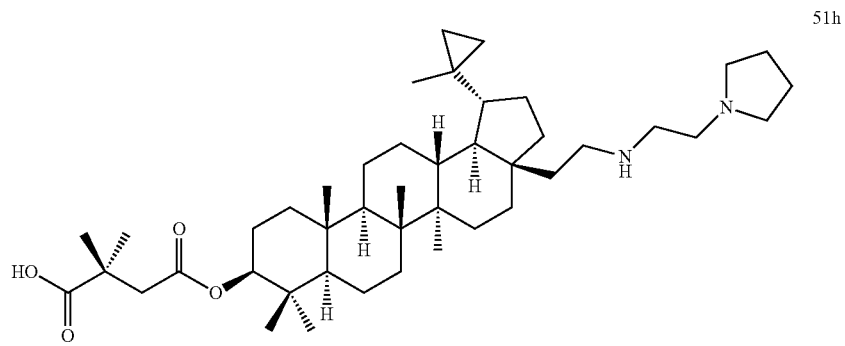

Amine 51h was obtained from aldehyde 30 and 2-(1-pyrrolidinyl)ethanamine as a white solid (3.5 mg, 9.1%) using Method A1: $^1$H NMR (200 MHz, CD$_3$OD) δ 4.52-4.37 (m, 1H), 3.2-2.32 (m, 12H), 2.20-0.60 (m, 55H), 0.44-0.15 (m, 4H); LCMS, purity 95.4% (based on total ion count), m/z calcd for $C_{44}H_{75}N_2O_4^+$ [M+H] 695.6, found 695.7.

Example 32. Preparation of (3β)-17-[2-[[3-(4-Methylpiperazin-1-yl)propyl]amino]ethyl]-20,29-methano-28-norlupan-3-ol, 3-(1-Hydrogen 2,2-Dimethylbutanedioate) (51i)

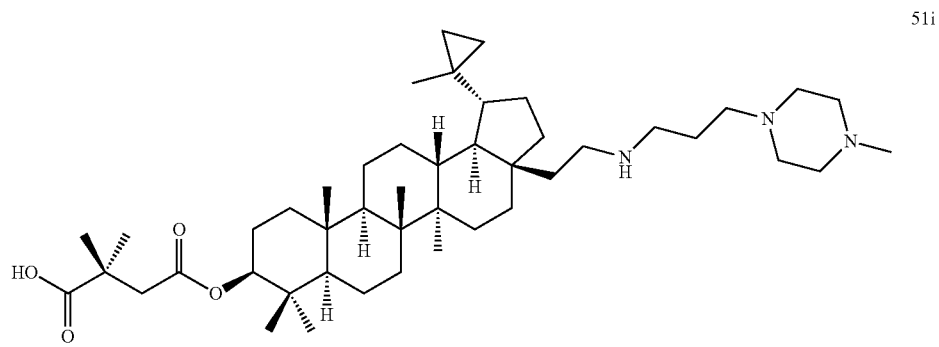

Amine 51i was obtained from aldehyde 30 and 3-(4-methylpiperazin-1-yl)propanamine as a white solid (1.8 mg, 4.3%) using Method A1: H NMR (200 MHz, CD$_3$OD) δ 4.51-4.4 (m, 1H), 3.20-2.9 (m, 9H), 2.80-2.65 (m, 5H), 2.65-2.50 (m, 5H), 2.10-0.75 (m, 53H), 0.45-0.18 (m, 4H); LCMS, purity 97.0% (based on total ion count), m/z calcd for $C_{46}H_{80}N_3O_4^+$ [M+H]+ 738.6, found 738.7.

Example 33. Preparation of (3β)-17-[2-[[(4-Dimethylamino)butyl]amino]ethyl]-20,29-methano-28-norlupan-3-ol, 3-(1-Hydrogen 2,2-Dimethylbutanedioate) (51j)

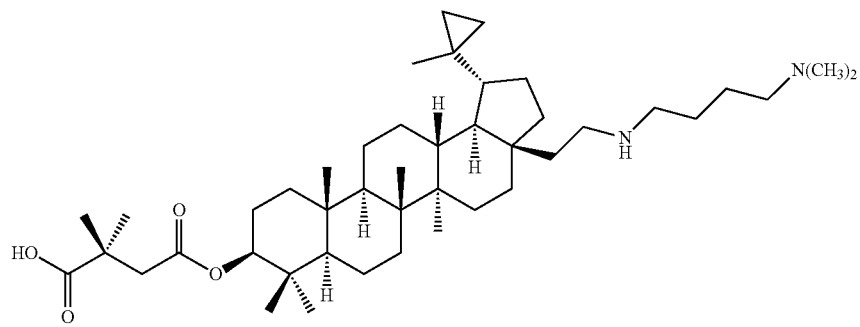

Amine 51j was obtained from aldehyde 30 and 4-(dimethylamino)butanamine as a white solid (2.4 mg, 6.2%) using Method A1: $^1$H NMR (200 MHz, CD$_3$OD) δ 4.58-4.39 (m, 1H), 2.60 (m, 2H), 2.05-0.78 (m, 68H), 0.45-0.15 (m, 4H); LCMS, purity 100% (based on total ion count), m/z calcd for $C_{44}H_{77}N_2O_4^+$ [M+H]$^+$ 697.6, found 697.6.

Example 34. Preparation of (3β)-17-[2-[2-[(1-Ethylpiperidin-4-yl]amino]ethyl]-20,29-methano-28-norlupan-3-ol, 3-(1-Hydrogen 2,2-Dimethylbutanedioate) (51k)

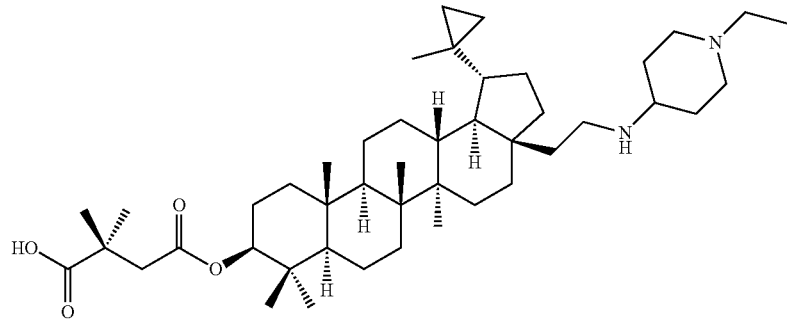

Amine 51k was obtained from aldehyde 30 and 1-ethyl-4-piperidinamine as a white solid (1.9 mg, 4.9%) using Method A1: $^1$H NMR (200 MHz, CD$_3$OD) δ 4.51-4.38 (m, 1H), 3.10-2.80 (m, 4H), 2.81-2.51 (m, 5H), 2.42-0.72 (m, 60H), 0.47-0.19 (m, 4H); LCMS, purity 100% (based on total ion count), m/z calcd for $C_{45}H_{77}N_2O_4^+$ [M+H]$^+$ 709.5, found 709.6.

Example 35. Preparation of (3β)-17-[2-[[2-[4-(4-Fluorophenylmethyl)piperazin-1-yl]ethyl]amino]ethyl]-28-norlup-20(29)-en-3-ol, 3-(1-Hydrogen 2,2-Dimethylbutanedioate) (51l)

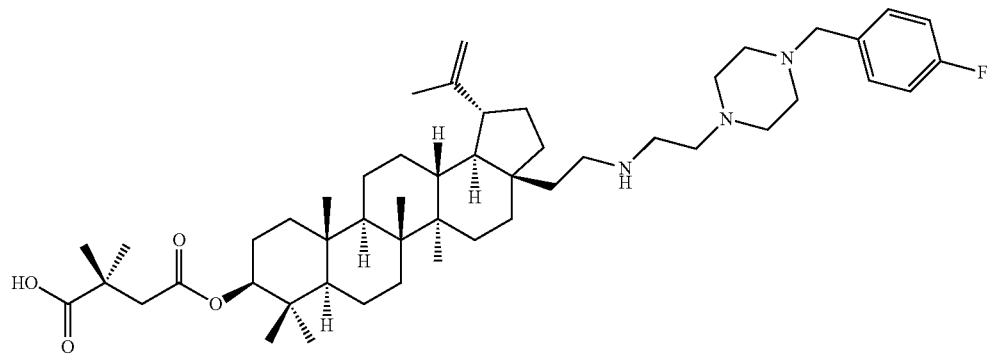

Amine 51l was obtained from aldehyde 6a and amine 43e as a white solid (45 mg) using Method A1: $^1$H NMR (400 MHz, CDCl$_3$) δ 7.30-7.23 (m, 2H), 6.99 (t, J=8.4 Hz, 2H), 4.67 (s, 1H), 4.57 (s, 1H), 4.47-4.39 (m, 1H), 3.54 (s, 2H), 3.23-2.24 (m, 18H), 2.02-0.61 (m, 50H); HPLC purity 100%; m/z calcd for $C_{50}H_{79}FN_3O_4^+$ [M+H]$^+$ 804.6049, found 804.6049.

Example 36. Preparation of (3β)-17-[2-[[2-[4-(3-Fluorophenylmethyl)piperazin-1-yl]ethyl]amino]ethyl]-28-norlup-20(29)-en-3-ol, 3-(1-Hydrogen 2,2-Dimethylbutanedioate) (51m)

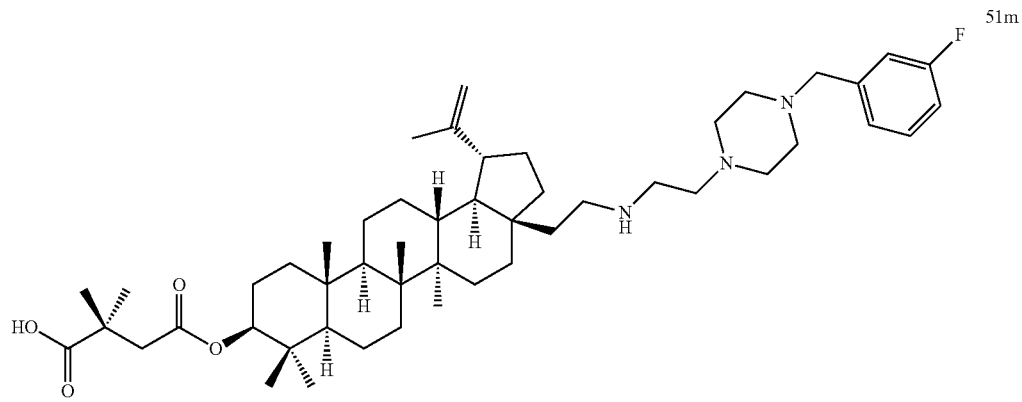

Amine 51m was obtained from aldehyde 6a and amine 43f as a white solid (40 mg) using Method A: $^1$H NMR (400 MHz, CDCl$_3$) δ 7.30-7.25 (m, 1H), 7.11-7.01 (m, 2H), 7.00-6.93 (m, 1H), 4.67 (s, 1H), 4.57 (s, 1H), 4.43 (t, J=7.9 Hz, 1H), 3.58 (s, 2H), 3.28-2.25 (m, 18H), 2.01-0.68 (m, 50H); HPLC purity 90%; m/z calcd for $C_{50}H_{79}FN_3O_4^+$ [M+H]$^+$ 804.6049, found 804.6026.

Example 37. Preparation of (3β)-17-[2-[[2-[4-(4-Chlorophenylmethyl)piperazin-1-yl]ethyl]amino]ethyl]-28-norlup-20(29)-en-3-ol, 3-(1-Hydrogen 2,2-Dimethylbutanedioate) (51n)

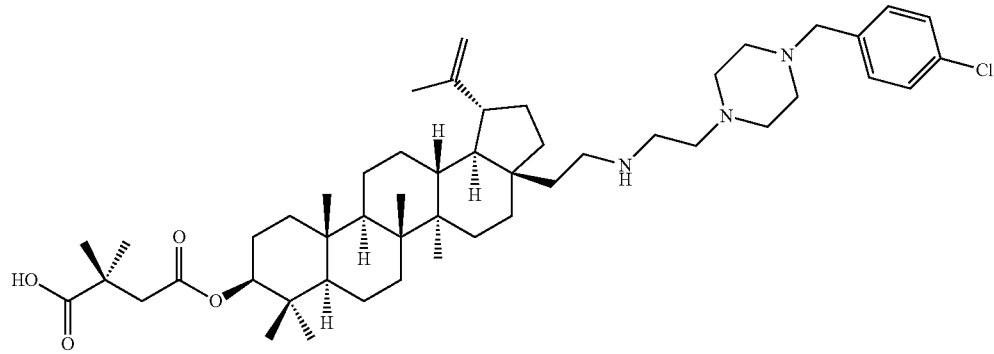

Amine 51n was obtained from aldehyde 6a and amine 43g as a white solid (47 mg) using Method A1: $^1$H NMR (400 MHz, CDCl$_3$) δ 7.31-7.21 (m, 4H), 4.67 (s, 1H), 4.58 (s, 1H), 4.44 (t, J=8.0 Hz, 1H), 3.54 (s, 2H), 3.15-2.32 (m, 18H), 1.97-0.68 (m, 50H); HPLC 100%; m/z calcd for $C_{50}H_{79}CN_3O_4^+$ [M+H]820.5754, found 820.5757.

Example 38. Preparation of (3β)-17-[2-[[2-[4-(3-Chlorophenylmethyl)piperazin-1-yl]ethyl]amino]ethyl]-28-norlup-20(29)-en-3-ol, 3-(1-Hydrogen 2,2-Dimethylbutanedioate) (51o)

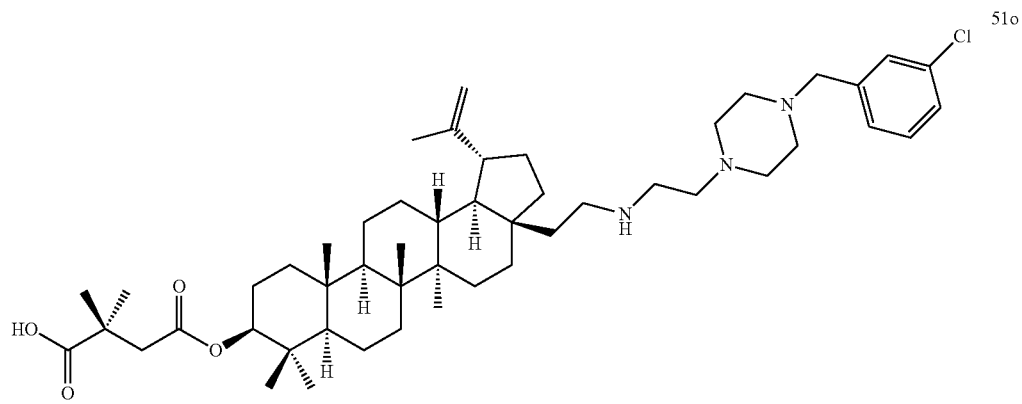

Amine 51o was obtained from aldehyde 6a and amine 43h as a white solid (15 mg) using Method A1: $^1$H NMR (400 MHz, CDCl$_3$) δ 7.34-7.30 (m, 1H), 7.28-7.24 (m, 2H), 7.21-7.16 (m, 1H), 4.70-4.65 (m, 1H), 4.58 (s, 1H), 4.43 (t, J=8.0 Hz, 1H), 3.58 (s, 2H), 3.14-2.35 (m, 18H), 2.08-0.70 (m, 50H); HPLC purity 100%; m/z calcd for $C_{50}H_{79}CN_3O_4^+$ [M+H]$^+$ 820.5754, found 820.5748.

Example 39. Preparation of (3β)-17-[2-[[2-(4-Phenylpiperazin-1-yl)ethyl]amino]ethyl]-28-norlup-20(29)-en-3-ol, 3-(1-Hydrogen 2,2-Dimethylbutanedioate) (51p)

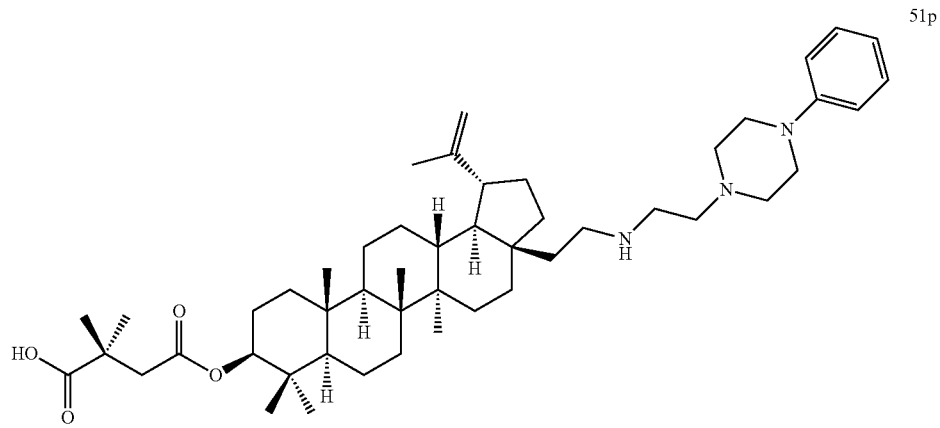

Amine 51p was obtained from aldehyde 6a and amine 43n as a white solid (25 mg) using Method A1: $^1$H NMR (400 MHz, CDCl$_3$) δ 7.28-7.21 (m, 2H), 6.93-6.83 (m, 3H), 4.70-4.65 (m, 1H), 4.58 (s, 1H), 4.42 (s, 1H), 3.27-2.31 (m, 18H), 1.99-0.65 (m, 50H); HPLC purity 100%; m/z calcd for $C_{49}H_7N_3O_4^+$ [M+H]$^+$ 772.5987, found 772.5974.

Example 40. Preparation of (3β)-17-[2-[[2-[4-(1-Naphthalenylmethyl)piperazin-1-yl]ethyl]amino]ethyl]-28-norlup-20(29)-en-3-ol, 3-(1-Hydrogen 2,2-Dimethylbutanedioate) (51q)

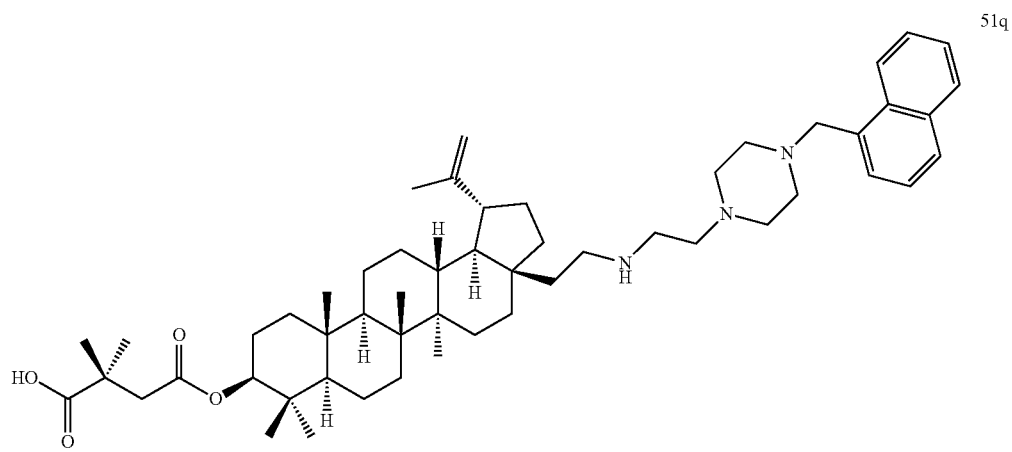

Amine 51q was obtained from aldehyde 6a and amine 43i as a white solid (30 mg) using Method A1: $^1$H NMR (400 MHz, CDCl$_3$) δ 8.23 (dd, J=7.8, 1.8 Hz, 1H), 7.88-7.73 (m, 2H), 7.54-7.36 (m, 4H), 4.68 (s, 1H), 4.58 (s, 1H), 4.43 (t, J=7.9 Hz, 1H), 3.97 (s, 2H), 3.27-2.46 (m, 18H), 2.08-0.61 (m, 50H); HPLC purity 100%; m/z calcd for $C_{54}H_{82}N_3O_4^+$ [M+H]$^+$ 836.6300, found 836.6296.

Example 41. Preparation of (3β)-17-[2-[[2-[4-(2-Naphthalenylmethyl)piperazin-1-yl]ethyl]amino]ethyl]-28-norlup-20(29)-en-3-ol, 3-(1-Hydrogen 2,2-Dimethylbutanedioate) (51r)

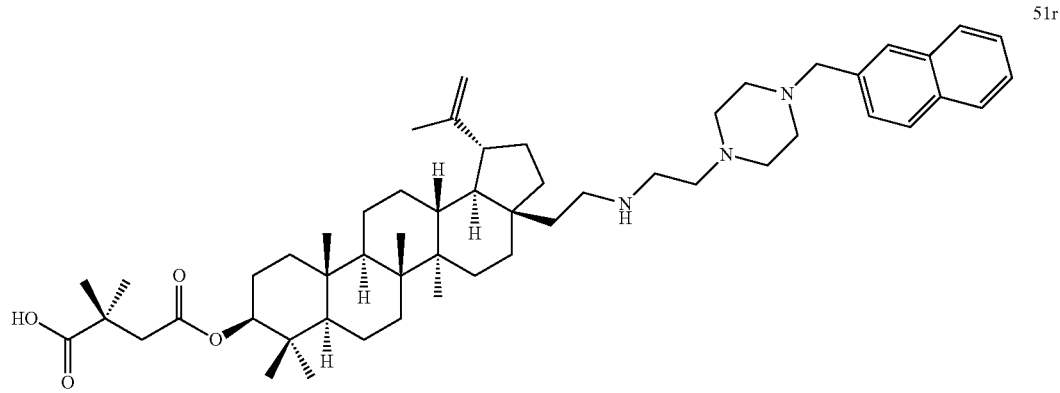

Amine 51r was obtained from aldehyde 6a and amine 43j as a white solid (50 mg) using Method A1: $^1$H NMR (400 MHz, CDCl$_3$) δ 7.86-7.69 (m, 4H), 7.49-7.42 (m, 3H), 4.67 (s, 1H), 4.58 (s, 1H), 4.42 (t, J=8.1 Hz, 1H), 3.82 (s, 2H), 3.18-2.27 (m, 18H), 1.96-0.62 (m, 50H); HPLC purity 100%; m/z calcd for $C_{54}H_2N_3O_4^+$ [M+H]$^+$ 836.6300, found 836.6305.

Example 42. Preparation of (3β)-17-[2-[[2-[4-(Cyclohexylmethyl)piperazin-1-yl]ethyl]amino]ethyl]-28-norlup-20(29)-en-3-ol, 3-(1-Hydrogen 2,2-Dimethylbutanedioate) (51s)

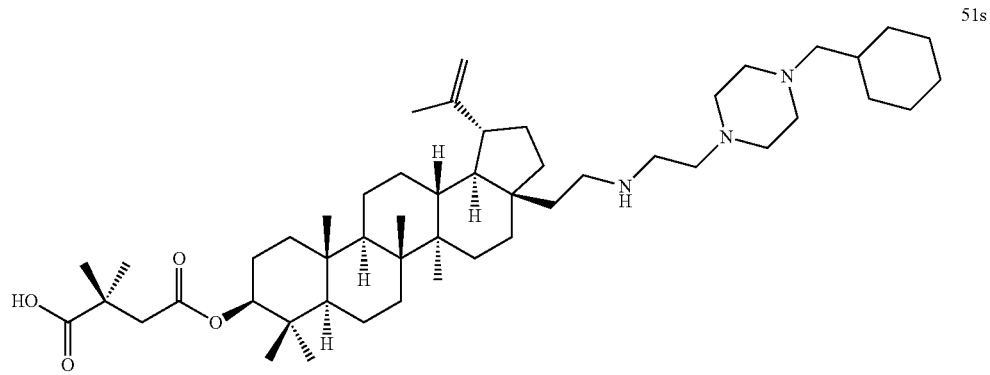

Amine 51s was obtained from aldehyde 6a and amine 43m as a white solid (45 mg) using Method A1: $^1$H NMR (400 MHz, CDCl$_3$) δ 4.67 (s, 1H), 4.58 (s, 1H), 4.44 (t, J=8.1 Hz, 1H), 3.35-2.26 (m, 26H), 2.04-0.63 (m, 55H); m/z calcd for $C_{50}H_{86}N_3O_4^+$ [M+H]$^+$ 792.6613, found 792.6601.

Example 43. Preparation of (3β)-17-[2-[[2-[4-(2-Quinolinylmethyl)piperazin-1-yl]ethyl]amino]ethyl]-28-norlup-20(29)-en-3-ol, 3-(1-Hydrogen 2,2-Dimethylbutanedioate) (51t)

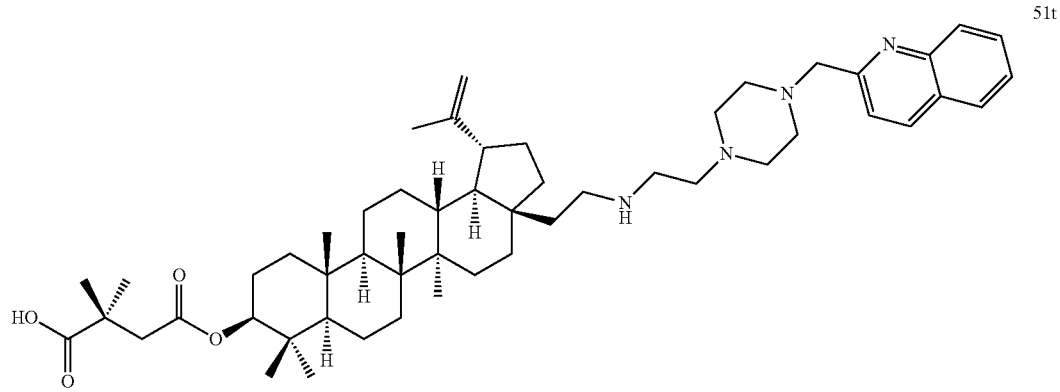

Amine 51t was obtained from aldehyde 6a and amine 43l as a white solid (50 mg) using Method A1: $^1$H NMR (400 MHz, CDCl$_3$) δ 8.14-8.04 (m, 2H), 7.78 (dd, J=8.1 and 1.4 Hz, 1H), 7.68 (ddd, J=8.4, 6.9, and 1.5 Hz, 1H), 7.60-7.47 (m, 2H), 4.67 (s, 1H), 4.56 (s, 1H), 4.43 (d, J=8.5 Hz, 1H), 3.86 (s, 2H), 3.14-2.28 (m, 18H), 2.01-0.63 (m, 50H); HPLC purity 100%; m/z calcd for $C_{53}H_8N_4O_4^+$ [M+H]$^+$ 837.6252, found 837.6234.

Example 44. Preparation of (3β)-17-[2-[[2-[4-(2-Pyridinylmethyl)piperazin-1-yl]ethyl]amino]ethyl]-28-norlup-20(29)-en-3-ol, 3-(1-Hydrogen 2,2-Dimethylbutanedioate) (51u)

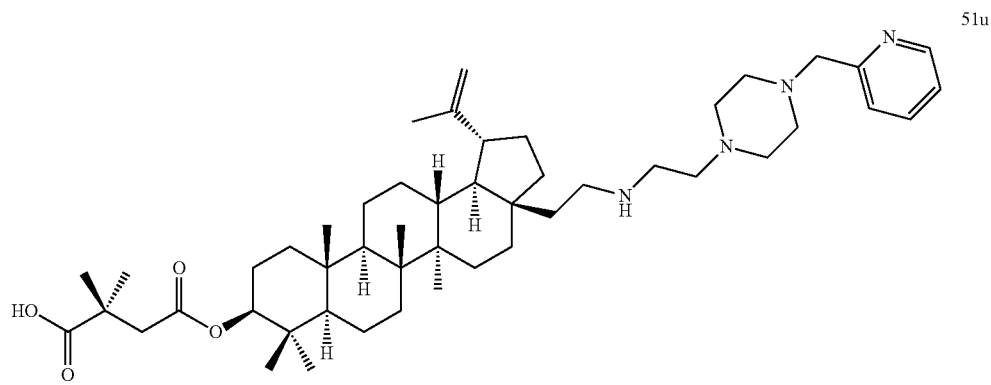

Amine 51u was obtained from aldehyde 6a and amine 43k as a white solid (55 mg) using Method A1: $^1$H NMR (400 MHz, CDCl$_3$) δ 8.56 (ddd, J=4.9, 1.8, and 0.9 Hz, 1H), 7.66 (td, J=7.7 and 1.8 Hz, 1H), 7.38 (dt, J=7.8 and 1.1 Hz, 1H), 7.19 (ddd, J=7.5, 4.8, and 1.2 Hz, 1H), 4.67 (s, 1H), 4.57 (s, 1H), 4.44 (t, J=8.0 Hz, 1H), 3.74 (s, 2H), 3.20-2.28 (m, 18H), 1.97-0.71 (m, 50H); HPLC purity 96%; m/z calcd for $C_{49}H_{79}N_4O_4^+$ [M+H]$^+$ 787.6096, found 787.6072.

Example 45. Preparation of (3β)-28-[[3-(1-Pyrrolidinyl)propyl]amino]lup-20(29)-en-3-ol, 3-(1-Hydrogen 2,2-Dimethylbutanedioate) Sulfate (51v)

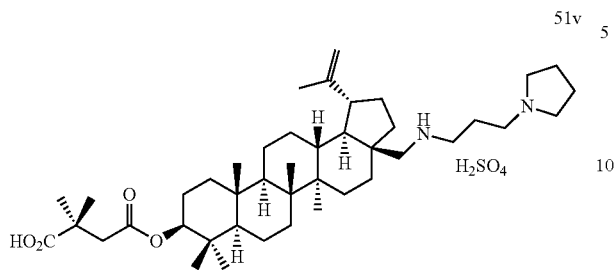

Amine 51v was obtained from aldehyde 3 and 3-(1-pyrrolidinyl)propylamine as a white solid (12.8 mg) using Method A2: H NMR (200 MHz, CD$_3$OD) δ 4.74 (s, 1H), 4.63 (s, 1H), 4.45 (t, 1H), 3.25-2.48 (m, 17H), 2.20-0.82 (m, 52H); LCMS, purity 97.3% (based on total ion count), m/z calcd for $C_{43}H_{73}N_2O_4^+$ [M+H]$^+$ 681.55, found 681.6.

Example 46. Preparation of (3β)-28-[[2-[4-(Phenylmethyl)piperazin-1-yl]ethyl]amino]lup-20(29)-en-3-ol, 3-(1-Hydrogen 2,2-Dimethylbutanedioate) Sesquisulfate (51w)

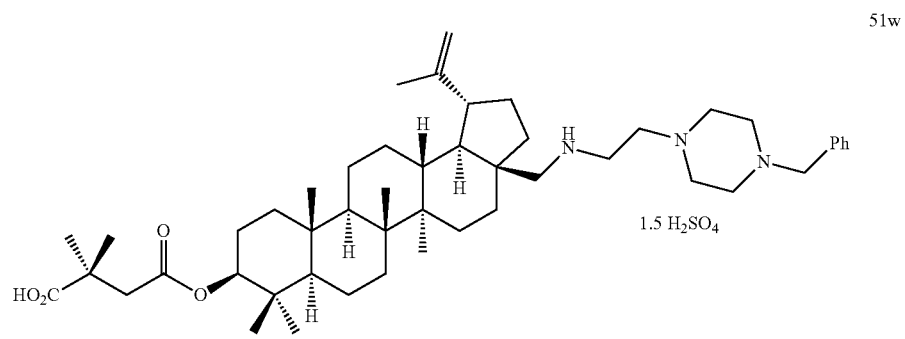

Amine 51w was obtained from aldehyde 3 and amine 43d as a white solid (14.6 mg) using Method A2: $^1$H NMR (200 MHz, CD$_3$OD) δ 7.57-7.46 (m, 5H), 4.74 (s, 1H), 4.63 (s, 1H), 4.46 (t, 1H), 4.35 (s, 1H), 2.96 (m, 6H), 2.60-2.57 (d, 2H), 1.72-0.86 (m, 60H); LCMS, purity, >99% (based on total ion count), n/z calcd for $C_{49}H_{78}N_3O_4^+$ [M+H]$^+$ 772.59, found 772.6.

Example 47. Preparation of (3β)-28-[[2-[4-(Methylsulfonyl)piperazin-1-yl]ethyl]amino]lup-20(29)-en-3-ol, 3-(1-Hydrogen 2,2-Dimethylbutanedioate) Sulfate (51x)

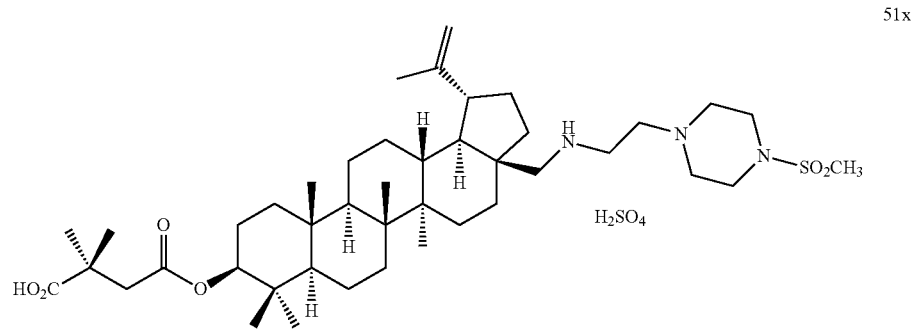

Amine 51x was obtained from aldehyde 3 and amine 43b as a white solid (21.4 mg) using Method A2: $^1$H NMR (200 MHz, CDCl$_3$) δ 4.60 (s, 1H), 4.50 (s, 1H), 4.37 (t, 1H), 3.52-3.12 (m, 10H), 2.78-2.72 (m, 6H), 2.57-2.48 (m, 10H), 2.30-2.20 (m, 2H), 1.92-0.67 (m, 36H); LCMS, purity >99% (based on total ion count), m/z calcd for C$_{43}$H$_4$N$_3$O$_6$S [M+H]$^+$ 760.52, found, 760.6.

Example 48. Preparation of (3β)-28-[[2-[(1,1-Dioxothiomorpholin-4-yl)]ethyl]amino]lup-20(29)-en-3-ol, 3-(1-Hydrogen 2,2-Dimethylbutanedioate) Sulfate (51y)

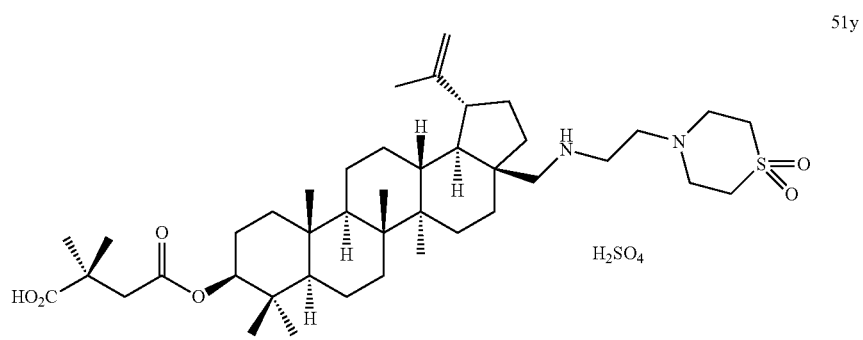

51y

Amine 51y was obtained from aldehyde 3 and amine 43a as a white solid (7.3 mg) using Method A2: $^1$H NMR (200 MHz, CDCl$_3$) δ 4.56 (s, 1H), 4.47 (s, 1H), 4.32 (t, 1H), 3.25 (m, 1H), 2.77-2.70 (m, 3H), 2.66-2.62 (m, 3H), 2.47-2.45 (d, 2H), 2.29-2.25 (d, 2H), 1.72-0.71 (m, 56H); LCMS, purity >99% (based on total ion count), m/z calcd for C$_{42}$H$_{71}$N$_2$O$_6$S [M+H]$^+$ 731.50, found 731.6.

Example 49. Preparation of (3β)-17-[2-[[3-(1-Pyrrolidinyl)propyl]amino]ethyl]-28-norlup-20(29)-en-3-ol, 3-(1-Hydrogen 2,2-Dimethylbutanedioate) Sulfate (51z)

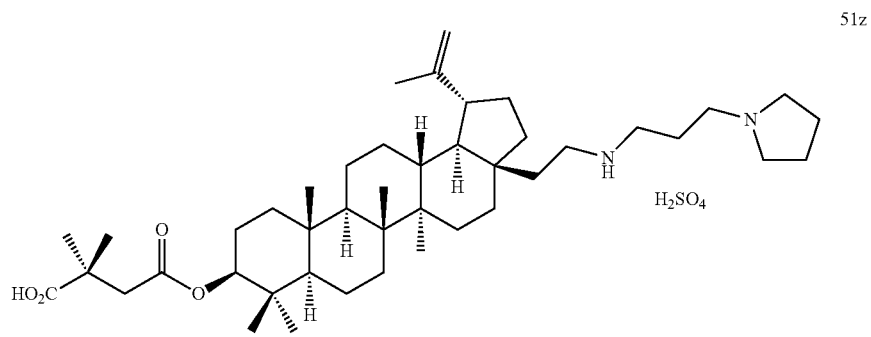

51z

Amine 51z was obtained from aldehyde 6a and 3-(1-pyrrolidinyl)propylamine as a white solid (22.5 mg) using Method A2: $^1$H NMR (200 MHz, CD$_3$OD) δ 4.70 (s, 1H), 4.60 (s, 1H), 4.43 (t, 1H), 2.99 (t, 1H), 2.85-2.74 (m, 8H), 2.54 (m, 2H), 1.94-0.88 (m, 59H); LCMS purity >99% (based on total ion count), m/z calcd for C$_{44}$H$_{75}$N$_2$O$_4$$^+$[M+H]$^+$ 695.56, found 695.6.

Example 50. Preparation of (3β)-17-[3-[[3-(1-Pyrrolidinyl)propyl]amino]propyl]-28-norlup-20(29)-en-3-ol, 3-(1-Hydrogen 2,2-Dimethylbutanedioate) Sulfate (51aa)

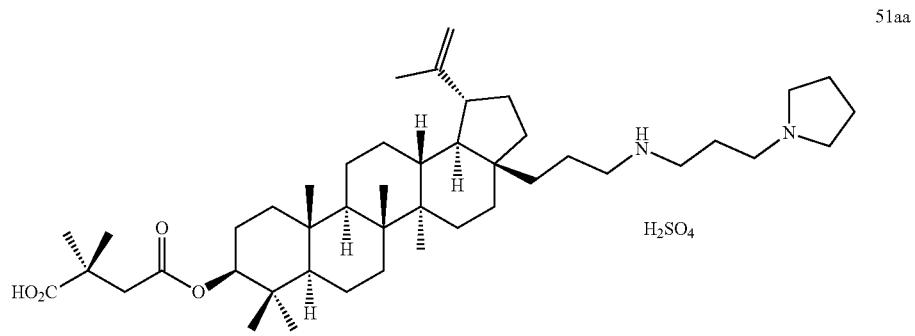

Amine 51aa was obtained from aldehyde 6b and 3-(1-pyrrolidinyl)propylamine as a white solid (15.2 mg) using Method A2: $^1$H NMR (200 MHz, CD$_3$OD) δ 4.69 (s, 1H), 4.57 (s, 1H), 4.45 (t, 1H), 4.08 (s, $^1$H), 3.63 (m, 1H), 3.15-2.98 (m, 6H), 2.58 (d, 2H), 2.09 (m, 6H), 1.69-0.85 (m, 57H); LCMS, purity >99%0 (based on total ion count), n/z calcd for C$_{45}$H$_{77}$N$_2$O$_4$ [M+H]$^+$ 709.58, found 709.7.

Example 51. Preparation of (3β)-17-[3-[[2-[4-(Phenylmethyl)piperazin-1-yl]ethyl]amino]propyl]-28-norlup-20(29)-en-3-ol, 3-(1-Hydrogen 2,2-Dimethylbutanedioate) Sesquisulfate (51bb)

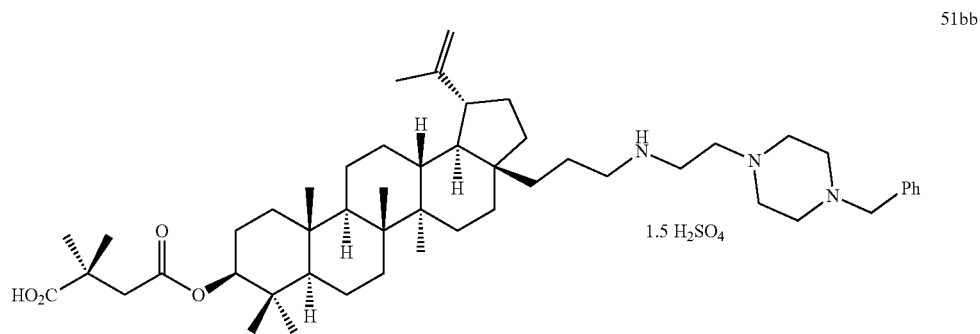

Amine 51bb was obtained from aldehyde 6b and amine 43d as a white solid (6.1 mg) using Method A2: $^1$H NMR (200 MHz, CD$_3$OD) δ 7.55-7.44 (m, 5H), 4.68 (s, 1H), 4.57 (s, 1H), 4.46 (t, 1H), 4.37 (s, 1H), 3.41 (t, 3H), 3.20 (t, 2H), 3.03 (t, 3H), 2.80-2.77 (m, 3H), 2.59-2.57 (d, 2H), 1.98-0.80 (m, 59H); LCMS purity >99% (based on total ion count [M+H]$^+$, [M+Na]$^+$), m/z calcd for C$_{51}$H$_{82}$N$_3$O$_4$, [M+H]$^+$ 800.63, found 800.6.

Example 52. Preparation of (3β)-17-[3-[[2-[4-(Methylsulfonyl)piperazin-1-yl]ethyl]amino]propyl]-28-norlup-20(29)-en-3-ol, 3-(1-Hydrogen 2,2-Dimethylbutanedioate) Sesquisulfate (51cc)

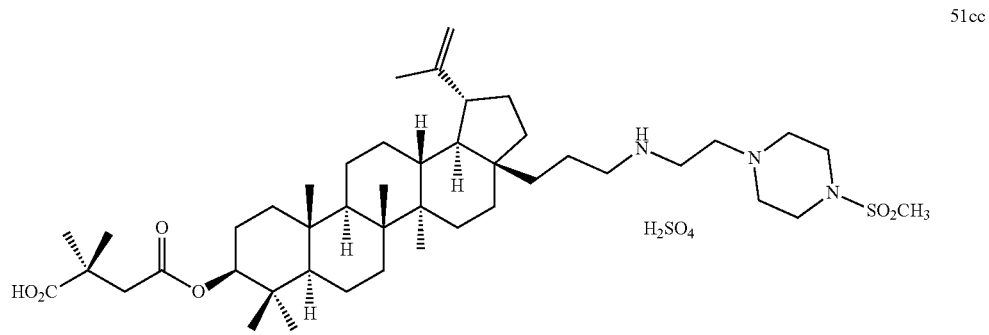

51cc

Amine 51cc was obtained from aldehyde 6b and amine 43b as a white solid (19.8 mg) using Method A2: $^1$H NMR (200 MHz, CD$_3$OD) δ 4.68 (s, 1H), 4.58 (s, 1H), 4.46 (t, 1H), 3.63 (s, 1H), 3.47 (m, 4H), 3.14-2.97 (m, 8H), 2.57 (d, 2H), 1.77-0.70 (m, 59H); LCMS purity >99% (based on total ion count), m/z calcd for C$_{45}$H$_{78}$N$_3$O$_6$S [M+H]$^+$ 788.56, found 788.5.

Example 53. Preparation of (3β)-17-[[[3-[2-(1,1-Dioxothiomorpholin-4-yl)]Ethyl]Amino]Propyl]-28-norlup-20(29)-en-3-ol, 3-(1-Hydrogen 2,2-Dimethylbutanedioate) Sulfate (51dd)

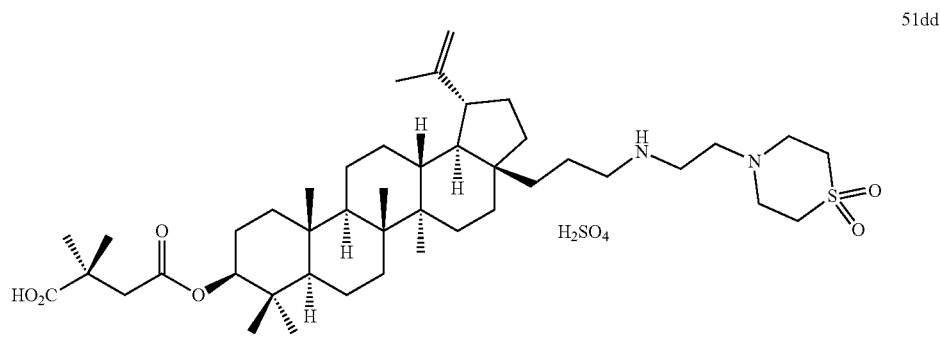

51dd

Amine 51dd was obtained from aldehyde 6b and amine 43a as a white solid (4.6 mg) using Method A2: $^1$H NMR (200 MHz, CD$_3$OD) δ 4.64 (s, 1H), 4.58 (s, 1H), 4.46-4.41 (t, 1H), 3.15-3.09 (t, 9H), 2.88-2.82 (t, 2H) 2.59-2.57 (d, 2H), 1.69-0.85 (m, 58H); LCMS purity 98.8% (based on total ion count), m/z calcd for C$_{44}$H$_{75}$N$_2$O$_6$S [M+H]$^+$ 759.53, found 759.6.

Example 54. Methods of the Syntheses of C-28 Alkylamines from C-28 Aldehydes and Homologated Aldehydes C-3 Esters Followed by Ester Protecting Group Removal Scheme 24. Reductive Amination of Aldehydes and Homologated Aldehydes C-3 Esters Followed by Ester Protecting Group Removal

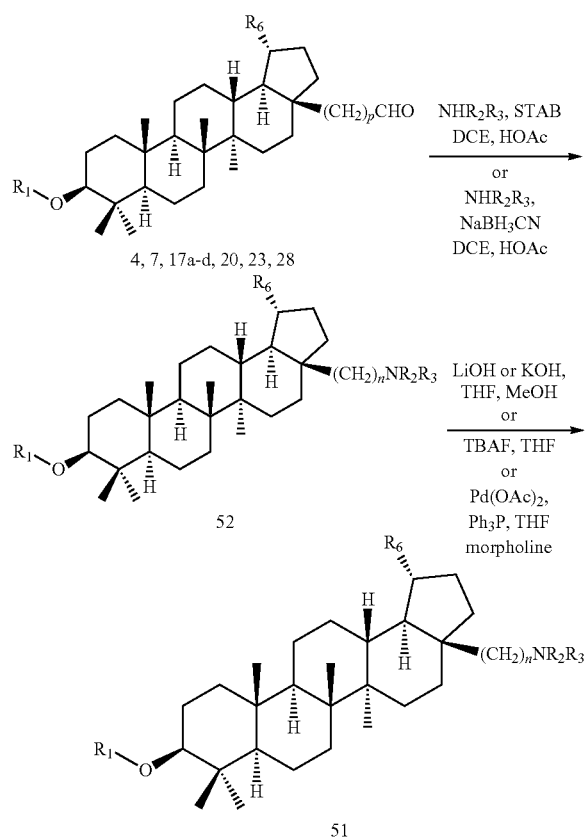

General procedure for the preparation of 52: To a solution of aldehyde (50 mg, 0.075 mmol) and amine (0.15 mmol) in DCE (2 mL) were added glacial acetic acid (15 μL, 0.5 mmol) and STAB (120 mg, 0.56 mmol). The mixture was stirred for 18 h, acidified with 10% $NaHSO_4$ and concd in vacuo. The crude product was purified by silica gel chromatography with the solvent gradient of 0-5% 10% $NH_4OH$ in MeOH and DCM. The fractions were analyzed by LCMS for purity, pure fractions pooled, and concd in vacuo providing amino esters 52 as viscous liquids. Alternatively, the crude product was redissolved in DCM, silica gel (1.0 g) was introduced and the solvent concd in vacuo. The dry-loaded substrate was purified by silica gel FCC (DCM/MeOH, 1-8% gradient) providing the amino esters 52.

General procedure for the preparation of 51 via basic ester hydrolysis using lithium hydroxide: To a solution of methyl ester 52 (0.15 mmol) in a 1:1 mixture of THF and methanol, 1 M LiOH (0.5 mL) was added and the mixture stirred at rt until completion of reaction (24 to 72 h). Additional 1 M LiOH was added if the reaction was incomplete. After completion of reaction the mixture was acidified with 10% $NaHSO_4$ and solvent concd in vacuo. The crude product was purified by silica gel chromatography with the solvent gradient of 0-20% 10% $NH_4OH$ in MeOH and DCM. The fractions were analyzed by LCMS for purity, pure fractions pooled and coned in vacuo providing 51 as solids.

General procedure for the preparation of 51 via basic ester hydrolysis using potassium hydroxide: To a solution of methyl or benzyl ester 52 (~0.20 mmol) in a 1:1 mixture of THF and methanol (10 mL) was added 2.5 M KOH (0.34 mL, 0.85 mmol) and the solution stirred at 20° C. for 7 d. The volatiles were removed in vacuo, water (5 mL) was added, and the pH adjusted to 7.0 with 1 M HCl. A pH 6.8 phosphate buffer solution (0.13 M $KH_2PO_4$ and 0.13 M $K_2HPO_4$, 0.10 mL) was added, the mixture stirred then filtered. The product obtained was purified as described above providing the amines 51.

General procedure for removal of 2-(trimethylsilyl)ethyl esters: To a solution of 2-(trimethylsilyl)ethyl ester 52 (0.30 mmol) in THF (3.0 mL) was introduced tetra-n-butylammonium fluoride (0.70 mL of a 1.0 M solution in THF, 0.70 mmol) and stirred at rt until the reaction was deemed complete. The reaction mixture was coned in vacuo, the residue re-dissolved in EtOAc (2.5 mL), washed with water (2×2.5 mL), dried ($Na_2SO_4$), filtered, and coned in vacuo. The residue obtained was purified as described above providing amines 51.

General procedure for the removal of allyl esters: To a degassed solution of allyl ester 52 (1 equ) in THF under an inert atmosphere were added palladium II acetate (1.05 equ), polymer bound triphenylphosphine (3.1 equ) and morpholine (20 equ). The reaction was stirred at 60° C. for 16 h, then cooled to rt, and filtered. The filtrate was diluted with EtOAc, washed with 1 M $KHSO_4$, water, dried ($Na_2SO_4$), filtered, and coned in vacuo. The residue obtained was purified as described above providing amines 51.

General procedure for the removal of benzyl esters: To a degassed solution of benzyl ester 52 (1 equ) in 1,4-dioxane (~20 mL/mmol) was added an equal weight of 10% Pd/C and 1,4-cyclohexadiene (10 equ) and then heated at 50° C. until reaction was deemed complete (2 h). The mixture was filtered through a pad of Celite® and the filter cake washed with DCM and MeOH. The filtrate was concd in vacuo and the residue purified as described above providing amines 51.

Example 55. Preparation of (3β)-17-[2-[[[2-(1,1-Dioxothiomorpholin-4-yl)]Ethyl]Amino]Ethyl]-28-norlup-20(29)-en-3-ol, 3-(1-Phenylmethyl 2,2-Dimethylbutanedioate) (52a)

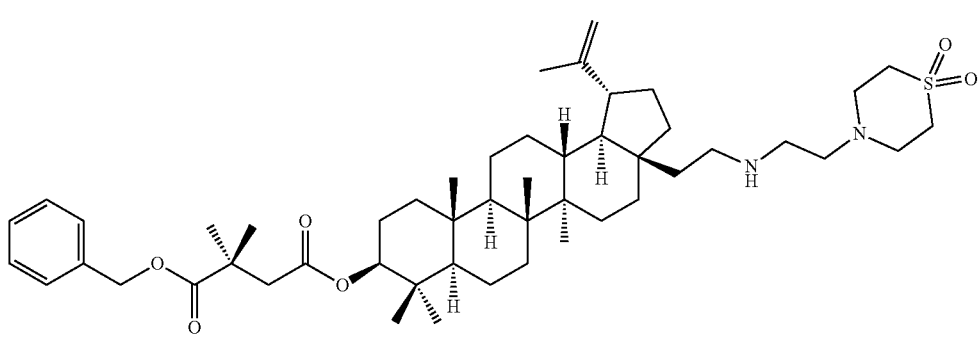

Reductive amination of aldehyde 7a with amine 43a provided ester 52a as a thick viscous liquid: (32 mg, 51.2%); $^1$H NMR (200 MHz, CD$_3$OD) δ 7.32 (s, 5H), 5.08 (s, 2H), 4.70 (s, 1H), 4.59 (s, 1H), 4.50-4.36 (m, 1H), 3.20-2.92 (m, 8H), 2.82-2.38 (m, 8H), 2.10-0.70 (m, 51H); LCMS m/z calcd for C$_{50}$H$_{79}$N$_2$O$_6$S$^+$ [M+H]$^+$ 835.0, found 834.9.

Example 56. Preparation of (3β)-17-[[[2-[2-(1,1-Dioxothiomorpholin-4-yl)]Ethyl]Amino]Ethyl]-28-norlup-20(29)-en-3-ol, 3-(1-Hydrogen 2,2-Dimethylbutanedioate) (51ee)

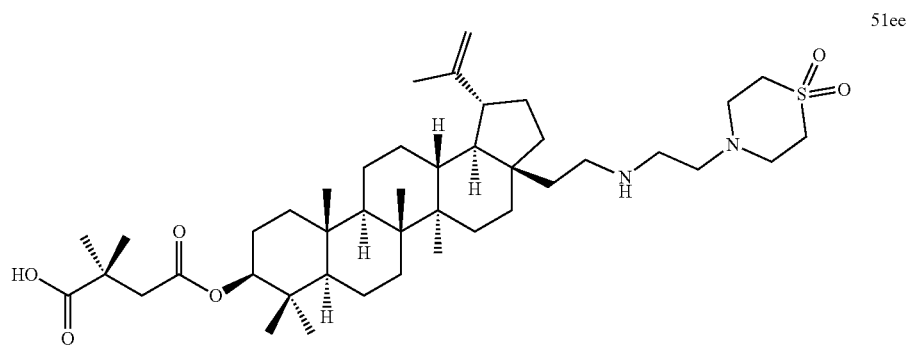

Hydrolysis of ester 52a using LiOH provided amine 51ee as a white solid (23.1 mg, 81.1%); $^1$H NMR (200 MHz, CD$_3$OD) δ 4.70 (s, 1H), 4.59 (s, 1H), 4.50-4.36 (m, 1H), 3.20-2.76 (m, 13H), 2.62-2.35 (m, 3H), 2.10-0.70 (m, 51H); LCMS, purity 100.0% (based on total ion count), m/z calcd for C$_{43}$H$_{73}$N$_2$O$_6$S$^+$ [M+H]$^+$ 745.0, found 744.9.

Example 57. Preparation of (3β)-17-[2-[[2-[4-(Methylsulfonyl)piperazin-1-yl]ethyl]amino]ethyl]-28-norlup-20(29)-en-3-ol, 3-(1-Phenylmethyl 2,2-Dimethylbutanedioate) (52b)

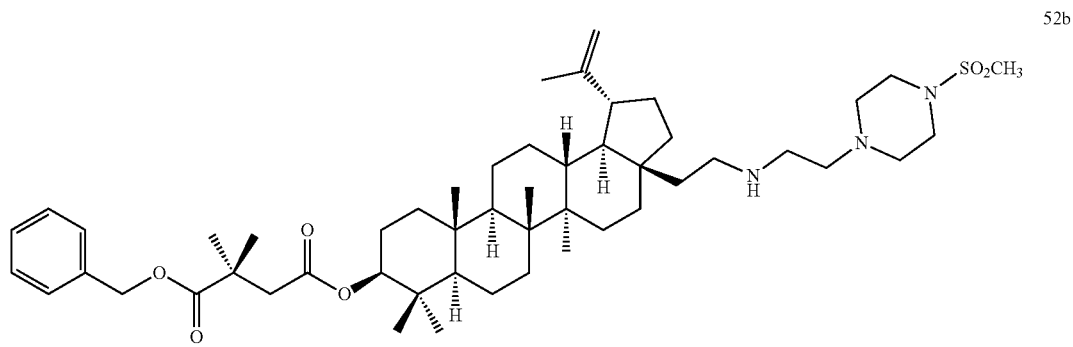

Reductive amination of aldehyde 7a with amine 43b provided ester 52b as a viscous liquid (22 mg, 34.0%): $^1$H NMR (200 MHz, CD$_3$OD) δ 7.34 (s, 5H), 5.12 (s, 2H), 4.70 (s, 1H), 4.60 (s, 1H), 4.50-4.40 (m, 1H), 3.80-3.20 (m, 10H), 3.20-2.80 (m, 5H), 2.80-2.20 (m, 4H), 2.10-0.60 (m, 51H); LCMS m/z calcd for C$_{51}$H$_{82}$N$_3$O$_6$S$^+$ [M+H]$^+$ 864.0, found: 864.0.

Example 58. Preparation of (3β)-17-[2-[[2-[4-(Methylsulfonyl)piperazin-1-yl]ethyl]amino]ethyl]-28-norlup-20(29)-en-3-ol, 3-(1-Hydrogen 2,2-Dimethylbutanedioate) (51ff)

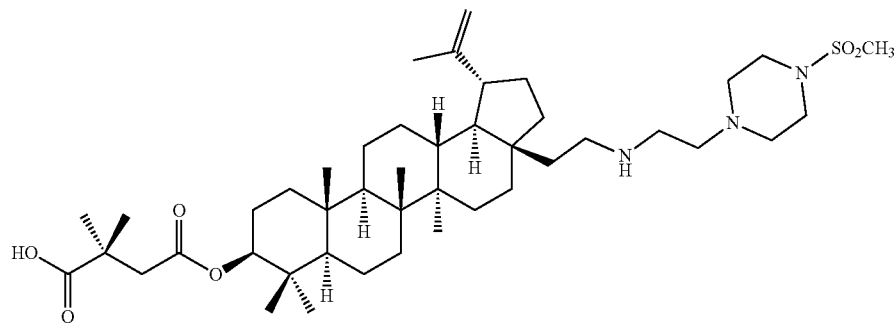

51ff

Hydrolysis of ester 52b using LiOH provided amine 51ff as a white solid (11.0 mg, 55.8%); $^1$H NMR (200 MHz, CD$_3$OD) δ 4.68 (s, 1H), 4.58 (s, 1H), 4.50-4.37 (M, 1H), 3.30-2.98 (m, 4H), 3.12-2.98 (m, 7H), 2.76-2.32 (m, 8H), 2.10-0.70 (m, 51H); LCMS, purity 100.0% (based on total ion count), m/z calcd for $C_{44}H_{76}N_3O_6S^+$ [M+H]$^+$ 774.0, found 774.0.

Example 59. Preparation of (3β)-17-[2-[[2-[4-(Methylsulfonyl)piperidin-1-yl]ethyl]amino]ethyl]-28-norlup-20(29)-en-3-ol, 3-(1-Phenylmethyl 2,2-Dimethylbutanedioate) (52c)

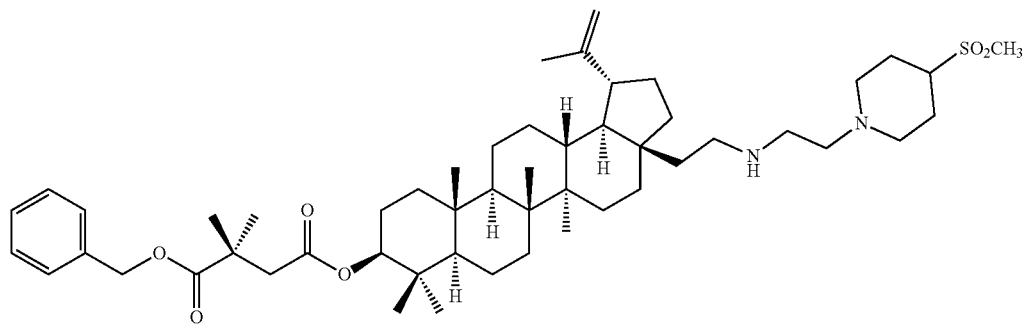

52c

Reductive amination of aldehyde 7a with amine 43c provided ester 52c as a viscous liquid (16 mg, 24.7%); $^1$H NMR (200 MHz. CD$_3$OD) δ 7.32 (s, 5H), 5.08 (s, 2H), 4.70 (s, 1H), 4.60 (s, 1H), 4.50-4.39 (m, 1H), 3.20-2.80 (m, 6H), 2.72-2.10 (m, 8H), 2.10-0.70 (m, 57H); LCMS m, calcd for $C_{52}H_{83}N_2O_6S^+$ [M+H]$^+$ 863.0, found 863.1.

Example 60. Preparation of (3β)-17-[2-[[2-[4-(Methylsulfonyl)piperidin-1-yl]ethyl]amino]ethyl]-28-norlup-20(29)-en-3-ol, 3-(1-Hydrogen 2,2-Dimethylbutanedioate) (51gg)

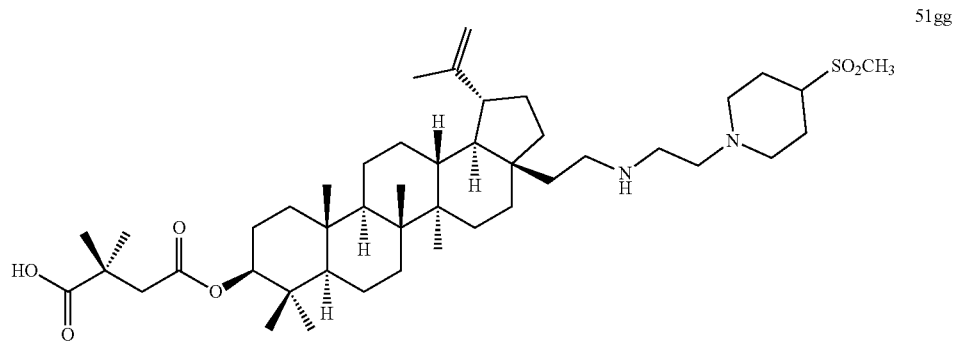

Hydrolysis of ester 52c using LiOH provided amine 51gg as a white solid (12.3 mg, 86.0%); $^1$H NMR (200 MHz, CD$_3$OD) δ 4.70 (s, 1H), 4.60 (s, 1H), 4.50-4.39 (m, 1H), 3.20-2.80 (m, 10H), 2.72-2.38 (m, 4H), 2.25-0.70 (m, 57H); LCMS, purity 97.9% (based on total ion count), m/z calcd for $C_{45}H_{77}N_2O_6S^+$ [M+H]$^+$ 773.0, found 773.1.

Example 61. Preparation of (3β)-17-[2-[[2-[4-(Phenylmethyl)piperazin-1-yl]ethyl]amino]ethyl]-28-norlup-20(29)-en-3-ol, 3-(1-Phenylmethyl 2,2-Dimethylbutanedioate) (52d)

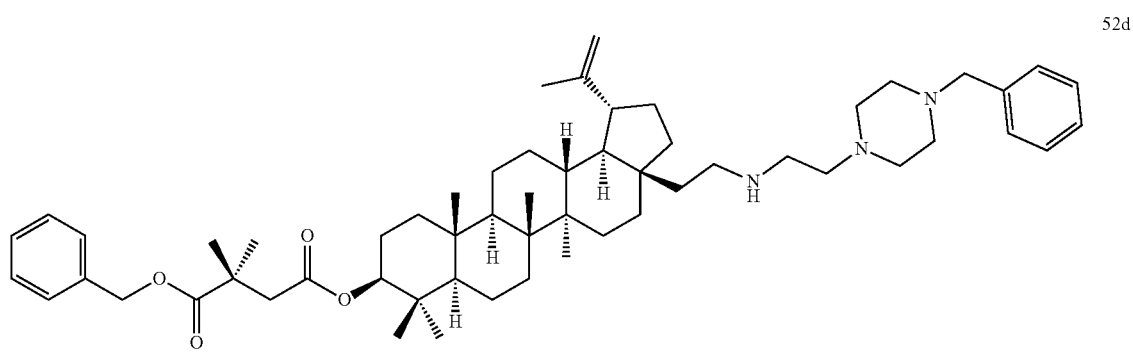

Reductive amination of aldehyde 7a with amine 43d provided ester 52d as a viscous liquid (22 mg, 33.5%); $^1$H NMR (200 MHz, CD$_3$OD) δ 7.20-7.40 (m, 10H), 5.20 (s, 2H), 4.70 (s, 1H), 4.58 (s, 1H), 4.50-4.33 (m, 1H), 3.57 (s, 2H), 3.20-2.22 (m, 16H), 2.20-0.70 (m, 51H); LCMS m, calcd for $C_{57}H_{56}N_3O_4^+$ [M+H]$^+$ 876.0, found 875.9.

Example 62. Preparation of (3β)-17-[2-[[2-[4-(Phenylmethyl)piperazin-1-yl]ethyl]amino]ethyl]-28-norlup-20(29)-en-3-ol, 3-(1-Hydrogen 2,2-Dimethylbutanedioate) (51hh)

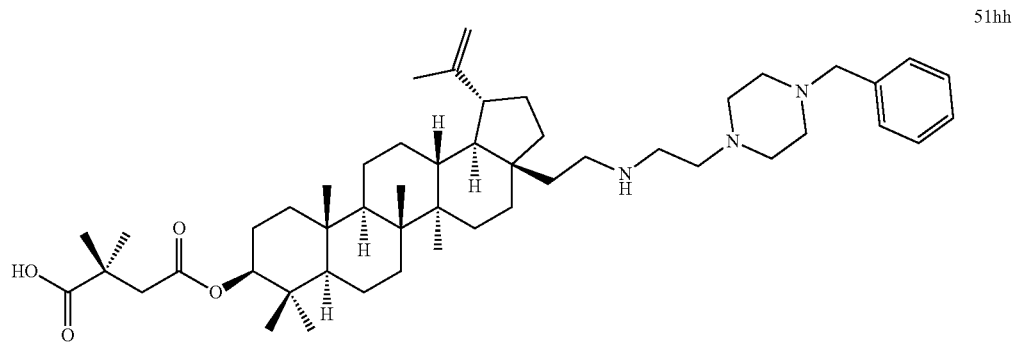

Hydrolysis of ester 52d using LiOH provided amine 51hh as a white solid (18.7 mg, 94.9%); $^1$H NMR (200 MHz, CD$_3$OD) δ 7.26 (m, 5H), 4.70 (s, 1H), 4.58 (s, 1H), 4.50-4.33 (m, 1H), 3.57 (s, 2H), 3.20-2.22 (m, 16H), 2.2-0.70 (m, 51H); LCMS, purity 100.0% (based on total ion count), m/z calcd for $C_{50}H_{80}N_3O_4^+$ [M+H]$^+$ 786.0, found 785.9.

Example 63. Preparation of (3β)-17-[2-[[2-(4-Hydroxypiperidin-1-yl)ethyl]amino]ethyl]-28-norlup-20(29)-en-3-ol, 3-(1-Phenylmethyl 2,2-Dimethylbutanedioate) (52e)

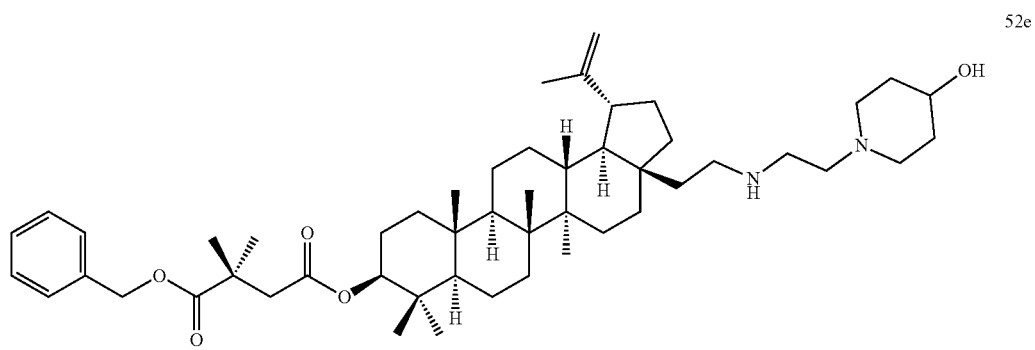

Reductive amination of aldehyde 7a with 1-(2-aminoethyl)piperidin-4-ol provided ester 52e as a viscous liquid (32 mg, 53.3%); $^1$H NMR (200 MHz, CD$_3$OD) δ 7.35 (s, 5H), 5.08 (s, 2H), 4.70 (s, 1H), 4.58 (s, 1H), 4.50-4.38 (m, 1H), 3.70-3.58 (m, 1H), 2.90-2.30 (m, 12H), 2.25-0.70 (m, 55H); LCMS m/z calcd for $C_{51}H_{81}N_2O_5^+$ [M+H]$^+$ 801.0, found 801.1.

Example 64. Preparation of (3β)-17-[2-[[2-(4-Hydroxypiperidin-1-yl)ethyl]amino]ethyl]-28-norlup-20(29)-en-3-ol, 3-(1-Hydrogen 2,2-Dimethylbutanedioate) (51ii)

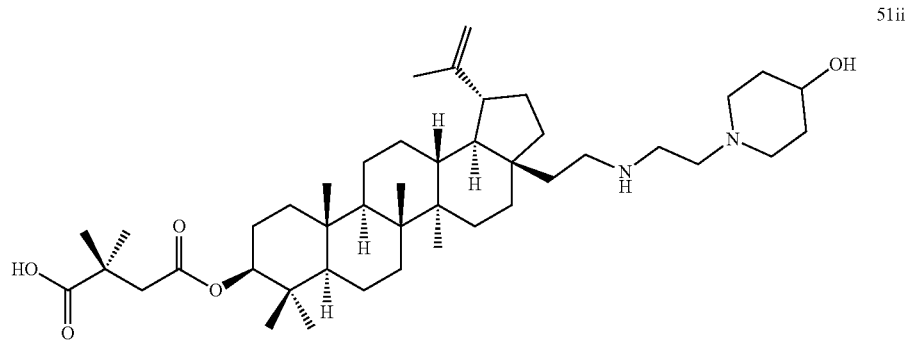

51ii

Hydrolysis of ester 52e using LiOH provided amine 51ii as a white solid (23.5 mg, 82.7%); $^1$H NMR (200 MHz, CD$_3$OD) δ 4.72 (s, 1H), 4.60 (s, 1H), 4.50-4.38 (m, 1H), 3.70-3.58 (m, 1H), 3.20-2.78 (m, 6H), 2.75-2.36 (m, 4H), 2.36-2.16 (m, 2H), 2.14-0.70 (m, 55H); LCMS, purity 100.0% (based on total ion count), m/z calcd for $C_{44}H_{75}N_2O_5^+$ [M+H]$^+$ 711.0, found 711.1.

Example 65. Compound Activity and Antiviral Assays

Cell culture, plasmids and transfections. The MT-4 T-cell line was maintained in RPMI-1640 medium supplemented with 10% (vol/vol) fetal bovine serum (FBS), 2 mM glutamine, 100 U/mL penicillin and 100 µg/mL streptomycin at 37° C. in a humidified 5% CO$_2$ atmosphere. HeLa and 293T cells were maintained in Dulbecco's modified Eagle's medium (DMEM) supplemented with 5% (vol/vol) FBS, 2 mM glutamine, 100 U/mL penicillin and 100 µg/mL streptomycin. Molecular clones used in this study were WT pNL4-3 and the derivative encoding a Val-to-Ala mutation at SP1 residue 7, referred to as SP1-V7A. The MT-4 T-cell line was transfected the DEAE/dextran procedure; HeLa and 293T cells were transfected with linear polyethylenimine (L-PEI) or Lipofectamine 2000 (Invitrogen) as recommended by the supplier.

CA-SP1 accumulation assay. For CA-SP1 accumulation assays, HeLa or 293T cells were transfected with WT pNL4-3 or the SP1-V7A derivative. At 24 h post-transfection, cells were starved in Met/Cys-free medium for 30 min and metabolically labeled with [$^{35}$S]Met/Cys-Pro-mix (Amersham) for 2-3 h. Maturation inhibitors were maintained in the cultures throughout the transfection and labeling period. Viruses were collected by ultracentrifugation at 99,000×g for 45-60 min. Virus pellets were resuspended in Triton X-100 lysis buffer [300 mM NaCl, 50 mM Tris-HCl (pH 7.5), 0.5% Triton X-100, 10 mM iodoacetamide, and protease inhibitor cocktail tablets (Roche)]. CA and CA-SP1 proteins were separated on 13.5-15% polyacrylamide gels by SDS-polyacrylamide gel electrophoresis, exposed to a phosphorimager plate (Fuji) and quantified by Quantity One software (Bio-Rad). CA-SP1 accumulation results are summarized in Table 1.

Antiviral assays. To produce HIV-1 stocks, 293T cells were transfected with WT pNL4-3 or the SP1-V7A derivative and culture supernatants were collected 24 h post transfection. RT-normalized virus supernatants were used to infect MT-4 cells at room temperature for 30 min. Cells were then cultured in the presence of serial dilutions of compounds. At 4 d post-infection, the culture supernatants were subjected to RT assay to monitor viral replication. The 50% inhibitory concentrations (IC$_{50}$s) were defined as compound concentrations that reduced RT levels to 50% those measured in the absence of inhibitor (DMSO only controls) using GraphPad Prism 6 software. The IC$_{50}$s in primary peripheral blood mononuclear cells (PBMCs) were calculated with a multi-clade panel of HIV-1 isolates by Southern Research Institute (Frederick, Md.). The PBMCs were stimulated with phytohemagglutinin (PHA) and IL-2 prior to use in the antiviral assays. IC$_{50}$s were calculated based on reductions in RT activity on day 6 post-infection as described above and are reported in Table 1.

Cytotoxicity assays. Cytotoxicity was measured with CellTiter-Blue® Cell Viability Assay according to the manufacturer's protocol (Promega). Two cell lines, MT-4 and HeLa, were used in this assay. Cells were incubated with serial dilution of compounds at 37° C. for 4 to 8 days and subjected to CellTiter-Blue Reagent. The fluorescent signal was measured at 560 nm Ex/590 nm Em by a plate reader (TECAN, Infinite® M1000 PRO). The 50% cytotoxic concentrations (CC$_{50}$s) were defined as compound concentrations at which the fluorescent signals were reduced by 50%/relative to the no-inhibitor (DMSO only) controls using GraphPad Prism 6 software and are reported in Table 1.

TABLE 1

CA-SP1 Accumulation, Antiviral, and Cytotoxicity Assays Results

| | % CA-SP1 Accumulation[a] | | | | Antiviral Assay[b] | | Cytotoxicity[c] | |
| | 100 nM | | 10 nM | | $IC_{50}$ (nM) | | $CC_{50}$ (nM) | |
| | SP1 | | SP1 | | SP1 | | | |
| Compound | NL4-3 | V7A | NL4-3 | V7A | NL4-3 | V7A | MT-4 | HeLa |
|---|---|---|---|---|---|---|---|---|
| 51a | 62.0 | 18.0 | | | | | | |
| 51b | 58.0 | 21.0 | | | | | | |
| 51c | 72.9 (3) | 29.2 (3) | | | | | | |
| 51d | 71.6 (3) | 20.4 (3) | | | | | | |
| 51e | 70.4 (3) | 23.1 (3) | | | | | | |
| 51f | 79.7 (3) | 43.4 (3) | | | 21 ± 19 | 8 ± 2 | 366 ± 44 | >1000 |
| 51g | 85.0 (2) | 46.5 (3) | | | 2 ± 0.5 | 19 ± 6 | 406 ± 48 | 551 ± 83 |
| 51h | 70.1 | 20.1 | | | | | | |
| 51i | 71.9 | 22.0 | | | | | | |
| 51j | 53.6 | 6.4 | | | | | | |
| 51k | 55.0 (2) | 27.3 (2) | | | | | | |
| 51l | | | 48.9 | 38.2 (3) | | | | |
| 51m | | | 53.7 | 40.3 (3) | | | | |
| 51n | | | 46.9 | 38.2 (3) | | | | |
| 51o | | | 55.7 | 39.4 (3) | | | | |
| 51p | | | 60.0 | 22.5 | | | | |
| 51q | | | 26.8 | 11.6 | | | | |
| 51r | | | 44.3 | 34.1 (3) | | | | |
| 51s | | | 48.7 | 14.5 | | | | |
| 51t | | | 56.1 | 18.6 | | | | |
| 51u | | | 53.8 | 30.2 (2) | | | | |
| 51v | 57.2 | 26.9 | 21.9 | 10.3 | | | | |
| 51w | 50.1 | 21.6 | 16.3 | 9.6 | | | | |
| 51x | 74.3 | 26.9 | 56.6 | 31.0 | | | | |
| 51y | 69.4 | 28.1 | 56.4 | 28.5 | | | | |
| 51z | 19.9 | 10.5 | 9.5 | 7.5 | | | | |
| 51aa | 45.2 | 14.4 | 12.5 | 5.3 | | | | |
| 51bb | 8.4 | 3.7 | 5.8 | 4.8 | | | | |
| 51cc | 58.4 | 19.3 | 26.0 | 12.5 | | | | |
| 51dd | 9.7 | 7.3 | 8.2 | 5.9 | | | | |
| 51ee | | | 73.5 | 35.1 | | | | |
| 51ff | | | 72.7 (3) | 31.1 (3) | | | | |
| 51gg | | | 57.7 | 30.9 | | | | |
| 51hh | | | 66.4 (3) | 42.1 (5) | | | | |
| 51ii | | | 70.1 | 29.5 (3) | | | | |

[a]Number in parenthesis represents the number of repeated independent assays
[b]The $IC_{50}$ values represent the mean ± SEM from four independent experiments.
[c]The $CC_{50}$ values represent the mean ± SEM from three independent experiments.

Example 66. Antiviral Compound Evaluation in Human Peripheral Blood Mononuclear Cells (PBMCs)

Virus Isolates. Compound evaluation against a panel of HIV-1 isolates were performed by the Southern Research Institute (SRI). The viruses were chosen to include one isolate from each of the seven HIV-1 Group M envelope subtypes A, B, C, D, E, F, and G, as well as isolates from HIV-1 Groups O and N. In addition, various drug resistant HIV-1 isolates were included for evaluation. The HIV-1 isolates selected include CCR5-tropic and CXCR4-tropic isolates. Unless otherwise noted, all virus isolates were obtained from the NIH AIDS Research and Reference Reagent Program. Virus isolate 1022-48 was obtained from Dr. William A. Schief of Merck Research Laboratories. MDR769 and MDR807 were obtained from Dr. Thomas C. Merigan of Stanford University. A low passage stock of each virus was prepared using fresh human PBMCs and stored in liquid nitrogen. Pre-titered aliquots of each virus were removed from the freezer and thawed rapidly to rt in a biological safety cabinet immediately before use.

Human PBMC Preparation. Fresh human PBMCs were isolated from screened donors, seronegative for HIV and HBV (Biological Specialty Corporation, Colmar, Pa.). Cells were pelleted/washed 2-3 times by low speed centrifugation and resuspension in Dulbecco's phosphate buffered saline (PBS) to remove contaminating platelets. The leukophoresed blood was then diluted 1:1 with PBS and layered over 14 mL of Ficoll-Hypaque density gradient (Lymphocyte Separation Medium, Cell Grow #85-072-CL, density 1.078+/−0.002 g/mL) in a 50 mL centrifuge tube and then centrifuged for 30 min at 600×g. Banded PBMCs were gently aspirated from the resulting interface and subsequently washed twice with PBS by low speed centrifugation. After the final wash, cells were enumerated by trypan blue exclusion and re-suspended at $1 \times 10^6$ cells/mL in RPMI 1640 supplemented with 15% Fetal Bovine Serum (FBS), 2 mM L-glutamine, 100 U/mL penicillin, 100 sg/mL streptomycin, and 4 µg/mL Phytohemagglutinin (PHA; Sigma, St. Louis, Mo.; cat #L1668). The cells were allowed to incubate for 48-72 h at 37° C. After incubation, PBMCs were centrifuged and resuspended in RPMI 1640 with 15% FBS, L-glutamine, penicillin, streptomycin, non-essential amino acids (MEM/NEAA; Hyclone; cat #SH30238.01), and 20 U/mL recombinant human IL-2 (R&D Systems Inc., Minneapolis, Minn.; cat #202IL). PBMCs were maintained in this medium at a concentration of $1\text{-}2 \times 10^6$ cells/mL, with twiceweekly medium changes until they were used in the assay protocol. Monocytes-derived-macrophages were depleted from the culture as the result of adherence to the tissue culture flask.

PBMC Assay. For the standard PBMC assay, PHA stimulated cells from at least two normal donors were pooled (mixed together), diluted in fresh medium to a final concentration of $1 \times 10^6$ cells/mL, and plated in the interior wells of a 96 well round bottom microplate at 50 µL/well (5×104 cells/well) in a standard formate developed by the Infectious Disease Research Department of the SRI. Pooling (mixing) of mononuclear cells from more than one donor was used to minimize the variability observed between individual donors, which results from quantitative and qualitative differences in HIV infection and overall response to the PHA and IL-2 of primary lymphocyte populations. Each plate contains virus control wells (cells plus virus) and experimental wells (drug plus cells plus virus). Test drug dilutions were prepared at a 2× concentration in microtiter tubes and 100 µL of each concentration was placed in appropriate wells using the standard format. 50 µL of a predetermined dilution of virus stock was placed in each test well (final MOI≈0.1). Separate plates were prepared identically without virus for drug cytotoxicity studies using an MTS assay system (described below; cytotoxicity plates also include compound control wells containing drug plus media without cells to control for colored compounds that affect the MTS assay). The PBMC cultures were maintained for seven days following infection at 37° C., 5% $CO_2$. After this period, cell-free supernatant samples were collected for analysis of reverse transcriptase activity, and compound cytotoxicity was measured by addition of MTS to the separate cytotoxicity plates for determination of cell viability. Wells were also examined microscopically and any abnormalities were noted.

Reverse Transcriptase Activity Assay. A microtiter plate-based reverse transcriptase (RT) reaction was utilized (Buckheit et al., AIDS Research and Human Retroviruses 7: 295-302, 1991). Tritiated thymidine triphosphate ($^3$H-TTP, 80 Ci/mmol, PerkinElmer) was received in 1:1 $dH_2O$/ethanol at 1 mCi/mL). Poly rA/oligo dT template/primer (GE HealthCare) was prepared as a stock solution by combining 150 µL poly rA (20 mg/mL) with 0.5 mL oligo dT (20 units/mL) and 5.35 mL sterile $dH_2O$ followed by aliquoting (1.0 mL) and storage at −20° C. The RT reaction buffer was prepared fresh on a daily basis and consisted of 125 µL 1.0 M EGTA, 125 µL $dH_2O$, 125 µL 20% Triton X100, 50 µL 1.0 M Tris (pH 7.4), 50 µL 1.0 M DTT, and 40 µL 1.0 M $MgCl_2$. The final reaction mixture was prepared by combining 1 part $^3$H-TTP, 4 parts $dH_2O$, 2.5 parts poly rA/oligo dT stock and 2.5 parts reaction buffer. Ten microliters of this reaction mixture was placed in a round bottom microtiter plate and 15 µL of virus-containing supernatant was added and mixed. The plate was incubated at 37° C. for 60 min. Following incubation, the reaction volume was spotted onto DE81 filter-mats (Wallac), washed 5 times for 5 min each in a 5% sodium phosphate buffer or 2×SSC (Life Technologies), 2 times for 1 min each distilled water, 2 times for 1 min each in 70% ethanol, and then dried. Incorporated radioactivity (counts per minute, CPM) was quantified using standard liquid scintillation techniques.

MTS Staining for PBMC Viability to Measure Cytotoxicity. At assay termination, the uninfected assay plates were stained with the soluble tetrazolium-based dye MTS (Cell-Titer 96 Reagent, Promega) to determine cell viability and quantify compound toxicity. MTS is metabolized by the mitochondria enzymes of metabolically active cells to yield a soluble formazan product, allowing the rapid quantitative analysis of cell viability and compound cytotoxicity. This reagent is a stable, single solution that does not require preparation before use. At termination of the assay, 20-25 mL of MTS reagent was added per well and the microtiter plates were then incubated at 37° C., 5% $CO_2$ to assess cell viability. Adhesive plate sealers were used in place of the lids, the sealed plate was inverted several times to mix the soluble formazan product and the plate was read spectrophotometrically at 490/650 nm with a Molecular Devices SPECTRAmax I3 plate reader.

Data Analysis. Using an SRI computer program, the PBMC data analysis included the calculation of $IC_{50}$ (50% inhibition of virus replication) and $CC_{50}$ (50% cytotoxicity); calculated values are reported in Table 2.

TABLE 2

Compound Antiviral Activity Against a Panel of HIV-1 Isolates

| Isolate | 51f | | 51ee | | 51ff | |
|---|---|---|---|---|---|---|
| | $IC_{50}$ nM | $CC_{50}$ nM | $IC_{50}$ nM | $CO_{50}$ nM | $IC_{50}$ nM | $CC_{50}$ nM |
| 92UG031 | >1,000 | >1,000 | | | | |
| 92RW009 | | | 20.7 | >1,000 | 39.4 | >1,000 |
| 92BR030 | 100 | >1,000 | 455.0 | >1,000 | >1000 | >1,000 |
| 93IN101 | 89.0 | >1,000 | 2.7 | >1,000 | 14.2 | >1,000 |
| 92UG001 | | | 0.4 | >1,000 | <0.15 | >1,000 |
| 99UGA07412MI | 8.2 | >1,000 | 2.2 | >1,000 | 4.3 | >1,000 |
| CMU02 | 316 | >1,000 | 110.0 | >1,000 | 217.0 | >1,000 |
| 93BR020 | | | 1.8 | >1,000 | 2.4 | >1,000 |
| 93BR029 | 5.1 | >1,000 | 0.9 | >1,000 | 1.1 | >1,000 |
| JV1083 | 477 | >1,000 | 126.0 | >1,000 | 460.0 | >1,000 |
| YBF30 | 14.8 | >1,000 | 8.4 | >1,000 | 3.6 | >1,000 |
| BCF02 | 4.6 | >1,000 | 1.7 | >1,000 | 2.8 | >1,000 |
| MDR769 | 5.9 | >1,000 | 1.4 | >1,000 | 1.7 | >1,000 |
| MDR807 | >1,000 | >1,000 | | | | |
| 1064-52 | | | 0.5 | >1,000 | 0.7 | >1,000 |
| A17 (IIIB) | 8.2 | >1,000 | 1.4 | >1,000 | 1.8 | >1,000 |
| 1022-48 | 18.9 | >1,000 | 1.1 | >1,000 | 1.3 | >1,000 |
| NL4-3 | 4.0 | >1,000 | 0.8 | >1,000 | 0.8 | >1,000 |
| NL4-3 gp41(36G) N42T, N43K | 5.6 | >1,000 | 1.3 | >1,000 | 1.4 | >1,000 |
| 4736_4 (NL4-3) | 3.3 | >1,000 | 1.0 | >1,000 | 0.8 | >1,000 |

| Isolate | 51hh | | 51m | | 51o | |
|---|---|---|---|---|---|---|
| | $IC_{50}$ nM | $CC_{50}$ nM | $IC_{50}$ nM | $CC_{50}$ nM | $IC_{50}$ nM | $CC_{50}$ nM |
| 92UG031 | | | | | | |
| 92RW009 | 10.4 | >1,000 | 27.9 | >1,000 | 60.9 | >1,000 |
| 92BR030 | >1000 | >1,000 | | | | |
| 93IN101 | 5.6 | >1,000 | 21.5 | >1,000 | 24.8 | >1,000 |
| 92UG001 | 1.2 | >1,000 | 7.9 | >1,000 | 8.1 | >1,000 |
| 99UGA07412MI | 8.0 | >1,000 | 17.8 | >1,000 | 33.2 | >1,000 |
| CMU02 | 11.1, 7.1 | >1,000 | 18.8 | >1,000 | 25.0 | >1,000 |
| 93BR020 | 3.0 | >1,000 | 8.4 | >1,000 | 13.2 | >1,000 |
| 93BR029 | 4.1 | >1,000 | 10.8 | >1,000 | 14.8 | >1,000 |
| JV1083 | 17.1 | >1,000 | >1000 | >1,000 | 220.0 | >1,000 |
| YBF30 | 132.0 | >1,000 | | | | |
| BCF02 | 3.8 | >1,000 | 16.7 | >1,000 | 38.1 | >1,000 |
| MDR769 | 4.4 | >1,000 | | | | |
| MDR807 | | | | | | |
| 1064-52 | 1.7 | >1,000 | | | | |
| A17 (IIIB) | 6.1 | >1,000 | | | | |
| 1022-48 | 3.2 | >1,000 | | | | |
| NL4-3 | 1.4 | >1,000 | | | | |
| NL4-3 gp41(36G) N42T, N43K | 3.8 | >1,000 | | | | |
| 4736_4 (NL4-3) | 1.4 | >1,000 | | | | |

TABLE 2-continued

Compound Antiviral Activity Against a Panel of HIV-1 Isolates

| Isolate | 51n IC$_{50}$ nM | 51n CC$_{50}$ nM | 51r IC$_{50}$ nM | 51r CC$_{50}$ nM |
|---|---|---|---|---|
| 92UG031 | | nM | | nM |
| 92RW009 | 25.9 | >1,000 | >1000 | >1,000 |
| 92BR030 | | | | |
| 93IN101 | 23.3 | >1,000 | 207.0 | >1,000 |
| 92UG001 | 5.3 | >1,000 | 25.5 | >1,000 |
| 99UGA07412MI | 31.4 | >1,000 | 370.0 | >1,000 |
| CMU02 | 17.3 | >1,000 | >1000 | >1,000 |
| 93BR020 | 12.8 | >1,000 | 26.0 | >1,000 |
| 93BR029 | 18.4 | >1,000 | 22.3 | >1,000 |
| JV1083 | 311.0 | >1,000 | >1000 | >1,000 |
| YBF30 | | | | |
| BCF02 | 22.0 | >1,000 | 62.3 | >1,000 |
| MDR769 | | | | |
| MDR807 | | | | |
| 1064-52 | | | | |
| A17 (IIIB) | | | | |
| 1022-48 | | | | |
| NL4-3 | | | | |
| NL4-3 gp41(36G) | | | | |
| N42T, N43K | | | | |
| 4736_4 (NL4-3) | | | | |

Example 67. Antiviral Compound Evaluation Against HIV-1 Clade C

Compound evaluation was performed against a panel of HIV-1 Clade C isolates K3016, pindieC1, and ZM247. The three isolates all contain the SP1-A7V. Clade B NL4-3 was included as the SP1A7 control.

Plasmids, tissue culture and transfections. HIV-1 clade B molecular clone NL4-3 and cade C clones K3016, ZM247 were obtained from Dr. Christina Ochsenbauer, University of Alabama, USA. Both K3016 and ZM247 were constructed using viral strains from South Africa. The HIV-1 clade C molecular clone pindieC1 was obtained from Dr. Uday Ranga, JNCASR, India. This clone was constructed using an HIV strain from India. HEK-293T and TZM-bl cells were propagated in Dulbecco's modified Eagle's medium (DM4EM) containing 10% fetal bovine serum (FBS). HUT-R5 cells were propagated in RPM 1640 medium supplemented with 10% FBS. For transfections, HEK-293T cells were grown in six well plates to about 80% confluency. Cells were transfected using Lipofectamine 2000 (invitrogen, USA) following manufacturer's recommendations. For viral replication assays, HUT-R5 T-cells were transfected using DEAE dextran as described in Waheed, A. A., Ono, A., and Freed, E. O.; Methods for the study of HIV-1 assembly; *Methods Mol. Biol. Clifton N.J.* 485, 163-184 (2009).

Preparation of viral stocks. Virus stocks were prepared by transfecting HEK-293T cells with HIV-1 DNAs (3 μg). 24 h post-transfection, the culture medium was replaced with fresh DMEM and incubated for another 2 h. Compounds tested were maintained in the culture throughout transfection. The culture supernatant was centrifuged at 845×g for 3 min to remove cellular debris. The clarified supernatants were filtered (pore size 0.45 m filter disc) to remove residual cellular contaminants. For determination of viral infectivity, the un-concentrated virus was used to infect TZM-bl cells. For the CA-SP1 accumulation assay, the virus was pelleted by ultra-centrifugation at 210,100×g for 1 h at 4° C. using SW41Ti rotor (Beckman Coulter, USA).

CA-SP1 accumulation assay. To measure accumulation of CA-SP1, immunoblot analysis of virus-associated proteins was performed. The virus pellet was resuspended in radio-immunoprecipitation assay (RIPA) buffer (50 mM Tris-HCl pH 8.0, 150 mM sodium chloride, 1.0% NP-40, 0.5% sodium deoxycholate, 0.1% SDS) containing 1×protease inhibitor cocktail (Roche, Germany). The viral lysates were subjected to SDS-polyacrylamide gel electrophoresis (15% gel). Proteins were transferred to polyvinylidene difluoride membranes and reacted with HIV-IgG obtained from the NIH AIDS Reagent Program (catalog no. 3957) followed by incubation with HRP-conjugated anti-human secondary antibodies (GE Healthcare, UK). The proteins were visualized by enhanced chemiluminescence (Pierce, USA) and the bands were quantified using ImageJ software (http://imagej.nih.gov/ij/).

Viral infectivity assays. The virus stocks were normalized for p24 antigen using an HIV-1 p24 Antigen Capture kit (ABL, USA). Equal amounts of virus were used to infect TZM-bl cells ($5 \times 10^4$/well) in the presence of 20 μg DEAE-dextran per mL in 24 well plate. Single-round infectivity assays were performed as previously described in Checkley, M. A. et al; Reevaluation of the Requirement for TIP47 in Human Immunodeficiency Virus Type 1 Envelope Glycoprotein Incorporation; *J. Virol.* 87, 3561-3570 (2013). The luciferase activity in the cell lysates was measured using the Steady-Glo luciferase assay kit (Promega, USA) following manufacturer's recommendations.

Antiviral assays. HUT-R5 cells were infected with normalized HIV-1 clade C K3016 virus stocks at 37° C. for 1 h. Cells were then maintained for 8 days in the presence of serial dilutions of the compounds assayed. After 8 days, the HIV-1 p24 concentration in the virus supernatants was measured to monitor virus replication. The 50% inhibitory concentrations ($IC_{50}$s) were determined that reduced HIV-1 p24 levels to 50% relative to DMSO-only controls.

Cytotoxicity assays. Cytotoxicity assays were performed using the CellTitre-Blue Cell Viability Assay kit (Promega, USA) as per manufacturer's recommendations. HEK-293T and HUT-R5 cell lines were maintained in the presence of serial dilutions of the compounds for 4 days and treated with CellTitre-Blue reagent for 4 h at 37° C. The fluorescent signals were recorded at $530/25_{excision}$ and $590/35_{emission}$ using BioTek microplate reader. The 50% cytotoxicity concentrations ($CC_{50}$s) were determined as the compound concentrations that reduced the fluorescent signals to 50% relative to DMSO only controls.

TABLE 3

CA-SP1 Accumulation Results Against HIV-1 Clade C isolates

| Compound | % CA-SP1 Accumulation | | | | | |
|---|---|---|---|---|---|---|
| | K3016 | | K3016 | | K3016 | |
| | 10 nM | 100 nM | 10 nM | 100 nM | 10 nM | 100 nM |
| 51hh | 35.8 | 62.9 | 26.7 | 43.8 | 7.0 | 27.2 |
| 51ee | 53.8 | 66.4 | 41.8 | 48.3 | 14.2 | 32.6 |
| 51ff | 49.8 | 54.4 | 36.7 | 39.1 | 12.8 | 19.1 |
| DMSO | 0 | 0 | 0 | 0 | 0 | 0 |

TABLE 4

Relative Infectivity, Antiviral, and Cytotoxicity Assays Results Against HIV-1 Clade C Isolates

| Com-pound | % Relative Infectivity | | | | Antiviral Activity[a] | Cytotoxicity | |
|---|---|---|---|---|---|---|---|
| | NL4-3 | | K3016 | | K3016 | $CC_{50}$ | |
| | 10 nM | 100 nM | 10 nM | 100 nM | $IC_{50}$ nM | HEK293T | HUTR5 |
| 51hh | 41.4 | 3.3 | 48.6 | 32.3 | 3.89 ± 0.18 | >100 nM | >500 nM |
| 51ee | 15.4 | 4.4 | 32.0 | 7.8 | 3.60 ± 0.22 | >100 nM | >500 nM |
| 51ff | 20.1 | 2.9 | 43.3 | 24.4 | 2.27 ± 0.56 | >100 nM | >500 nM |
| DMSO | 100 | 100 | 100 | 100 | | | |

[a]The $IC_{50}$ values represent the mean ± SEM from 2 independent experiments

What is claimed is:

1. A compound according to Formula I:

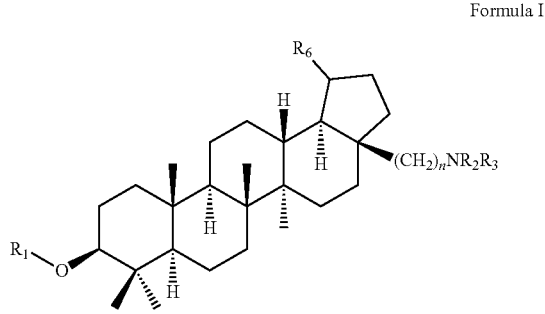

Formula I or a pharmaceutically acceptable salt, tautomer thereof, wherein:

$R_1$ is selected from the group consisting of substituted or unsubstituted $C_3$-$C_{20}$ alkanoyl, carboxyalkanoyl, carboxycyloalkylalkanoyl, carboxyalkylcycloalkylalkanoyl, carboxycyloalkylcarbonyl, carboxyalkylcycloalkylcarbonyl, alkoxycarbonylcycloalkylcarbonyl, alkoxycarbonylalkylcycloalkylcarbonyl, trialkylsilylalkoxycarbonylcyloalkylcarbonyl, trialkylsilylalkoxycarbonylalkylcycloalkylcarbonyl, arylalkyloxycarbonylcycloalkylcarbonyl, arylalkyloxycarbonylalkylcycloalkylcarbonyl, alkoxycarbonylalkanoyl, alkoxycarbonylcyloalkylalkanoyl, alkoxycarbonylalkylcycloalkylalkanoyl, trialkylsilylalkoxycarbonylalkanoyl, trialkylsilylalkoxycarbonylcyloalkylalkanoyl, trialkylsilylalkoxycarbonylalkylcycloalkylalkanoyl, arylalkyloxycarbonylalkanoyl, arylalkyloxycarbonylcyloalkylalkanoyl, and arylalkyloxycarbonylalkylcycloalkylalkanoyl, wherein any alkyl or cycloalkyl group is independently substituted with one or more groups selected from the group consisting of hydrido, halo, or $C_1$-$C_6$ alkyl groups;

n is an integer from one to six;

$R_2$ is hydrido, and $R_3$ is selected from the group consisting of heteroaryl$(CR_aR_b)_m$—, heterocyclyl$(CR_aR_b)_m$—, and $R_4R_5N(CR_aR_b)_m$—, wherein said heteroaryl or heterocyclyl is independently substituted with one or more groups selected from the group consisting of oxo, arylalkyl substituted with a halogen, haloalkyl, alkylsulfonyl, haloalkylsulfonyl, arylsulfonyl, heteroarylsulfonyl, heterocyclylsulfonyl, $(R_cR_dN)$sulfonyl, and $(R_cR_dN)$sulfonylalkyl and wherein, when the heterocyclyl is pyrrolidinyl, the pyrrolidinyl is not substituted with oxo;

$R_4$ and $R_5$ are independently selected from the group consisting of hydrido, alkylsulfonyl, haloalkylsulfonyl, arylsulfonyl, heteroarylsulfonyl, heterocyclylsulfonyl, $(R_cR_dN)$sulfonyl, and $(R_cR_dlN)$sulfonylalkyl, $R_6$ is isopropyl, isopropenyl, or 1-methyl-1-cyclopropyl;

$R_a$ and $R_b$ are independently selected from the group consisting of hydrido and $C_1$-$C_6$ alkyl, $R_a$ and $R_b$ are taken together with the carbon atom to form an oxo or substituted or unsubstituted cycloalkyl;

$R_c$ and $R_d$ are independently selected from the group consisting of hydrido, $C_1$-$C_6$ alkyl, cycloalkyl, alkoxyalkyl, hydroxyalkyl, alkylthioalkyl, alkylsulfinylalkyl, alkylsulfonylalkyl, carboxyalkyl, hydroxyl, aryl, arylalkyl, heteroaryl, heteroarylalkyl, heterocyclyl, and heterocyclylalkyl groups, or $R_c$ and $R_d$ can together with the nitrogen atom to which they are attached form a heterocyclyl or heteroaryl group, wherein the heterocyclyl or heteroaryl can optionally include one or more heteroatoms selected from the group consisting of nitrogen, sulfur and oxygen; and m is an integer from zero to six.

2. The compound of claim 1, wherein $R_3$ heteroaryl $(CR_aR_b)_m$—.

3. The compound of claim 2, wherein the heteroaryl of heteroaryl$(CR_aR_b)_m$—is a nitrogen containing heteroaryl.

4. The compound of claim 2, wherein the heteroaryl of heteroaryl$(CR_aR_b)_m$—is selected from the group consisting of furanyl, thiophenyl, pyrrolyl, isoxazolyl, oxazolyl, isothiazolyl, thiazolyl, pyrazolyl, imidazolyl, triazolyl, oxadiazolyl, thiadiazolyl, tetrazolyl, pyridinyl, pyrimidinyl, pyrazinyl, benzofuranyl, benzothiophenyl, indolyl, benzopyrrolidinyl, benzimidizolyl, indazolyl, benzotriazolyl, benzisoxazolyl, benzoxazolyl, benzisothiazolyl, benzothiazolyl, dihydroquinolinyl, tetrahydroquinolinyl, benzoxazinyl, quinolinyl, and isoquinolinyl.

5. The compound of claim 1, wherein n is 1, 2 or 3.

6. The compound of claim 1, wherein m is 0, 1, 2 or 3.

7. The compound of claim 1, wherein $R_3$ is heterocyclyl $(CR_aR_b)_m$—.

8. The compound of claim 7, wherein the heterocyclyl of heterocyclyl$(CR_aR_b)_m$—is a nitrogen containing heterocyclyl.

9. The compound of claim 7, wherein the heterocyclyl of heterocyclyl$(CR_aR_b)_m$—is selected from the group consisting of oxiranyl, thiaranyl, aziridinyl, oxetanyl, thiatanyl, azetidinyl, dihydrofuranyl, tetrahydrofuranyl, dihydrothiophenyl, tertahydrothiophenyl, pyrrolinyl, pyrrolidinyl, pyrazolinyl, pyrazolidinyl, imidazolyl, imidazolidinyl, isoxazolinyl, isoxazolidinyl, oxazolinyl, oxazolyl, isothiazolinyl, isothiazolidinyl, thiazolinyl, thiazolidinyl, dihydropyranyl, tetrahydropyranyl, tetrahydrothiopyranyl, dihydropyridinyl, tertahydropyridinyl, piperidinyl, dioxanyl, oxathianyl, dithianyl, oxazinyl, morpholinyl, piperazinyl, thiazinyl, thiomorpholinyl, oxepanyl, thiepanyl, azepanyl, dioxepanyl, oxathiepanyl, oxazapanyl, dithiepanyl, thieazapanyl, diazapanyl, diazabicyclo[2.2.1]heptanyl, oxazabicyclo[2.2.1]heptanyl, thiazabicyclo[2.2.1]heptanyl, diazabicyclo[2.2.1]octanyl, oxazabicyclo[2.2.1]octanyl, and thiazabicyclo[2.2.1]octanyl.

10. The compound of claim 7, wherein the heterocyclyl of heterocyclyl$(CR_aR_b)_m$—is selected from the group consisting of a pyrrolidinyl, a morpholinyl, a piperidinyl, a piperazinyl, an imidazolyl, or an oxazolyl.

11. The compound of claim 7, wherein the heterocyclyl of heterocyclyl$(CR_aR_b)_m$—is piperidinyl or piperazinyl.

12. The compound of claim 1, wherein the heteroaryl or heterocyclyl is substituted with a group selected from alkylsulfonyl, haloalkylsulfonyl, arylsulfonyl, heteroarylsulfonyl, heterocyclylsulfonyl, $(R_cR_dN)$sulfonyl, and $(R_cR_dN)$sulfonylalkyl.

13. The compound of claim 1, wherein the heteroaryl or heterocyclyl is substituted with haloalkyl or haloalkylaryl.

14. The compound of claim 1, wherein $R_3$ is $R_4R_5N(CR_aR_b)_m-$.

* * * * *

UNITED STATES PATENT AND TRADEMARK OFFICE
CERTIFICATE OF CORRECTION

PATENT NO. : 11,236,122 B2
APPLICATION NO. : 17/254189
DATED : February 1, 2022
INVENTOR(S) : Theodore J. Nitz et al.

It is certified that error appears in the above-identified patent and that said Letters Patent is hereby corrected as shown below:

In the Claims

Column 299, Line 36 (Claim 1):
"a pharmaceutically acceptable salt, tautomer thereof"
Should be replaced with:
--a pharmaceutically acceptable salt or tautomer thereof--.

Column 300, Line 6 (Claim 1):
"($R_cR_dIN$)sulfonylalkyl"
Should be replaced with:
--($R_cR_dN$)sulfonylalkyl--.

Column 300, Line 9 (Claim 1):
"$C_1$-$C_6$ alkyl, $R_a$ and $R_b$"
Should be replaced with:
--$C_1$-$C_6$ alkyl, or $R_a$ and $R_b$--.

Column 300, Line 24 (Claim 2):
"$R_3$ heteroaryl$(CR_aR_b)_m$—"
Should be replaced with:
--$R_3$ is heteroaryl$(CR_aR_b)_m$— --.

Column 300, Lines 27 and 29 (Claims 3 and 4):
"heteroaryl$(CR_aR_b)_m$—is"
Should be replaced with:
--heteroaryl$(CR_aRb)_m$— is--.

Column 300, Lines 43, 46, 63, and 67 (Claims 8-11):
"heterocyclyl$(CR_aR_b)_m$—is"

Signed and Sealed this
Third Day of May, 2022

*Katherine Kelly Vidal*
Director of the United States Patent and Trademark Office Should be replaced with:
--heterocyclyl$(CR_aR_b)_m$— is--.